United States Patent
Lee et al.

(10) Patent No.: US 10,333,081 B2
(45) Date of Patent: Jun. 25, 2019

(54) COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

(71) Applicant: SAMSUNG SDI CO., LTD., Yongin-si, Gyeonggi-do (KR)

(72) Inventors: Han-Ill Lee, Uiwang-si (KR);
Dong-Wan Ryu, Uiwang-si (KR);
Sung-Hyun Jung, Uiwang-si (KR);
Mi-Young Chae, Uiwang-si (KR);
Dal-Ho Huh, Uiwang-si (KR);
Jin-Seok Hong, Uiwang-si (KR);
Jun-Seok Kim, Uiwang-si (KR);
Dong-Kyu Ryu, Uiwang-si (KR);
Yu-Na Jang, Uiwang-si (KR);
Young-Kyoung Jo, Uiwang-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/869,149

(22) Filed: Jan. 12, 2018

(65) Prior Publication Data
US 2018/0138423 A1    May 17, 2018

Related U.S. Application Data

(60) Division of application No. 14/613,699, filed on Feb. 4, 2015, now Pat. No. 9,899,607, which is a
(Continued)

(30) Foreign Application Priority Data

Aug. 21, 2012 (KR) .................... 10-2012-0091340

(51) Int. Cl.
*H01L 51/00* (2006.01)
*C07D 405/04* (2006.01)
(Continued)

(52) U.S. Cl.
CPC ........ *H01L 51/0072* (2013.01); *C07D 405/04* (2013.01); *C07D 405/14* (2013.01);
(Continued)

(58) Field of Classification Search
None
See application file for complete search history.

(56) References Cited

U.S. PATENT DOCUMENTS

| | | |
|---|---|---|
| 2010/0012931 A1 | 1/2010 | Kato et al. |
| 2011/0201778 A1 | 8/2011 | Stoessel et al. |
| 2011/0272684 A1 | 11/2011 | Parham et al. |

FOREIGN PATENT DOCUMENTS

| | | |
|---|---|---|
| CN | 102056899 A | 5/2011 |
| CN | 102056911 A | 5/2011 |

(Continued)

OTHER PUBLICATIONS

Du, Chunyan, et al., "Synthesis of novel fluorene benzothiophene compounds and application thereof in organic light-emitting diodes", The 8th National Symposium on Electronic Process in Organic Solids, p. 180, Jun. 17, 2010.

(Continued)

*Primary Examiner* — Robert S Loewe
(74) *Attorney, Agent, or Firm* — Lee & Morse, P.C.

(57) ABSTRACT

A compound for an organic optoelectronic device, an organic light emitting diode including the same, and a display device including the organic light emitting diode are disclosed and the compound for an organic optoelectronic device represented by a combination of the following Chemical Formulae 1 and 2 provides an organic light (Continued)

emitting diode having life-span characteristics due to excellent electrochemical and thermal stability, and high luminous efficiency at a low driving voltage.

17 Claims, 1 Drawing Sheet

Related U.S. Application Data continuation of application No. PCT/KR2013/005197, filed on Jun. 12, 2013.

(51) Int. Cl.
| | |
|---|---|
| C07D 409/04 | (2006.01) |
| C09K 11/06 | (2006.01) |
| H05B 33/10 | (2006.01) |
| C07D 405/14 | (2006.01) |
| C07D 409/14 | (2006.01) |
| H01L 51/50 | (2006.01) |

(52) U.S. Cl.
CPC ......... *C07D 409/04* (2013.01); *C07D 409/14* (2013.01); *C09K 11/06* (2013.01); *H01L 51/0073* (2013.01); *H01L 51/0074* (2013.01); *H05B 33/10* (2013.01); *C09K 2211/1029* (2013.01); *C09K 2211/1088* (2013.01); *C09K 2211/1092* (2013.01); *H01L 51/0052* (2013.01); *H01L 51/0054* (2013.01); *H01L 51/0081* (2013.01); *H01L 51/5012* (2013.01); *H01L 51/5016* (2013.01); *H01L 51/5056* (2013.01); *H01L 51/5072* (2013.01); *H01L 2251/308* (2013.01)

(56) References Cited

FOREIGN PATENT DOCUMENTS

| | | |
|---|---|---|
| DE | 10 2009 005 289 A1 | 7/2010 |
| JP | 2003-306454 A | 10/2003 |
| KR | 10-2008-0015865 A | 2/2008 |
| KR | 10-2008-0031808 A | 4/2008 |
| KR | 10-2008-0108115 A | 12/2008 |
| KR | 10-2009-0120381 A | 11/2009 |
| KR | 10-2010-0006071 A | 1/2010 |
| KR | 10-2010-0106415 A | 10/2010 |
| KR | 10-2011-0013445 A | 2/2011 |
| KR | 10-2011-0025906 A | 3/2011 |
| KR | 10-2011-0057400 A | 6/2011 |
| KR | 10-2011-0070251 A | 6/2011 |
| KR | 10-2011-0077032 A | 7/2011 |
| KR | 10-2011-0092264 A | 8/2011 |
| KR | 10-2011-0122129 A | 11/2011 |
| KR | 10-2011-0122130 A | 11/2011 |
| KR | 10-2012-0047706 A | 5/2012 |
| KR | 10-2012-0078301 A | 7/2012 |
| WO | WO 2006/122630 A1 | 11/2006 |
| WO | WO 2009/148015 A | 12/2009 |
| WO | WO 2010/083873 A1 | 7/2010 |

OTHER PUBLICATIONS

Search Report dated Oct. 16, 2015 in corresponding Chinese Patent Application No. 2013800435473.
Extended European Search Report dated Jan. 21, 2016 in corresponding European Application No. 13830964.6; Lee, et al.
Extended European Search Report dated May 17, 2016 in Corresponding European Patent Application No. 13830964.6.

COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

CROSS-REFERENCE TO RELATED APPLICATIONS

This is a divisional application based on pending application Ser. No. 14/613,699, filed Feb. 4, 2015, the entire contents of which is hereby incorporated by reference.

This application is a continuation of pending International Application No. PCT/KR2013/005197, entitled "Compound for Organic Optoelectronic Device, Organic Light Emitting Diode Including the Same and Display Including the Organic Light Emitting Diode," which was filed on Jun. 12, 2013, the entire contents of which are hereby incorporated by reference.

Korean Patent Application No. 10-2012-0091340, filed on Aug. 21, 2012, and Korean Patent Application No. 10-2013-0067316, filed on Jun. 12, 2013, in the Korean Intellectual Property Office, and entitled: "Compound for Organic Optoelectronic Device, Organic Light Emitting Diode Including the Same and Display Including the Organic Light Emitting Diode," are incorporated by reference herein in their entirety.

BACKGROUND

1. Field

A compound for an organic optoelectronic device being capable of providing an organic optoelectronic device having excellent life-span, efficiency, electrochemical stability, and thermal stability, and an organic light emitting diode and a display device including the organic light emitting diode are disclosed.

2. Description of the Related Art

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer includes a multi-layer including different materials, for example a hole injection layer (HIL), a hole transport layer (HTL), an emission layer, an electron transport layer (ETL), and an electron injection layer (EIL), in order to improve efficiency and stability of an organic photoelectric device.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic photoelectric device in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

The low molecular organic light emitting diode is manufactured as a thin film in a vacuum deposition method and can have good efficiency and life-span performance. A polymer organic light emitting diode is manufactured in an Inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristic compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Based on these advantages, they have been remarkably developed to have 80 times efficiency and more than 100 times life-span since they come out for the first time in the late 1980s. Recently, they keep being rapidly larger such as a 40-inch organic light emitting diode panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons. Accordingly, while increasing electron injection and mobility from a cathode and simultaneously preventing movement of holes is required.

In order to improve life-span, a material crystallization caused by Joule heats generated during device operating is required to be prevented. Accordingly, there has been a strong need for an organic compound having excellent electron injection and mobility, and high electrochemical stability.

SUMMARY

A compound for an organic optoelectronic device that may act as hole injection and transport material or an electron injection and transport material, and also act as a light emitting host along with an appropriate dopant is provided.

An organic light emitting diode having excellent life-span, efficiency, driving voltage, electrochemical stability and thermal stability and a display device including the same are provided.

In one embodiment of the present invention, a compound for an organic optoelectronic device represented by a combination of the following Chemical Formulae 1 and 2 is provided.

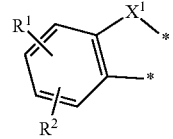

[Chemical Formula 1]

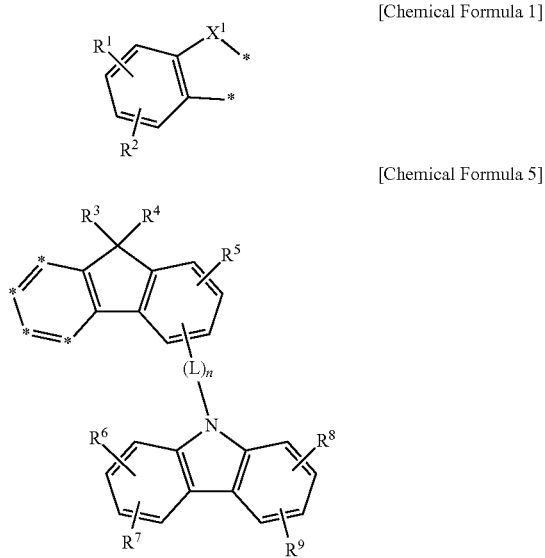

[Chemical Formula 5]

in the Chemical Formulae 1 and 2, $X^1$ is —O—, —S—, —S(O)— or —S(O)$_2$—, $R^1$ to $R^9$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 2 to form a fused ring.

The compound for an organic optoelectronic device may be represented by a combination of the following Chemical Formulae 1 and 3.

[Chemical Formula 1]

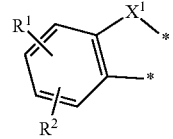

[Chemical Formula 3]

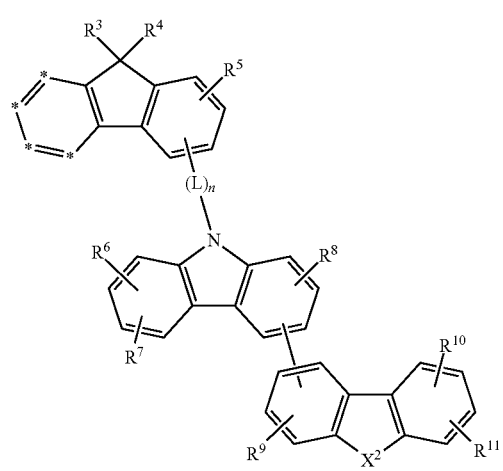

In the Chemical Formulae 1 and 3, $X^1$ is —O—, —S—, —S(O)— or —S(O)$_2$—, $X^2$ is —O—, —S—, —S(O)—, —S(O)$_2$—, —CR'R"— or —NR'—, wherein the R' and R" are independently, hydrogen, deuterium, a substituted or unsubstituted C1 to C10 alkyl group, a substituted or unsubstituted C6 to C30 aryl group or a substituted or unsubstituted C2 to C30 heteroaryl group, $R^1$ to $R^{11}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 3 to form a fused ring.

The compound for an organic optoelectronic device may be represented by a combination of the following Chemical Formulae 1 and 4.

[Chemical Formula 1]

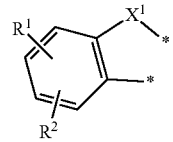

-continued

[Chemical Formula 4]

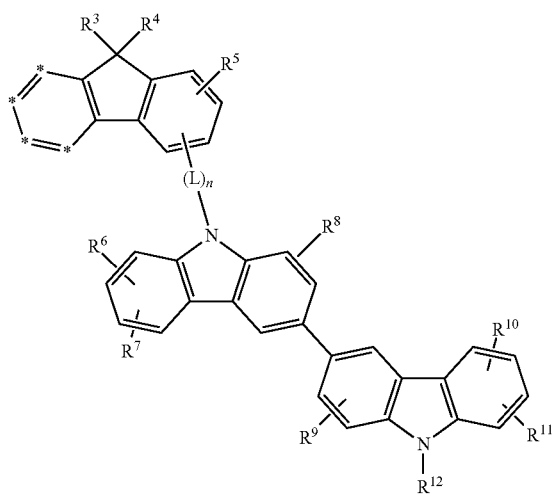

in the Chemical Formulae 1 and 4, $X^1$ is —O—, —S—, —S(O)— or —S(O)$_2$—, $R^1$ to $R^{12}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 4 to form a fused ring.

In another embodiment of the present invention, a compound for an organic optoelectronic device represented by a combination of the following Chemical Formulae 1 and 5 is provided.

[Chemical Formula 1]

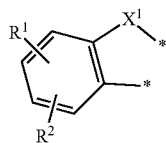

[Chemical Formula 5]

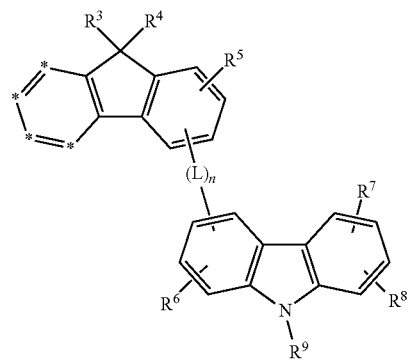

In the Chemical Formulae 1 and 5, $X^1$ is —O—, —S—, —S(O)— or —S(O)$_2$—, $R^1$ to $R^9$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 5 to form a fused ring.

The compound for an organic optoelectronic device may be represented by a combination of the following Chemical Formulae 1 and 6.

[Chemical Formula 1]

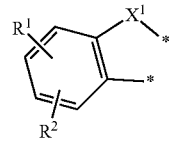

[Chemical Formula 6]

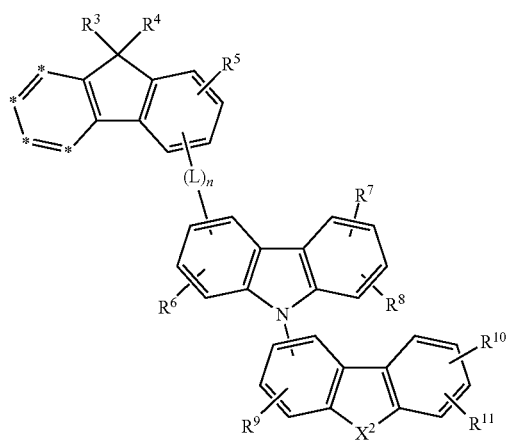

In the Chemical Formulae 1 and 5, $X^1$ is —O—, —S—, —S(O)— or —S(O)$_2$—, $X^2$ is —O—, —S—, —S(O)—, —S(O)$_2$—, —CR'R"— or —NR'—, wherein the R' and R" are independently, hydrogen, deuterium, a substituted or unsubstituted C1 to C10 alkyl group, a substituted or unsubstituted C6 to C30 aryl group or a substituted or unsubstituted C2 to C30 heteroaryl group, $R^1$ to $R^{11}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 6 to form a fused ring.

The compound for an organic optoelectronic device may be represented by a combination of the following Chemical Formulae 1 and 7.

[Chemical Formula 1]

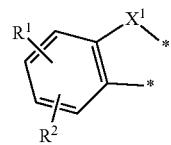

-continued

[Chemical Formula 7]

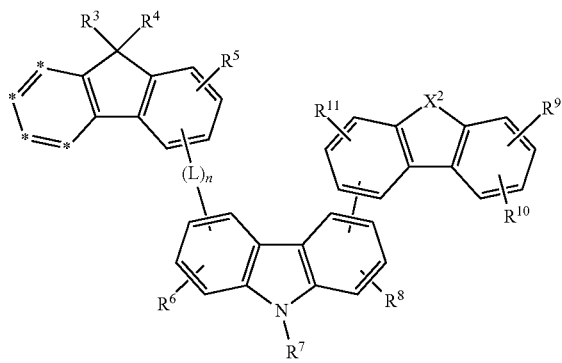

In the Chemical Formulae 1 and 7, $X^1$ is —O—, —S—, —S(O)— or —S(O)$_2$—, $X^2$ is —O—, —S—, —S(O)—, —S(O)$_2$—, —CR'R"— or —NR'—, wherein the R' and R" are independently, hydrogen, deuterium, a substituted or unsubstituted C1 to C10 alkyl group, a substituted or unsubstituted C6 to C30 aryl group or a substituted or unsubstituted C2 to C30 heteroaryl group, $R^1$ to $R^{11}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 7 to form a fused ring.

The $R^1$ to $R^9$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

In another embodiment of the present invention, a compound for an organic optoelectronic device represented by the following Chemical Formulae AD-1 and AD-2 is provided.

[Chemical Formula AD-1]

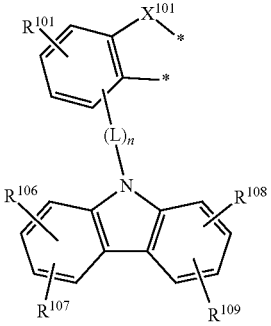

[Chemical Formula AD-2]

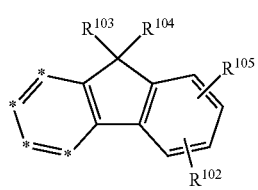

In the Chemical Formulae AD-1 and AD-2, $X^{101}$ is —O—, —S—, —S(O)— or —S(O)$_2$—, $R^{101}$ to $R^{109}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-1 are bonded with adjacent two *'s of four *'s of the Chemical Formula AD-2 to form a fused ring.

The compound for an organic optoelectronic device may be represented by a combination of the following Chemical Formulae AD-3 and AD-2.

[Chemical Formula AD-3]

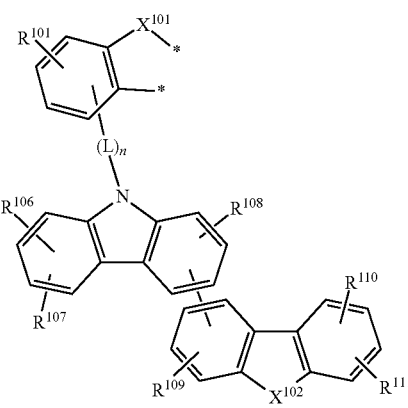

-continued

[Chemical Formula AD-2]

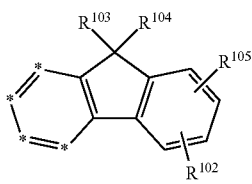

In the Chemical Formulae AD-3 and AD-2, $X^{101}$ is —O—, —S—, —S(O)— or —S(O)$_2$—, $X^{102}$ is —O—, —S—, —S(O)—, —S(O)$_2$—, —CR'R''— or —NR'—, wherein the R' and R'' are independently, hydrogen, deuterium, a substituted or unsubstituted C1 to C10 alkyl group, a substituted or unsubstituted C6 to C30 aryl group or a substituted or unsubstituted C2 to C30 heteroaryl group, $R^{101}$ to $R^{111}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-3 are bonded with adjacent two *'s of four *'s of the Chemical Formula AD-2 to form a fused ring.

The compound for an organic optoelectronic device may be represented by a combination of the following Chemical Formulae AD-4 and AD-2.

[Chemical Formula AD-4]

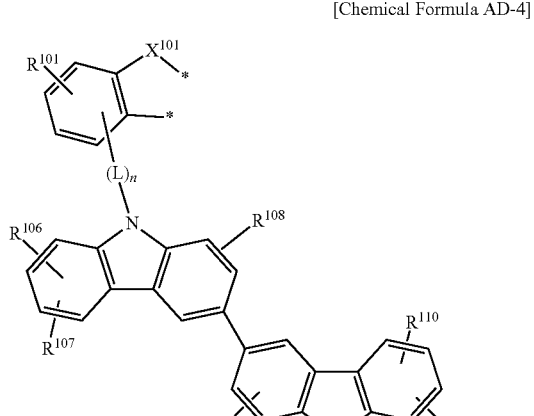

[Chemical Formula AD-2]

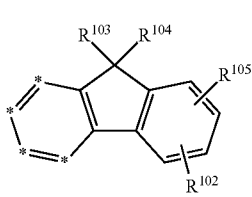

In the Chemical Formulae AD-4 and AD-2, $X^{101}$ is —O—, —S—, —S(O)— or —S(O)$_2$—, $R^{101}$ to $R^{112}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-4 are bonded with adjacent two *'s of four *'s of the Chemical Formula AD-2 to form a fused ring.

In another embodiment of the present invention, a compound for an organic optoelectronic device represented by the following Chemical Formulae AD-5 and AD-2 is provided.

[Chemical Formula AD-5]

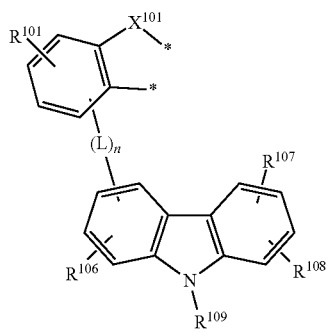

[Chemical Formula AD-2]

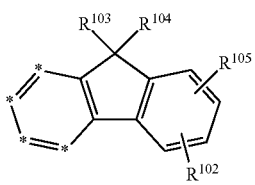

In the Chemical Formulae AD-5 and AD-2, $X^{101}$ is —O—, —S—, —S(O)— or —S(O)$_2$—, $R^{101}$ to $R^{109}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-5 are bonded with adjacent two *'s of four *'s of the Chemical Formula AD-2 to form a fused ring.

The compound for an organic optoelectronic device may be represented by a combination of the following Chemical Formulae AD-6 and AD-2.

[Chemical Formula AD-6]

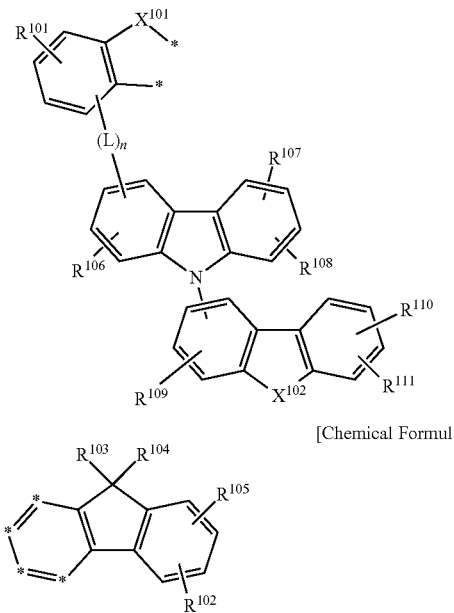

[Chemical Formula AD-2]

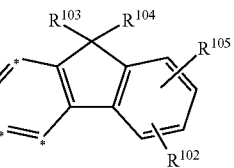

In the Chemical Formulae AD-6 and AD-2, $X^{101}$ is —O—, —S—, —S(O)— or —S(O)$_2$—, $X^{102}$ is —O—, —S—, —S(O)—, —CR'R"—, —S(O)$_2$— or —NR'—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^{101}$ to $R^{111}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-6 are bonded with adjacent two *'s of four *'s of the Chemical Formula AD-2 to form a fused ring.

The compound for an organic optoelectronic device may be represented by a combination of the following Chemical Formulae AD-7 and AD-2.

[Chemical Formula AD-7]

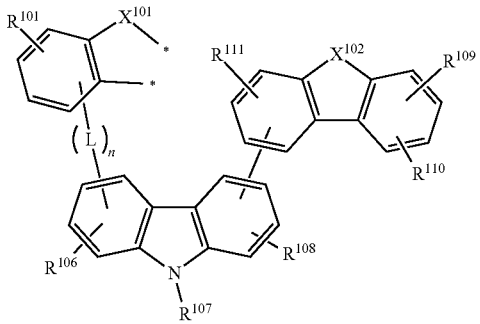

[Chemical Formula AD-2]

In the Chemical Formulae AD-7 and AD-2, $X^{101}$ is —O—, —S—, —S(O)— or —S(O)$_2$—, $X^{102}$ is —O—, —S—, —S(O)—, —S(O)$_2$—, —CR'R"— or —NR'—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^{101}$ to $R^{11}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-7 are bonded with adjacent two *'s of four *'s of the Chemical Formula AD-2 to form a fused ring.

The $R^{101}$ to $R^{109}$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

The compound for an organic optoelectronic device may have triplet exciton energy (T1) of greater than or equal to 2.0 eV.

The organic optoelectronic device may be selected from the group consisting of an organic photoelectric device, an organic light emitting diode, an organic solar cell, an organic transistor, an organic photo-conductor drum, and an organic memory device.

In another embodiment of the present invention, provided is an organic light emitting diode including an anode, a cathode, and at least one organic thin layer interposed between the anode and cathode, wherein at least one of the organic thin layers includes the compound for an organic optoelectronic device.

The organic thin layer may be selected from the group consisting of an emission layer, a hole transport layer, a hole injection layer, an electron transport layer, an electron injection layer, a hole blocking layer, and a combination thereof.

The compound for an organic optoelectronic device may be included in a hole transport layer (HTL) or a hole injection layer (HIL).

The compound for an organic optoelectronic device may be included in an emission layer.

The compound for an organic optoelectronic device may be used as a phosphorescent or fluorescent host material in an emission layer.

In yet another embodiment of the present invention, a display device including the organic light emitting diode is provided.

A compound having high hole or electron transport properties, film stability, thermal stability, and high triplet exciton energy may be provided.

Such a compound may be used as a hole injection/transport material, host material, or electron injection/transport material of an emission layer. An organic optoelectronic device using the same has improved life-span characteristics and high luminous efficiency at a low driving voltage due to excellent electrochemical and thermal stability.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
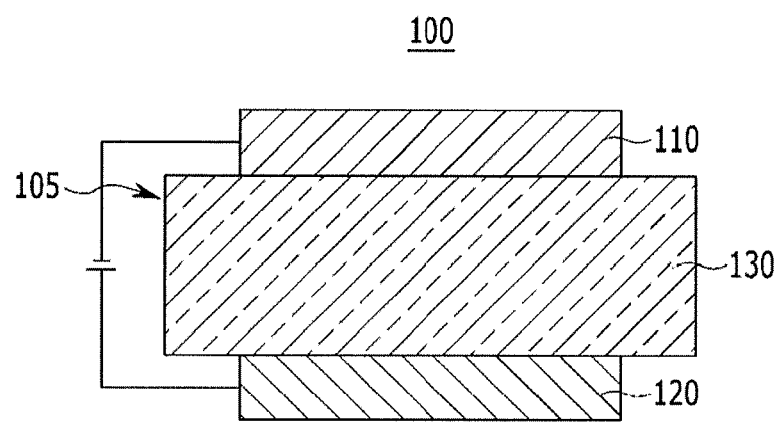
FIGS. 1 and 2 illustrate cross-sectional views showing organic light emitting diodes according to various embodiments of the present invention including the compound for an organic optoelectronic device according to one embodiment.

Hereinafter, embodiments of the present invention are described in detail. However, these embodiments are exemplary, and the present invention is not limited thereto and is limited by the claims.

In the present specification, when a definition is not otherwise provided, "substituted" refers to one substituted with deuterium, a halogen, hydroxy group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

The two adjacent substituents selected from the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring.

In the present specification, when specific definition is not otherwise provided, "hetero" refers to one including 1 to 3 hetero atoms selected from the group consisting of N, O, S, and P, and remaining carbons in one functional group.

In the present specification, when a definition is not otherwise provided, "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond.

The alkyl group may be a branched, linear, or cyclic alkyl group.

The "alkenyl group" refers to a functional group of at least one carbon-carbon double bond of at least two carbons, and the "alkynyl group" refers to a functional group of at least one carbon-carbon triple bond of at least two carbons.

The alkyl group may be a C1 to C20 alkyl group. More specifically, the alkyl group may be a C1 to C10 alkyl group or a C1 to C6 alkyl group.

For example, a C1 to C4 alkyl group may have 1 to 4 carbon atoms in an alkyl chain which may be selected from the group consisting of methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

"Aromatic group" refers to a cyclic functional group where all elements have p-orbitals, and these p-orbitals forms conjugation. Specific examples are aryl group and a heteroaryl group.

"Aryl group" includes monocyclic or fused polycyclic (i.e., rings sharing adjacent pairs of carbon atoms) groups.

"Heteroaryl group" refers to aryl group including 1 to 3 hetero atoms selected from the group consisting of N, O, S, and P, and remaining carbons. When the heteroaryl group is a fused ring, each ring may include 1 to 3 hetero atoms.

In the present specification, the carbazole-based derivative may refer to a substituted structure where a nitrogen atom of a substituted or unsubstituted carbazolyl group is substituted with a hetero atom except nitrogen, or carbon. Specific examples may be dibenzofuran (dibenzofuranyl group), dibenzothiophene (dibenzothiophenyl group), fluorene (fluorenyl group), and the like.

In the present specification, hole characteristics refer to characteristics that holes formed in the anode is easily injected into the emission layer and transported in the emission layer due to conductive characteristics according to HOMO level.

Electron characteristics refer to characteristics that electron formed in the cathode is easily injected into the emission layer and transported in the emission layer due to conductive characteristics according to LUMO level.

In the present specification, a benzothiophene-based derivative includes a structure where S of a benzothiophene compound is substituted with another heteroatom except S. For specific examples, the heteroatom may include —O—, —S—, —S(O)—, —S(O)$_2$— or —NR'—.

A compound for an organic optoelectronic device according to one embodiment of the present invention has a structure where a substituted or unsubstituted carbazolyl group is bonded with a fluorene-based fused ring core.

The core structure may be used as a light emitting material, a hole injection material or a hole transport material of an organic optoelectronic device. Particularly, it may be appropriate for a hole injection material or a hole transport material.

The compound for an organic optoelectronic device includes a core moiety and various substituents for a substituent for substituting the core moiety and thus may have various energy bandgaps.

When the compound having an appropriate energy level depending on a substituent is used to manufacture an organic optoelectronic device, the compound reinforces hole transport capability or electron transport capability and thus, brings about excellent effects in terms of efficiency and a driving voltage, and also, has excellent electrochemical and thermal stability and thus, may improve life-span characteristics of the organic optoelectronic device.

According to one embodiment of the present invention, the compound for an organic optoelectronic device is a compound for an organic optoelectronic device represented by a combination of the following Chemical Formulae 1 and 2.

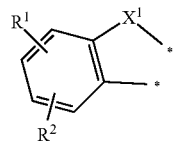

[Chemical Formula 1]

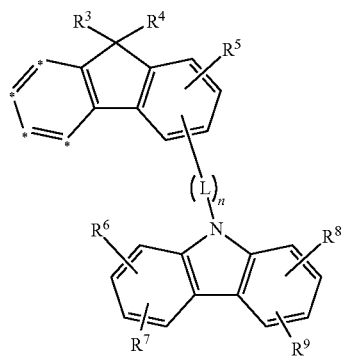

[Chemical Formula 2]

In the Chemical Formulae 1 and 2, $X^1$ is —O—, —S—, —S(O)— or —S(O)$_2$—, $R^1$ to $R^9$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 2 to form a fused ring.

Due to the carbazolyl group, electrons and holes in the fluorene-based fused core may be easily transported through whole the compound. Thereby a device including the compound for an organic optoelectronic device may have improved life-span characteristics. In addition, when it is directly boned with amine (N) of the carbazolyl group, the HOMO may be remarkably reduced, and an organic compound having large a band gap may be synthesized. Accordingly, the compound for an organic optoelectronic device may be applied to a device variously.

The $X^1$ may be —O—, —S—, —S(O)— or —S(O)$_2$—. When the $X^1$ is —O—, life-span characteristics of a device may be improved, and when the $X^1$ is —S—, efficiency characteristics of a device may be improved.

More specifically, the $X^1$ may be —O— or —S—. In this case, an interaction with an electrode may be easy due to unshared electron pairs such as —O— and —S, and thus mobility is high. Because of this, a driving voltage may be lowered. At the same time, molecular interactions is small, crystallization may be suppressed and thus a manufacture yield of a device is improved, and a life-span of a device may be longer.

The $R^3$ and $R^4$ may be a substituted or unsubstituted C6 to C30 aryl group. More specifically, they may be a phenyl group. When the $R^3$ and $R^4$ are a substituted or unsubstituted C6 to C30 aryl group, thermal stability of the compound may be improved.

In addition, the compound may suppress has a small molecular interaction due to steric hindrance, and thus crystallization may be suppressed. Thereby, a manufacture yield of a device is improved. In addition, life-span characteristics of a device may be improved.

The compound has a relatively large molecular weight, and a compound decomposition may be suppressed during deposition.

The L may be selectively adjusted to determine an entire conjugation length of a compound, and thereby triplet energy bandgap may be adjusted. Thereby, material characteristics required for an organic photoelectric device may be realized. The triplet energy bandgap may be also adjusted by changing binding positions such as ortho, para, or meta.

Specific examples of the L may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted p-terphenyl group, a substituted or unsubstituted m-terphenyl group, a substituted or unsubstituted perylenyl group, and the like.

More specifically, the compound for an organic optoelectronic device may be represented by a combination of the following Chemical Formulae 1 and 3.

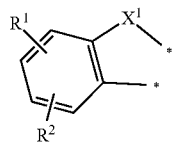

[Chemical Formula 1]

[Chemical Formula 3]

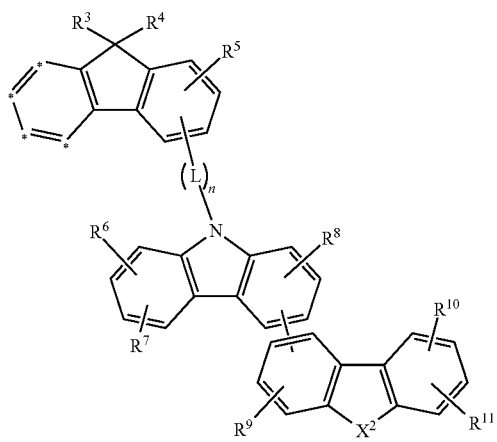

[Chemical Formula 4]

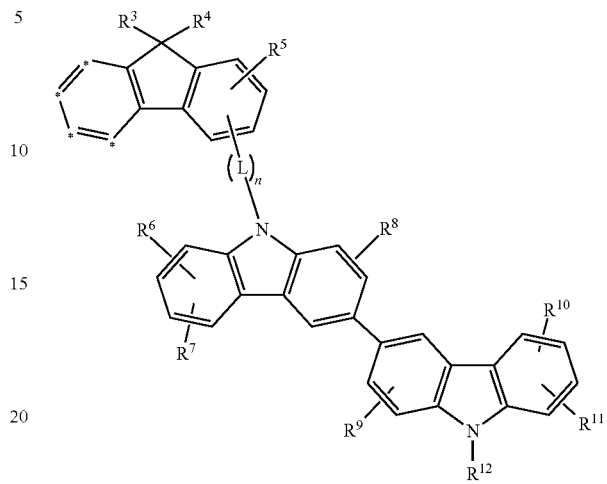

In the Chemical Formulae 1 and 3, $X^1$ is —O—, —S—, —S(O)— or —S(O)$_2$—, $X^2$ is —O—, —S—, —S(O)—, —S(O)$_2$—, —CR'R"— or —NR'—, wherein the R' and R" are independently, hydrogen, deuterium, a substituted or unsubstituted C1 to C10 alkyl group, a substituted or unsubstituted C6 to C30 aryl group or a substituted or unsubstituted C2 to C30 heteroaryl group, $R^1$ to $R^{11}$, are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 3 to form a fused ring.

When the compound for an organic optoelectronic device is represented by the combination of the Chemical Formulae 1 and 3, electrons and holes of the fluorene fused structure may be spread into the entire compound through binding with carbazole and life-span of a device may be longer.

Through the structure of the Chemical Formula 3, efficiency characteristics of a device may be improved.

More specifically, the compound for an organic optoelectronic device may be represented by a combination of the following Chemical Formulae 1 and 4.

In the Chemical Formulae 1 and 4, $X^1$ is —O—, —S—, —S(O)— or —S(O)$_2$—, $R^1$ to $R^{12}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 4 to form a fused ring.

When the compound for an organic optoelectronic device is represented by a combination of the Chemical Formulae 1 and 4, a biscarbazole structure may be included. Specifically, when a carbazole structure is included in Chemical Formula 4, triplet energy is remarkably increased, and thus luminous efficiency of a phosphorescence device may be improved.

In another embodiment of the present invention, a compound for an organic optoelectronic device represented by a combination of the following Chemical Formulae 1 and 5 is provided.

[Chemical Formula 1]

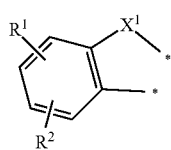

[Chemical Formula 1]

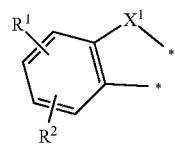

[Chemical Formula 5]

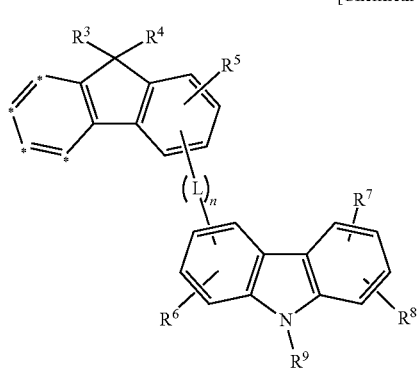

[Chemical Formula 6]

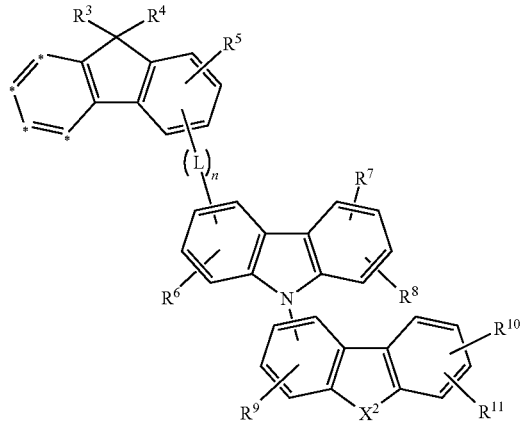

In the Chemical Formulae 1 and 5, $X^1$ is —O—, —S—, —S(O)— or —S(O)$_2$—, $R^1$ to $R^9$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 5 to form a fused ring.

The compound for an organic optoelectronic device represented by a combination of the Chemical Formulae 1 and 5 includes a carbazolyl group at a different binding position from that of the compound for an organic optoelectronic device represented by a combination of the Chemical Formulae 1 and 2.

The compound for an organic optoelectronic device represented by a combination of the Chemical Formulae 1 and 5 may have higher HOMO than a compound having the above structure. In addition, the structure represented by a combination of the Chemical Formulae 1 and 5 may improve efficiency and life-span characteristics of a device.

Other substituents are the same as those of the compound for an organic optoelectronic device represented by a combination of the Chemical Formulae 1 and 2 and thus, will not be illustrated again.

More specifically, the compound for an organic optoelectronic device may be represented by a combination of the following Chemical Formulae 1 and 6.

[Chemical Formula 1]

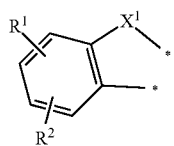

In the Chemical Formulae 1 and 6, $X^1$ is —O—, —S—, —S(O)— or —S(O)$_2$—, $X^2$ is —O—, —S(O)—, —CR'R''—, —S(O)$_2$— or —NR'—, wherein the R' and R'' are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^1$ to $R^{11}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 6 to form a fused ring.

More specifically, the compound for an organic optoelectronic device may be represented by a combination of the following Chemical Formulae 1 and 7.

[Chemical Formula 1]

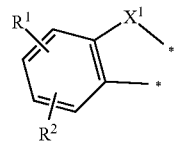

[Chemical Formula 7]

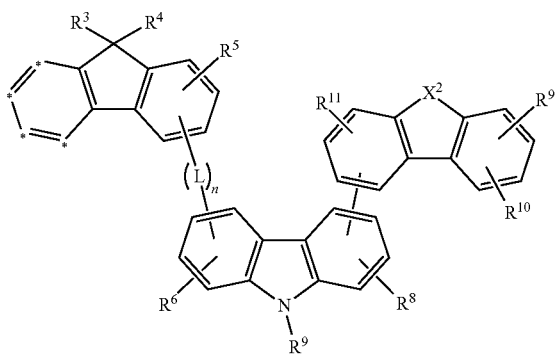

In the Chemical Formulae 1 and 7, $X^1$ is —O—, —S—, —S(O)— or —S(O)$_2$—, $X^2$ is —O—, —S—, —S(O)—, —S(O)$_2$—, —CR'R"— or —NR'—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, R$^1$ to R$^{11}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula 1 are bonded with adjacent two *'s of four *'s of the Chemical Formula 7 to form a fused ring.

When the compound for an organic optoelectronic device is binded with an additional carbazolyl-based substituent like the compounds represented by a combination of the following Chemical Formulae 1 and 6 and a combination of the following Chemical Formulae 1 and 7, triplet energy is remarkably increased, and thus, luminous efficiency of a phosphorescence device may be improved.

The R$^1$ to R$^9$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but is not limited thereto.

The substituents of R$^1$ to R$^9$ may be applied to R$^1$ to R$^{11}$ of all the above chemical formulae.

The compound for an organic optoelectronic device may have light emission, hole or electron characteristics; film stability; thermal stability and high triplet exciton energy (T1) due to the substituents.

In another embodiment of the present invention, a compound for an organic optoelectronic device represented by the following Chemical Formulae AD-1 and AD-2 is provided.

[Chemical Formula AD-1]

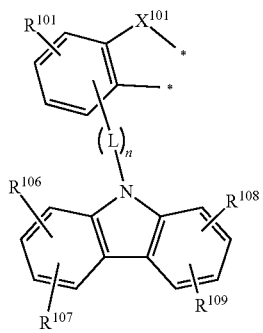

[Chemical Formula AD-2]

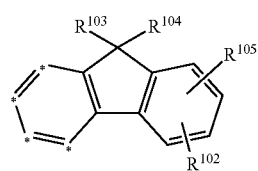

In the Chemical Formulae AD-1 and AD-2, X$^{101}$ is —O—, —S—, —S(O)— or —S(O)$_2$—, R$^{101}$ to R$^{109}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-1 are bonded with adjacent two *'s of four *'s of the Chemical Formula AD-2 to form a fused ring.

A compound represented by the Chemical Formula AD-1 and AD-2 includes a carbazolyl group at a different binding position from that of the compound represented by a combination of Chemical Formulae 1 and 2 according to one embodiment of the present invention.

Since the Chemical Formula 1 has higher hole-forming capability than Chemical Formula 2, a compound should have higher hole characteristics, but hole-forming capability of the compound may be adjusted, so that it may be applied to various devices.

Herein, the hole-forming capability may be adjusted by changing the binding position of the carbazolyl group through a combination of the Chemical Formulae AD-1 and AD-2. In addition, entire hole/electron mobility inside a molecule may be increased by directly connecting an AD-1 group having high hole/electron mobility to the carbazolyl group.

Other substituents are similar to those of the compound represented by a combination of Chemical Formulae 1 and 2 according to one embodiment of the present invention.

Specifically, the compound for an organic optoelectronic device may be represented by a combination of the following Chemical Formulae AD-3 and AD-2.

However, the combination of the Chemical Formulae AD-1 and AD-2 has a limit in adjusting hole/electron mobility. The reason is that the combination of the Chemical Formulae AD-1 and AD-2 has high electron mobility but may require higher mobility depending on a device. Accordingly, a carbazolyl group having high hole forming capability may be added to the carbazolyl group to promote hole formation and to increase hole transport capability, or a substituent substituted with —O—, or —S— may be used to provide higher hole/electron mobility. The compound may be widely applied to more devices through this structural change.

[Chemical Formula AD-3]

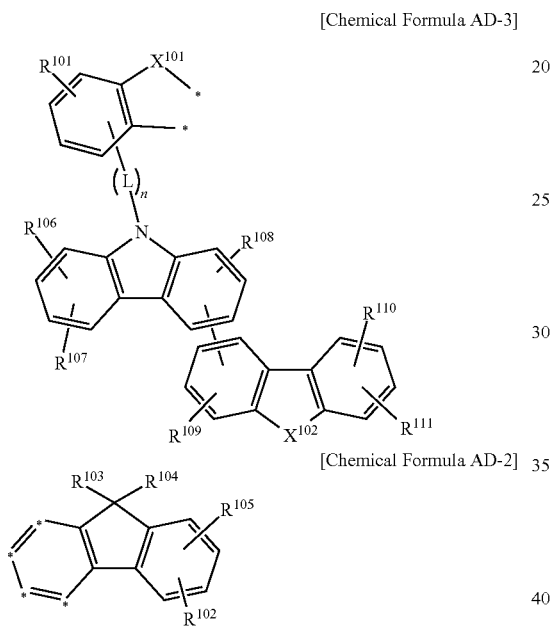

[Chemical Formula AD-2]

In the Chemical Formulae AD-3 and AD-2, $X^{101}$ is —O—, —S—, —S(O)— or —S(O)$_2$—, $X^{102}$ is —O—, —S—, —S(O)—, —S(O)$_2$—, —CR'R''— or —NR'—, wherein the R' and R'' are independently, hydrogen, deuterium, a substituted or unsubstituted C1 to C10 alkyl group, a substituted or unsubstituted C6 to C30 aryl group or a substituted or unsubstituted C2 to C30 heteroaryl group, $R^{101}$ to $R^{111}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-3 are bonded with adjacent two *'s of four *'s of the Chemical Formula AD-2 to form a fused ring.

More specifically, the compound for an organic optoelectronic device may be represented by a combination of the following Chemical Formulae AD-4 and AD-2.

When mobility is insufficient by the combination of Chemical Formulae AD-3 and AD-2, hole/electron mobility may be increased by connecting a substituent having fast mobility to the $R^{112}$. In addition, the entire HOMO level inside the molecule may be easily changed depending on a kind of substituent at the N position of a carbazolyl group. Accordingly, when the HOMO level is difficult to change by the combination of AD-3 and AD-2, the HOMO level may be changed by combining AD-4 and AD-2.

[Chemical Formula AD-4]

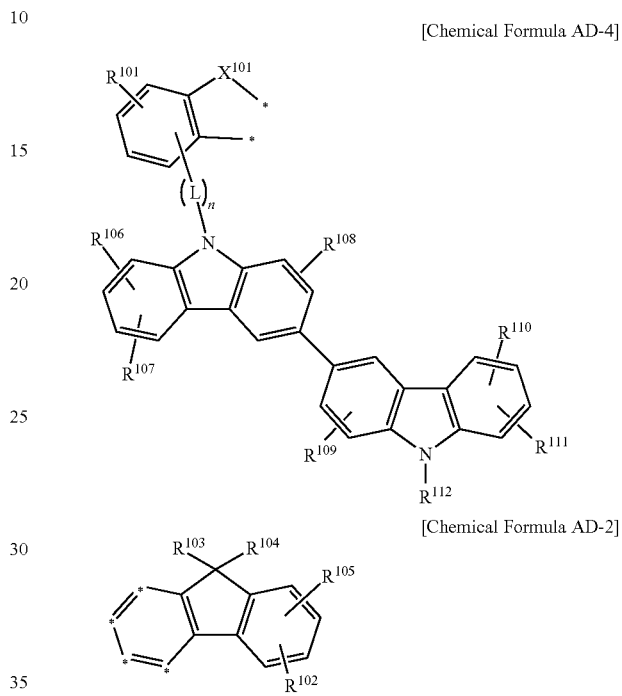

[Chemical Formula AD-2]

In the Chemical Formulae AD-4 and AD-2, $X^{101}$ is —O—, —S—, —S(O)— or —S(O)$_2$—, $R^{101}$ to $R^{112}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s in the Chemical Formula AD-4 are bonded with two neighboring *'s out of four *'s in the Chemical Formula AD-2 and form a fused ring.

In another embodiment of the present invention, a compound for an organic optoelectronic device represented by the following Chemical Formulae AD-5 and AD-2 is provided.

The compound needs a part capable of adjusting a bandgap inside a molecule, so that the compound may be applied to various organic light emitting diodes. As shown in the following combination of Chemical Formulae AD-5 and AD-2, when connected in other directions except the N direction of a carbazolyl group an HOMO level inside the molecule may be increased. For example, when the carbazole N bond has a HOMO level ranging from −5.3 eV to −5.5 eV, the following Chemical Formula may have a HOMO level ranging from −5.0 eV to −5.2 eV.

[Chemical Formula AD-5]

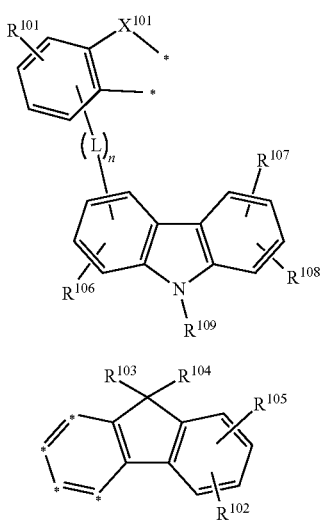

[Chemical Formula AD-2]

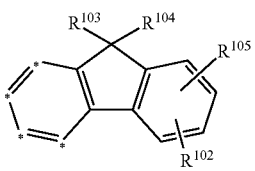

In the Chemical Formulae AD-5 and AD-2, $X^{101}$ is —O—, —S—, —S(O)— or —S(O)$_2$—, $R^{101}$ to $R^{109}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-5 are bonded with adjacent two *'s of four *'s of the Chemical Formula AD-2 to form a fused ring.

The compound for an organic optoelectronic device may be represented by a combination of the following Chemical Formulae AD-6 and AD-2.

When mobility is not sufficiently secured by a combination of the Chemical Formulae AD-5 and AD-2, a substituent having fast mobility is connected to $R^{102}$ to increase hole/electron mobility. In addition, an HOMO level inside an entire molecule may be easily changed depending on a kind of substituent at the N position of the carbazolyl group. Accordingly, when the HOMO level is difficult to change by the combination of AD-5 and AD-2, a combination of AD-6 and AD-2 may be used.

[Chemical Formula AD-6]

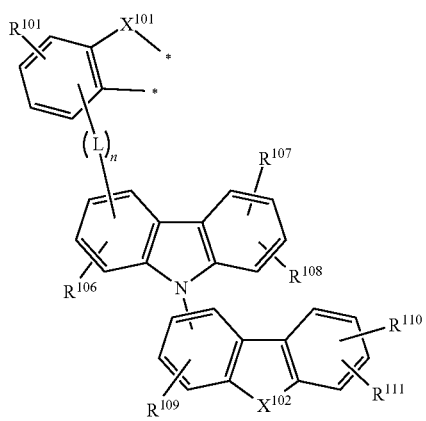

[Chemical Formula AD-2]

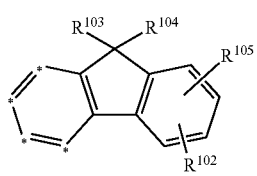

In the Chemical Formulae AD-6 and AD-2, $X^{101}$ is —O—, —S—, —S(O)— or —S(O)$_2$—, $X^{102}$ is —O—, —S—, —S(O)—, —CR'R"—, —S(O)$_2$— or —NR'—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^{101}$ to $R^{111}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-6 are bonded with adjacent two *'s of four *'s of the Chemical Formula AD-2 to form a fused ring.

The compound for an organic optoelectronic device may be represented by a combination of the following Chemical Formulae AD-7 and AD-2.

When the combination of AD-6 and AD-2 increases hole/electron mobility, the following combination of Chemical Formulae AD-7 and AD-2 may largely increase hole formation capability. Specifically, this effect may be obtained by adding a carbazolyl group to the carbazolyl group.

[Chemical Formula AD-7]

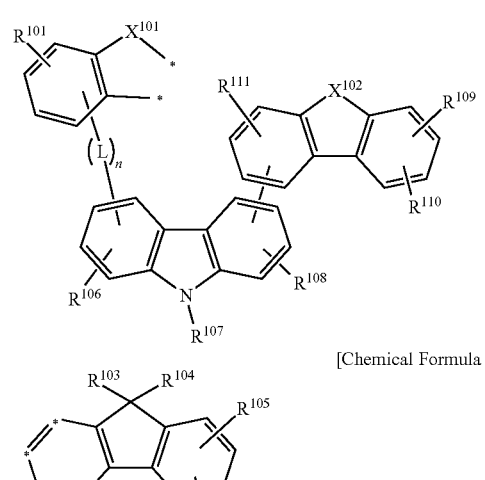

[Chemical Formula AD-2]

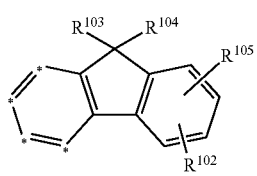

In the Chemical Formulae AD-7 and AD-2, $X^{101}$ is —O—, —S—, —S(O)— or —S(O)$_2$—, $X^{102}$ is —O—, —S—, —S(O)—, —S(O)$_2$—, —CR'R"— or —NR'—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^{101}$ to $R^{111}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and two *'s of the Chemical Formula AD-7 are bonded with adjacent two *'s of four *'s of the Chemical Formula AD-2 to form a fused ring.

The $R^{101}$ to $R^{109}$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

More specifically, the compound for an organic optoelectronic device may be represented by one of the following Chemical Formulae A-1 to A-136, but is not limited thereof.

[Chemical Formula A-1]

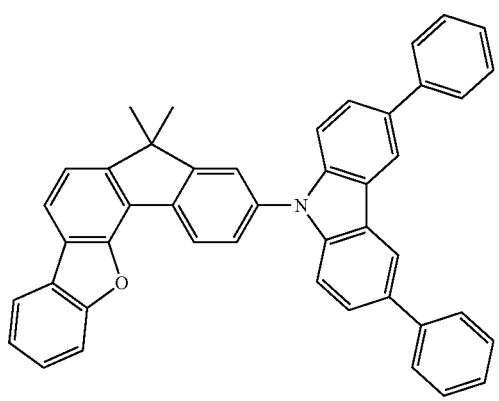

[Chemical Formula A-2]

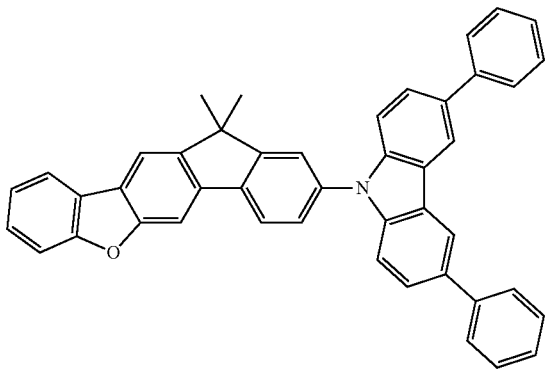

[Chemical Formula A-3]

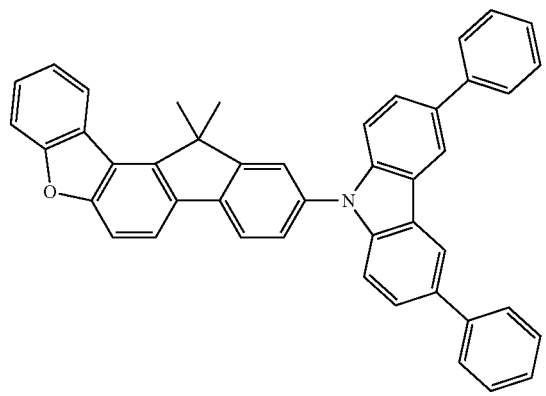

[Chemical Formula A-4]

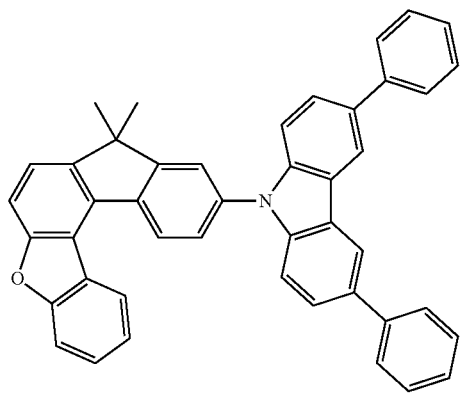

[Chemical Formula A-5]

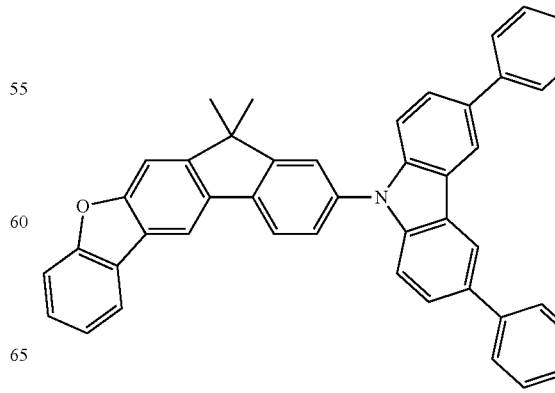

[Chemical Formula A-6]
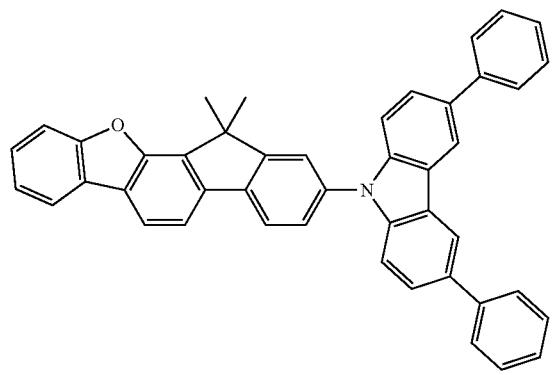
[Chemical Formula A-7]
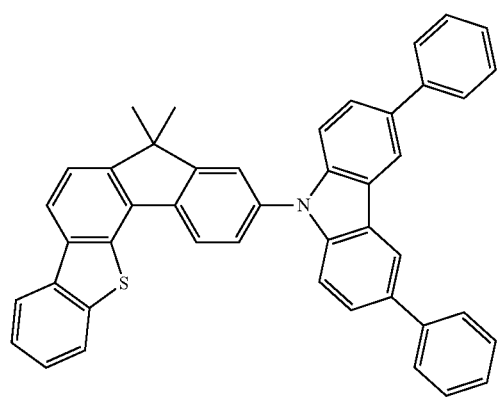
[Chemical Formula A-8]
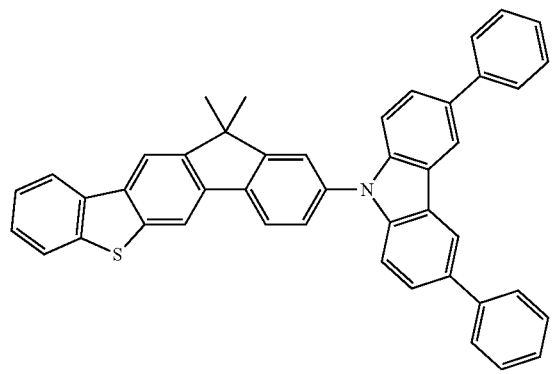
[Chemical Formula A-9]
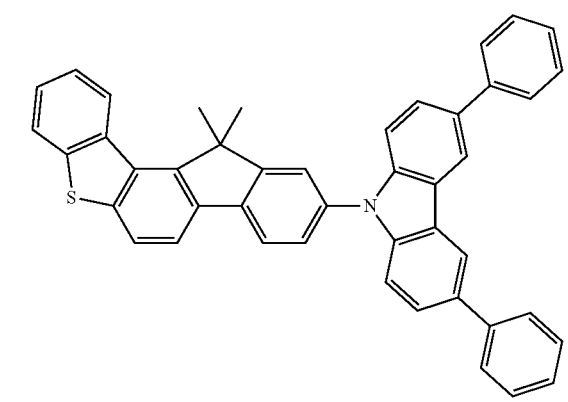
[Chemical Formula A-10]
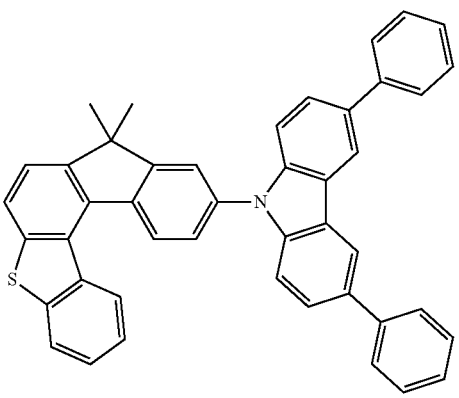
[Chemical Formula A-11]
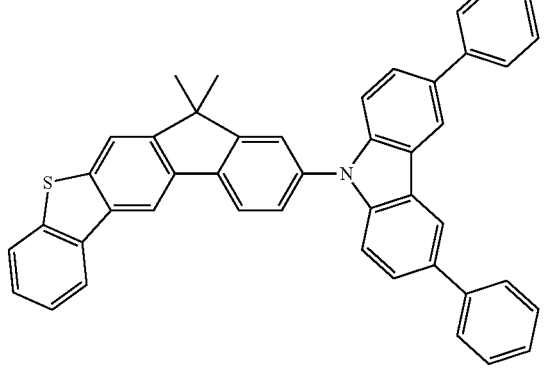
[Chemical Formula A-12]
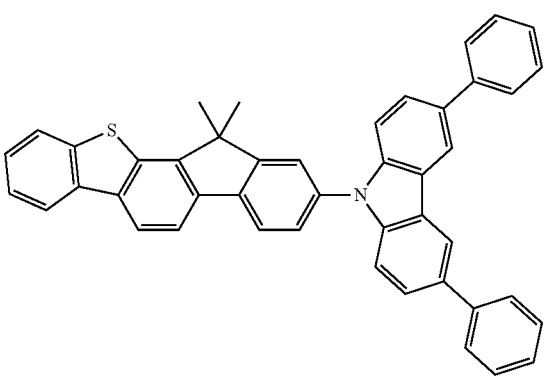
[Chemical Formula A-13]
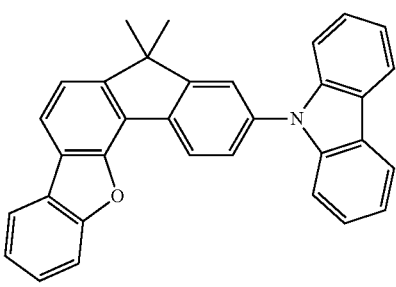

[Chemical Formula A-14]
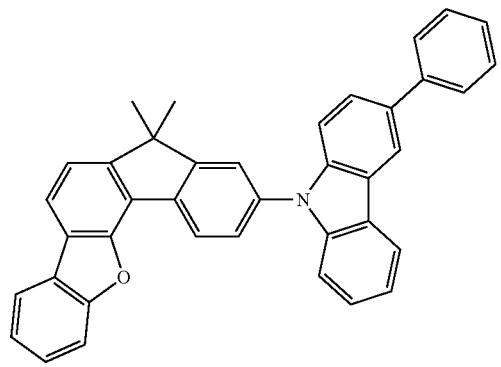
[Chemical Formula A-15]
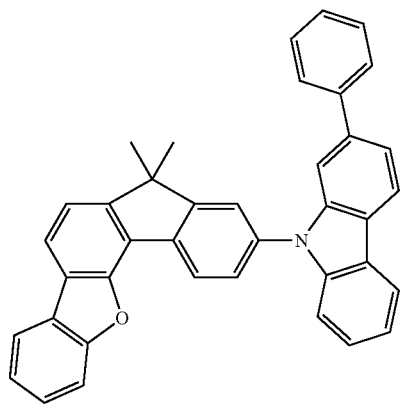
[Chemical Formula A-16]
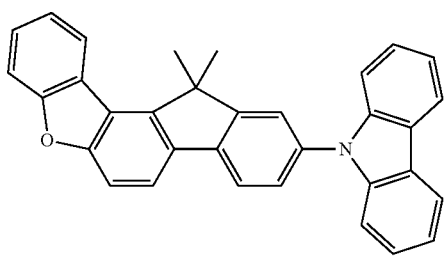
[Chemical Formula A-17]
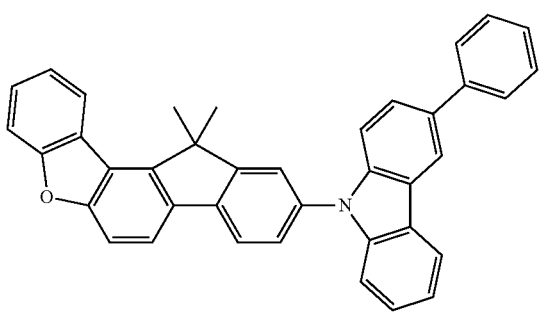
[Chemical Formula A-18]
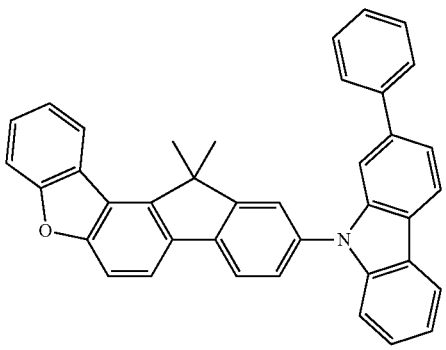
[Chemical Formula A-19]
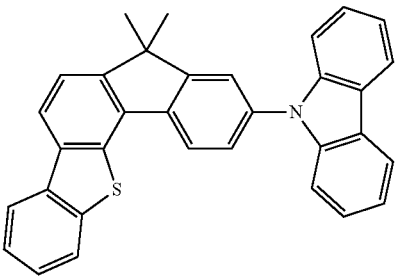
[Chemical Formula A-20]
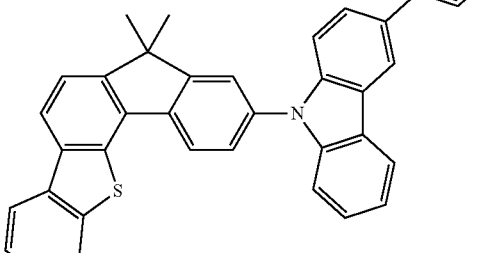
[Chemical Formula A-21]
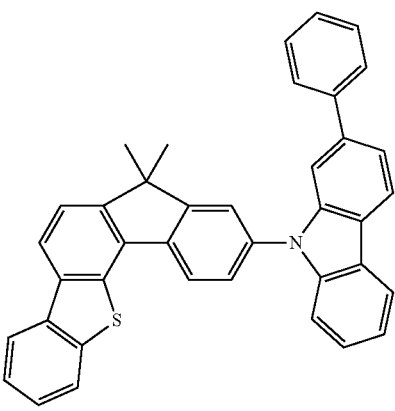

[Chemical Formula A-22]
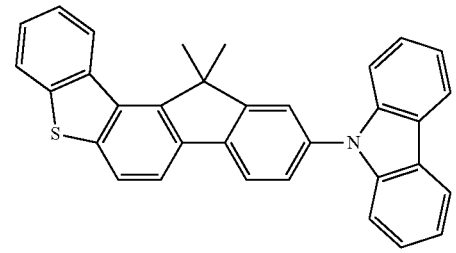
[Chemical Formula A-23]
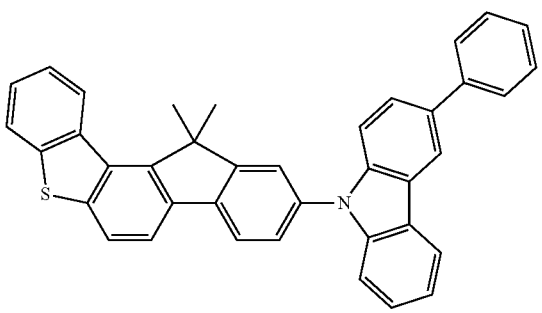
[Chemical Formula A-24]
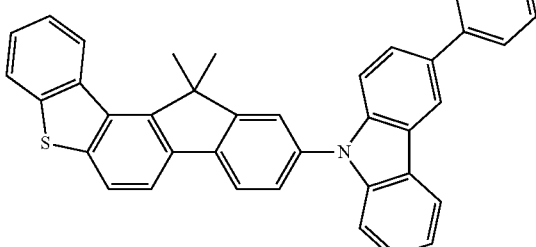
[Chemical Formula A-25]
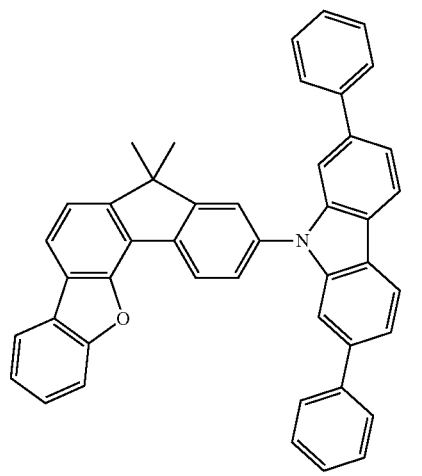
[Chemical Formula A-26]
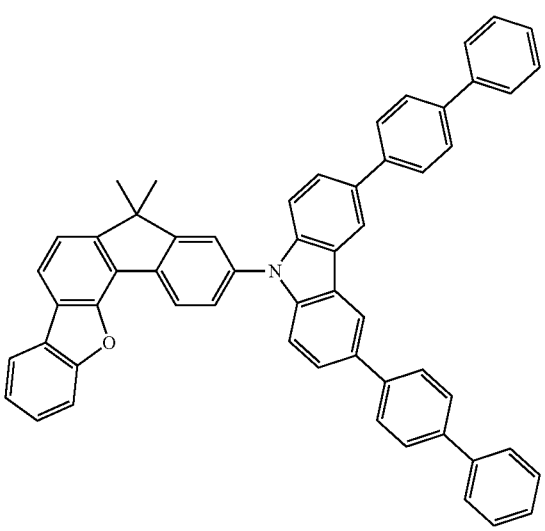
[Chemical Formula A-27]
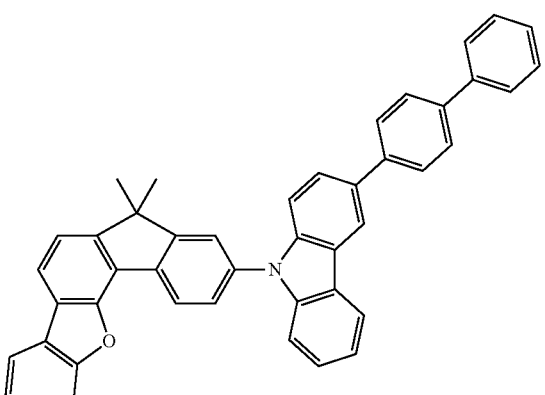
[Chemical Formula A-28]
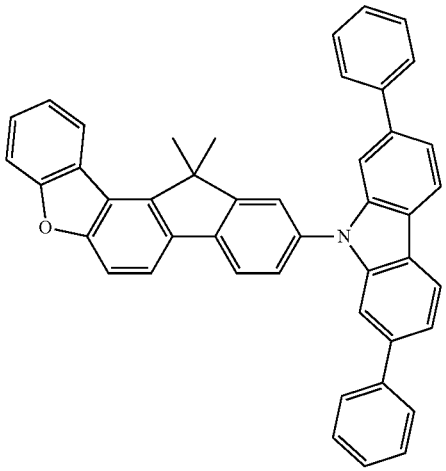

[Chemical Formula A-29]
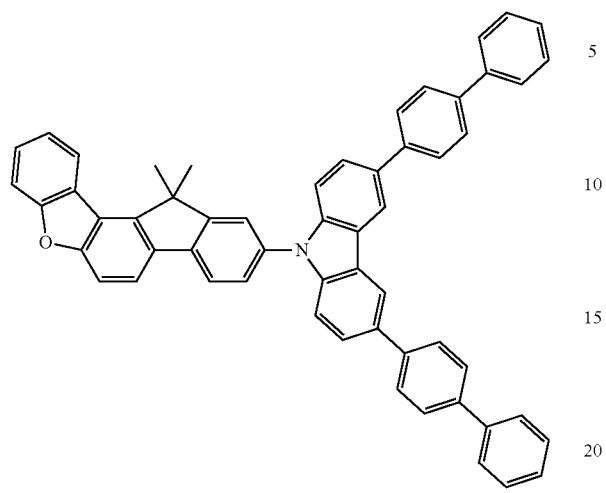
[Chemical Formula A-32]
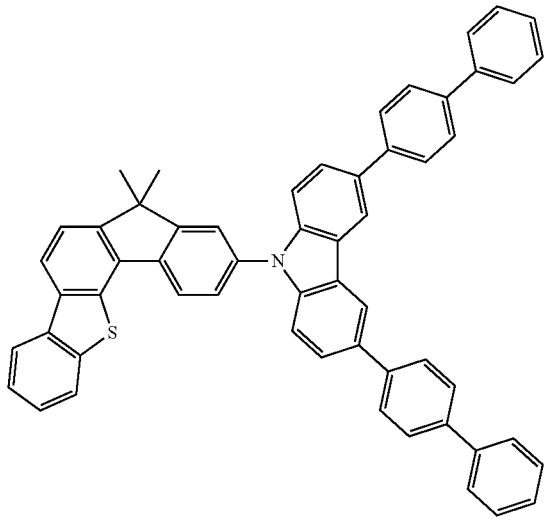
[Chemical Formula A-30]
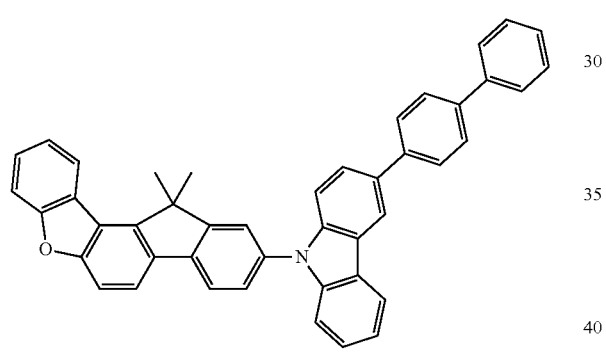
[Chemical Formula A-33]
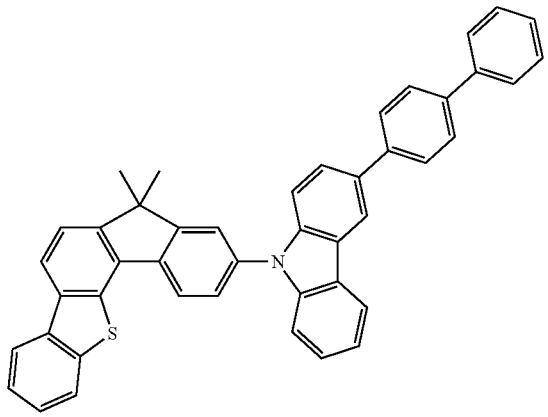
[Chemical Formula A-31]
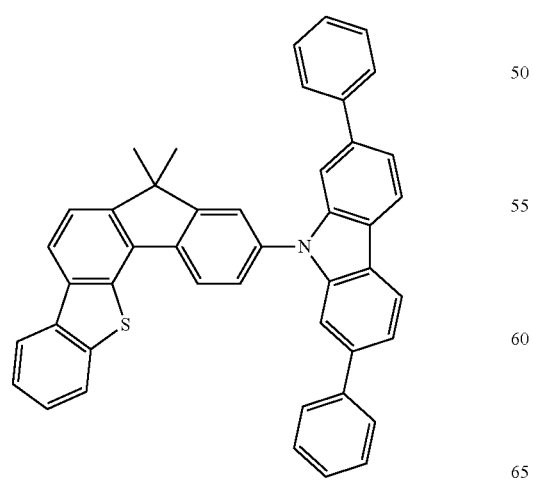
[Chemical Formula A-34]
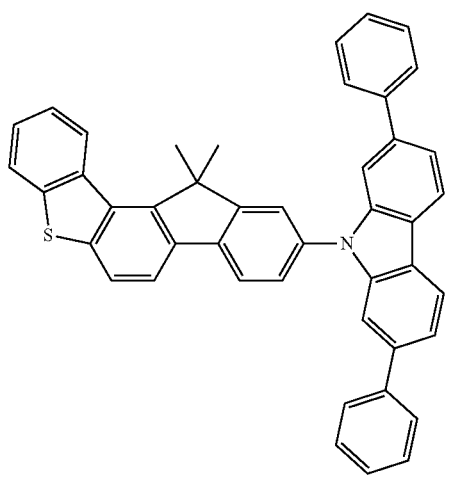

[Chemical Formula A-35]
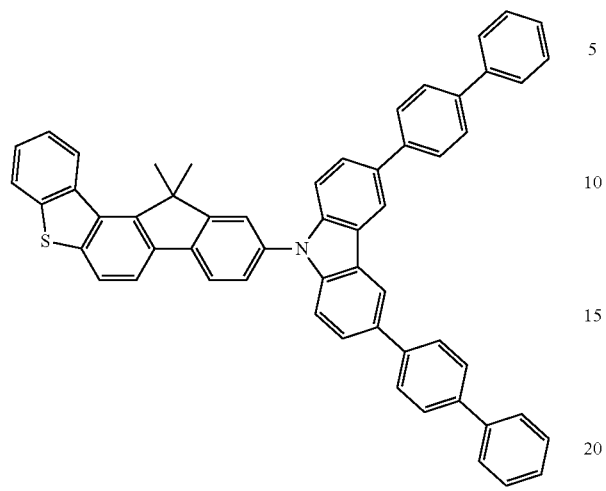
[Chemical Formula A-38]
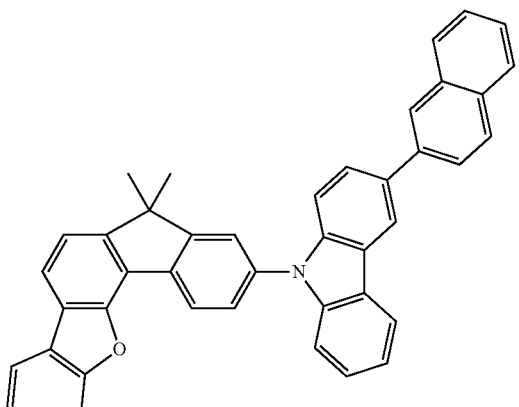
[Chemical Formula A-36]
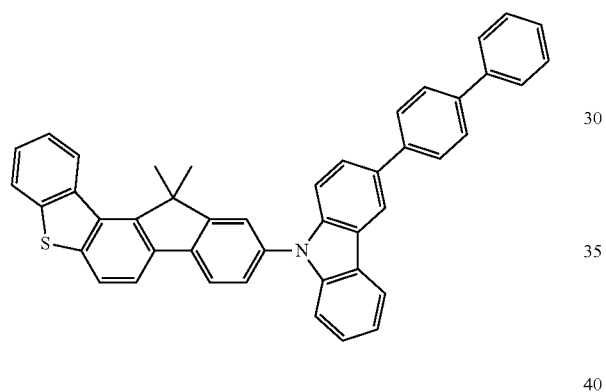
[Chemical Formula A-39]
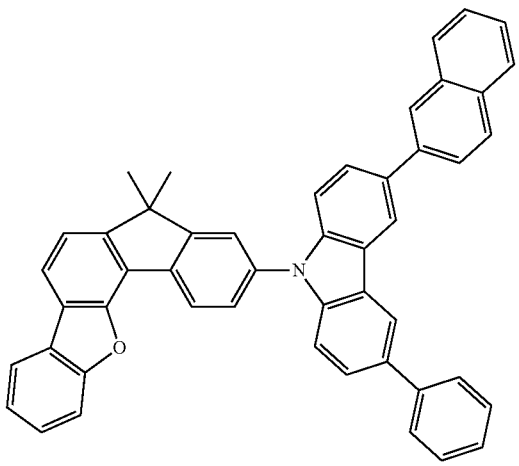
[Chemical Formula A-37]
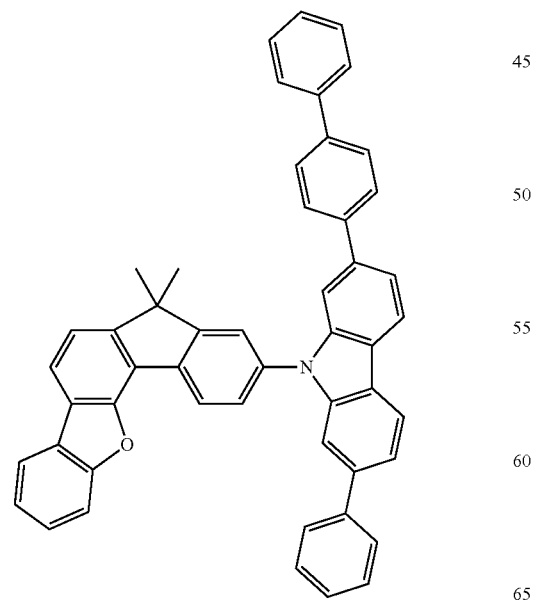
[Chemical Formula A-40]
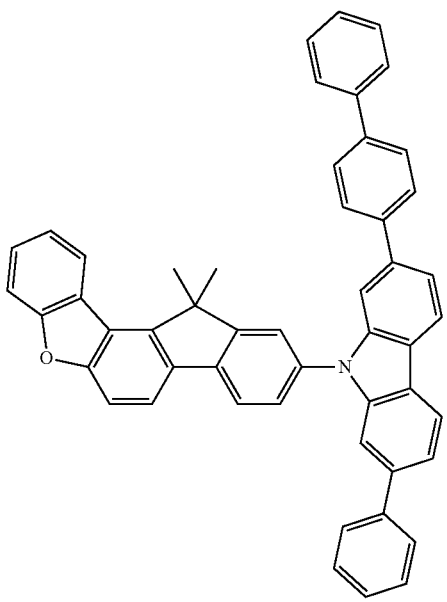

[Chemical Formula A-41]
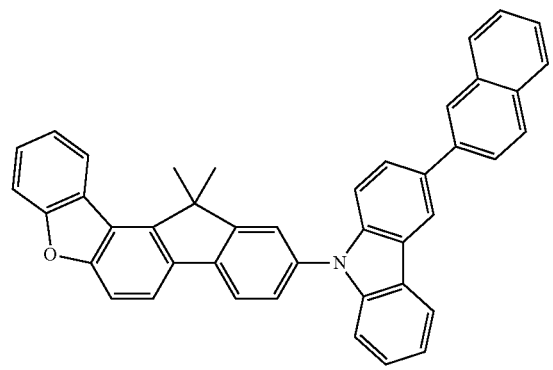
[Chemical Formula A-42]
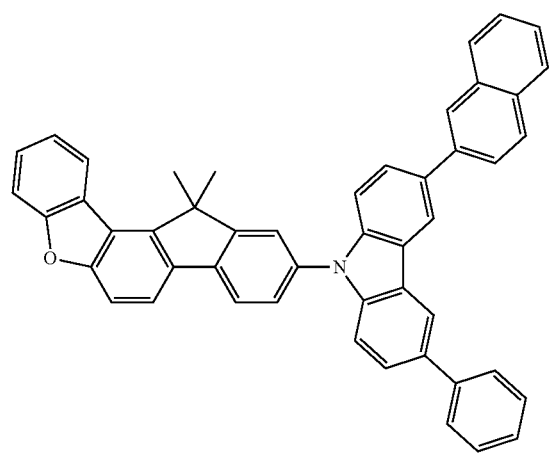
[Chemical Formula A-43]
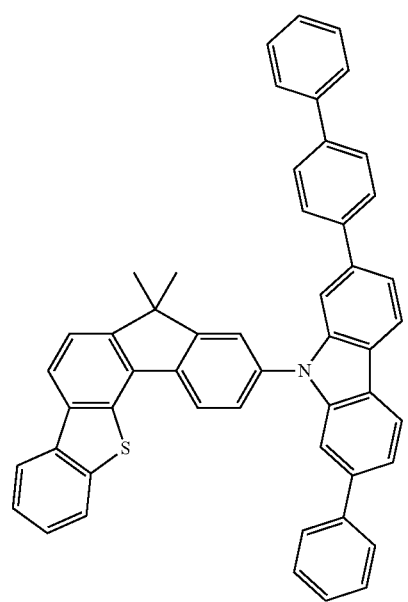
[Chemical Formula A-44]
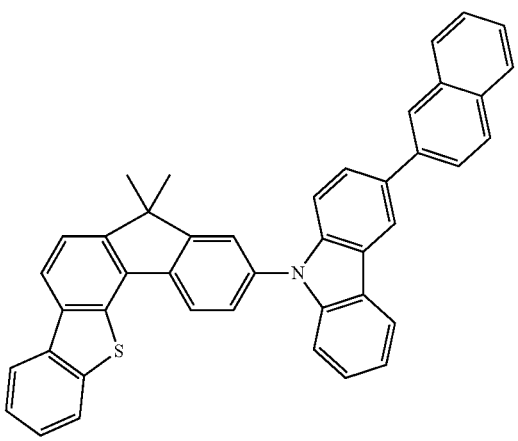
[Chemical Formula A-45]
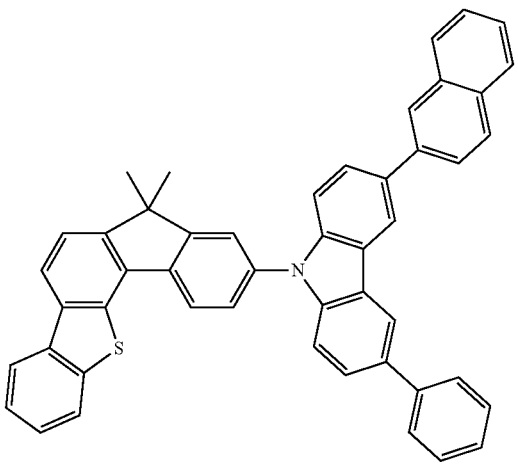
[Chemical Formula A-46]
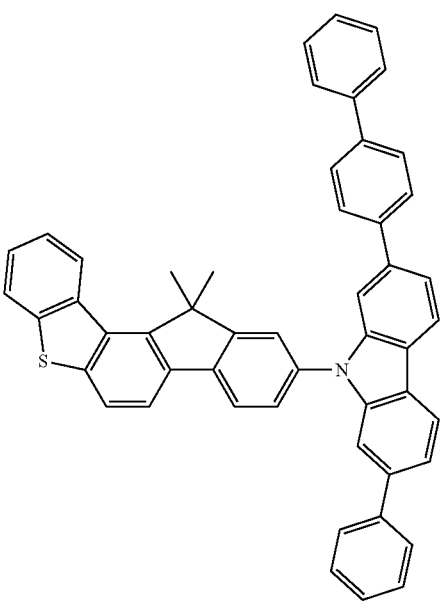

[Chemical Formula A-47]
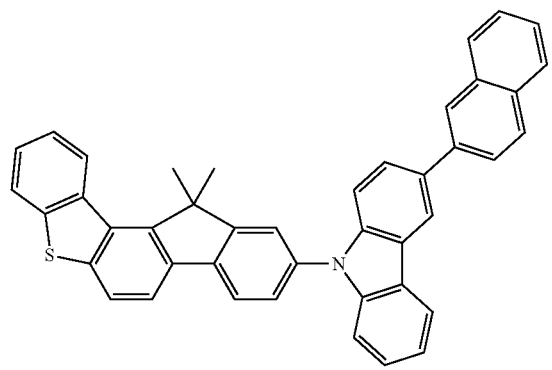
[Chemical Formula A-48]
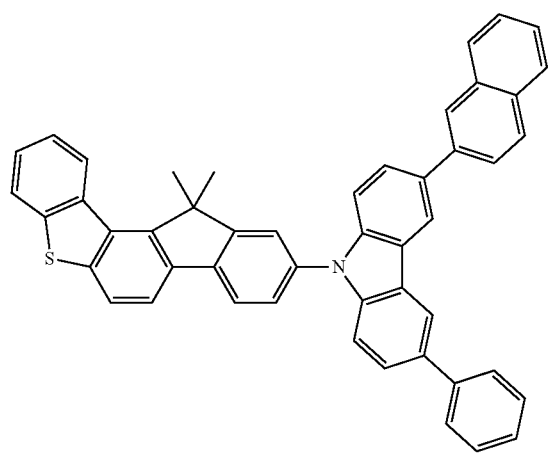
[Chemical Formula A-49]
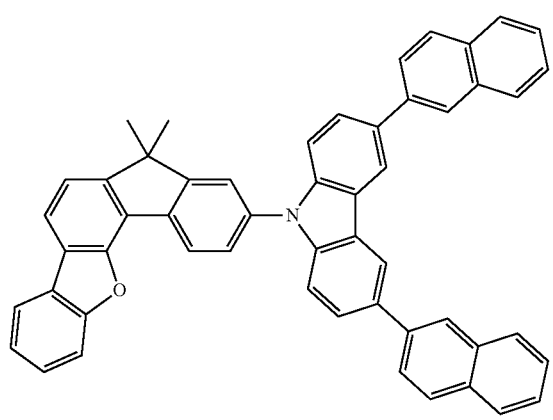
[Chemical Formula A-50]
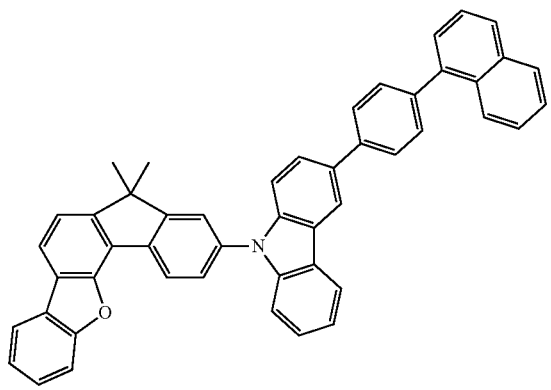
[Chemical Formula A-51]
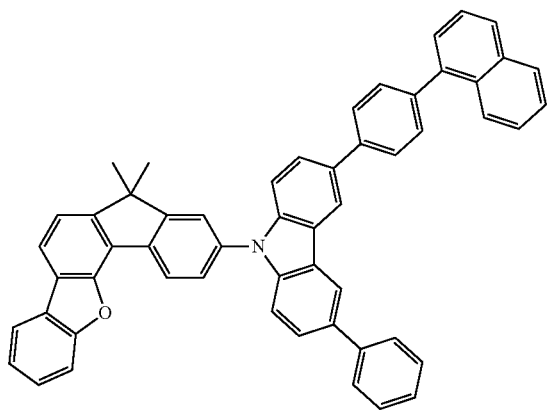
[Chemical Formula A-52]
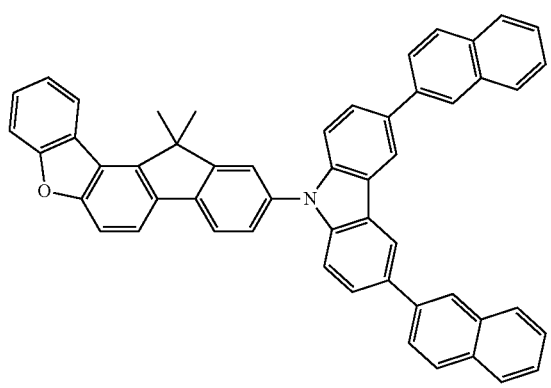
[Chemical Formula A-53]
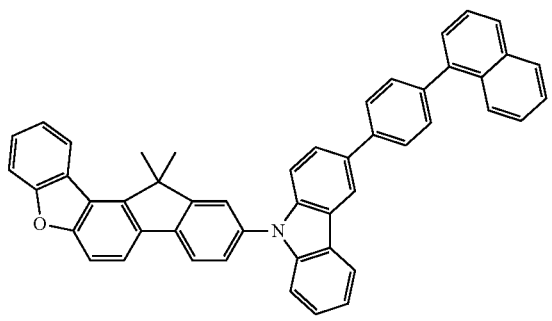

[Chemical Formula A-54]
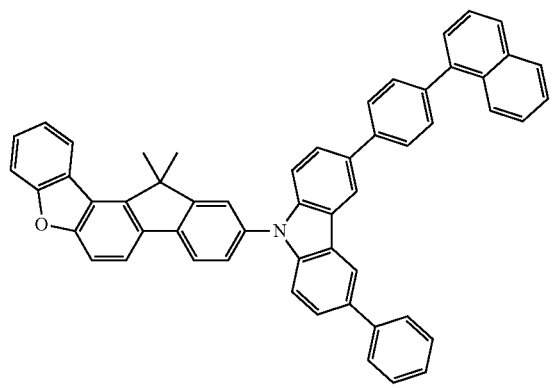
[Chemical Formula A-55]
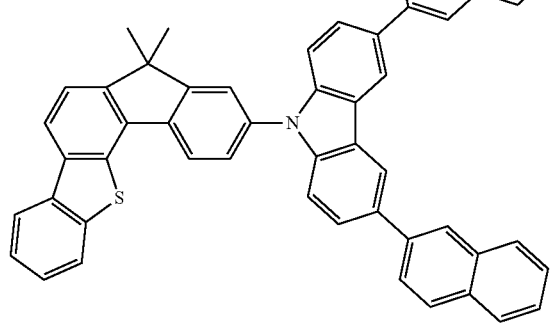
[Chemical Formula A-56]
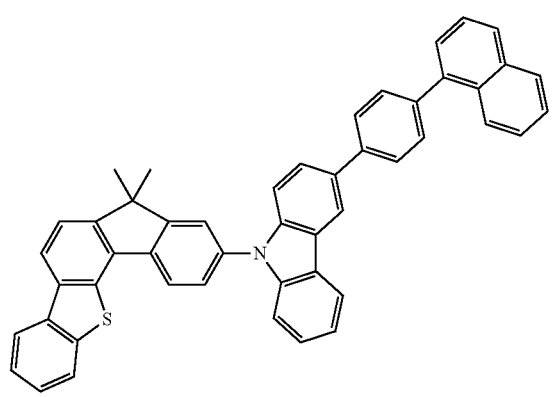
[Chemical Formula A-57]
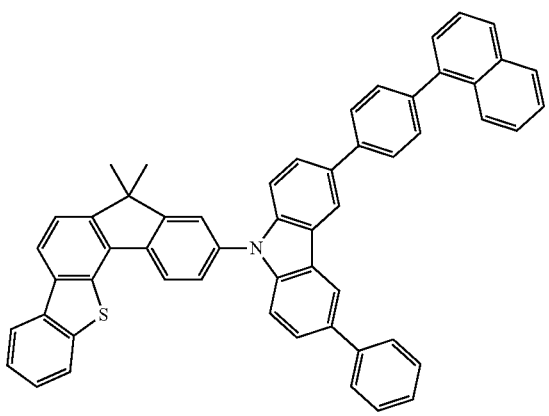
[Chemical Formula A-58]
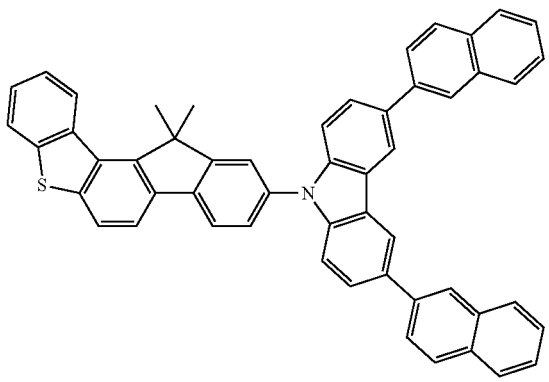
[Chemical Formula A-59]
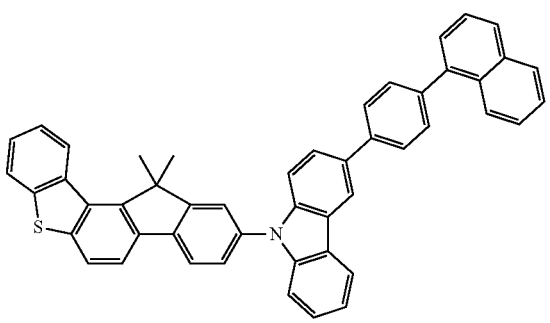
[Chemical Formula A-60]
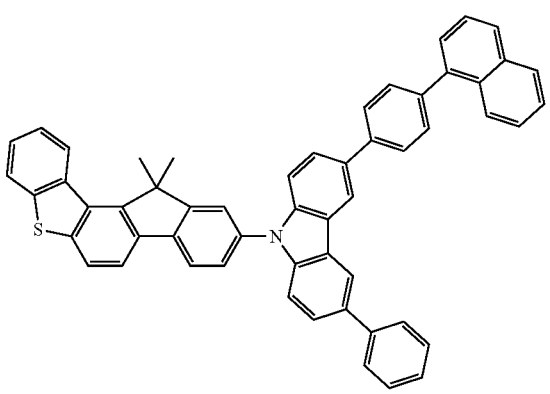

[Chemical Formula A-61]
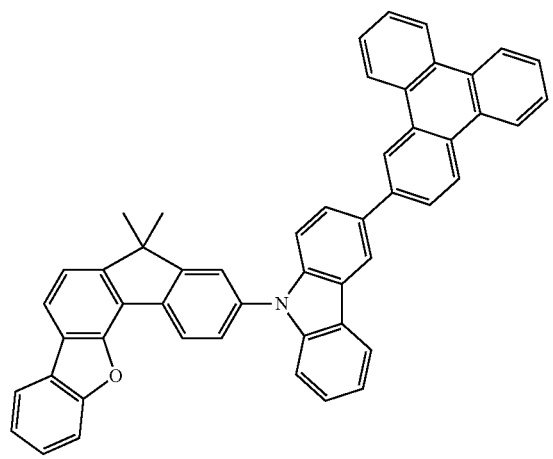
[Chemical Formula A-62]
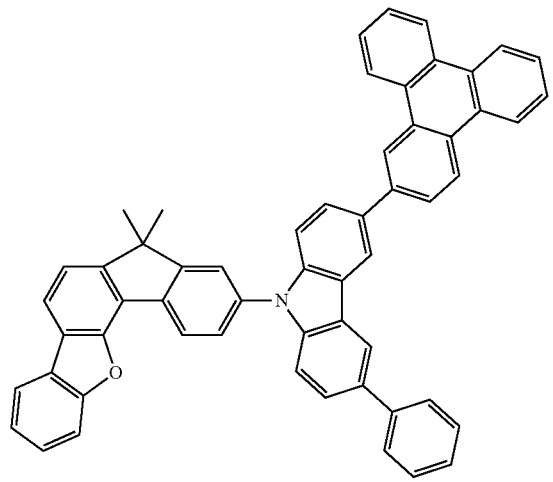
[Chemical Formula A-63]
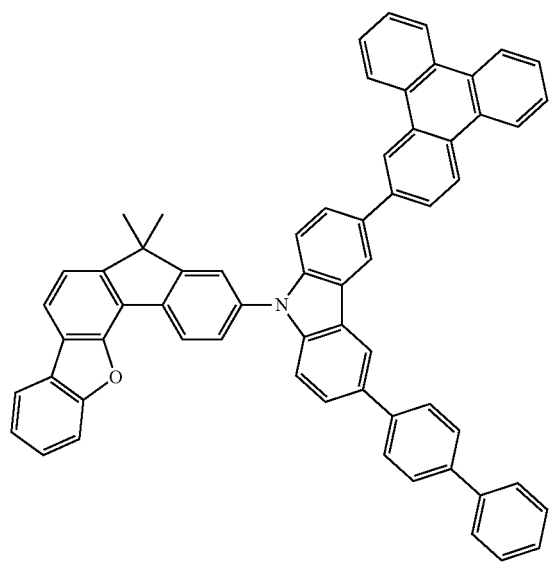
[Chemical Formula A-64]
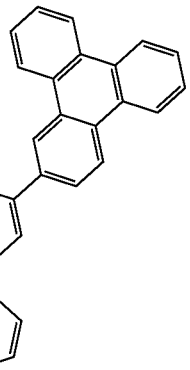
[Chemical Formula A-65]
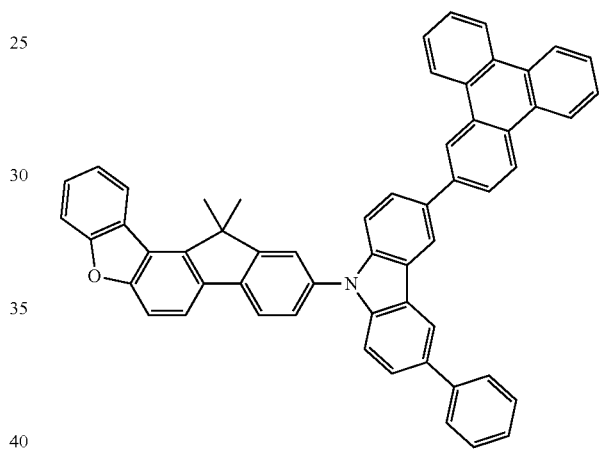
[Chemical Formula A-66]
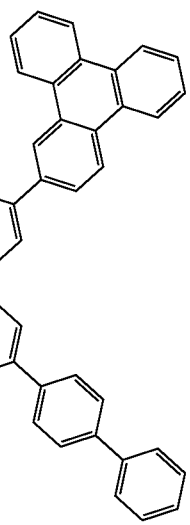

[Chemical Formula A-67]
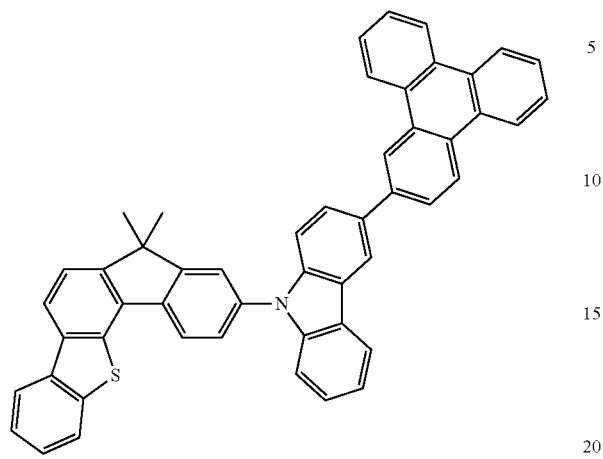
[Chemical Formula A-68]
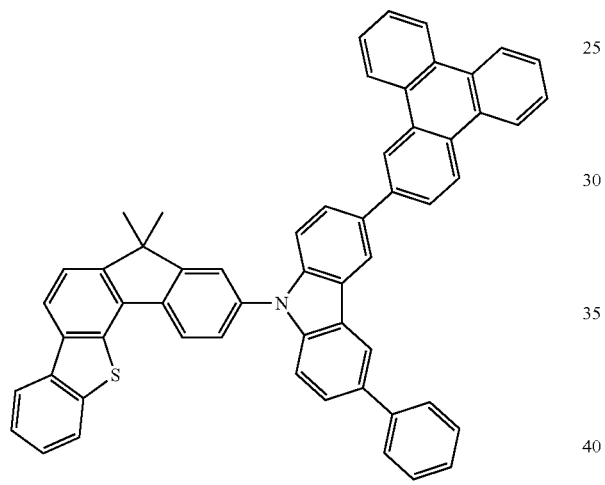
[Chemical Formula A-69]
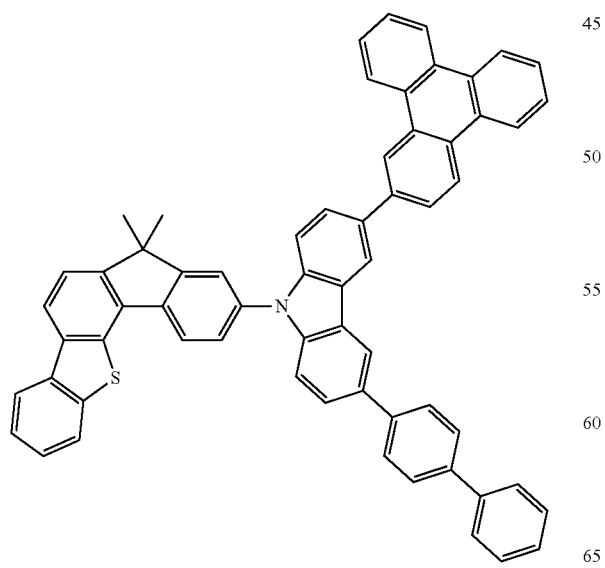
[Chemical Formula A-70]
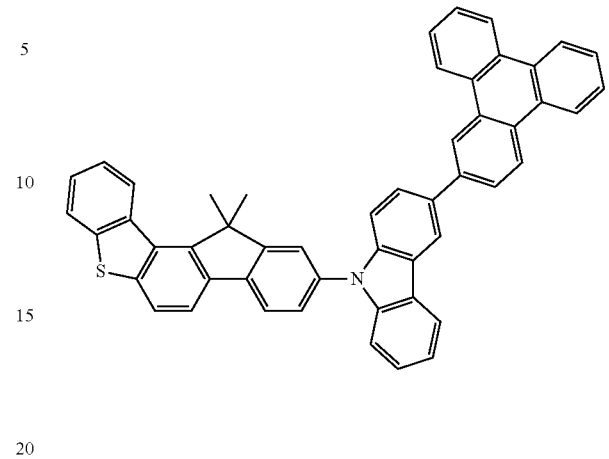
[Chemical Formula A-71]
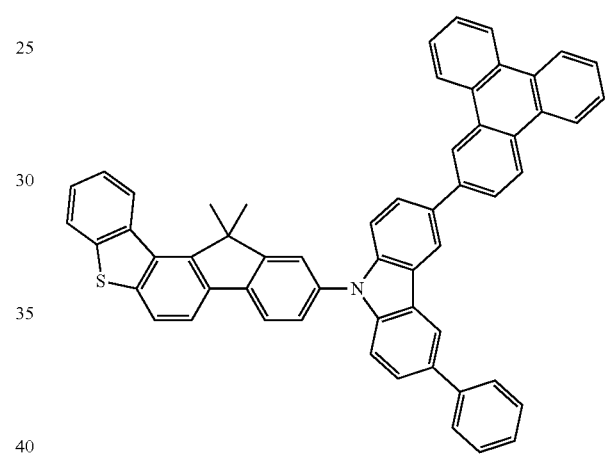
[Chemical Formula A-72]
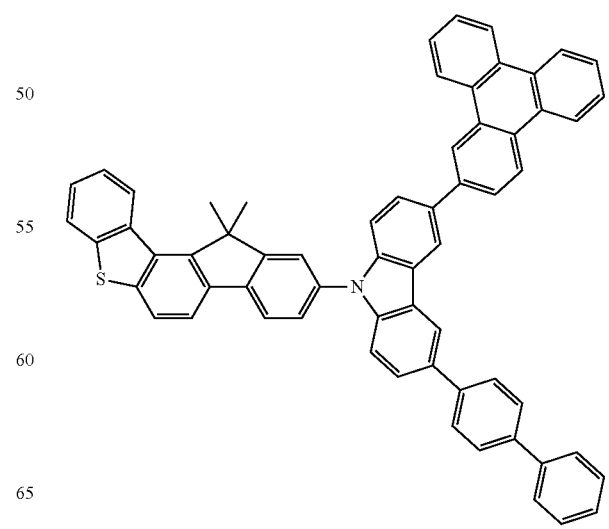

[Chemical Formula A-73]
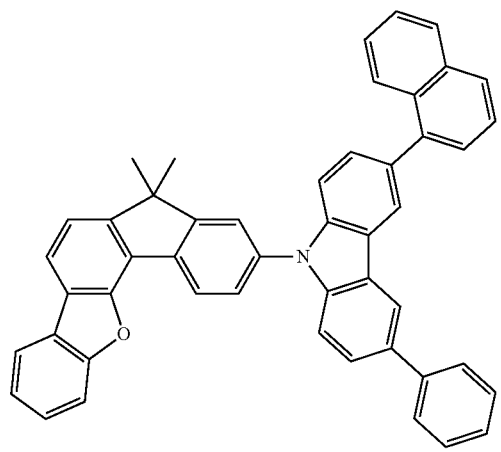
[Chemical Formula A-76]
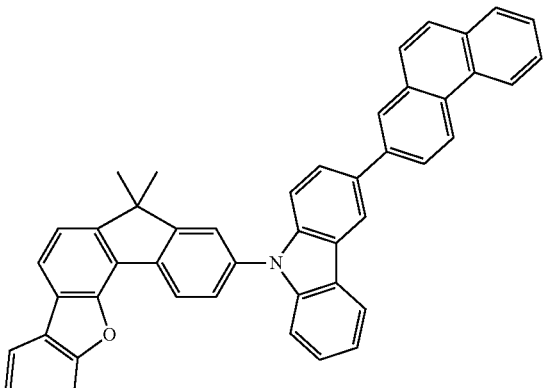
[Chemical Formula A-74]
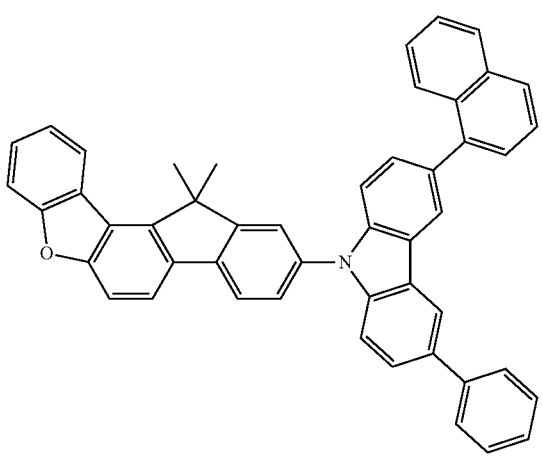
[Chemical Formula A-77]
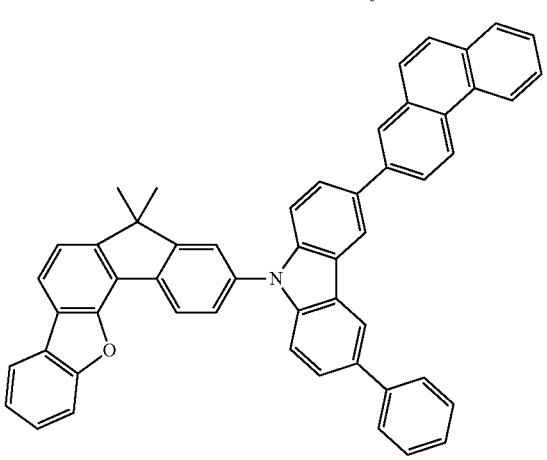
[Chemical Formula A-75]
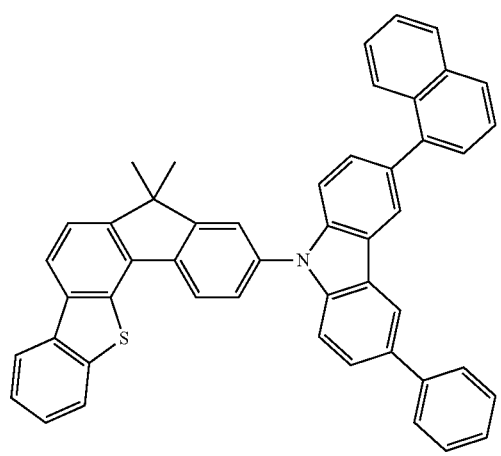
[Chemical Formula A-78]
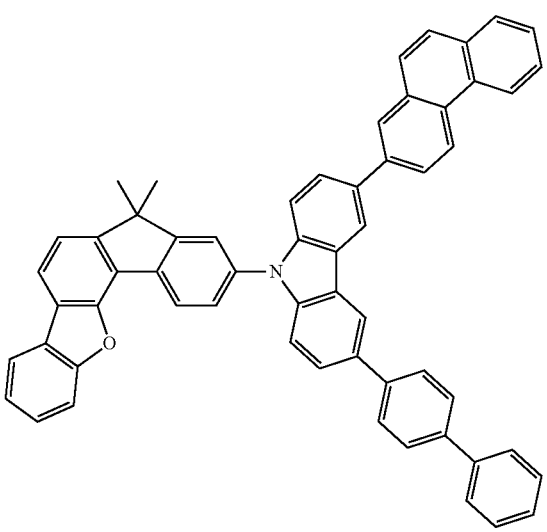

[Chemical Formula A-79]
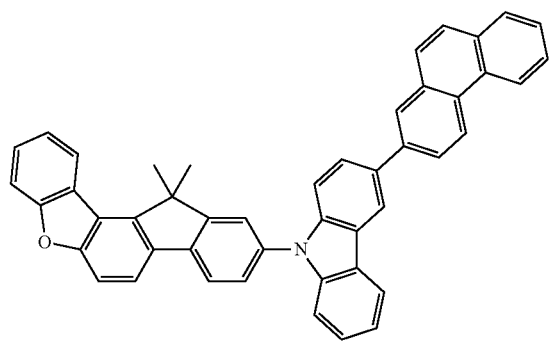
[Chemical Formula A-80]
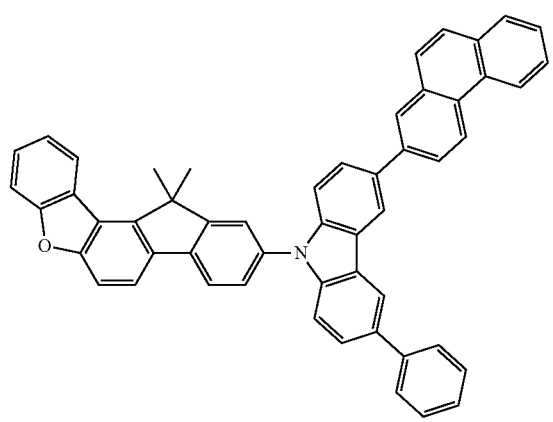
[Chemical Formula A-81]
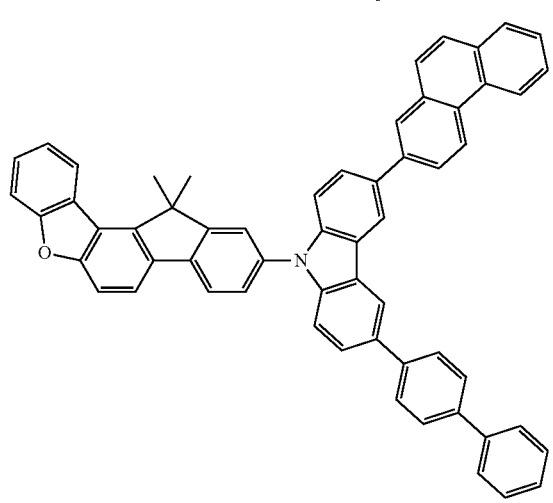
[Chemical Formula A-82]
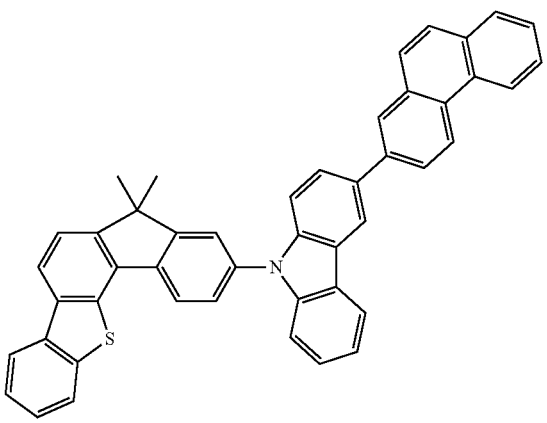
[Chemical Formula A-83]
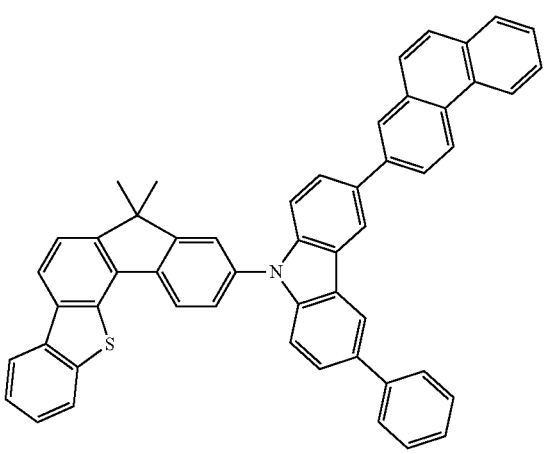
[Chemical Formula A-84]
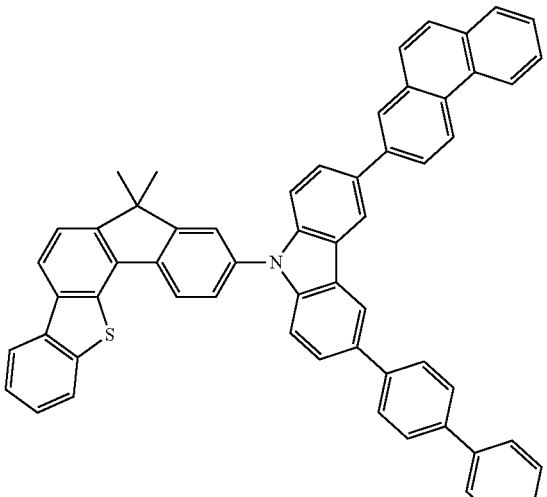

[Chemical Formula A-85]
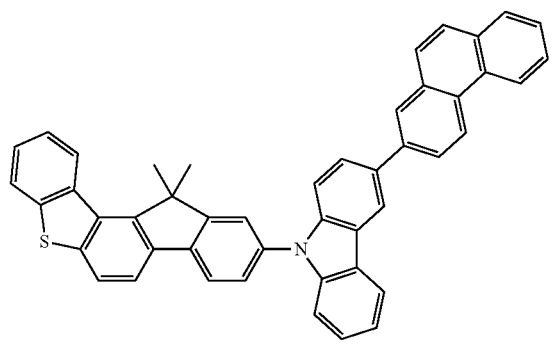
[Chemical Formula A-86]
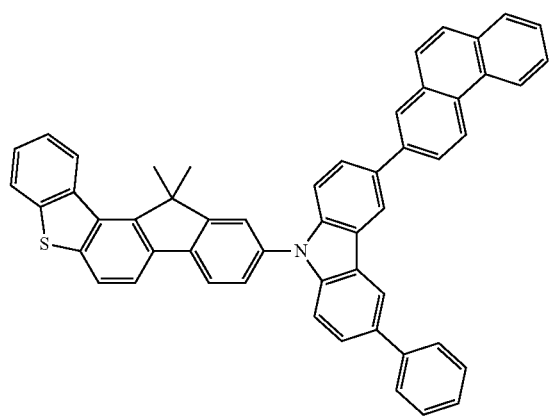
[Chemical Formula A-87]
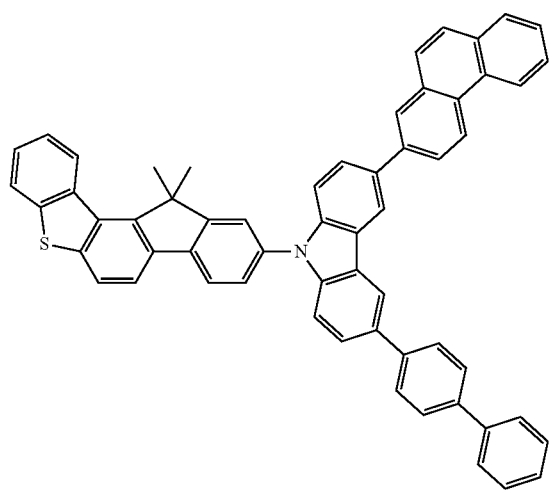
[Chemical Formula A-88]
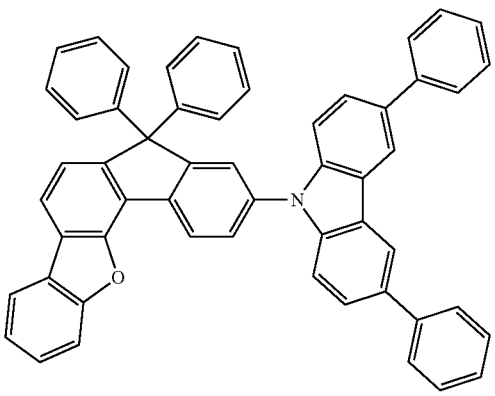
[Chemical Formula A-89]
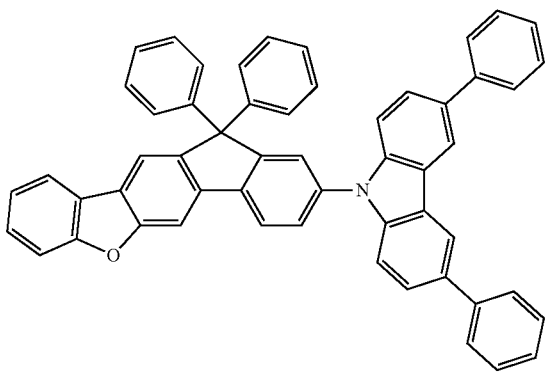
[Chemical Formula A-90]
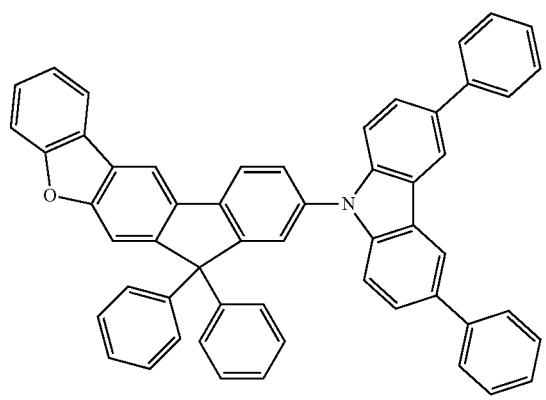
[Chemical Formula A-91]
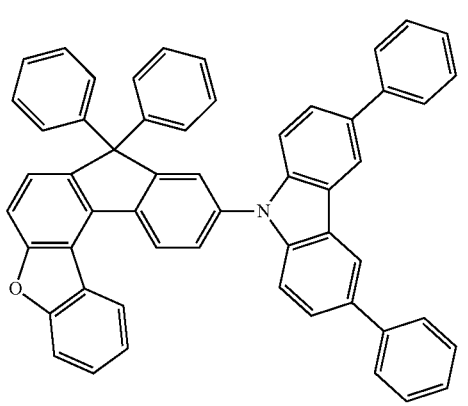

[Chemical Formula A-92]
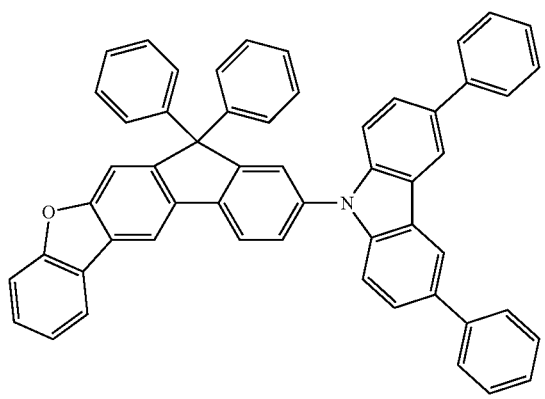
[Chemical Formula A-93]
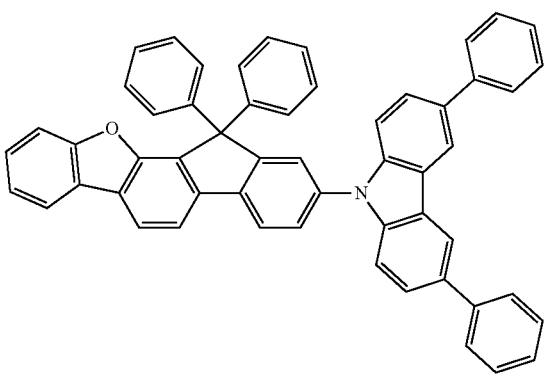
[Chemical Formula A-94]
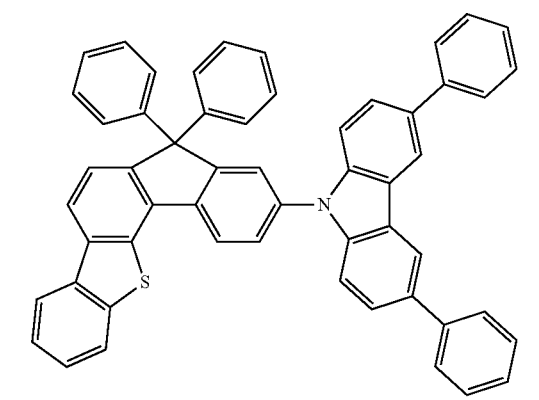
[Chemical Formula A-95]
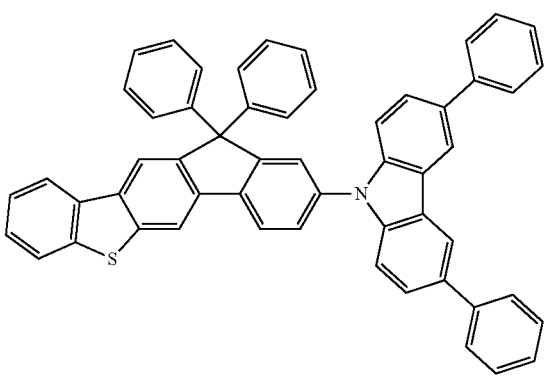
[Chemical Formula A-96]
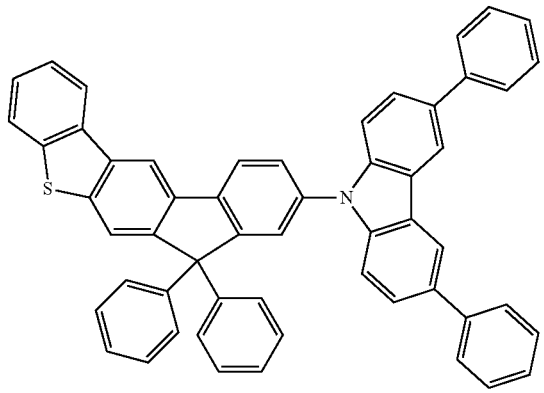
[Chemical Formula A-97]
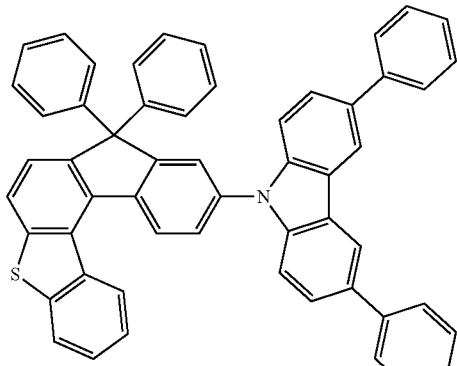
[Chemical Formula A-98]
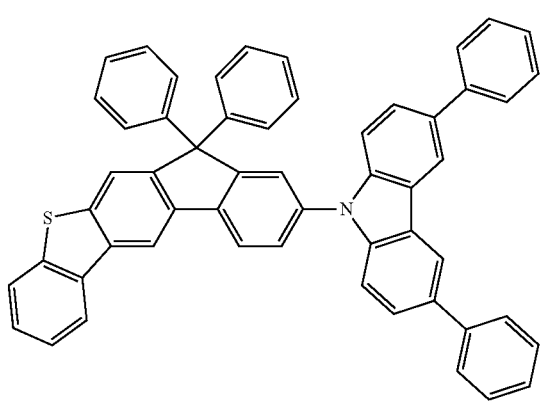
[Chemical Formula A-99]
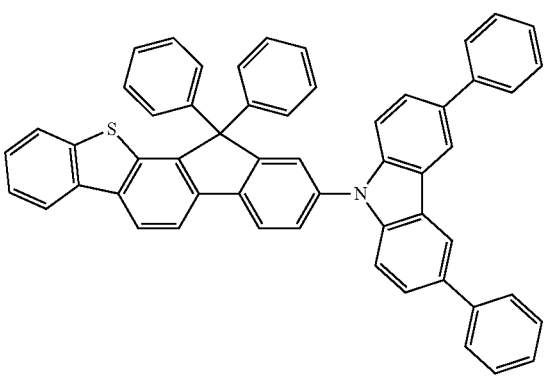

[Chemical Formula A-100]
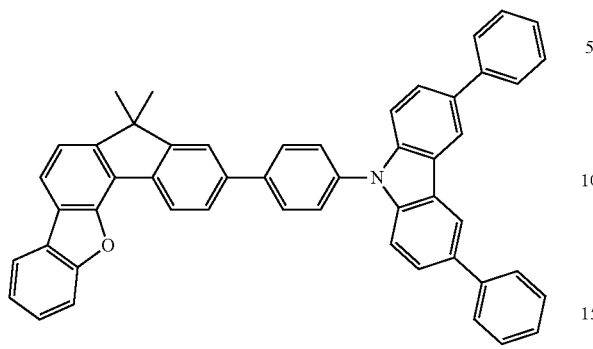
[Chemical Formula A-101]
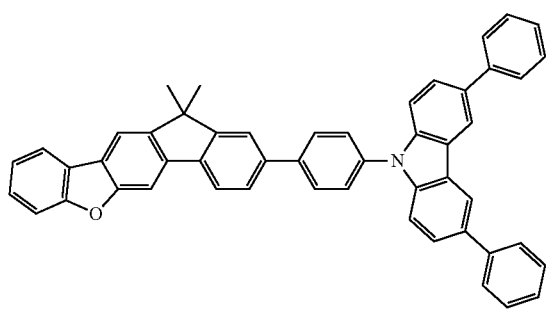
[Chemical Formula A-102]
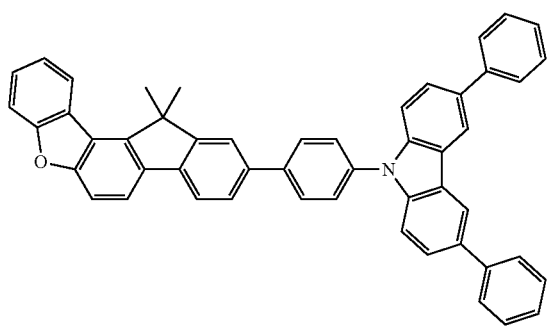
[Chemical Formula A-103]
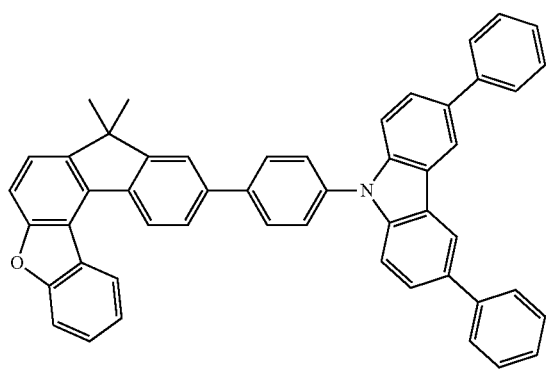
[Chemical Formula A-104]
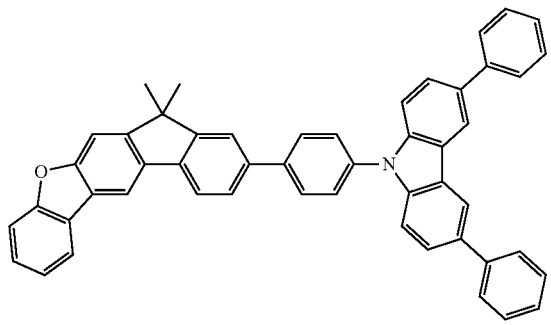
[Chemical Formula A-105]
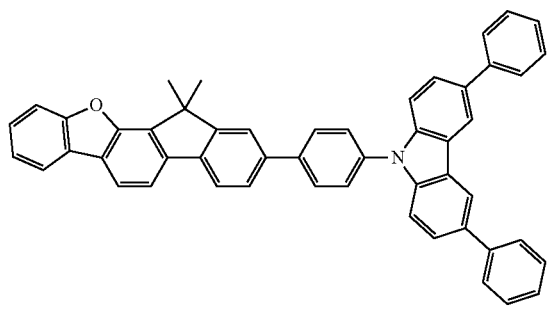
[Chemical Formula A-106]
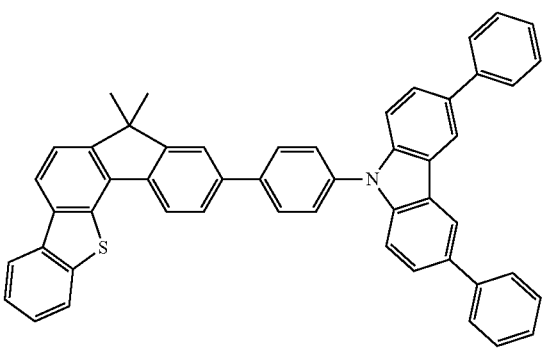
[Chemical Formula A-107]
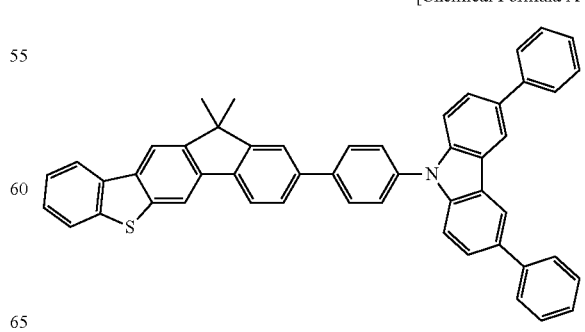

[Chemical Formula A-108]
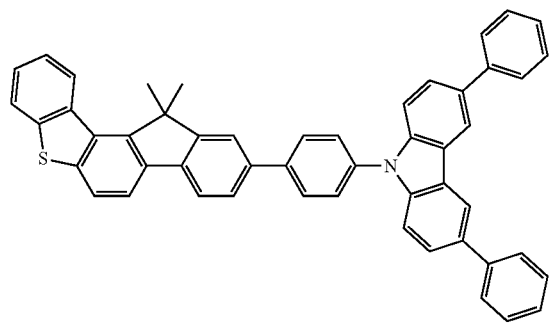
[Chemical Formula A-109]
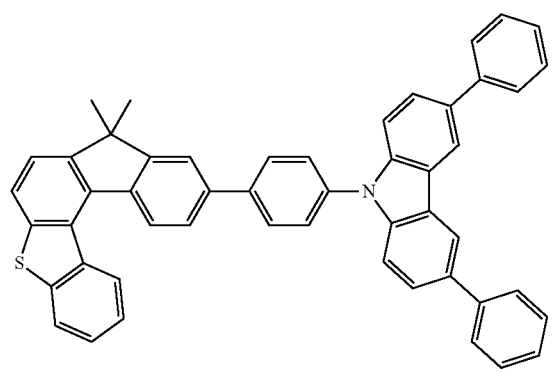
[Chemical Formula A-110]
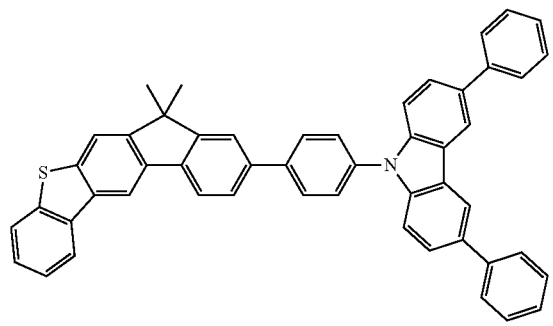
[Chemical Formula A-111]
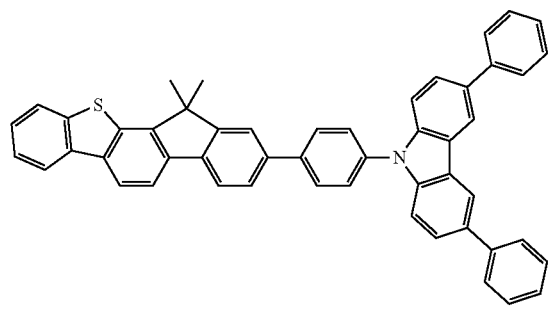
[Chemical Formula A-112]
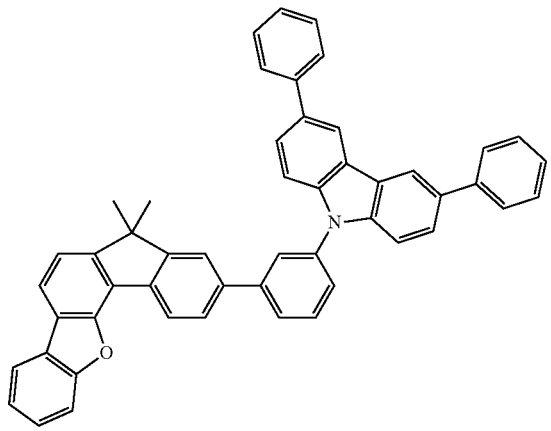
[Chemical Formula A-113]
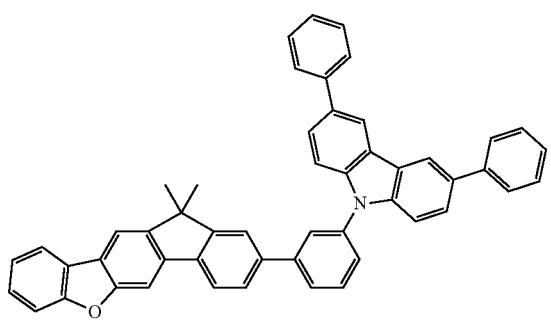
[Chemical Formula A-114]
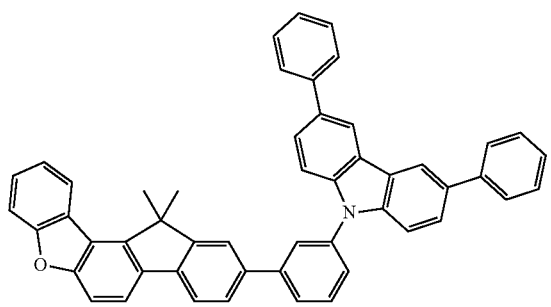
[Chemical Formula A-115]
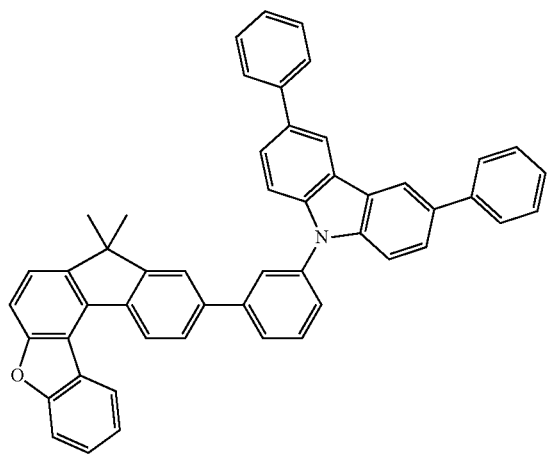

[Chemical Formula A-116]
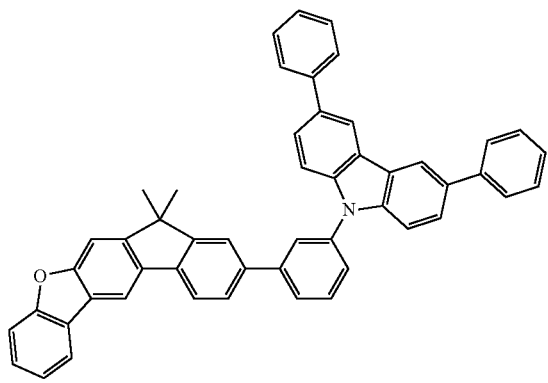
[Chemical Formula A-117]
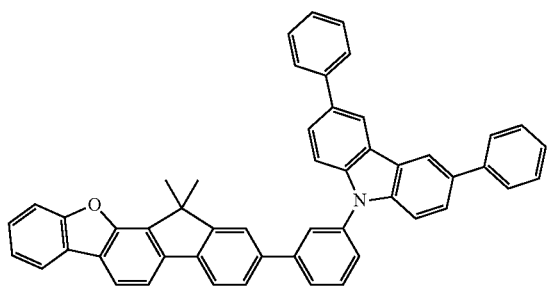
[Chemical Formula A-118]
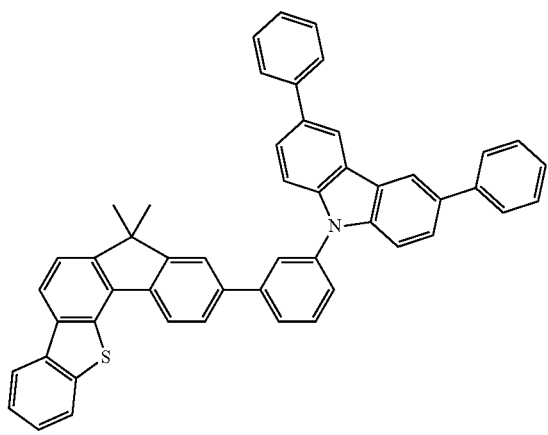
[Chemical Formula A-119]
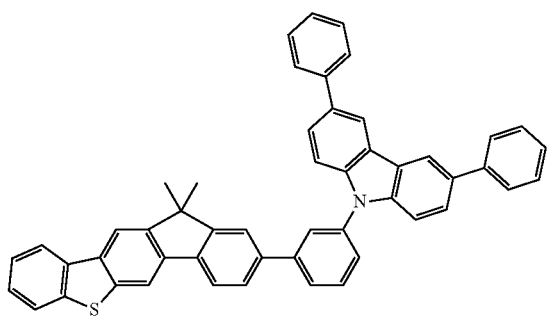
[Chemical Formula A-120]
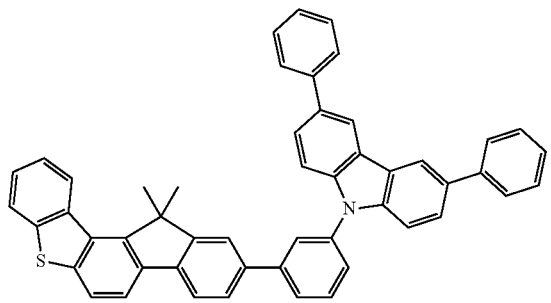
[Chemical Formula A-121]
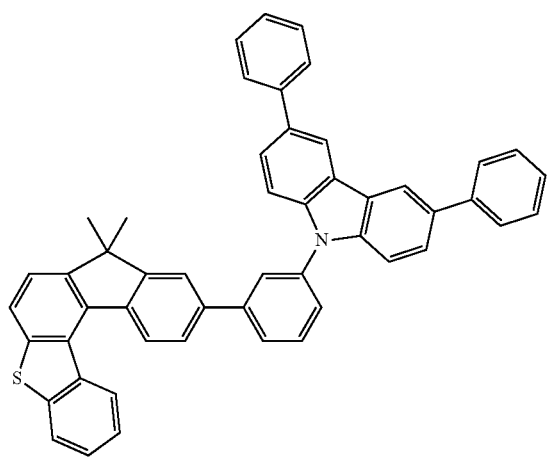
[Chemical Formula A-122]
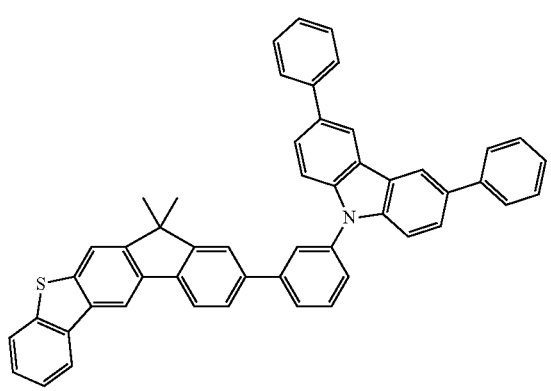
[Chemical Formula A-123]
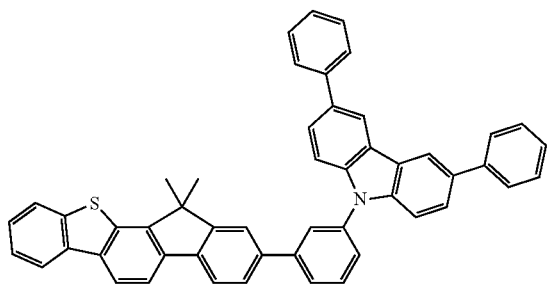

[Chemical Formula A-124]
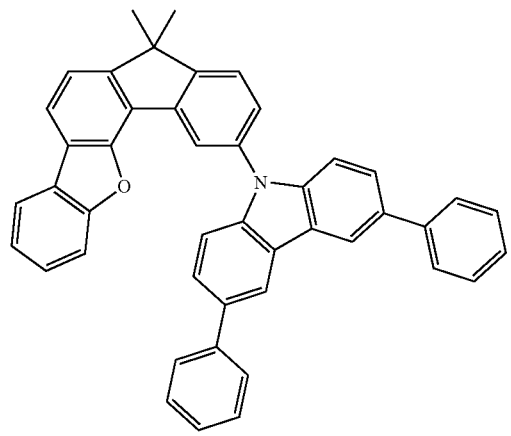
[Chemical Formula A-125]
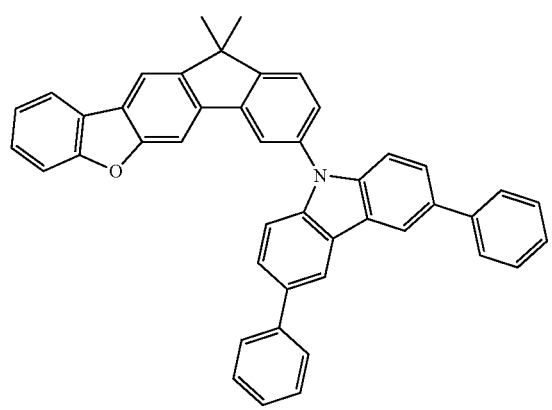
[Chemical Formula A-126]
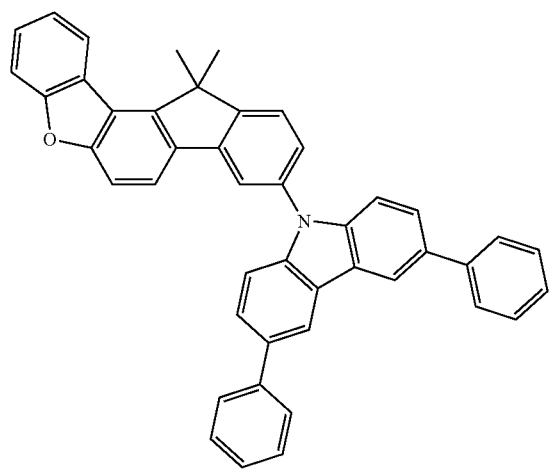
[Chemical Formula A-127]
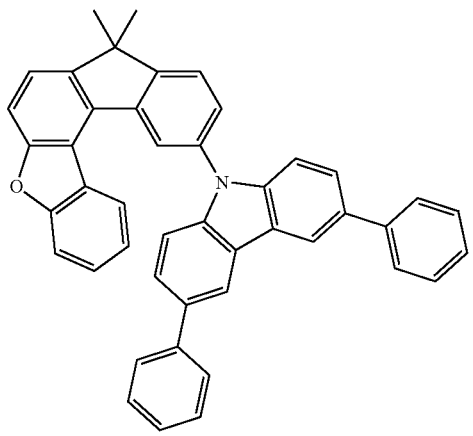
[Chemical Formula A-128]
[Chemical Formula A-129]
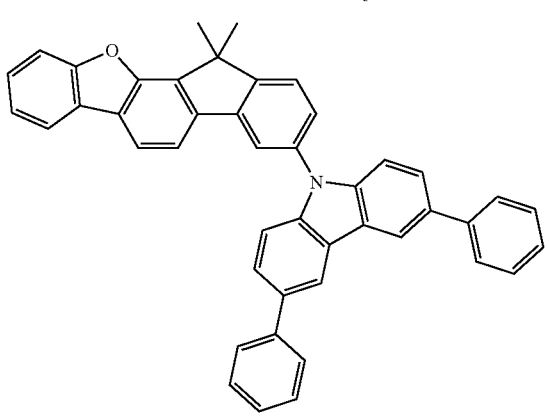

[Chemical Formula A-130]
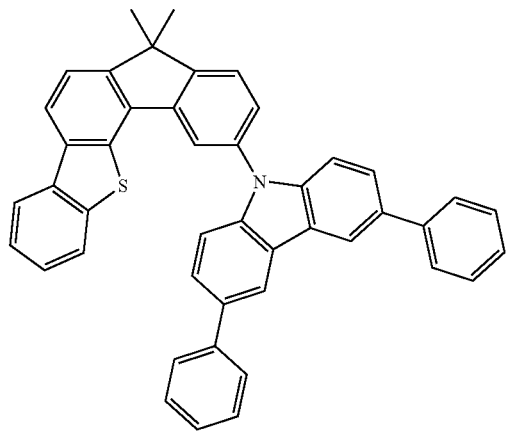
[Chemical Formula A-131]
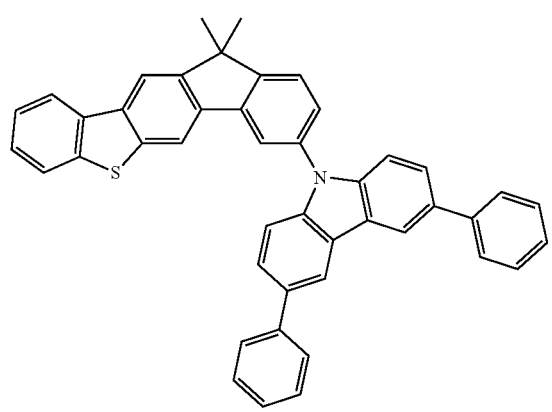
[Chemical Formula A-132]
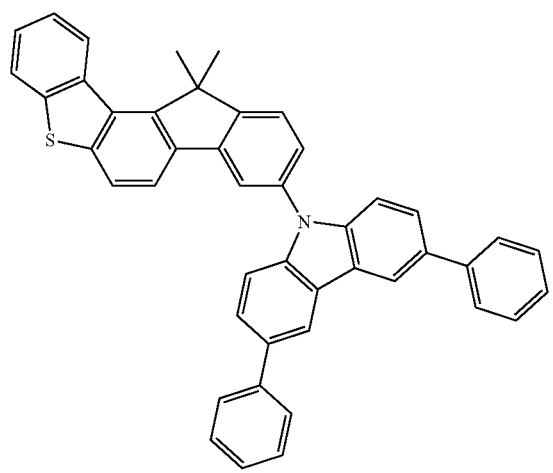
[Chemical Formula A-133]
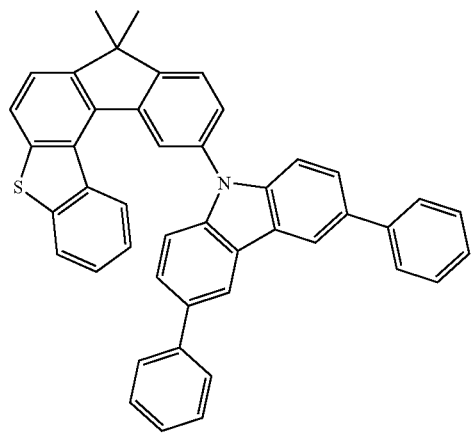
[Chemical Formula A-134]
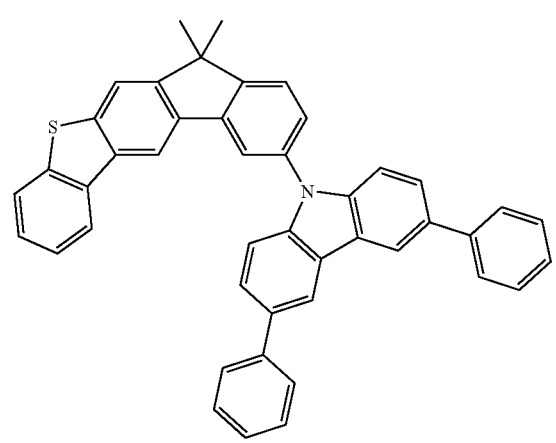
[Chemical Formula A-135]
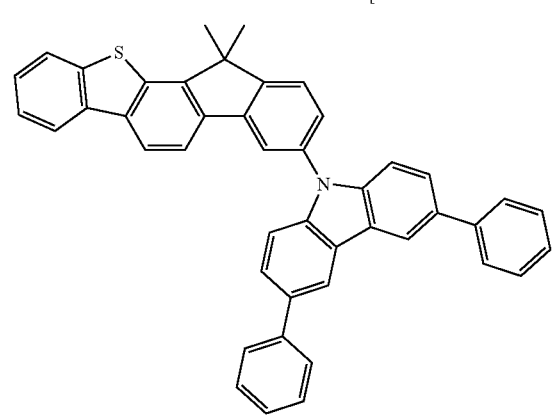

[Chemical Formula A-136]
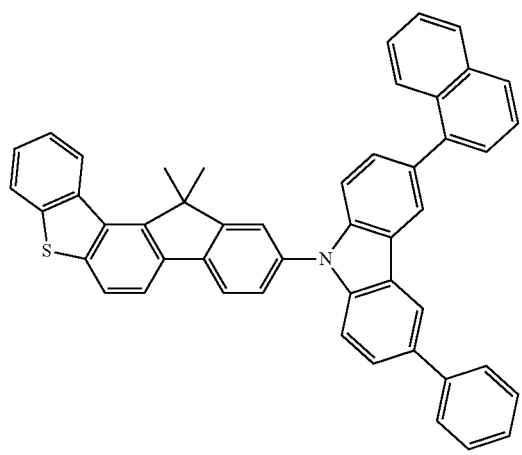
Specifically, the compound for an organic optoelectronic device may be represented by one of the following Chemical Formulae B-1 to B-68 but is not limited thereto.
[Chemical Formula B-1]
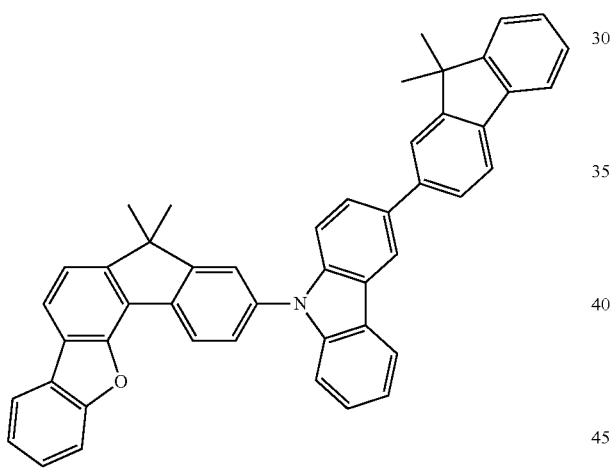
[Chemical Formula B-2]
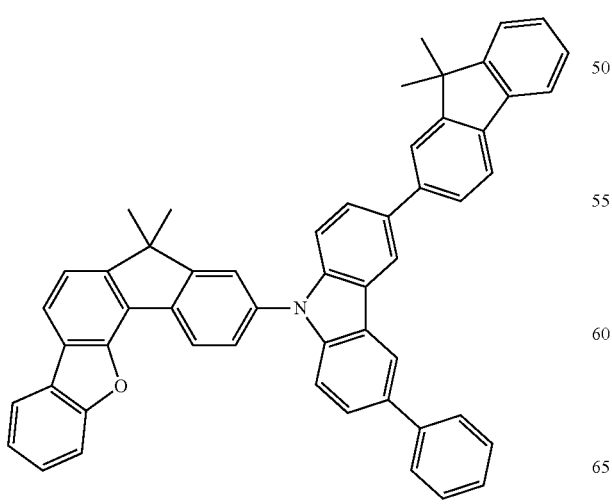
[Chemical Formula B-3]
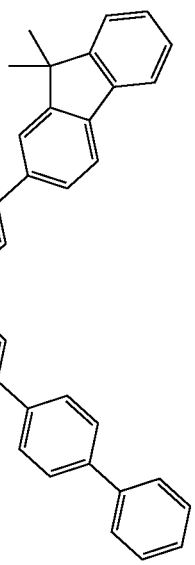
[Chemical Formula B-4]
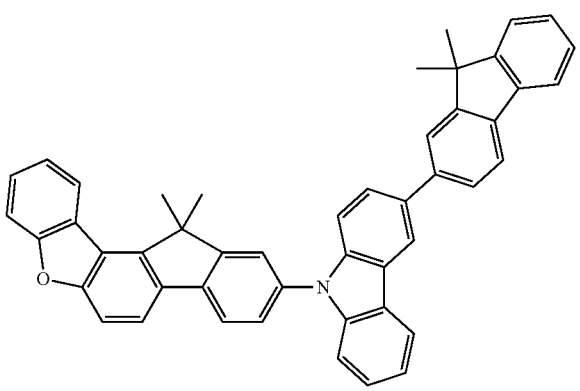
[Chemical Formula B-5]
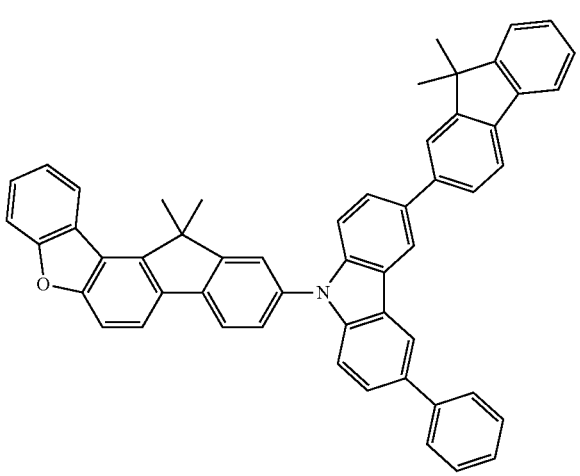

[Chemical Formula B-6]
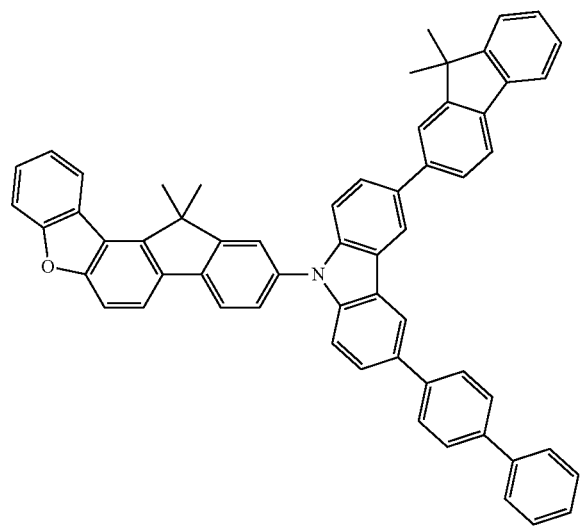
[Chemical Formula B-7]
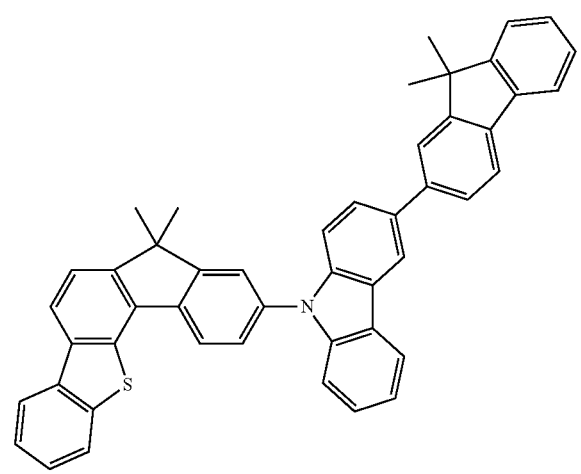
[Chemical Formula B-8]
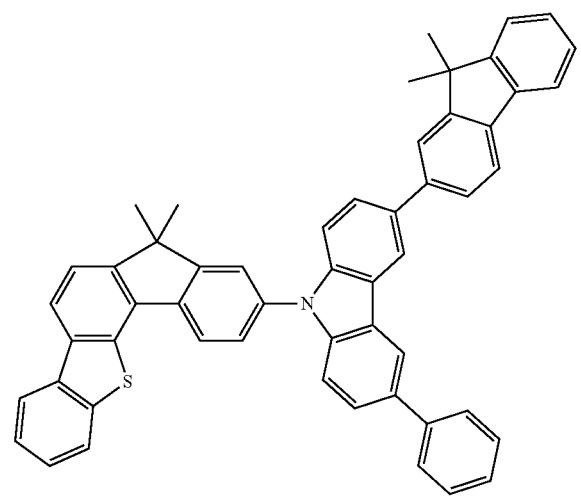
[Chemical Formula B-9]
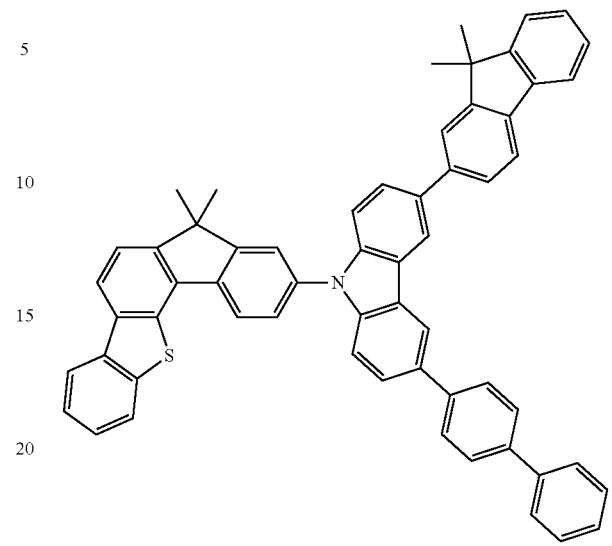
[Chemical Formula B-10]
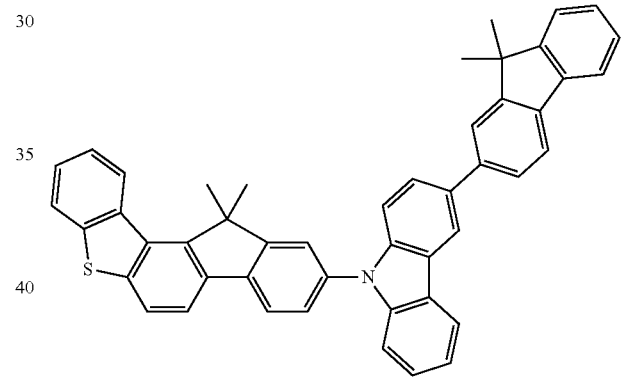
[Chemical Formula B-11]
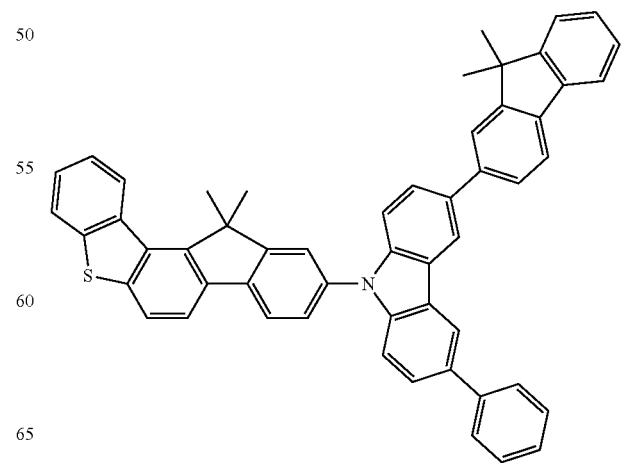

[Chemical Formula B-12]
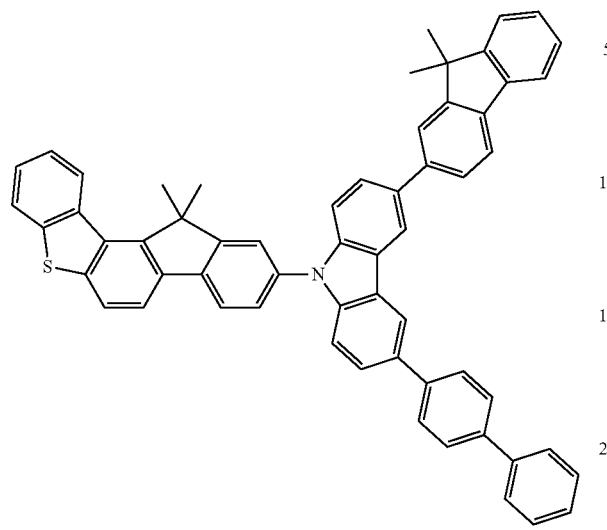
[Chemical Formula B-13]
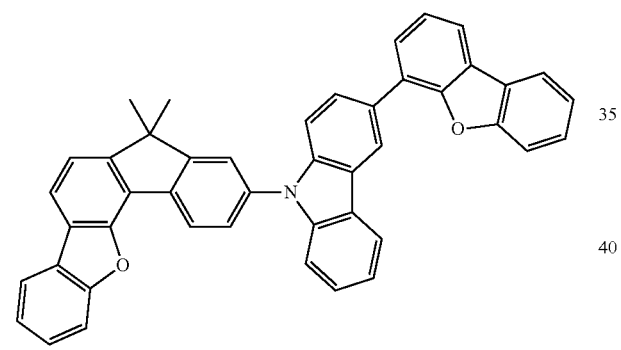
[Chemical Formula B-14]
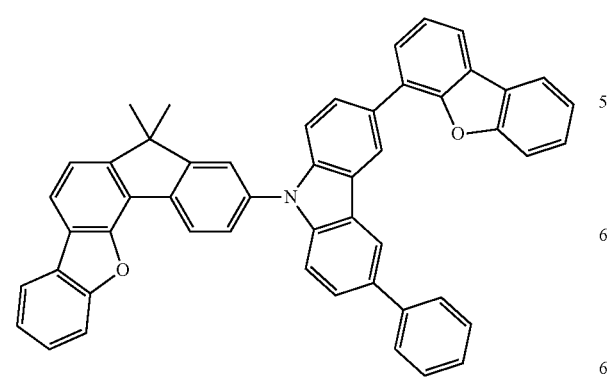
[Chemical Formula B-15]
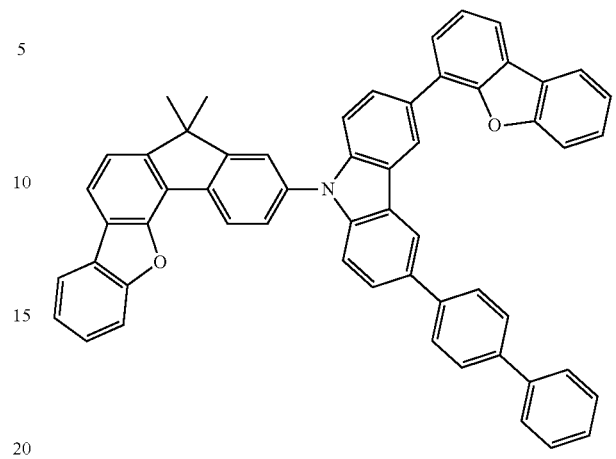
[Chemical Formula B-16]
[Chemical Formula B-17]
[Chemical Formula B-18]
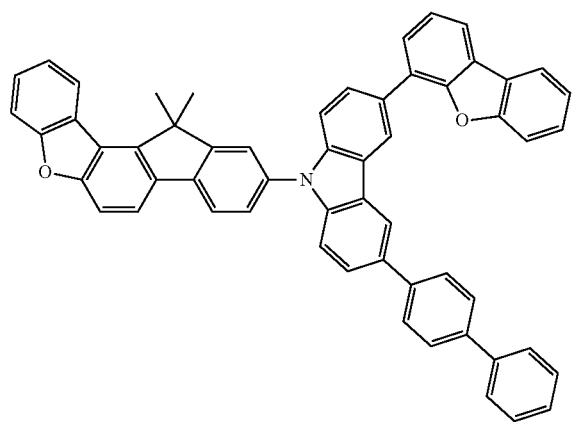

[Chemical Formula B-19]
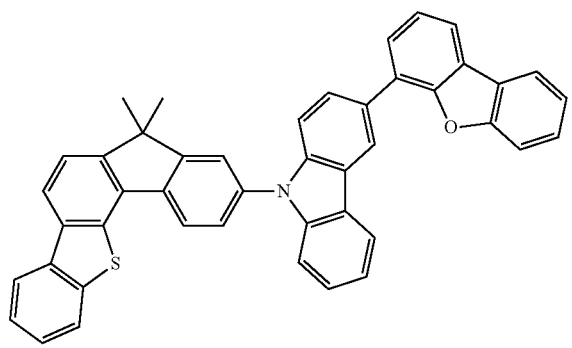
[Chemical Formula B-23]
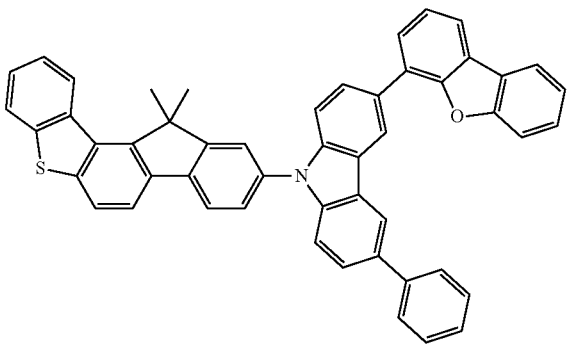
[Chemical Formula B-20]
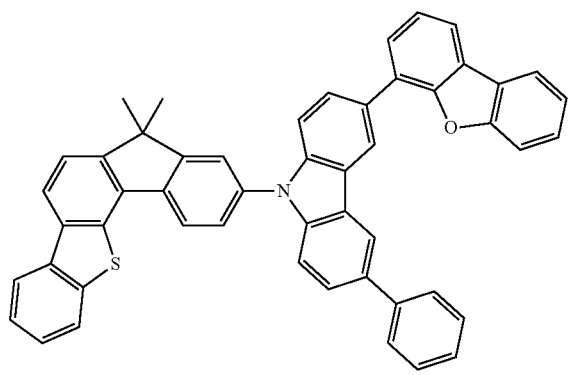
[Chemical Formula B-24]
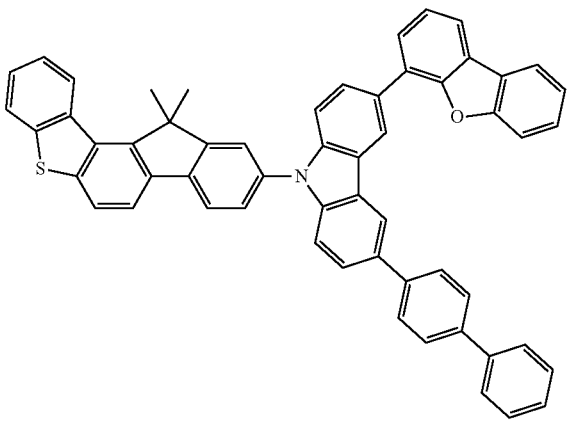
[Chemical Formula B-21]
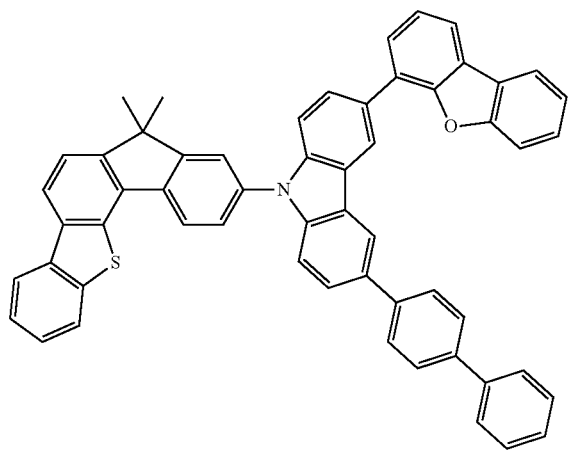
[Chemical Formula B-25]
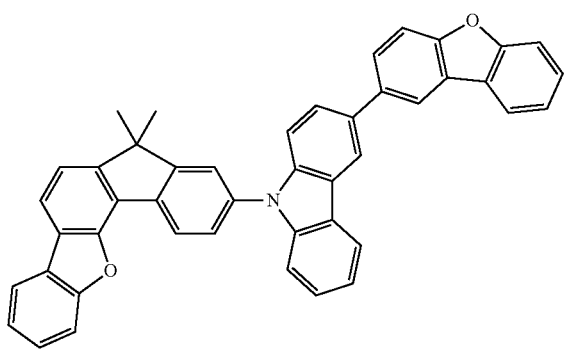
[Chemical Formula B-22]
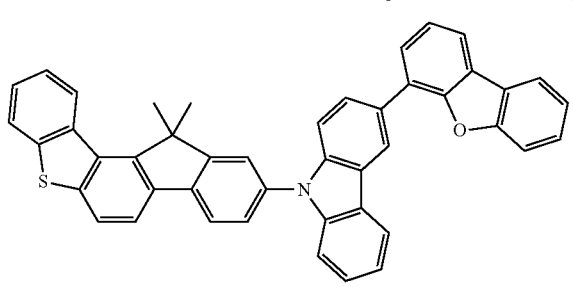
[Chemical Formula B-26]
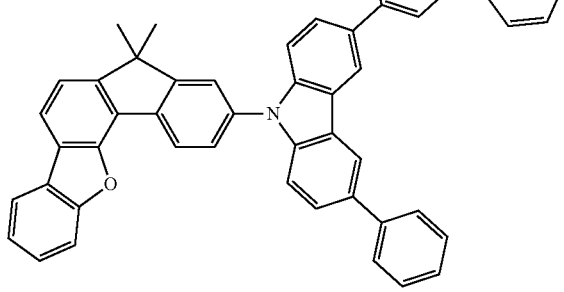

[Chemical Formula B-27]
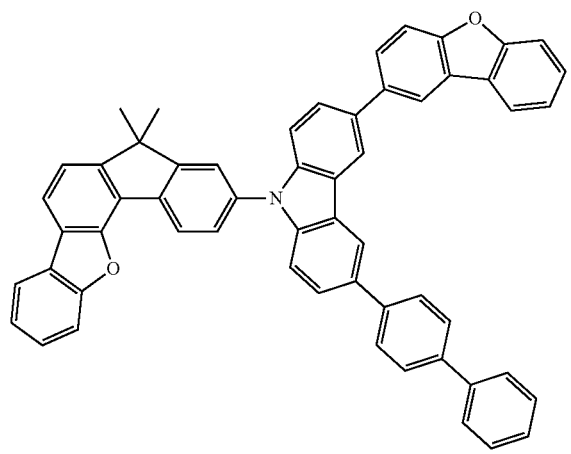
[Chemical Formula B-28]
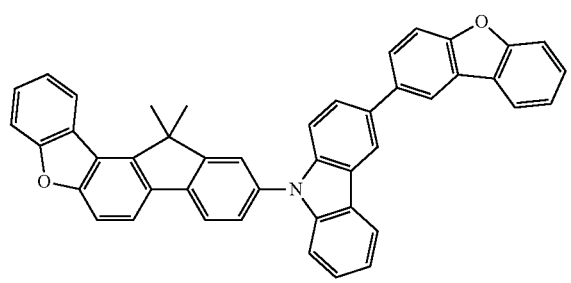
[Chemical Formula B-29]
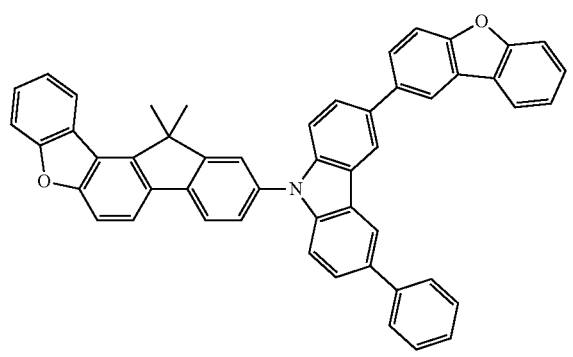
[Chemical Formula B-30]
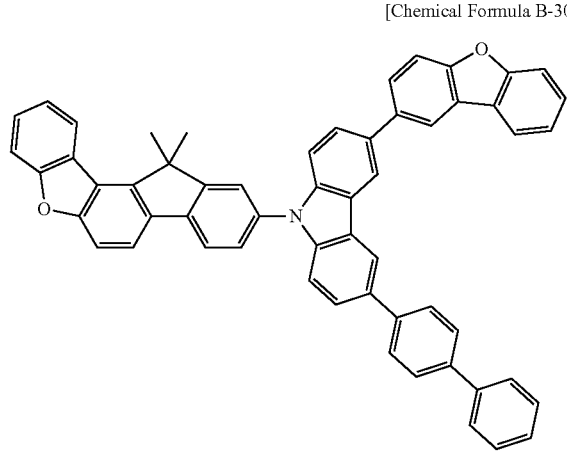
[Chemical Formula B-31]
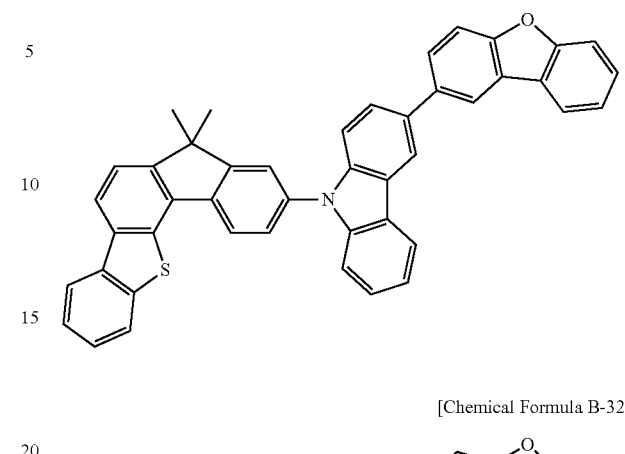
[Chemical Formula B-32]
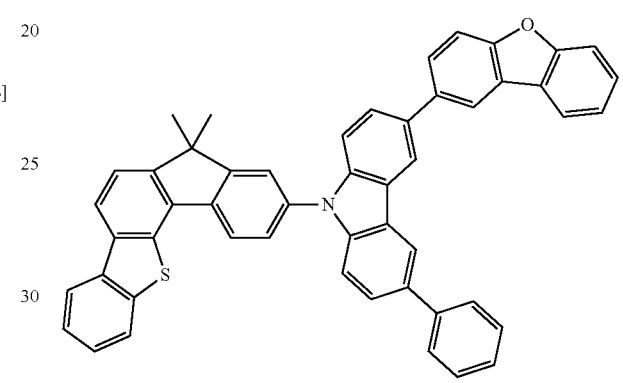
[Chemical Formula B-33]
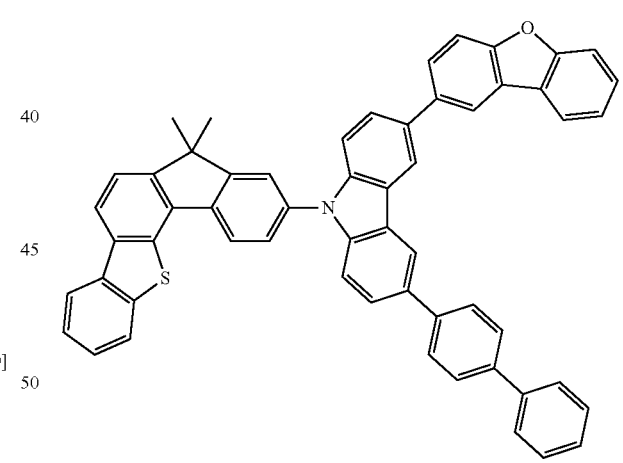
[Chemical Formula B-34]
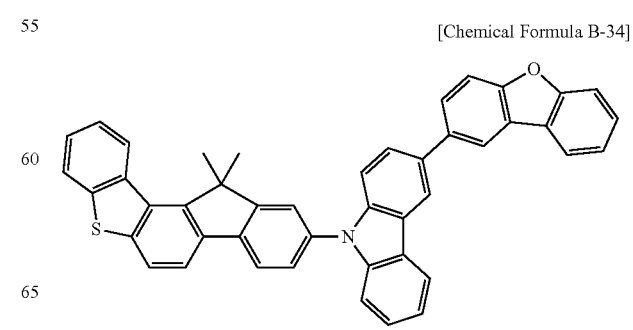

-continued
[Chemical Formula B-35]
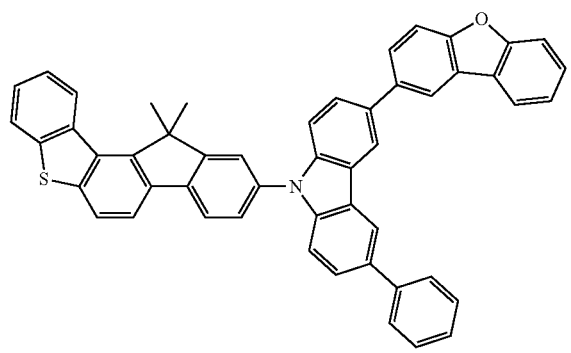
[Chemical Formula B-36]
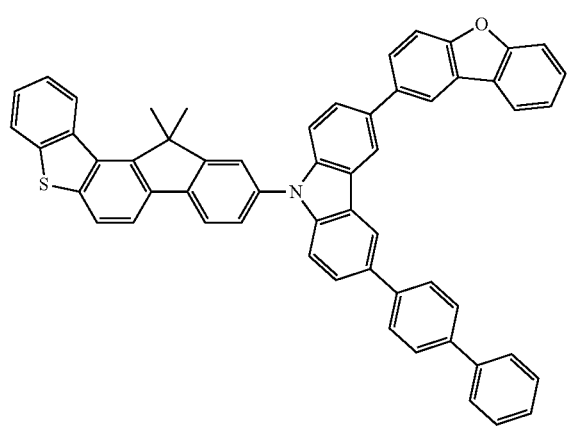
[Chemical Formula B-37]
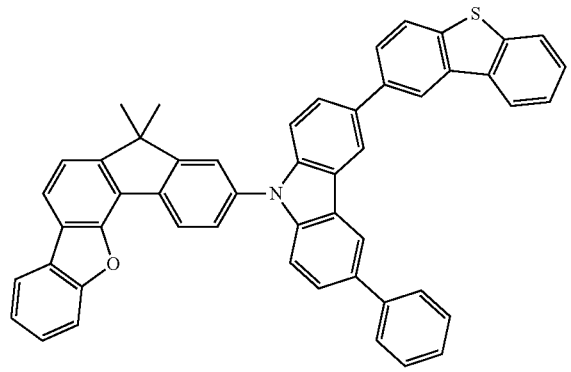
[Chemical Formula B-38]
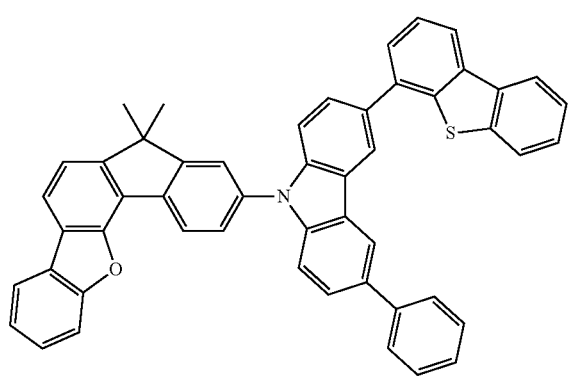
-continued
[Chemical Formula B-39]
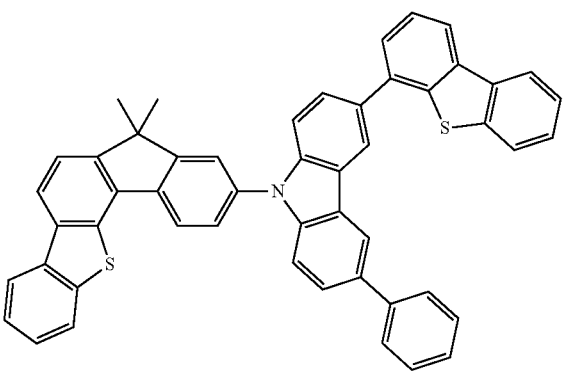
[Chemical Formula B-40]
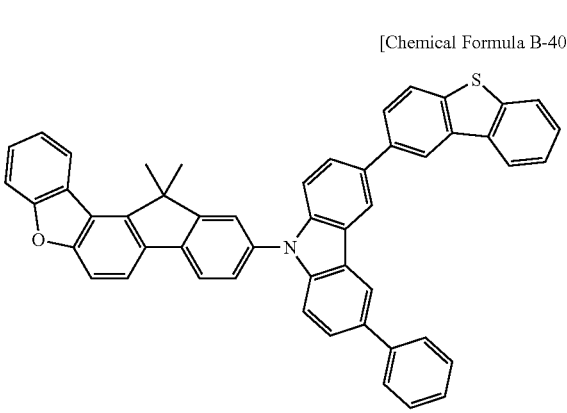
[Chemical Formula B-41]
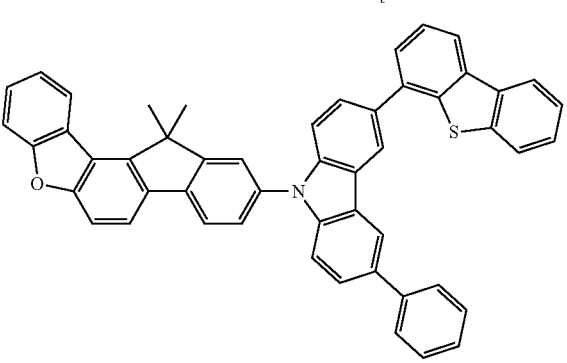
[Chemical Formula B-42]
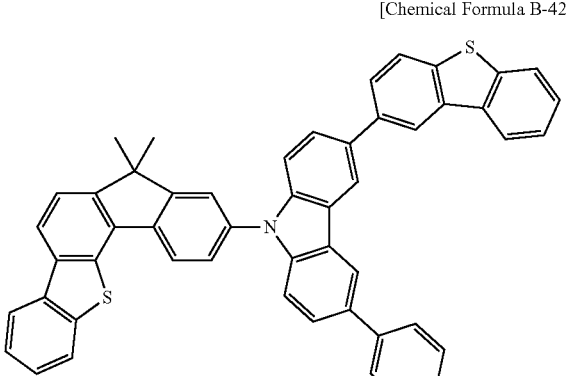

[Chemical Formula B-43]
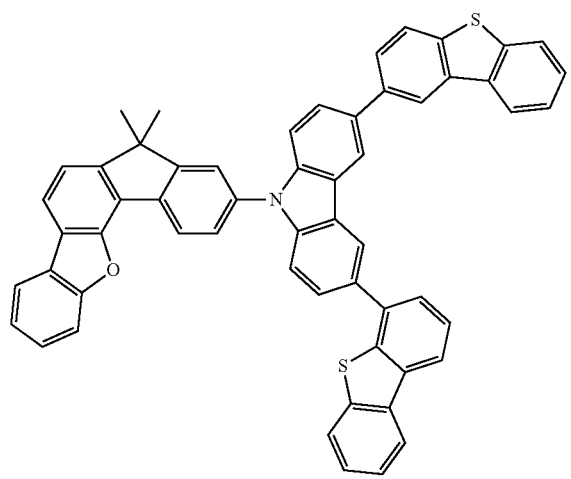
[Chemical Formula B-46]
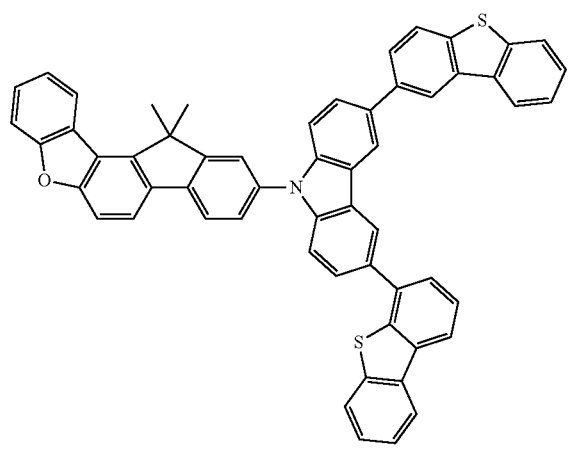
[Chemical Formula B-44]
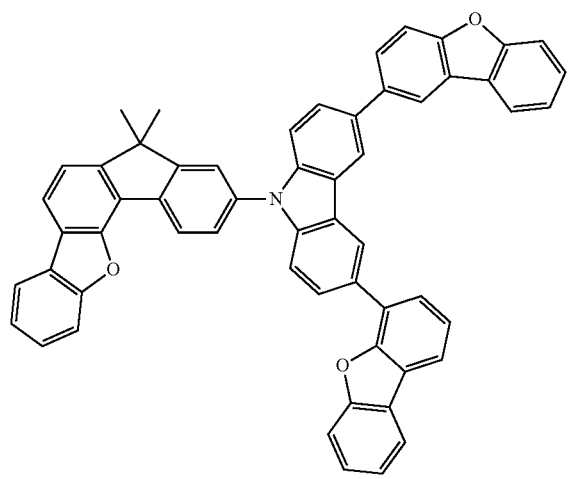
[Chemical Formula B-47]
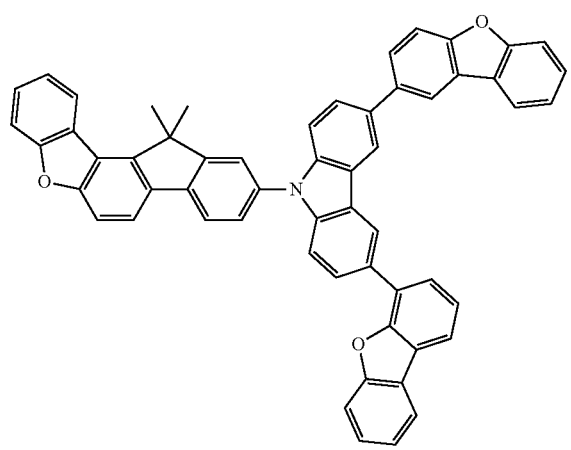
[Chemical Formula B-45]
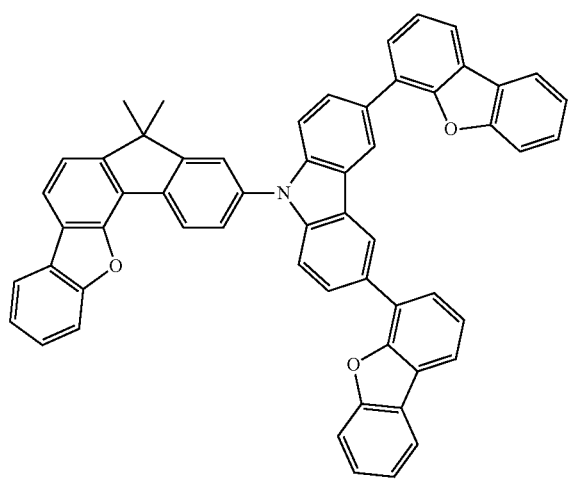
[Chemical Formula B-48]
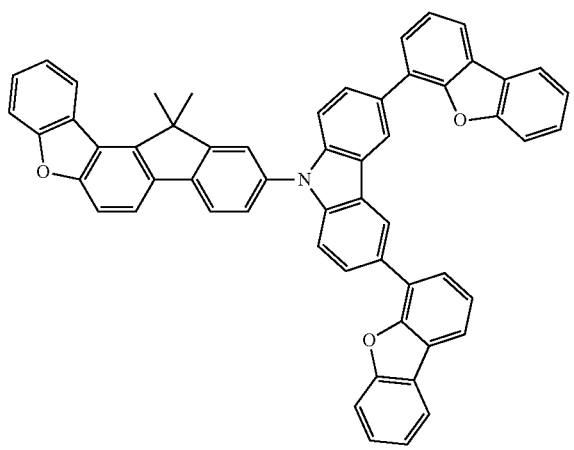

[Chemical Formula B-49]
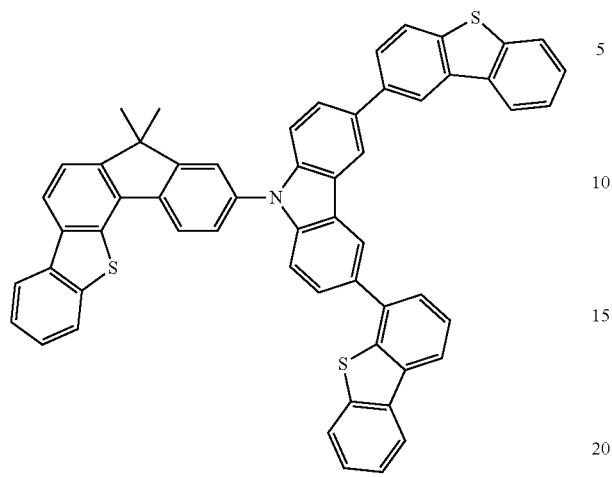
[Chemical Formula B-52]
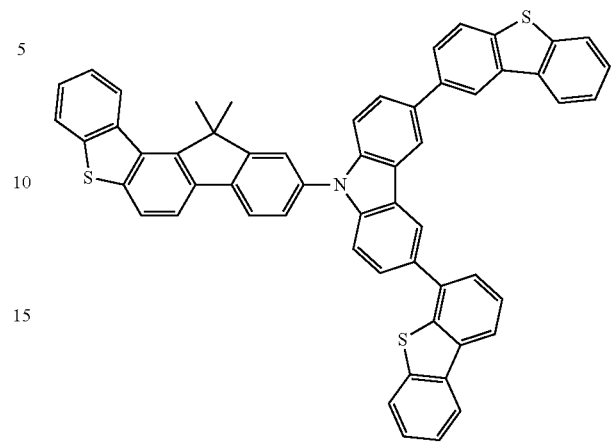
[Chemical Formula B-50]
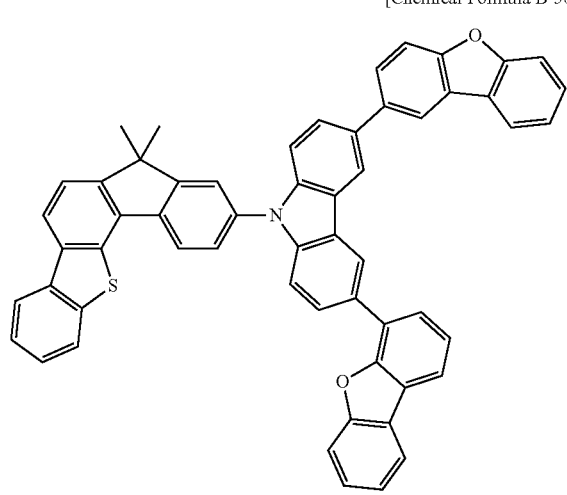
[Chemical Formula B-53]
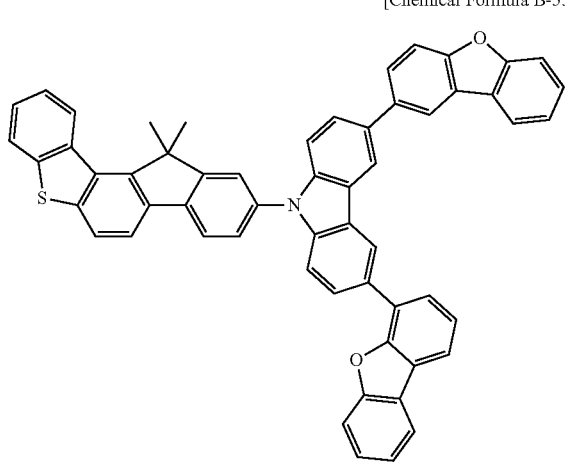
[Chemical Formula B-51]
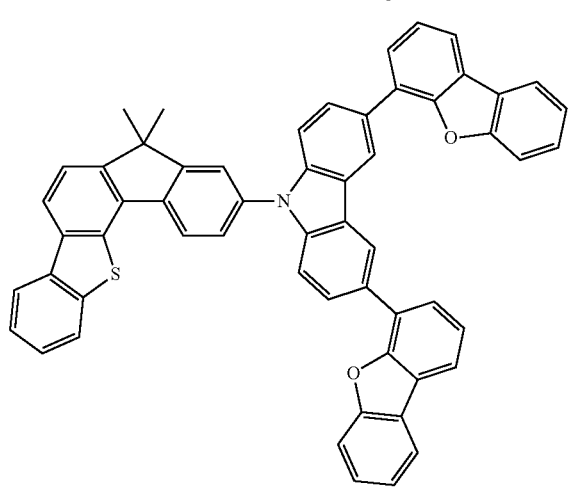
[Chemical Formula B-54]
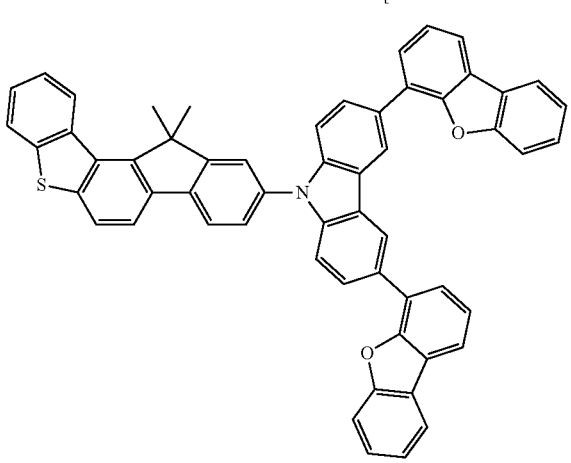

[Chemical Formula B-55]
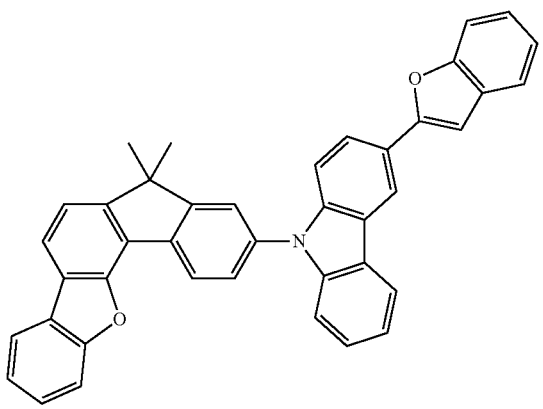
[Chemical Formula B-56]
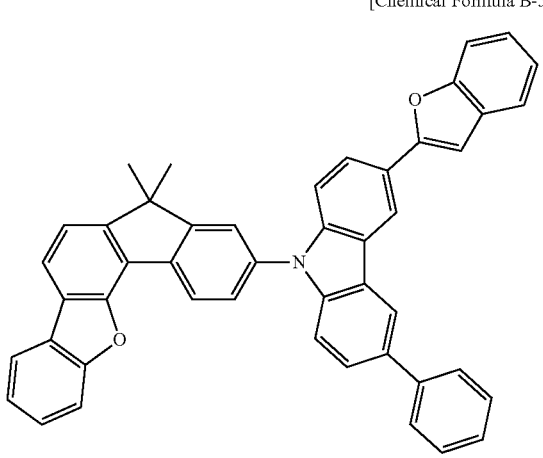
[Chemical Formula B-57]
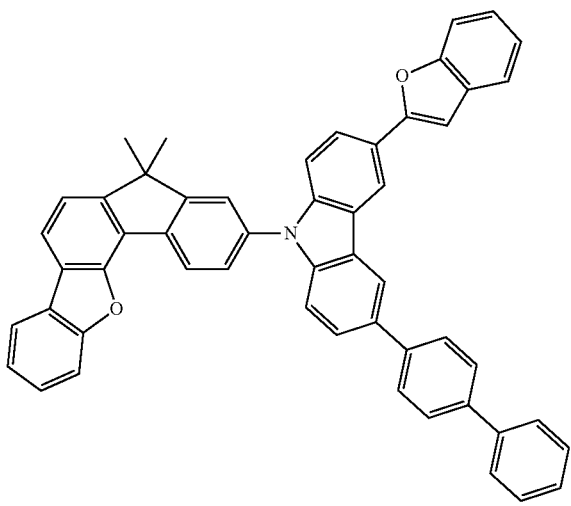
[Chemical Formula B-58]
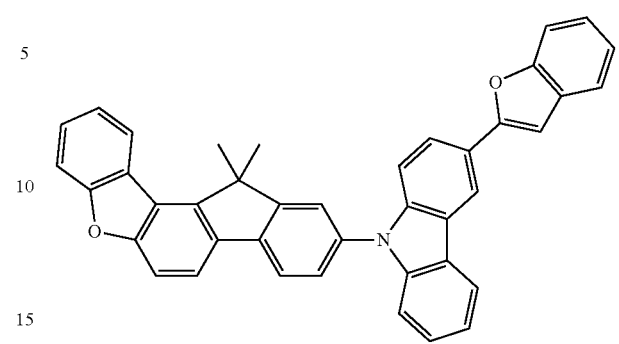
[Chemical Formula B-59]
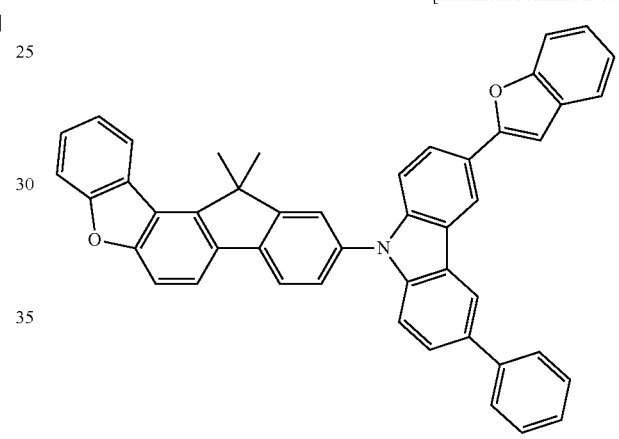
[Chemical Formula B-60]
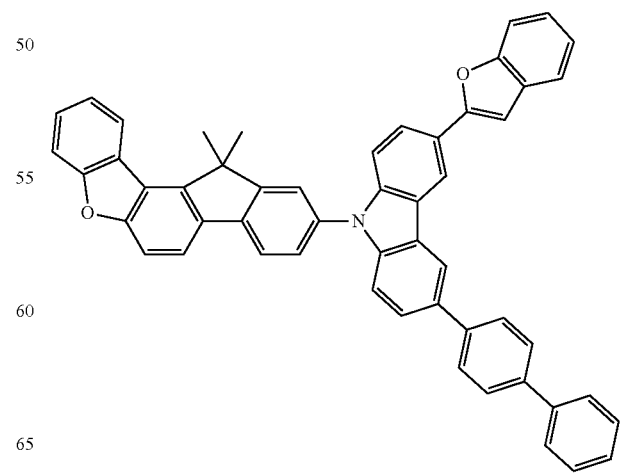

[Chemical Formula B-61]
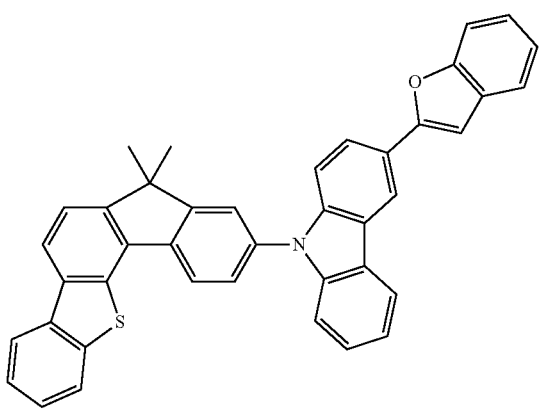
[Chemical Formula B-62]
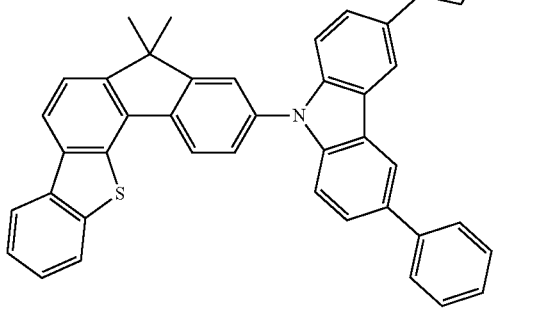
[Chemical Formula B-63]
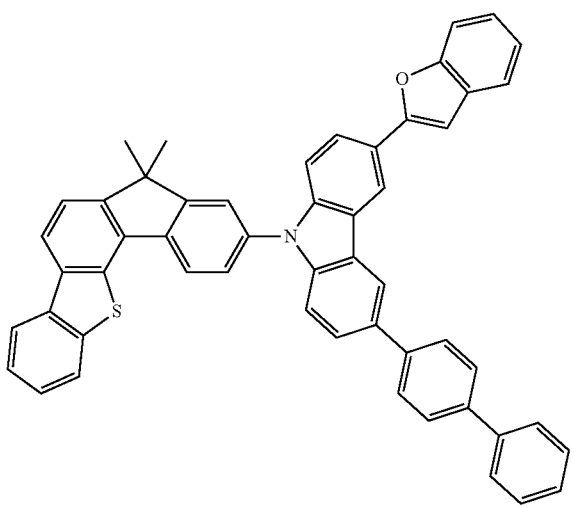
[Chemical Formula B-64]
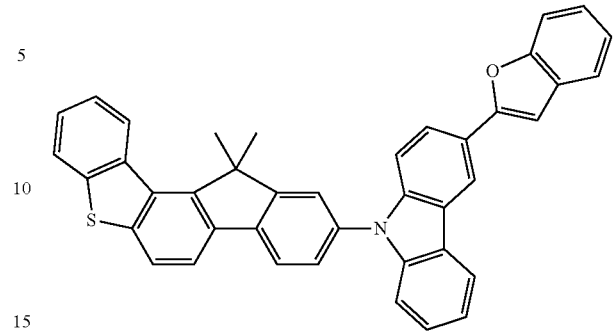
[Chemical Formula B-65]
[Chemical Formula B-66]
[Chemical Formula B-67]
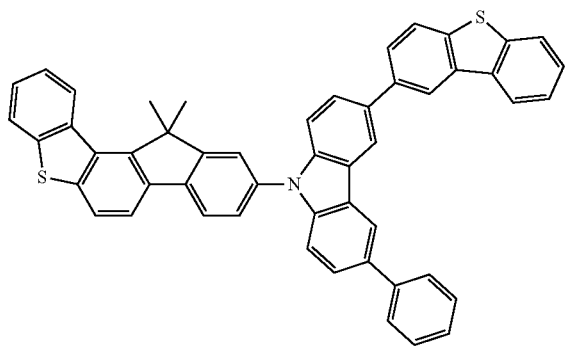

[Chemical Formula B-68]
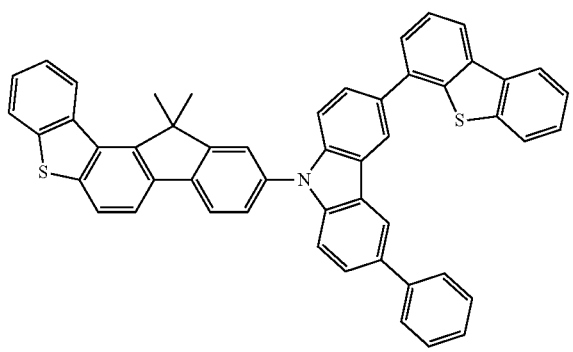
Specifically, the compound for an organic optoelectronic device may be represented by one of the following Chemical Formulae C-1 to C-78 but is not limited thereto.
[Chemical Formula C-1]
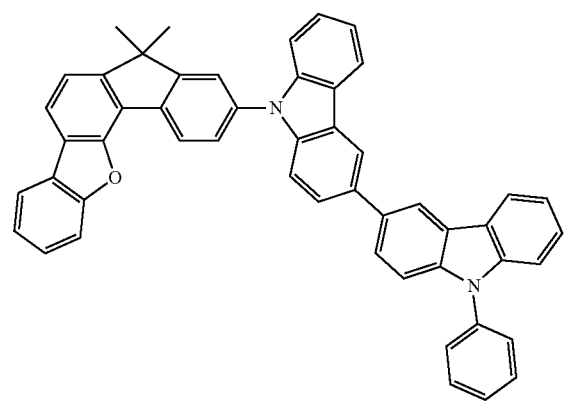
[Chemical Formula C-2]
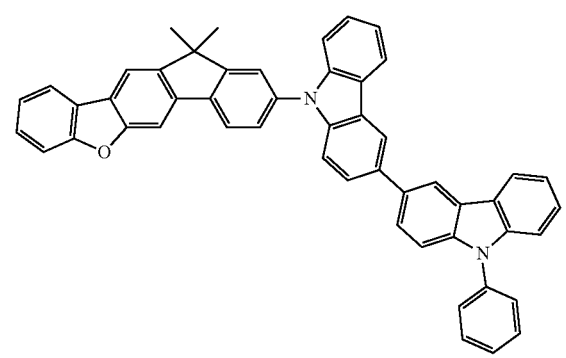
[Chemical Formula C-3]
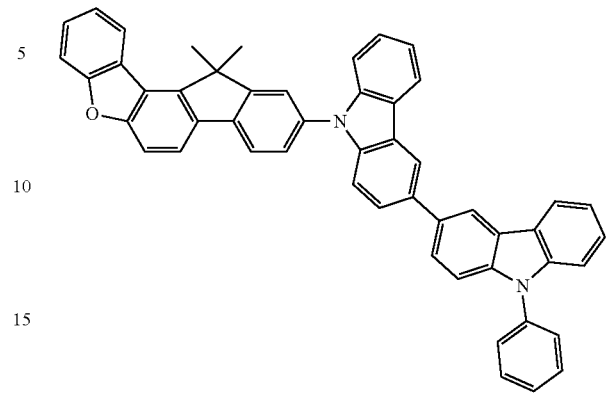
[Chemical Formula C-4]
[Chemical Formula C-5]
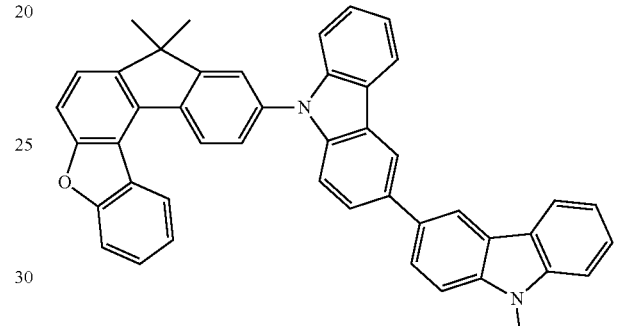
[Chemical Formula C-6]

[Chemical Formula C-7]
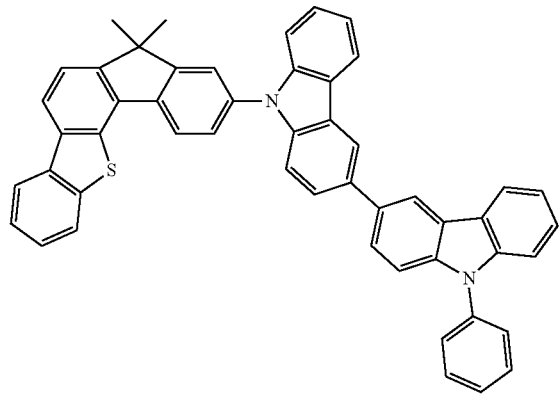
[Chemical Formula C-11]
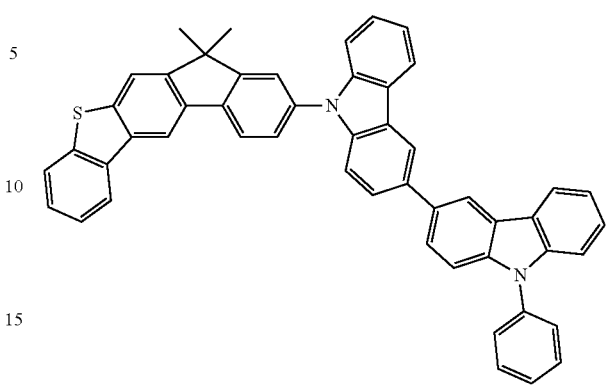
[Chemical Formula C-8]
[Chemical Formula C-12]
[Chemical Formula C-9]
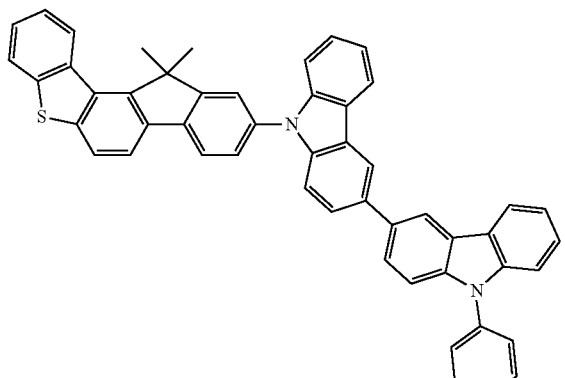
[Chemical Formula C-13]
[Chemical Formula C-10]
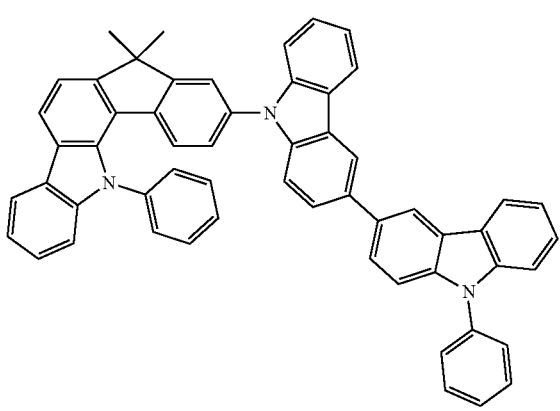
[Chemical Formula C-14]
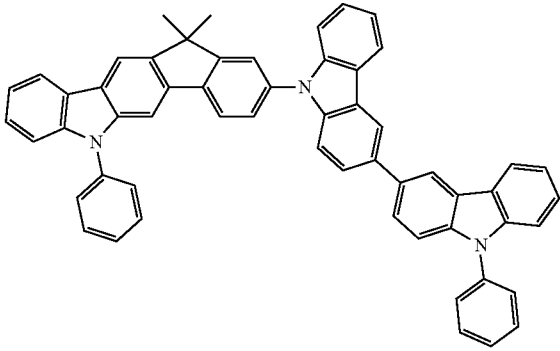

[Chemical Formula C-15]
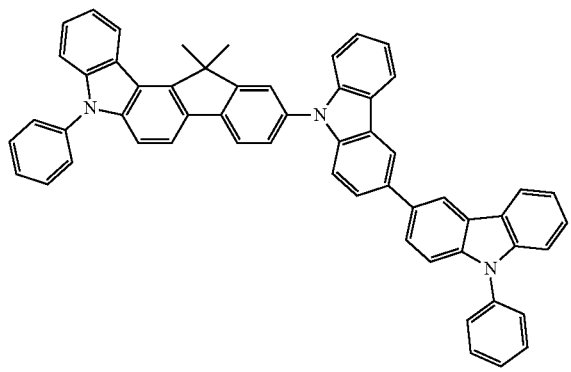
[Chemical Formula C-16]
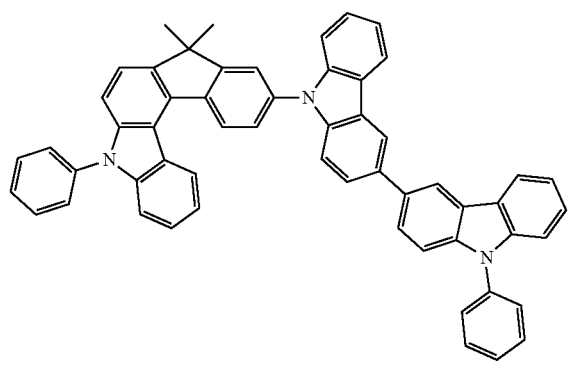
[Chemical Formula C-17]
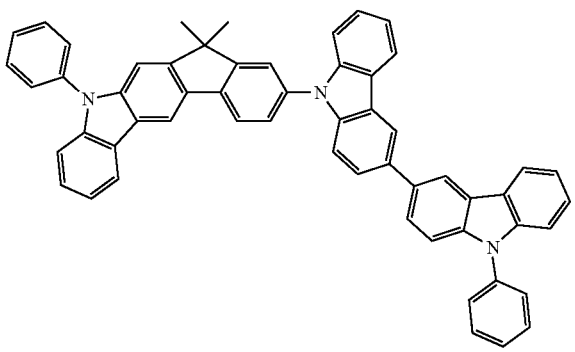
[Chemical Formula C-18]
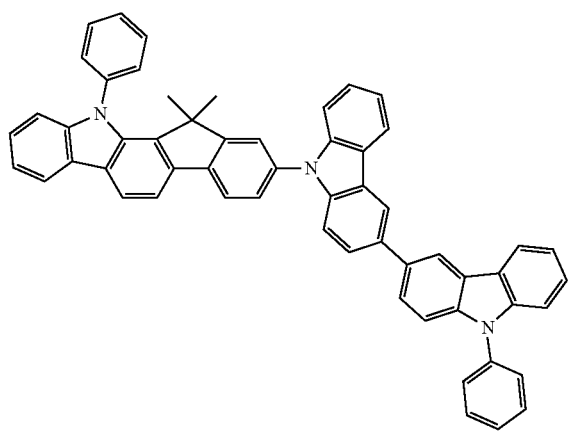
[Chemical Formula C-19]
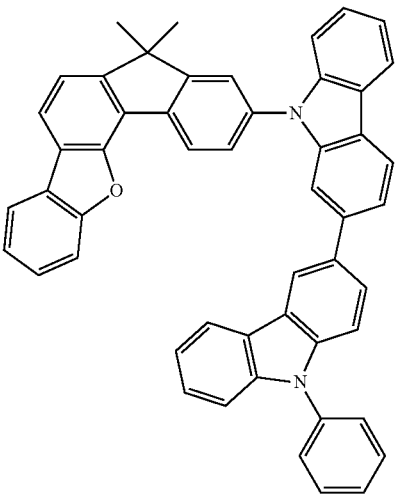
[Chemical Formula C-20]
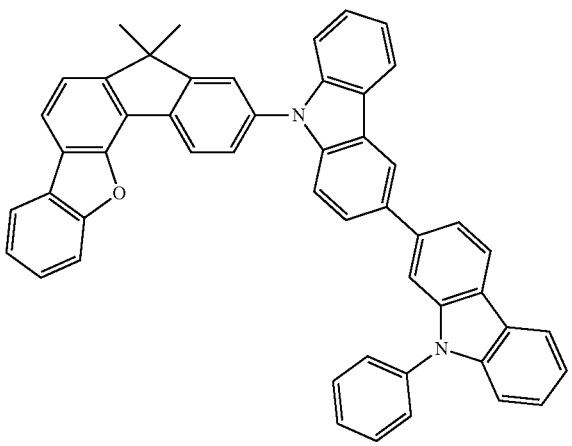
[Chemical Formula C-21]
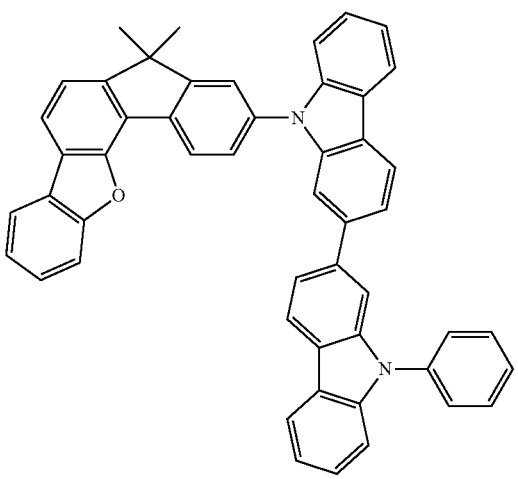

[Chemical Formula C-22]
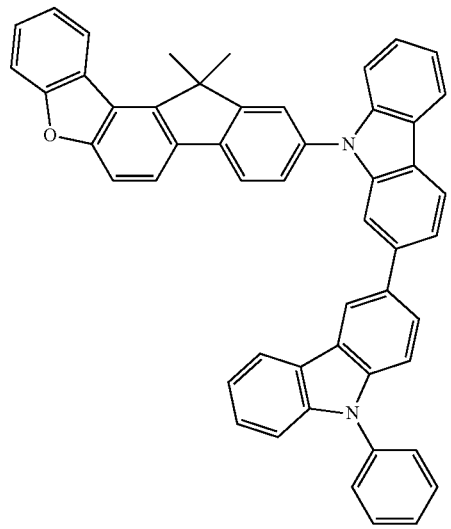
[Chemical Formula C-23]
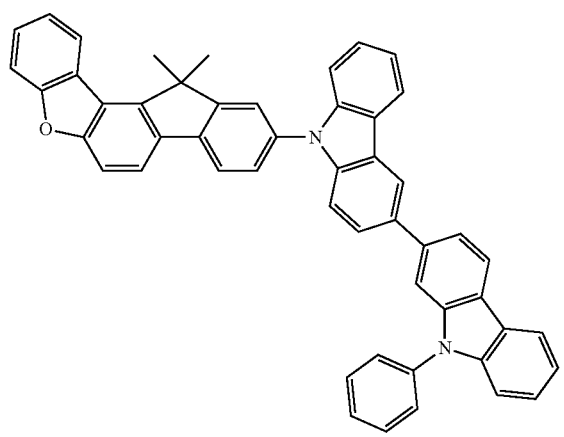
[Chemical Formula C-24]
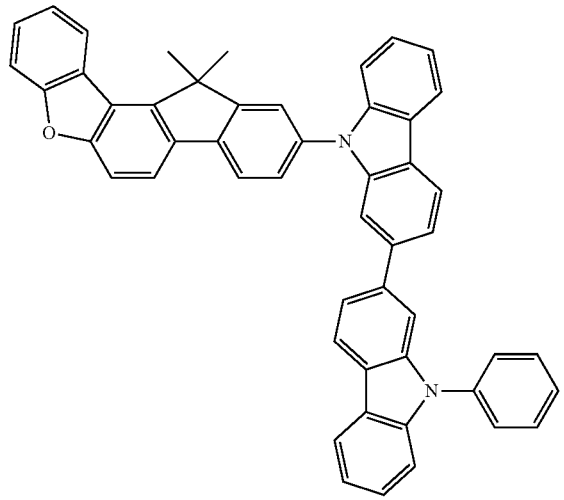
[Chemical Formula C-25]
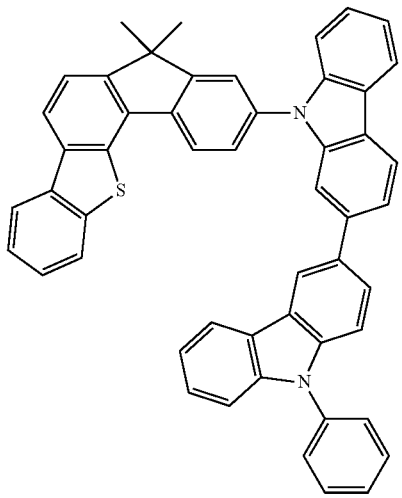
[Chemical Formula C-26]
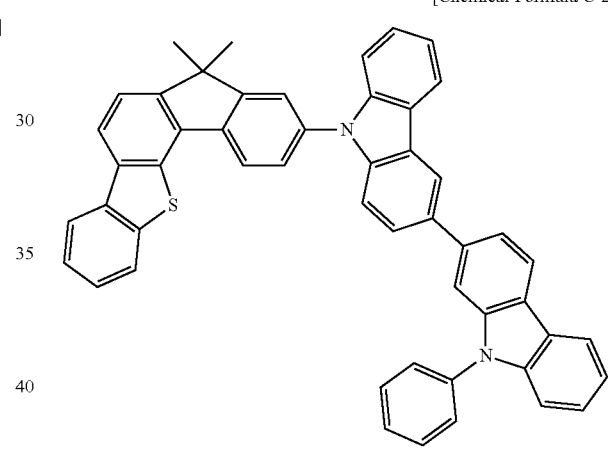
[Chemical Formula C-27]
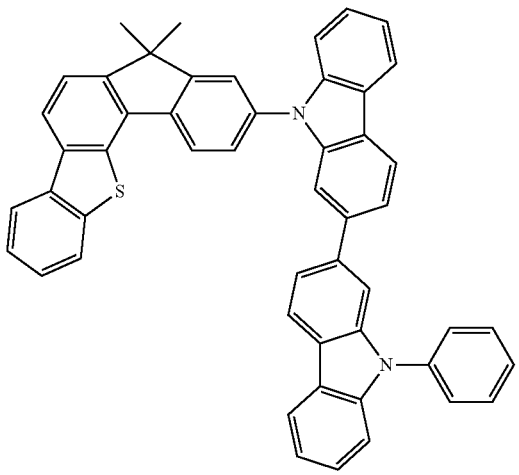

[Chemical Formula C-28]
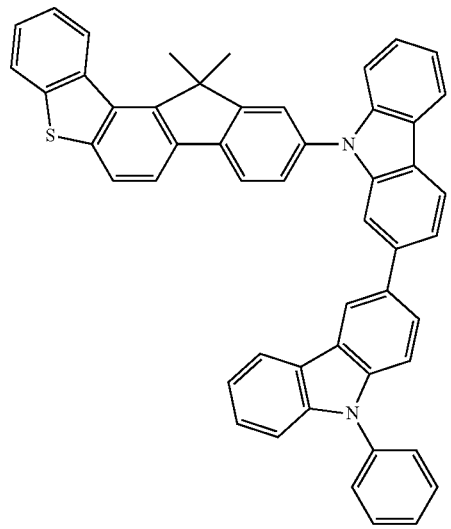
[Chemical Formula C-29]
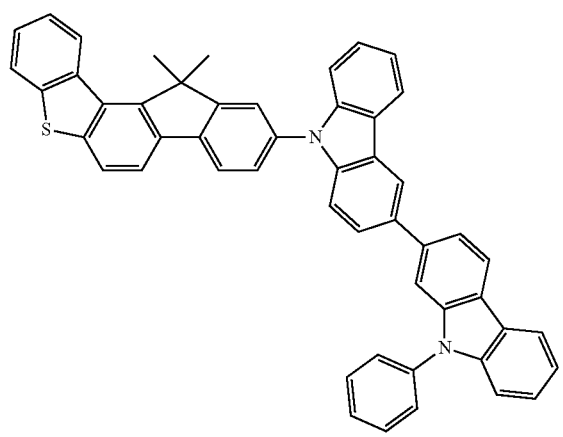
[Chemical Formula C-30]
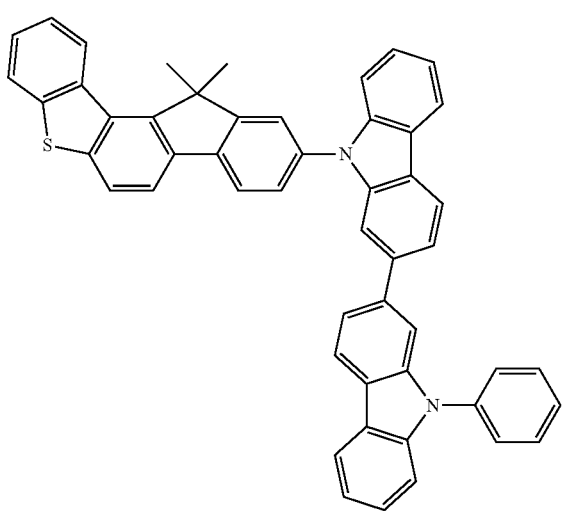
[Chemical Formula C-31]
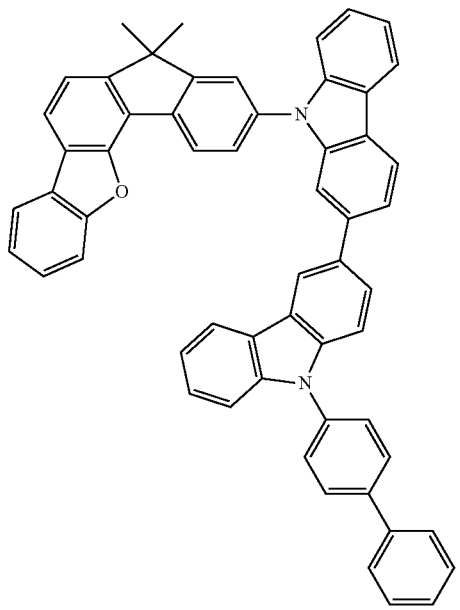
[Chemical Formula C-32]
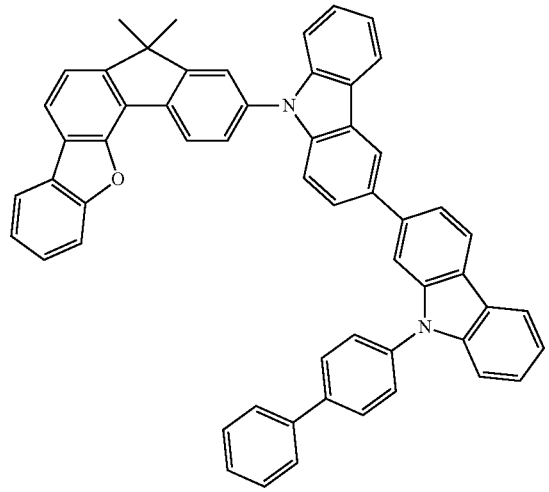
[Chemical Formula C-33]
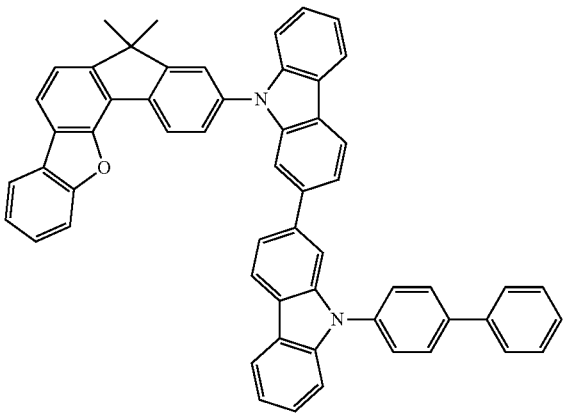

[Chemical Formula C-34]
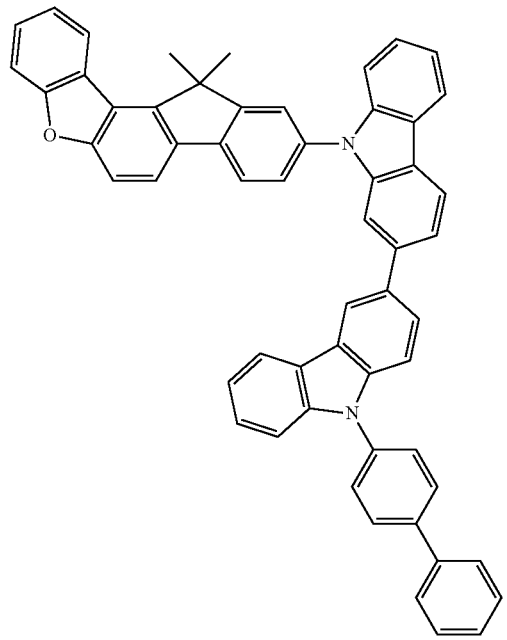
[Chemical Formula C-35]
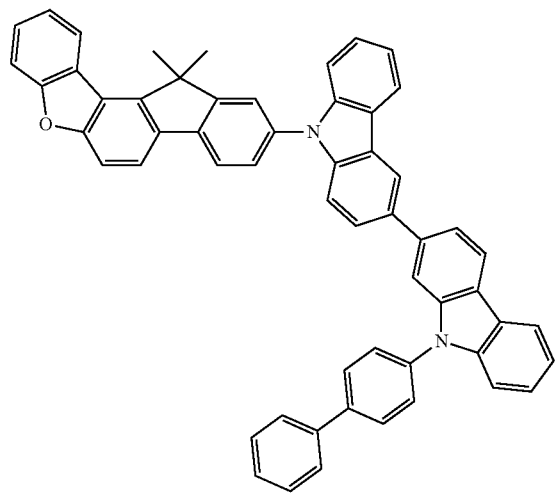
[Chemical Formula C-36]
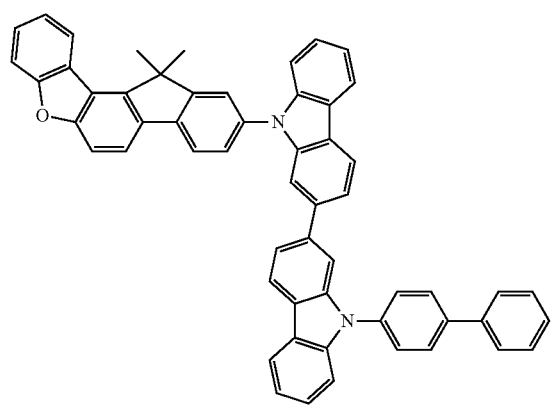
[Chemical Formula C-37]
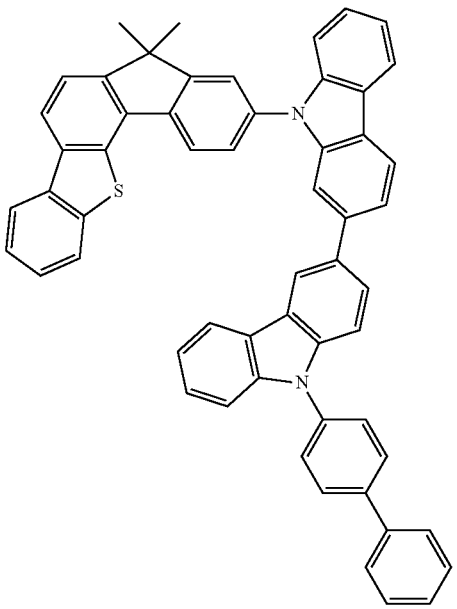
[Chemical Formula C-38]
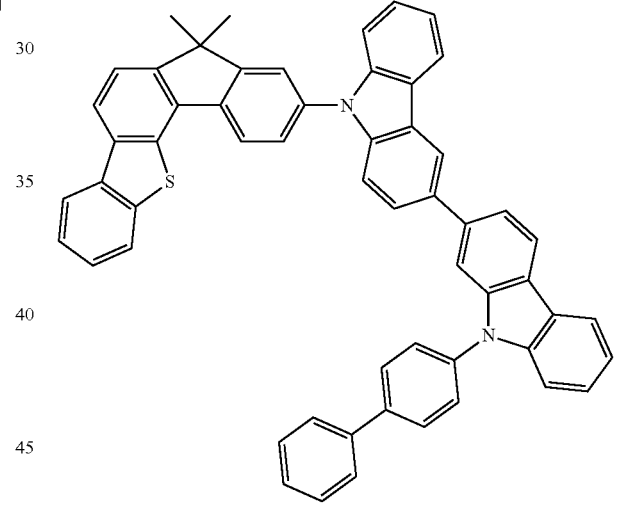
[Chemical Formula C-39]
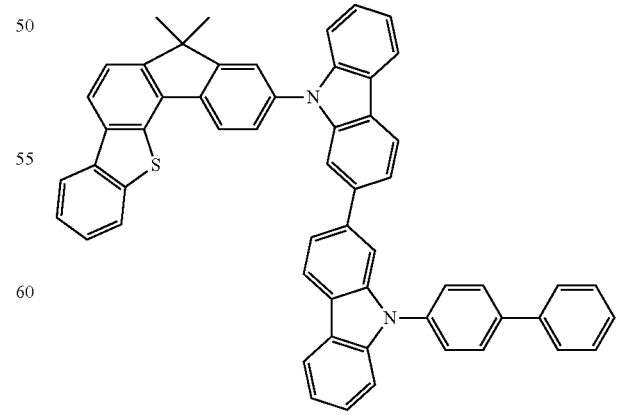

[Chemical Formula C-40]
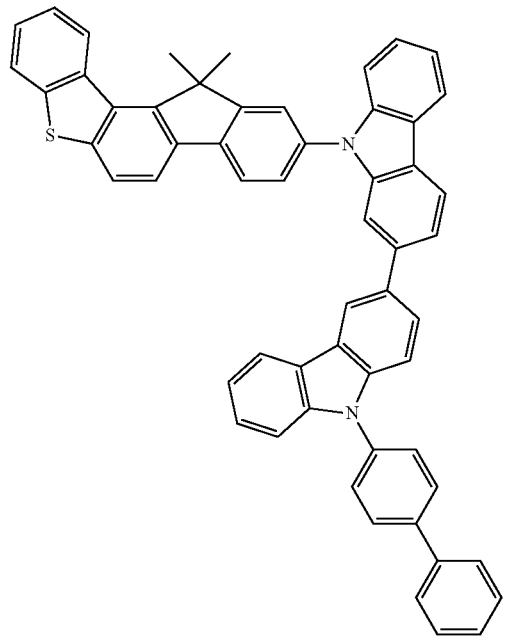
[Chemical Formula C-41]
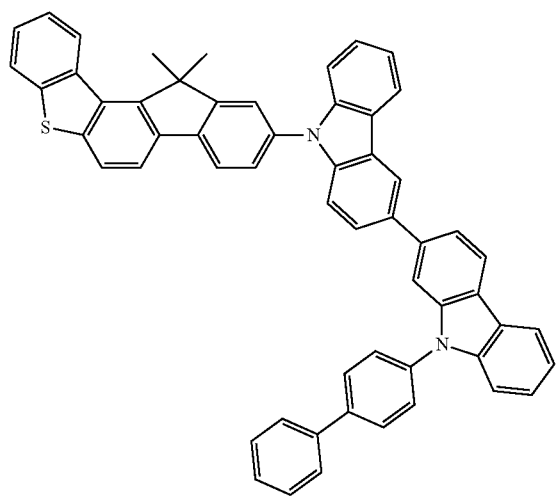
[Chemical Formula C-42]
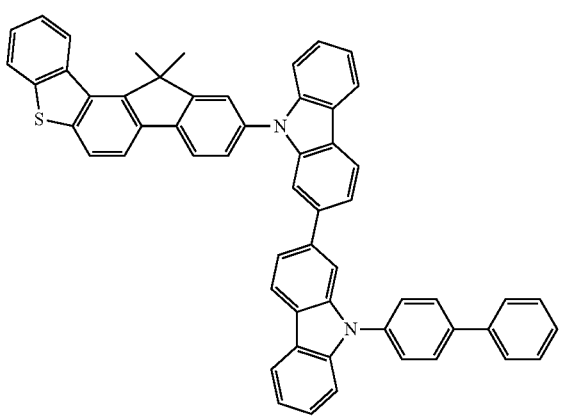
[Chemical Formula C-43]
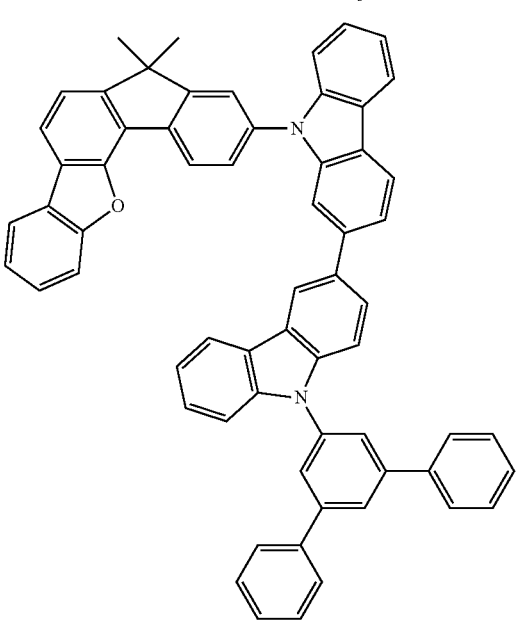
[Chemical Formula C-44]
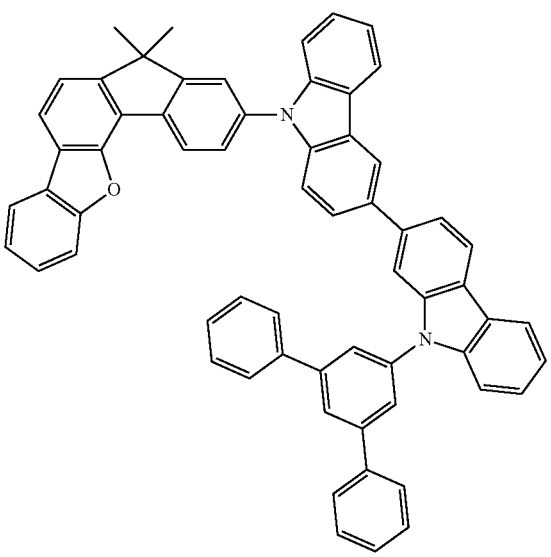

[Chemical Formula C-45]
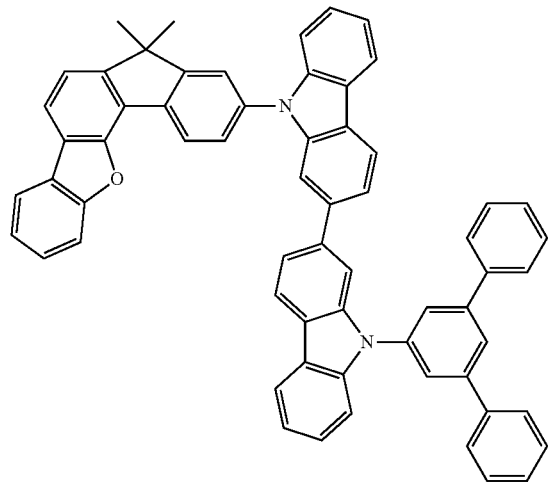
[Chemical Formual C-46]
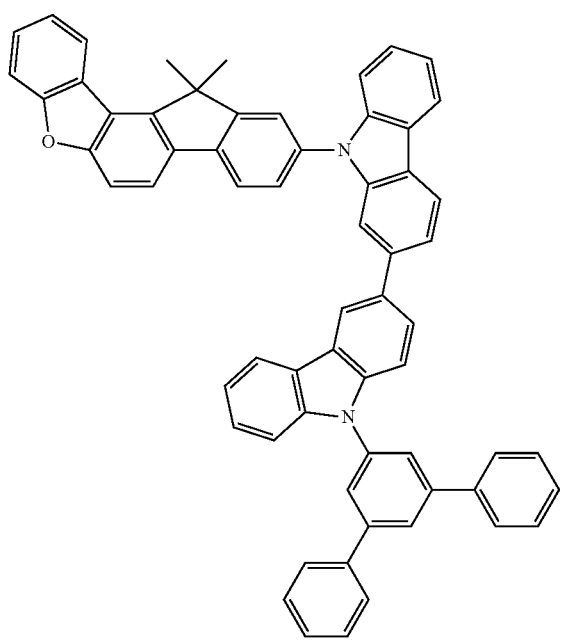
[Chemical Formula C-47]
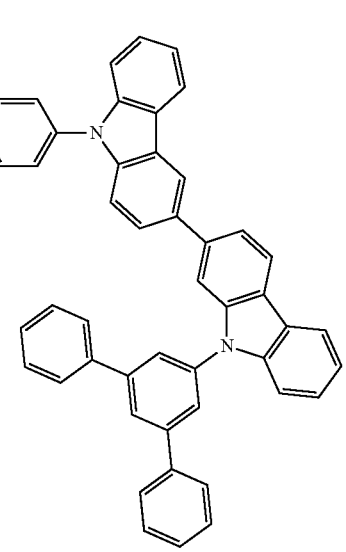
[Chemical Formula C-48]
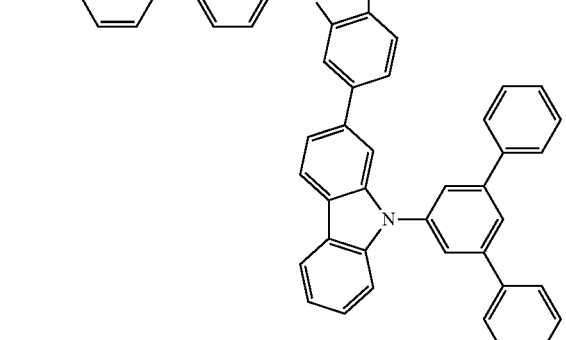

[Chemical Formula C-49]
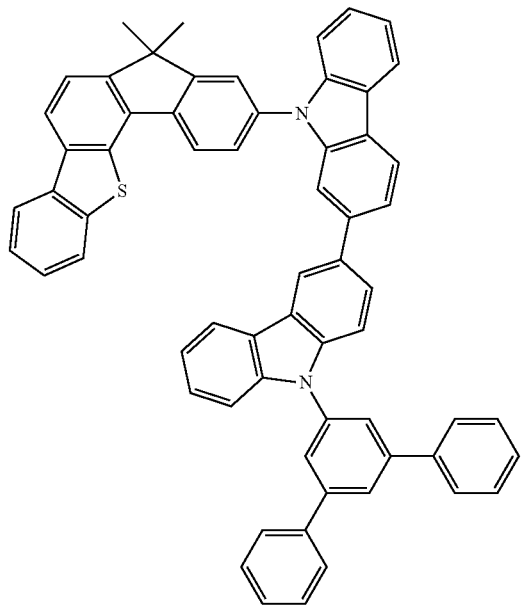
[Chemical Formula C-50]
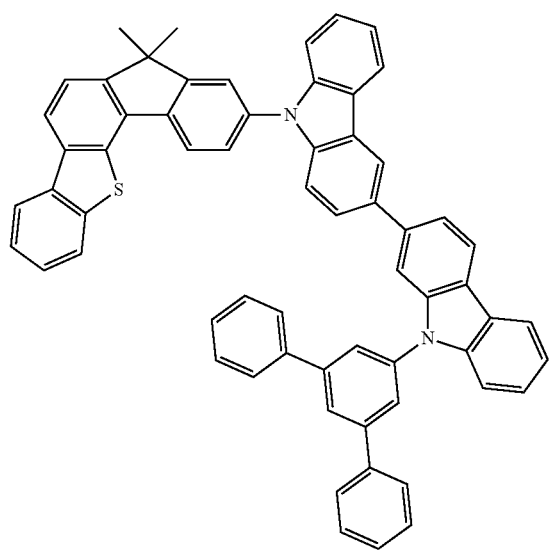
[Chemical Formula C-51]
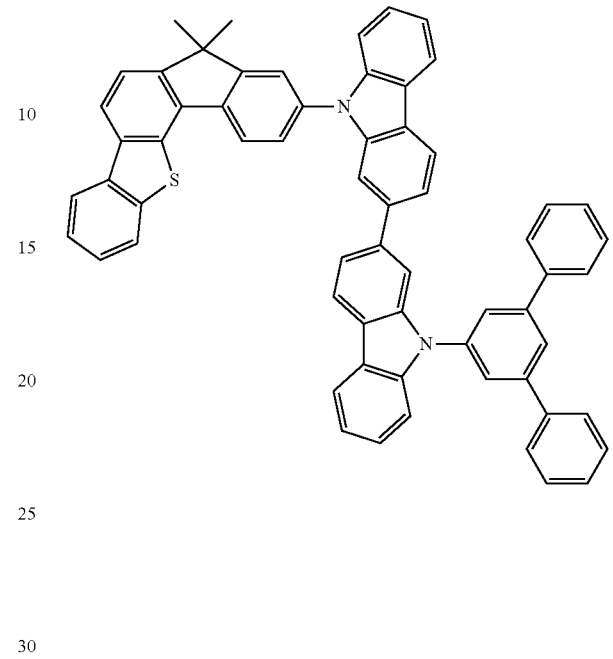
[Chemical Formula C-52]
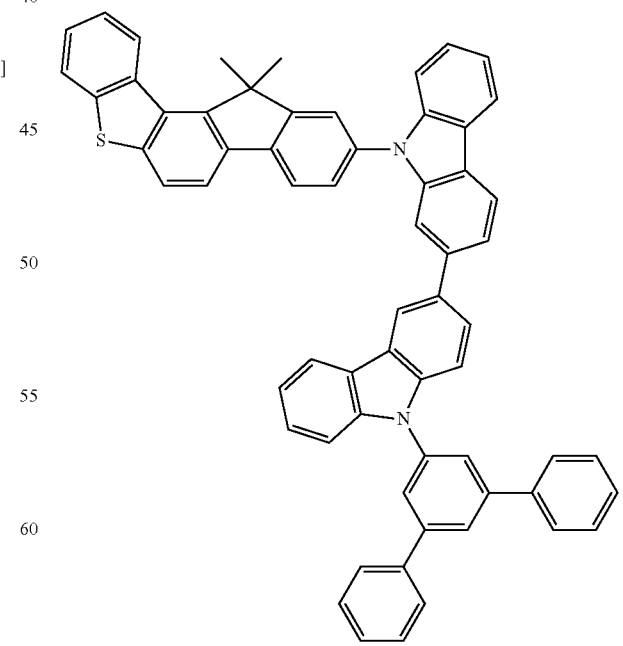

[Chemical Formula C-53]
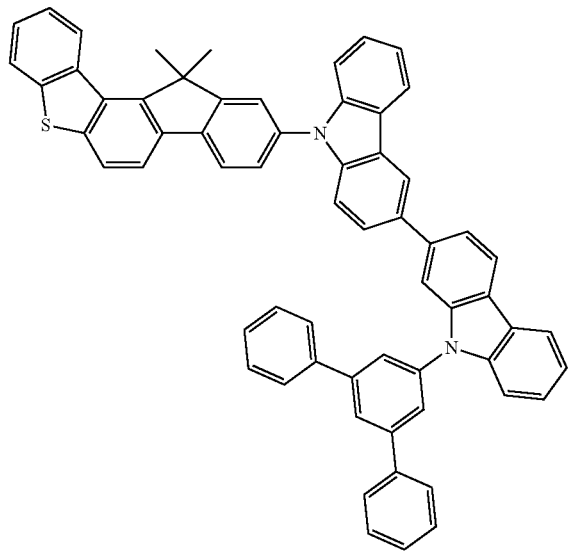
[Chemical Formula C-54]
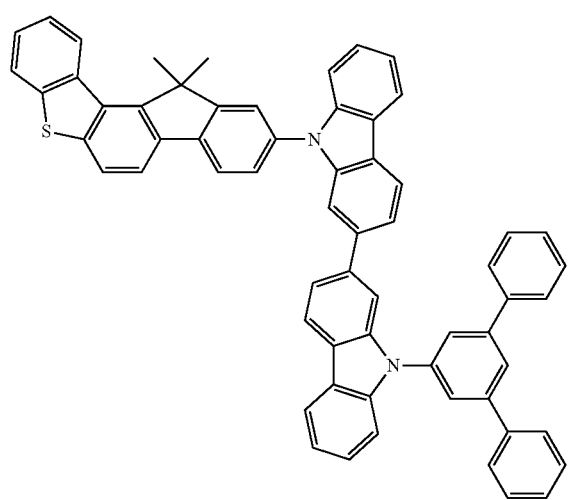
[Chemical Formula C-55]
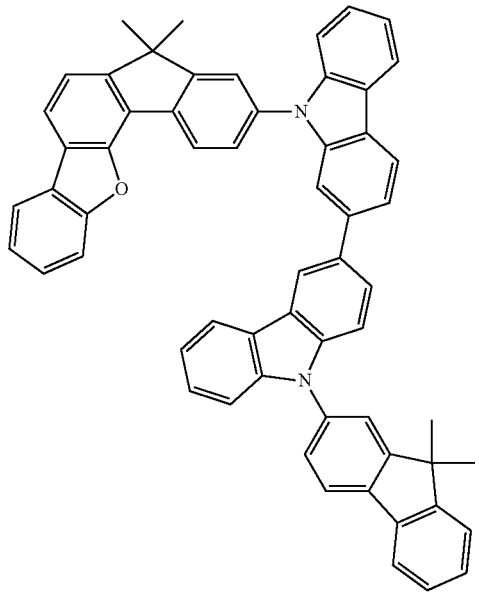
[Chemical Formula C-56]
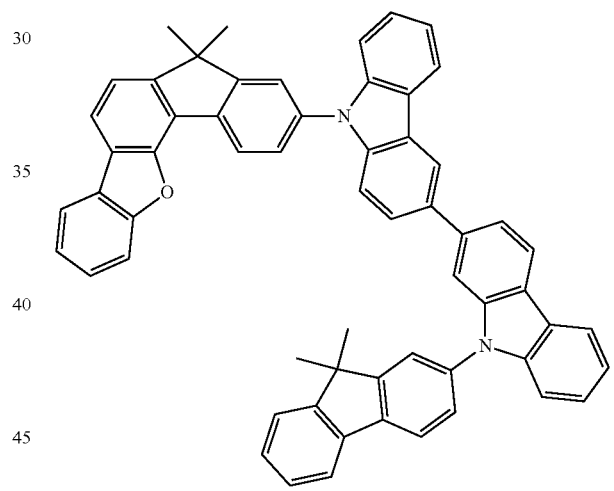
[Chemical Formula C-57]
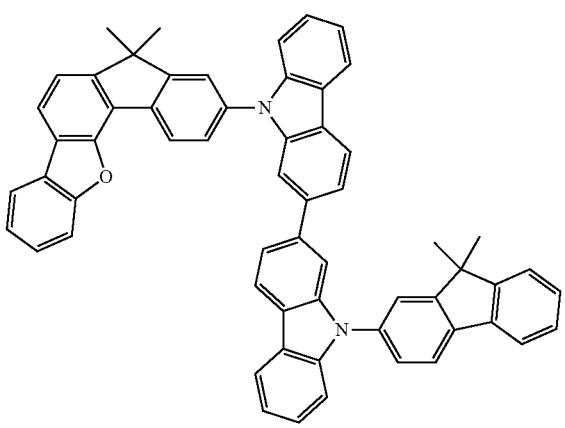

[Chemical Formula C-58]
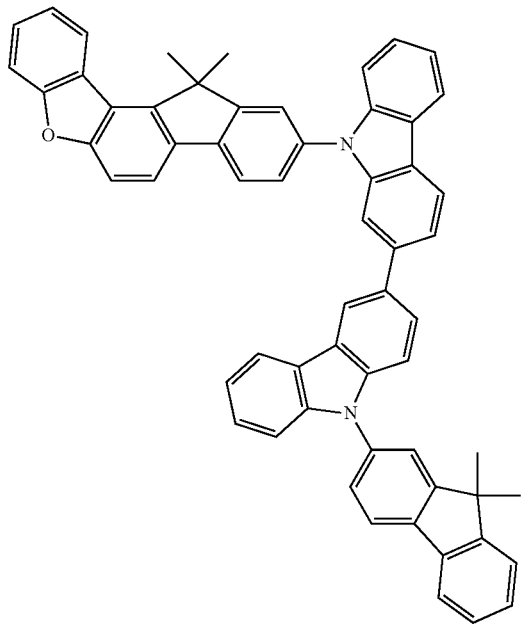
[Chemical Formula C-61]
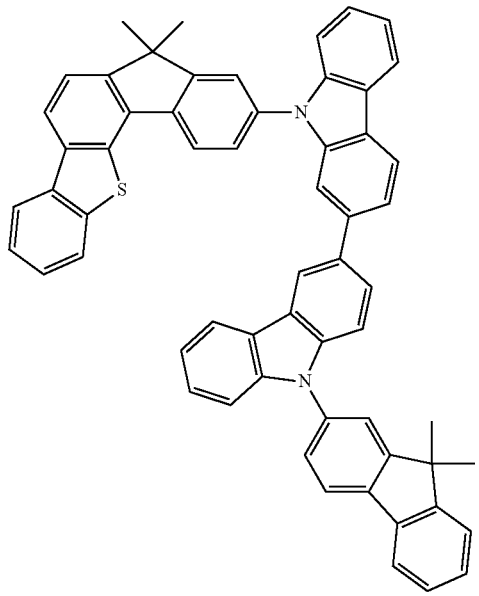
[Chemical Formula C-59]
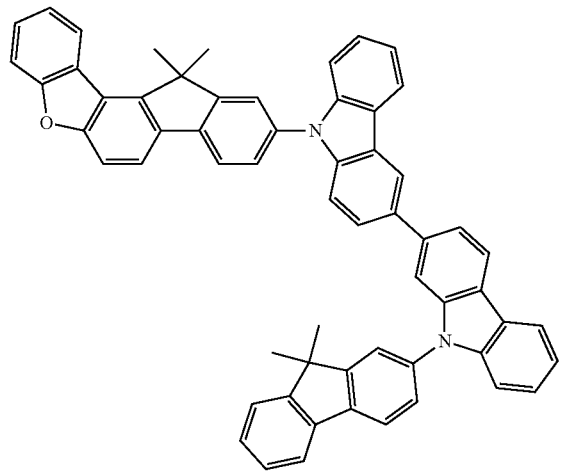
[Chemical Formula C-62]
[Chemical Formula C-60]
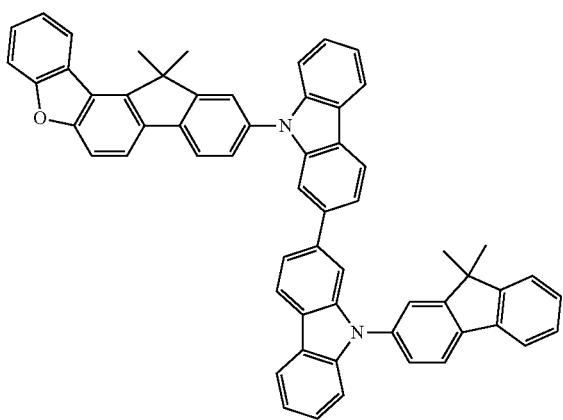
[Chemical Formula C-63]
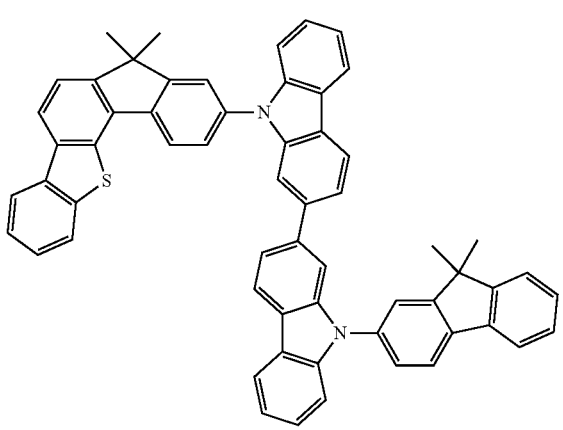

[Chemical Formula C-64]
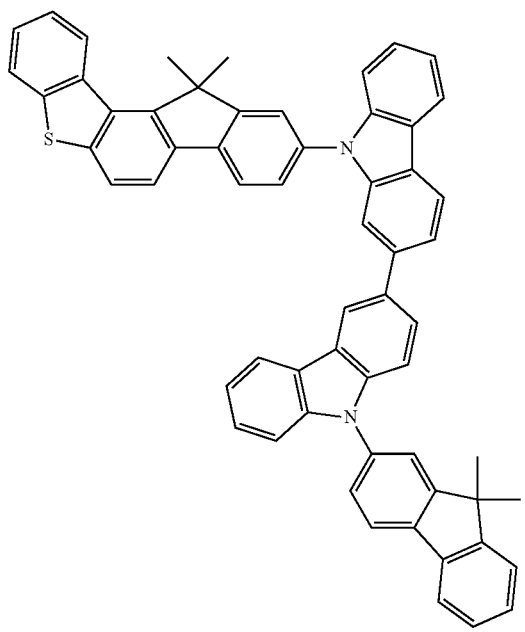
[Chemical Formula C-65]
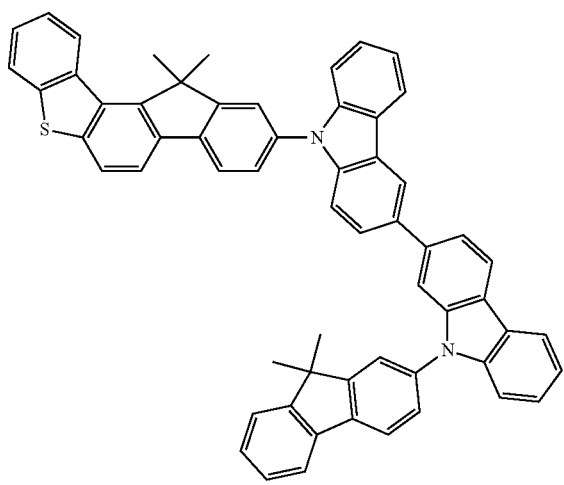
[Chemical Formula C-66]
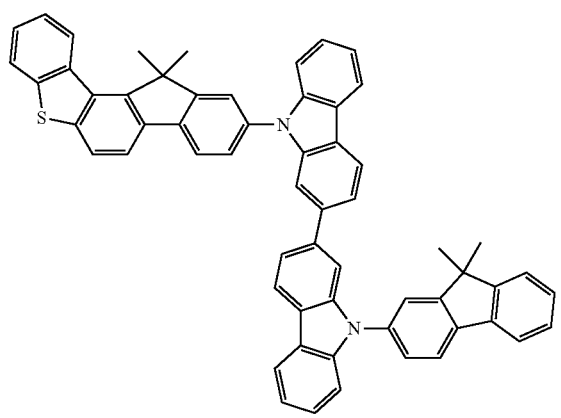
[Chemical Formula C-67]
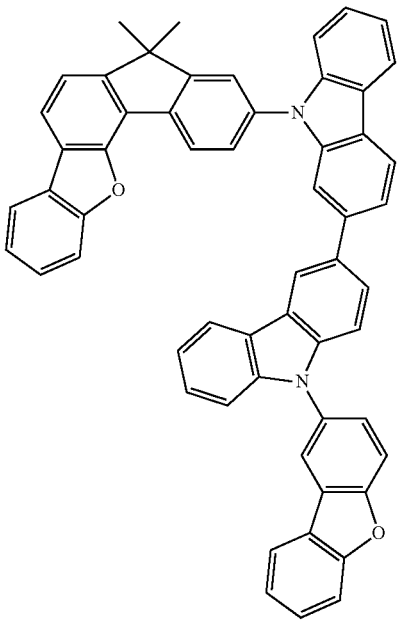
[Chemical Formula 68]
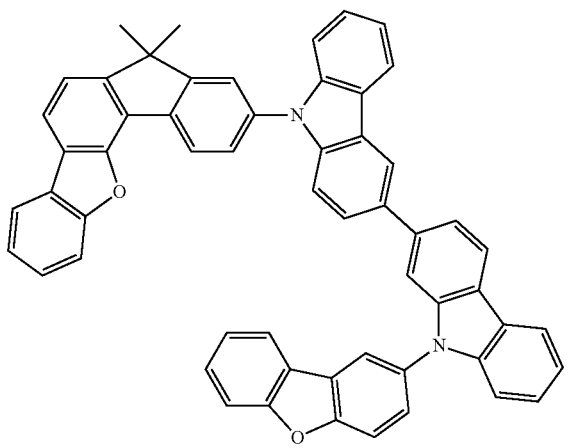
[Chemical Formula C-69]
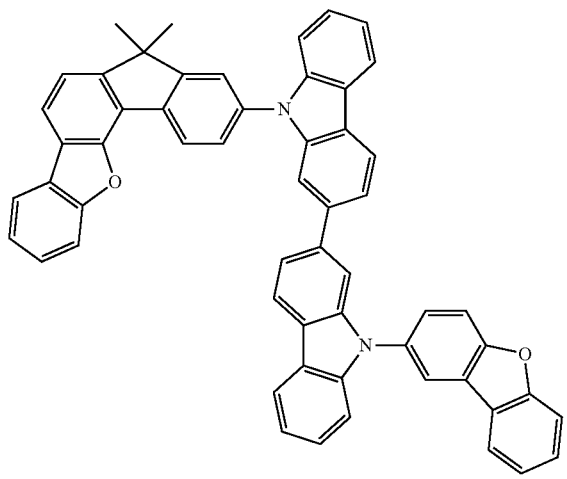

[Chemical Formula C-70]
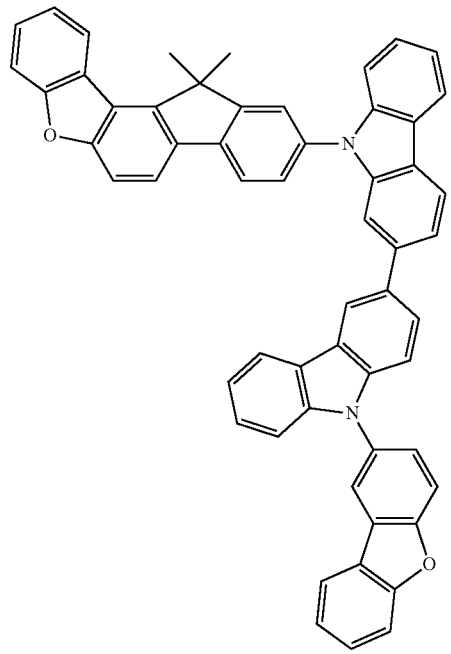
[Chemical Formula C-71]
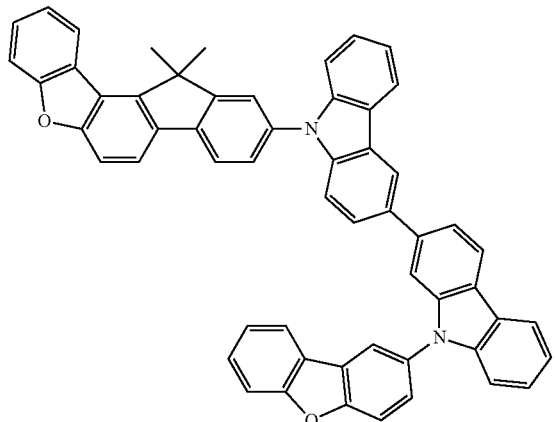
[Chemical Formula C-72]
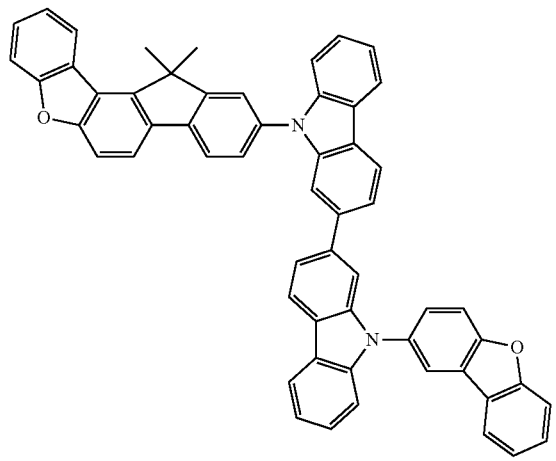
[Chemical Formula C-73]
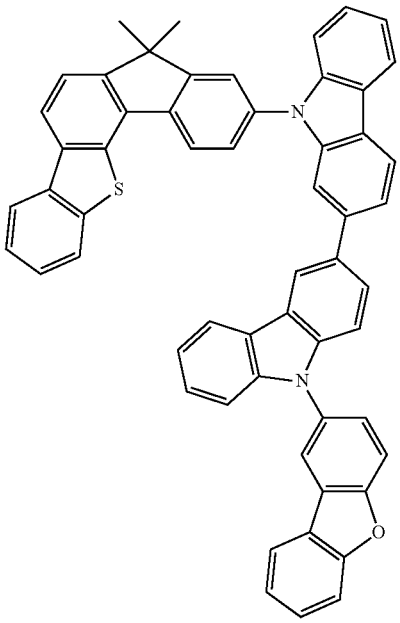
[Chemical Formula C-74]
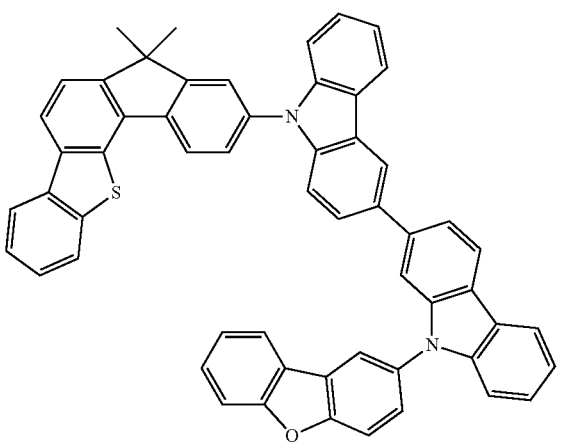
[Chemical Formula C-75]
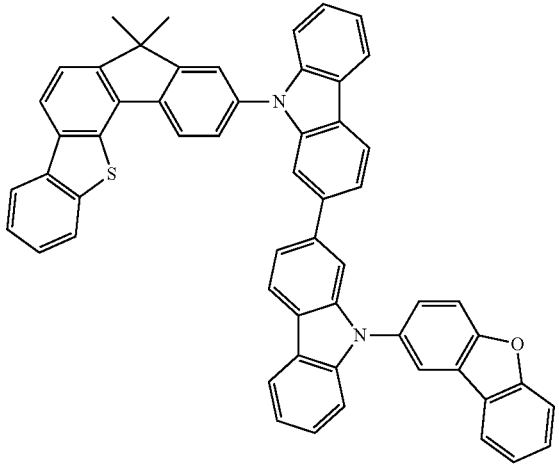

[Chemical Formula C-76]
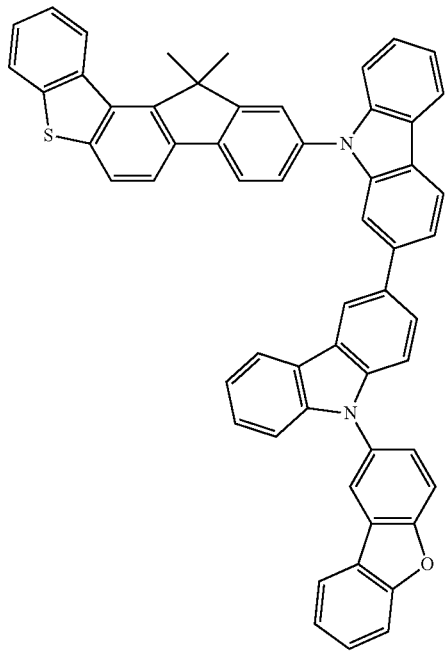
[Chemical Formula C-77]
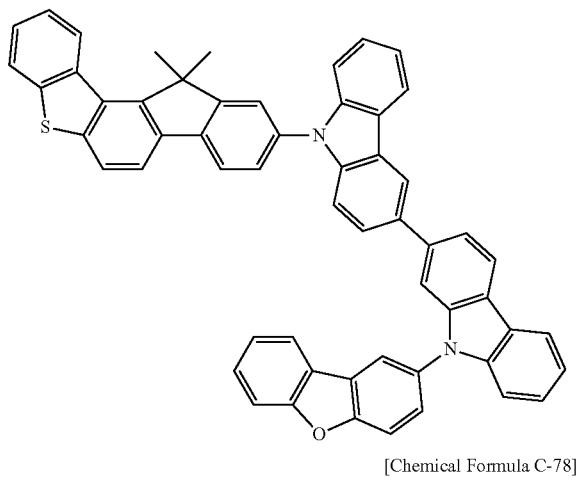
[Chemical Formula C-78]
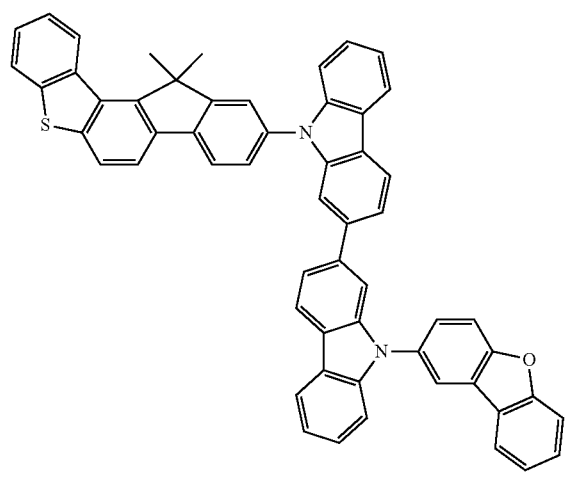
Specifically, the compound for an organic optoelectronic device may be represented by one of the following Chemical Formulae D-1 to D-210 but is not limited thereto.
[Chemical Formula D-1]
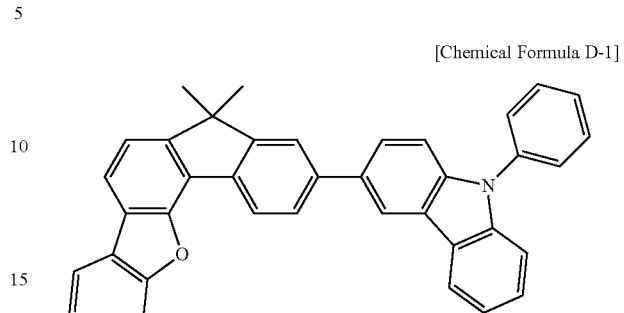
[Chemical Formula D-2]
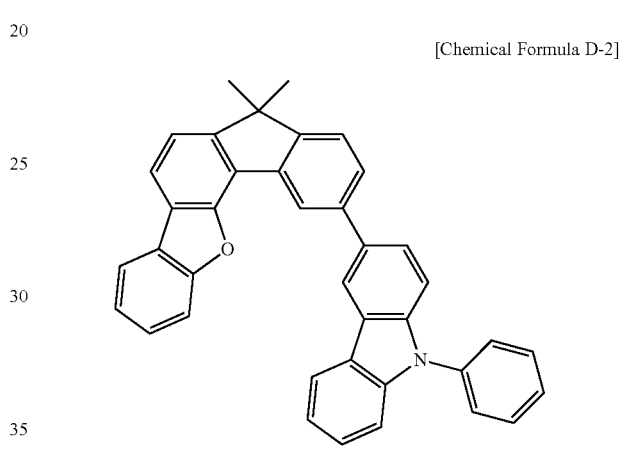
[Chemical Formula D-3]
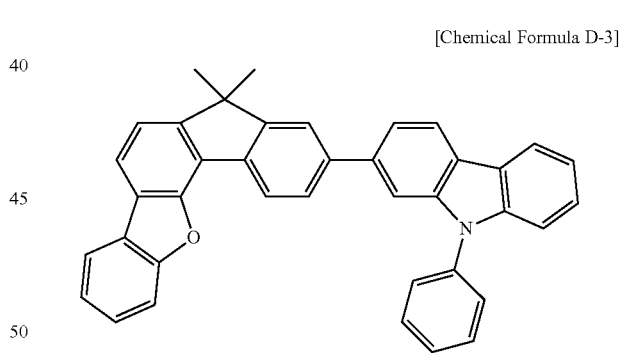
[Chemical Formula D-4]
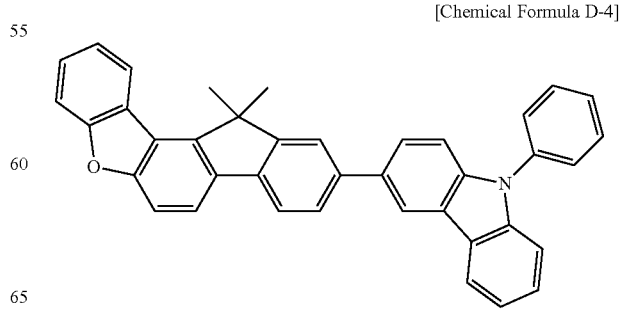

[Chemical Formula D-5]
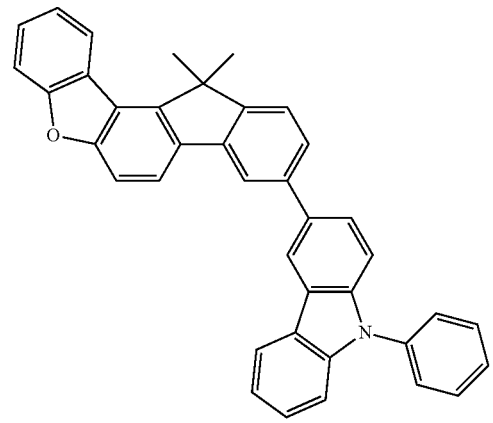
[Chemical Formula D-6]
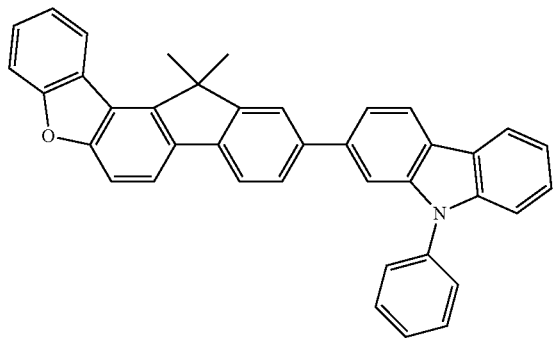
[Chemical Formula D-7]
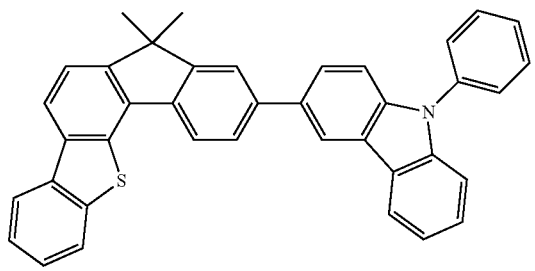
[Chemical Formula D-8]
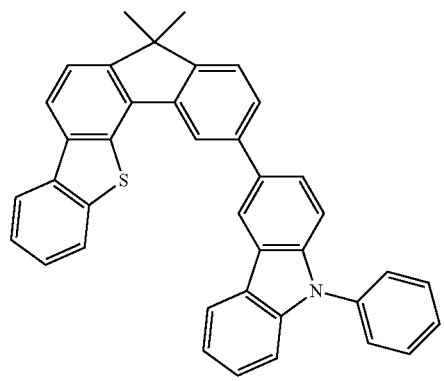
[Chemical Formula D-9]
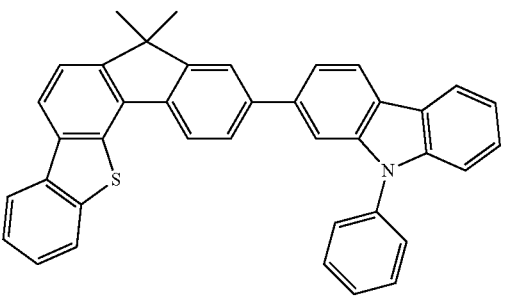
[Chemical Formula D-10]
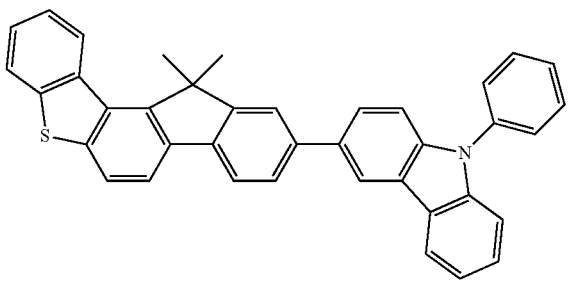
[Chemical Formula D-11]
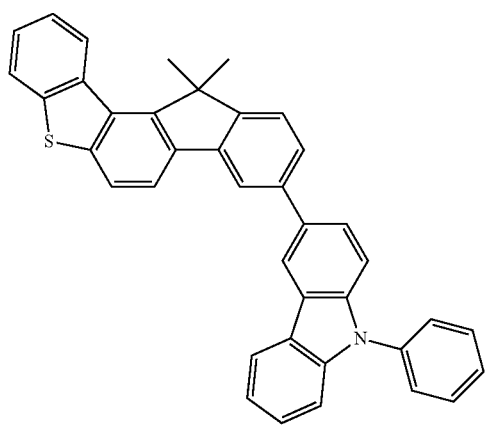
[Chemical Formula D-12]
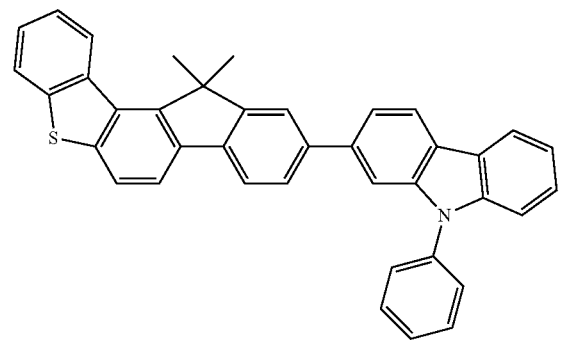

[Chemical Formula D-13]
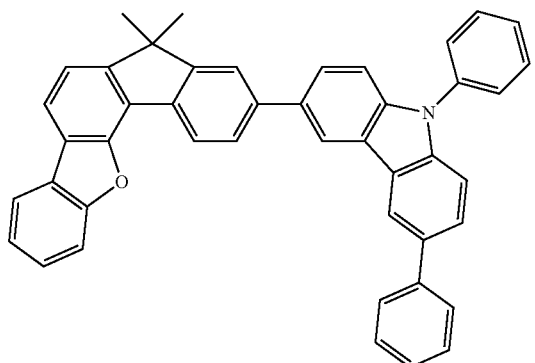
[Chemical Formula D-14]
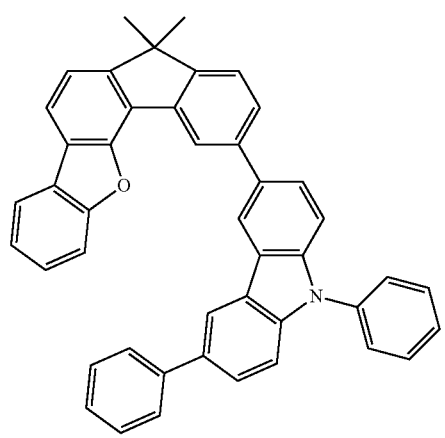
[Chemical Formula D-15]
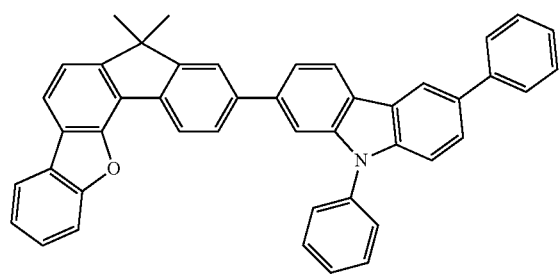
[Chemical Formula D-16]
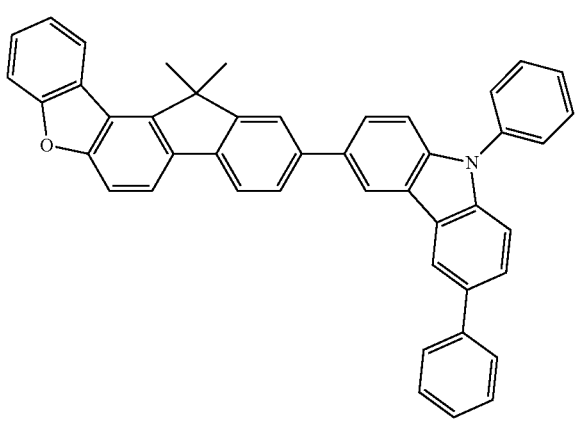
[Chemical Formula D-17]
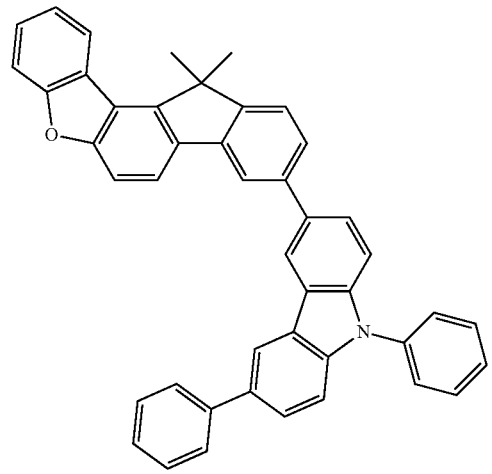
[Chemical Formula D-18]
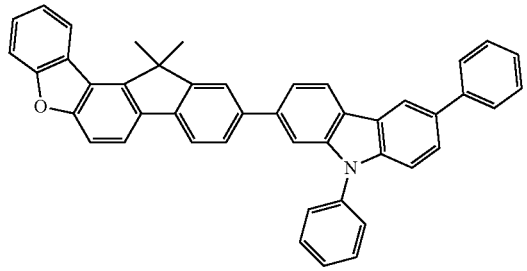
[Chemical Formula D-19]
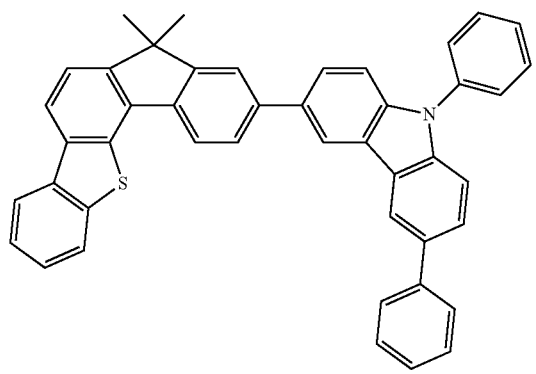
[Chemical Formula D-20]
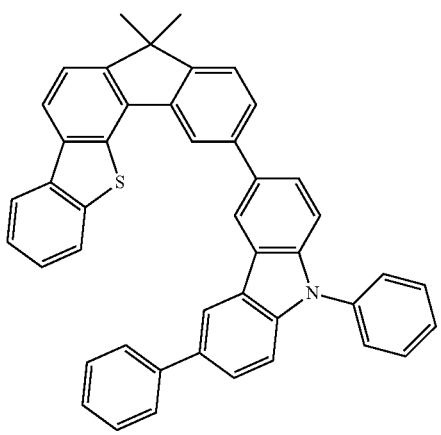

[Chemical Formula D-21]
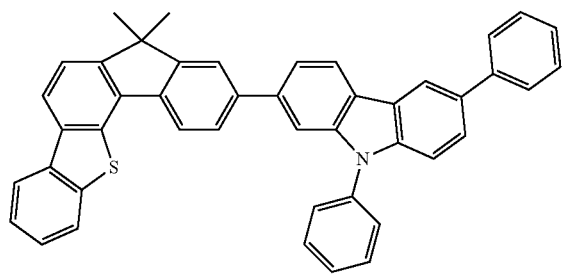
[Chemical Formula D-22]
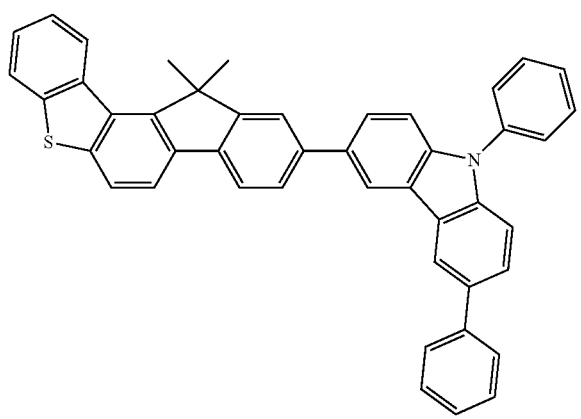
[Chemical Formula D-23]
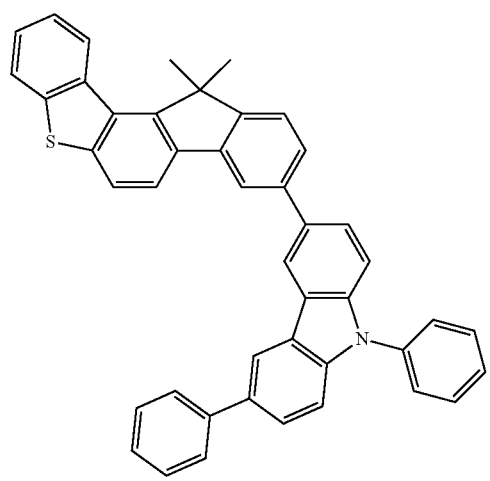
[Chemical Formula D-24]
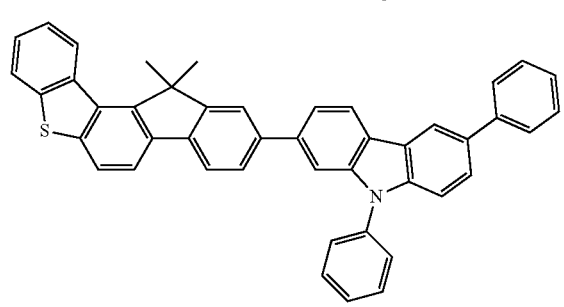
[Chemical Formula D-25]
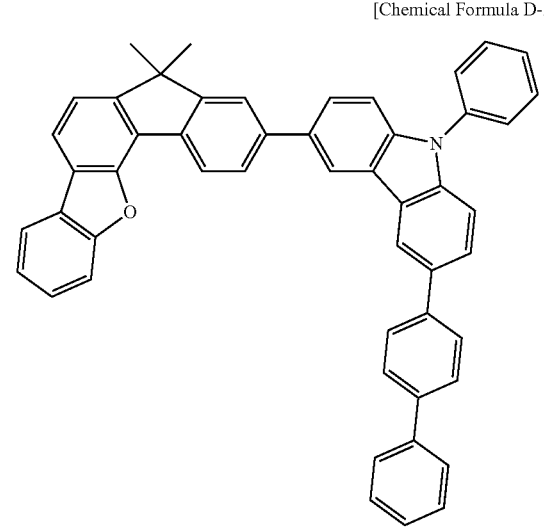
[Chemical Formula D-26]
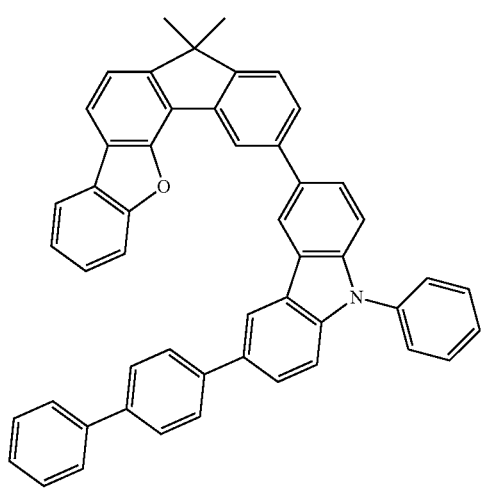
[Chemical Formula D-27]

-continued
[Chemical Formula D-28]
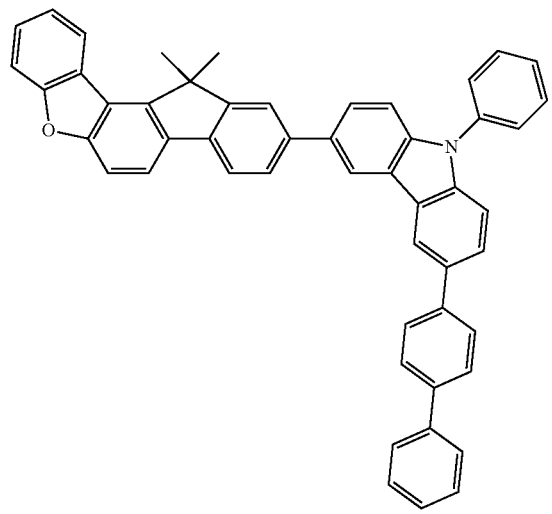
[Chemical Formula D-29]
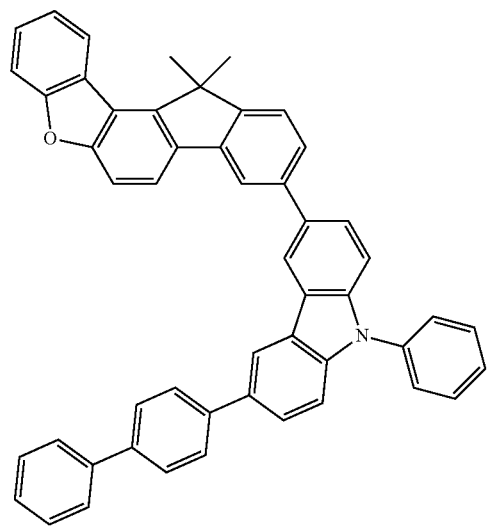
[Chemical Formula D-30]
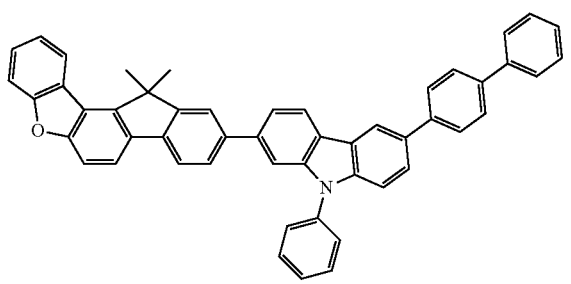
-continued
[Chemical Formula D-31]
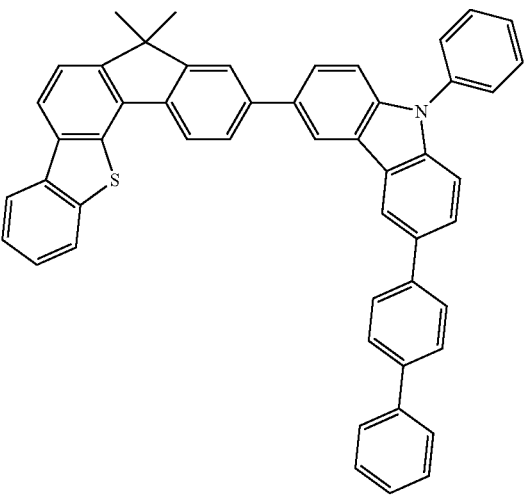
[Chemical Formula D-32]
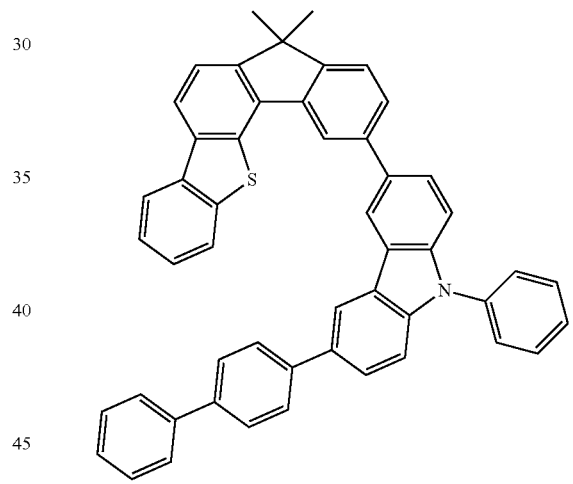
[Chemical Formula D-33]
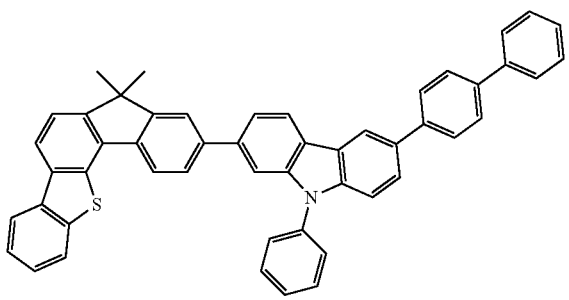

[Chemical Formula D-34]
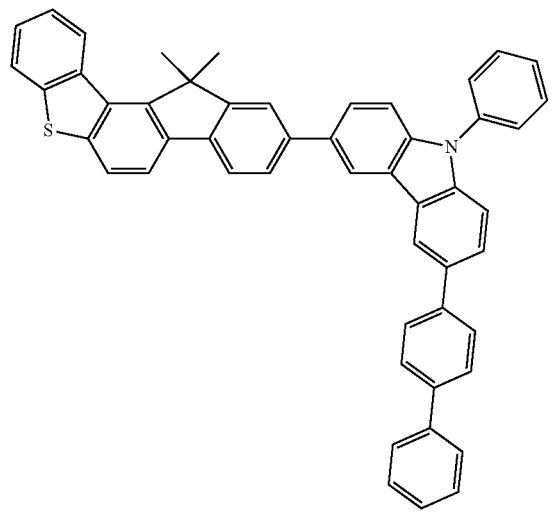
[Chemical Formula D-35]
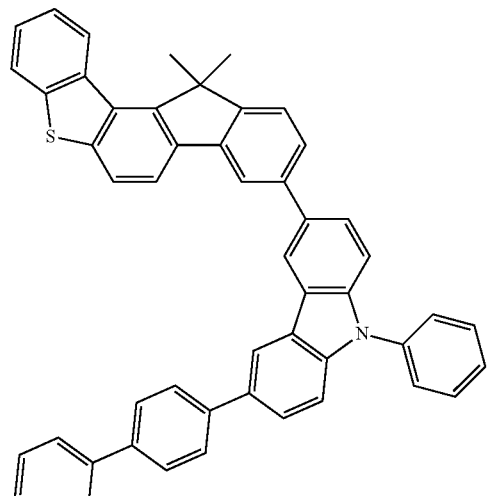
[Chemical Formula D-36]
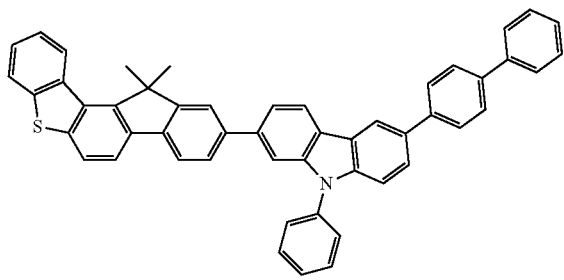
[Chemical Formula D-37]
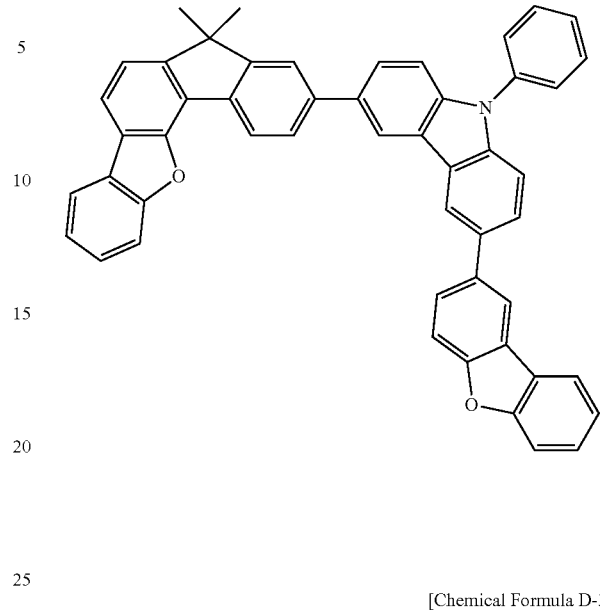
[Chemical Formula D-38]
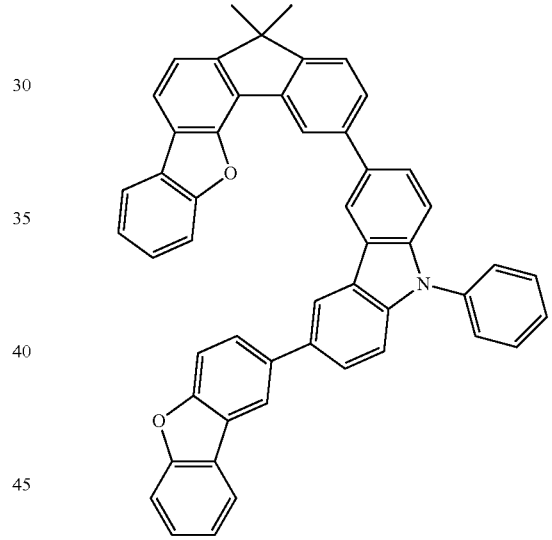
[Chemical Formula D-39]
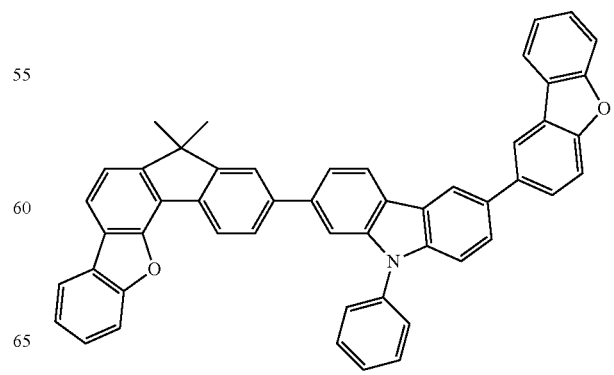

[Chemical Formula D-40]
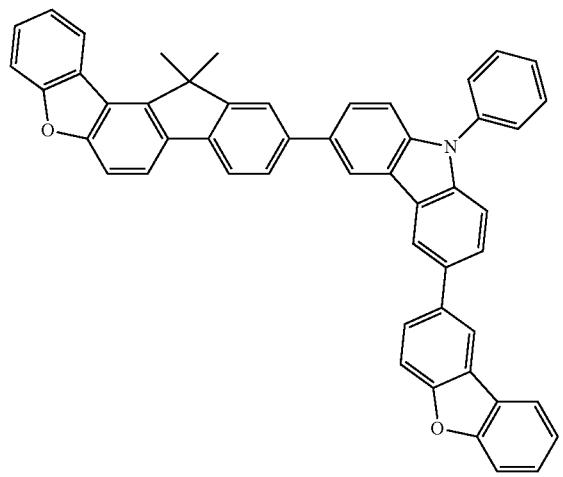
[Chemical Formula D-43]
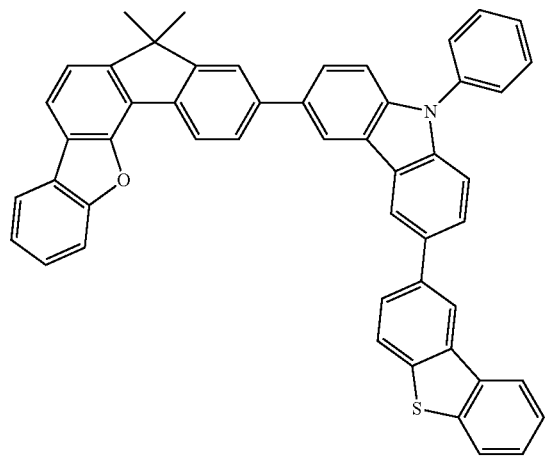
[Chemical Formula D-41]
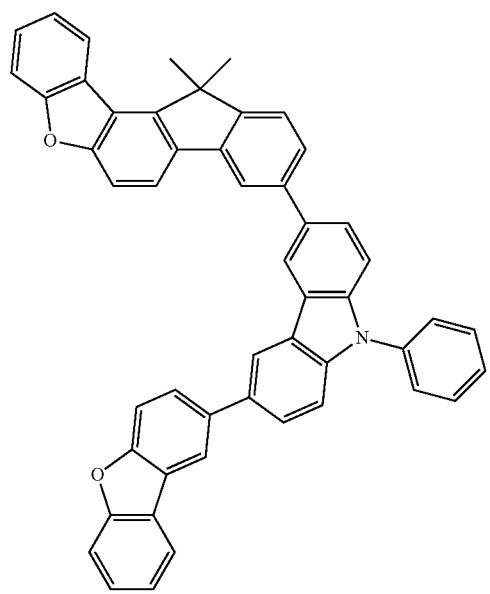
[Chemical Formula D-44]
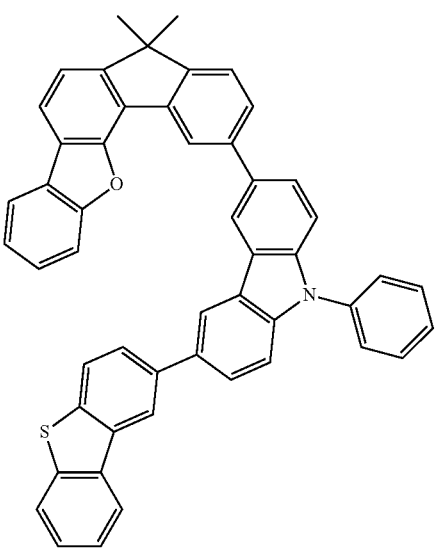
[Chemical Formula D-42]
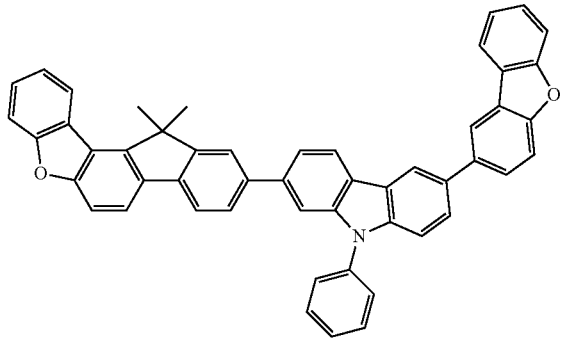
[Chemical Formula D-45]
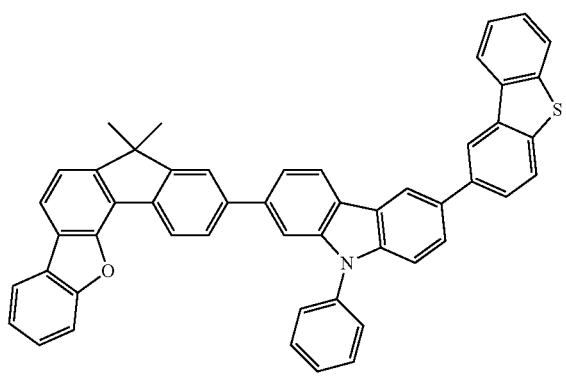

[Chemical Formula D-46]
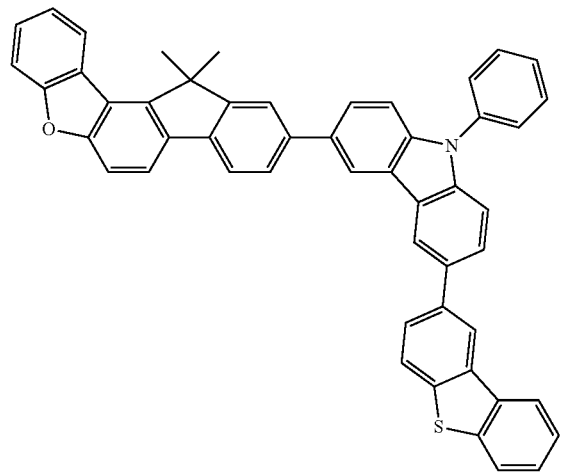
[Chemical Formula D-47]
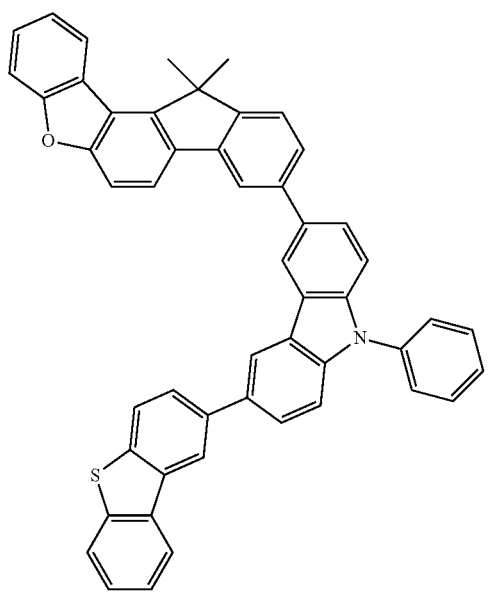
[Chemical Formula D-48]
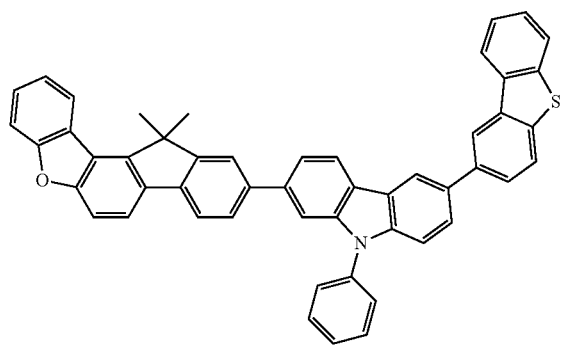
[Chemical Formula D-49]
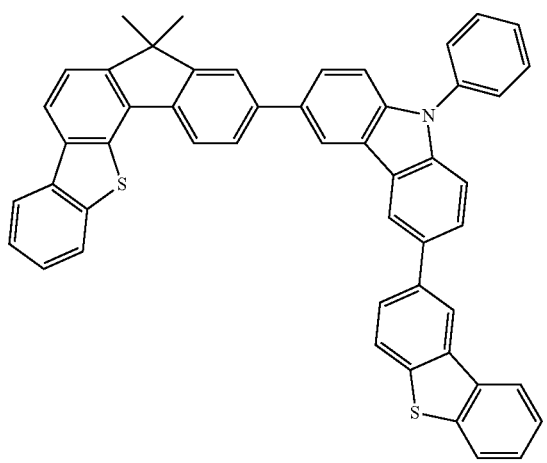
[Chemical Formula D-50]
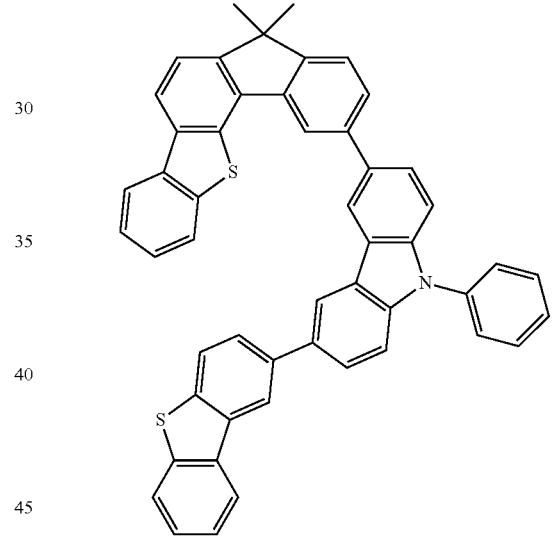
[Chemical Formula D-51]
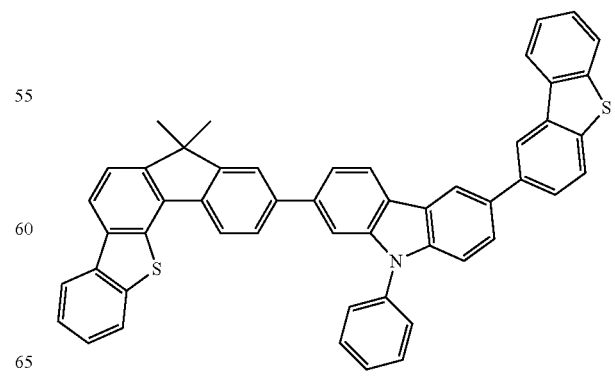

[Chemical Formula D-52]
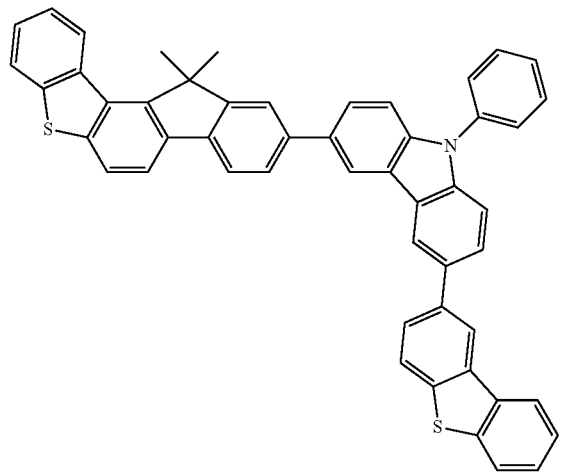
[Chemical Formula D-55]
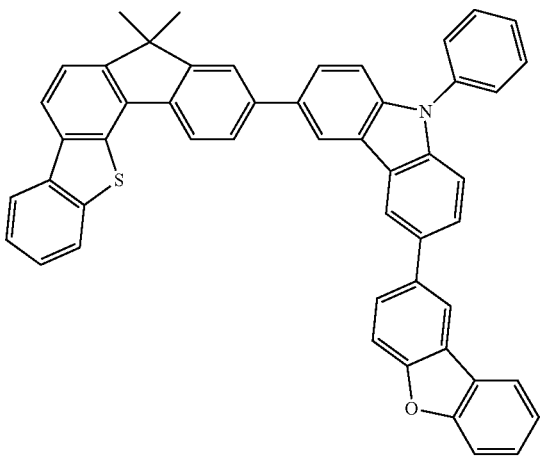
[Chemical Formula D-53]
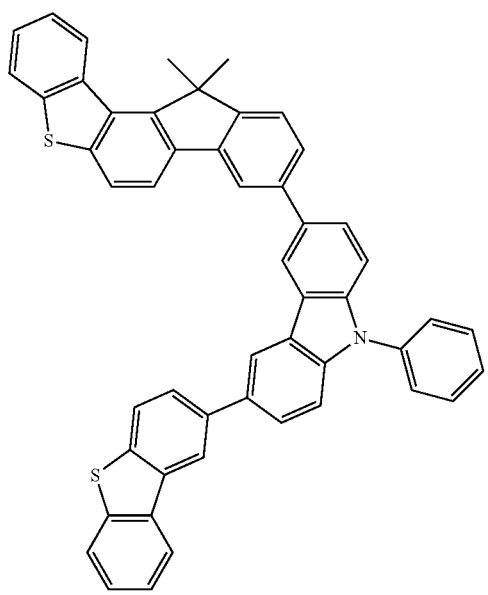
[Chemical Formula D-56]
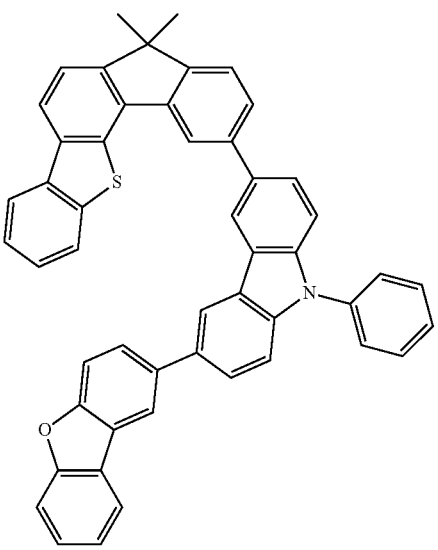
[Chemical Formula D-54]
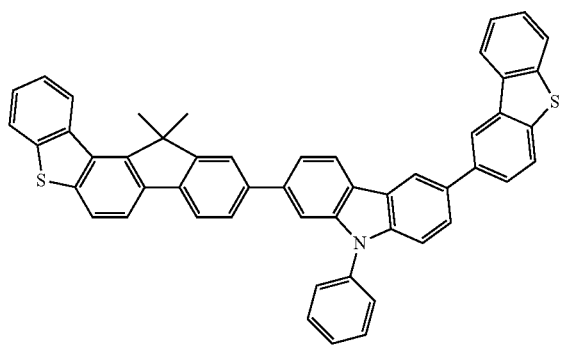
[Chemical Formula D-57]
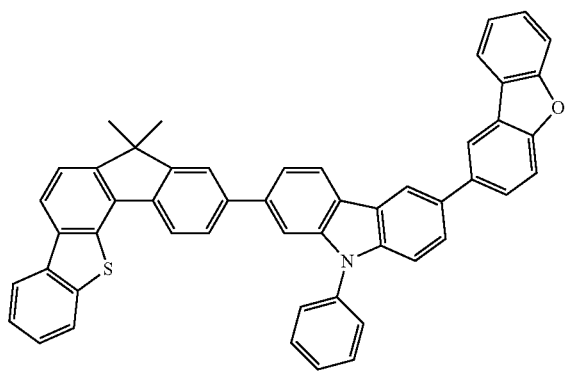

[Chemical Formula D-58]
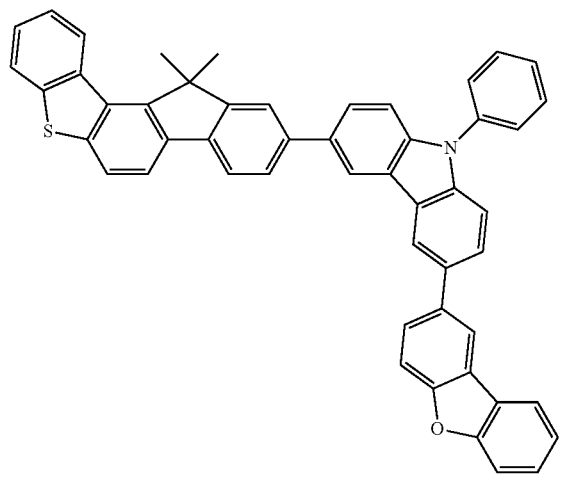
[Chemical Formula D-61]
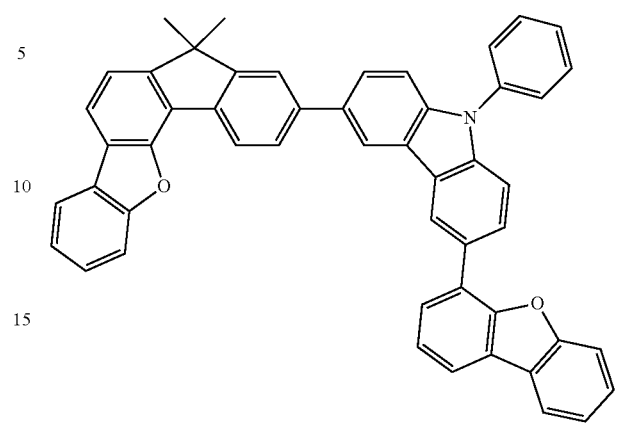
[Chemical Formula D-59]
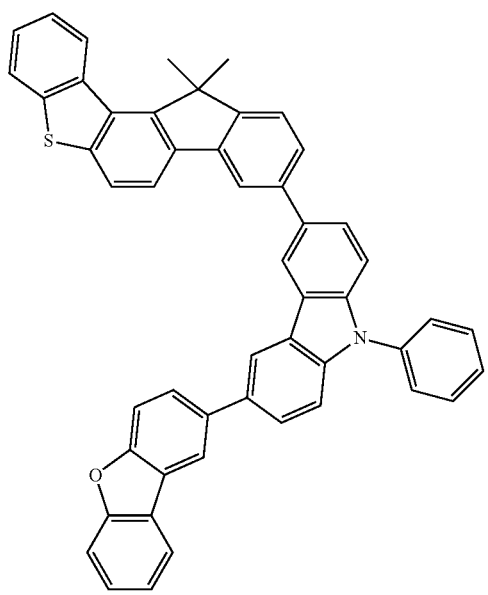
[Chemical Formula D-62]
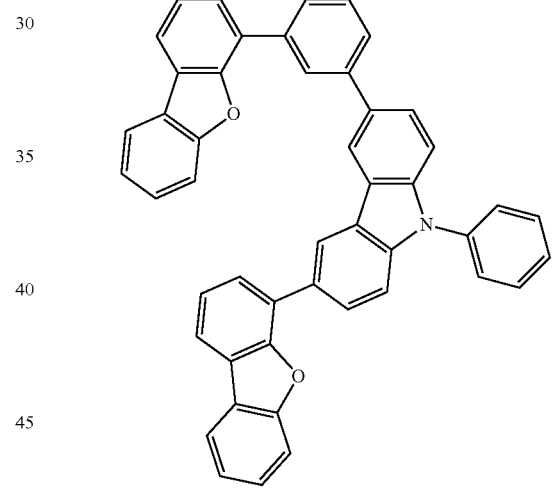
[Chemical Formula D-60]
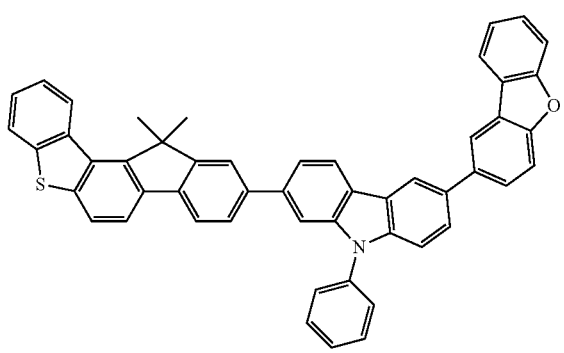
[Chemical Formula D-63]
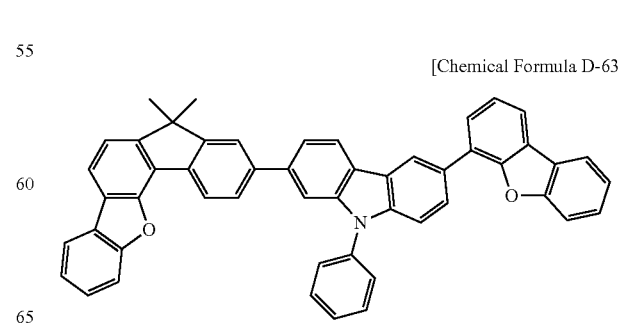

[Chemical Formula D-64]
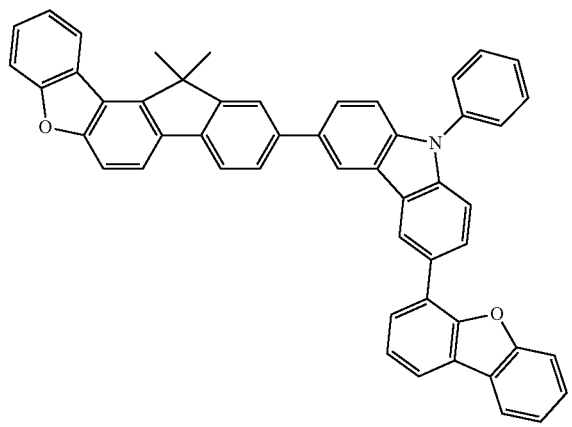
[Chemical Formula D-65]
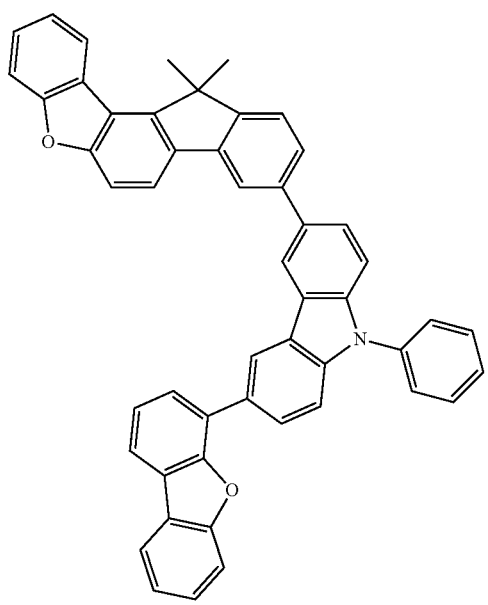
[Chemical Formula D-66]
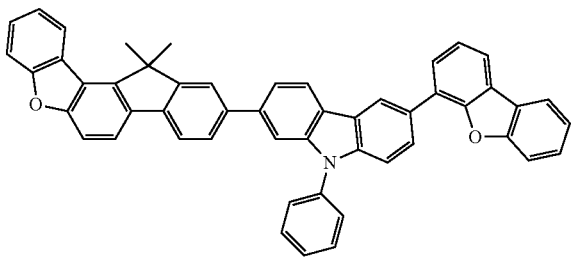
[Chemical Formula D-67]
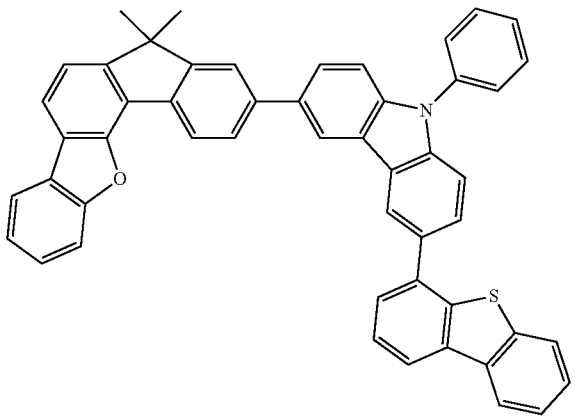
[Chemical Formula D-68]
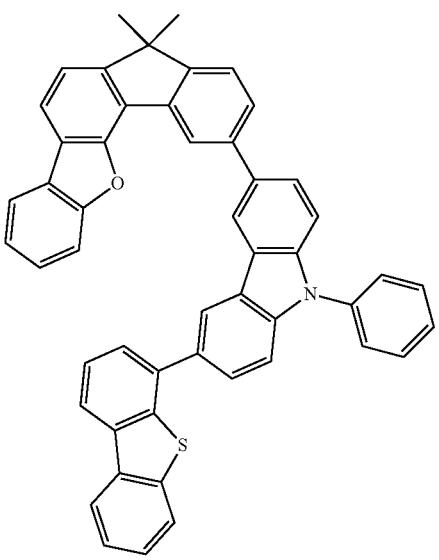
[Chemical Formula D-69]
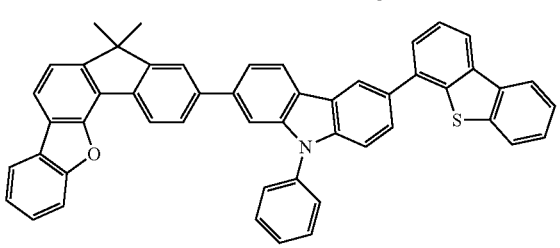

[Chemical Formula D-70]
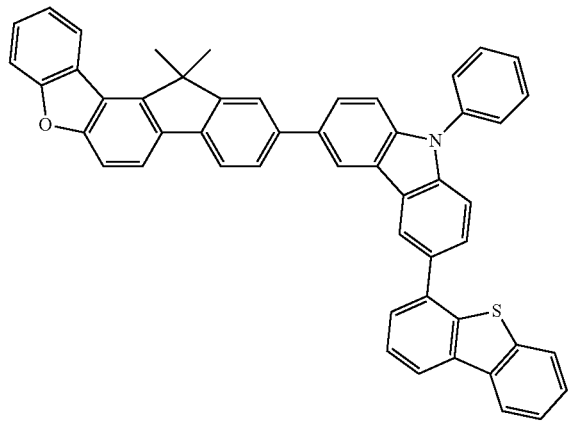
[Chemical Formula D-73]
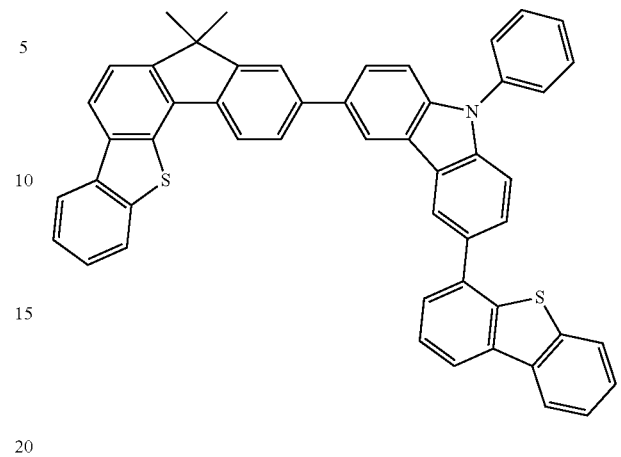
[Chemical Formula D-71]
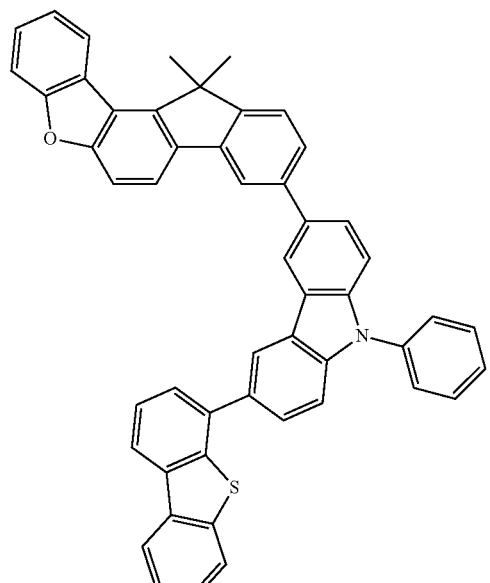
[Chemical Formula D-74]
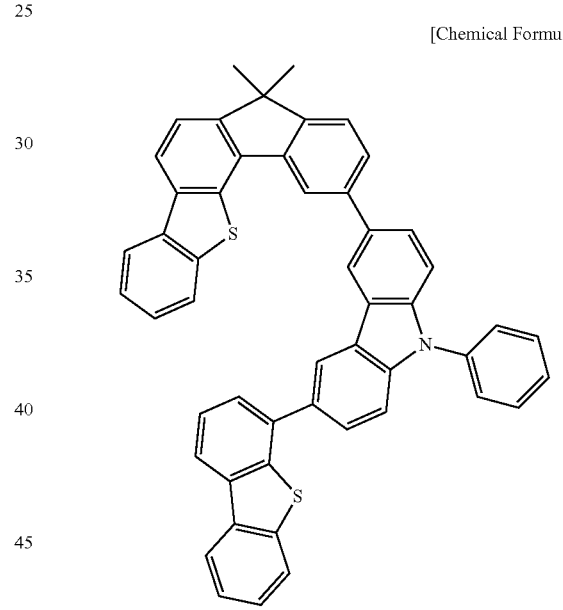
[Chemical Formula D-72]
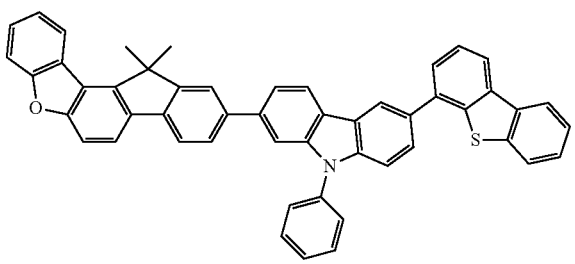
[Chemical Formula D-75]
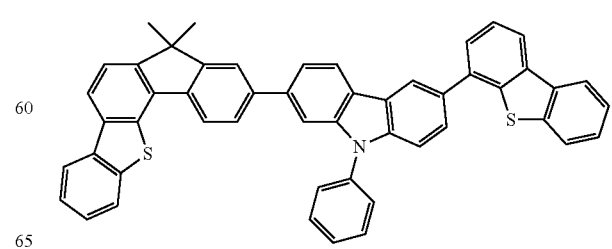

[Chemical Formula D-76]
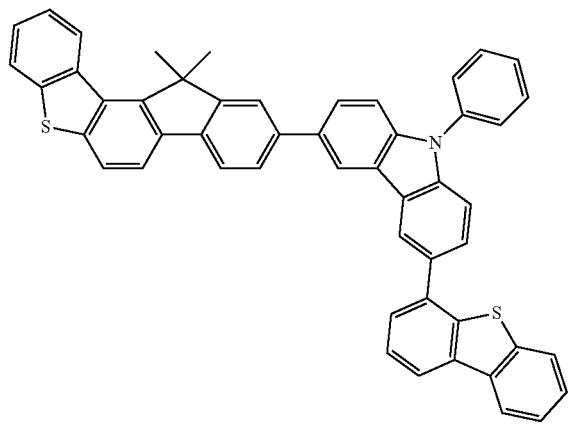
[Chemical Formula D-77]
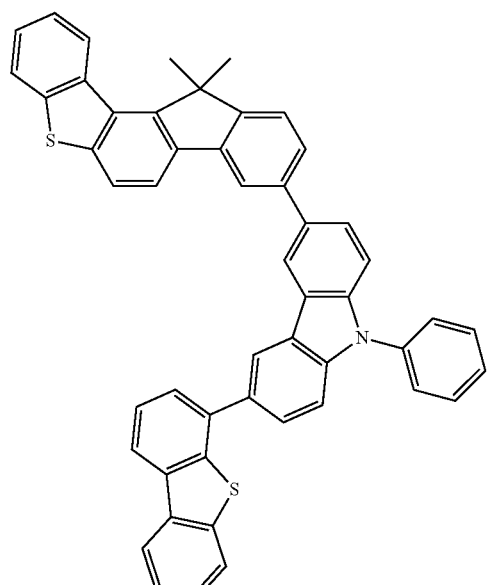
[Chemical Formula D-78]
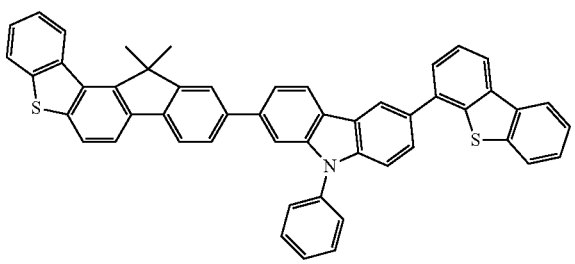
[Chemical Formula D-79]
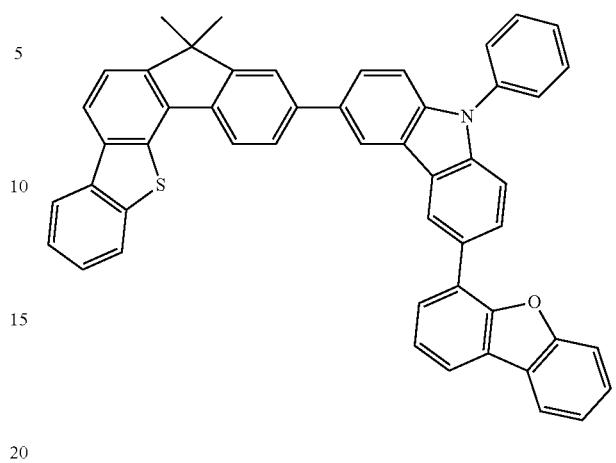
[Chemical Formula D-80]
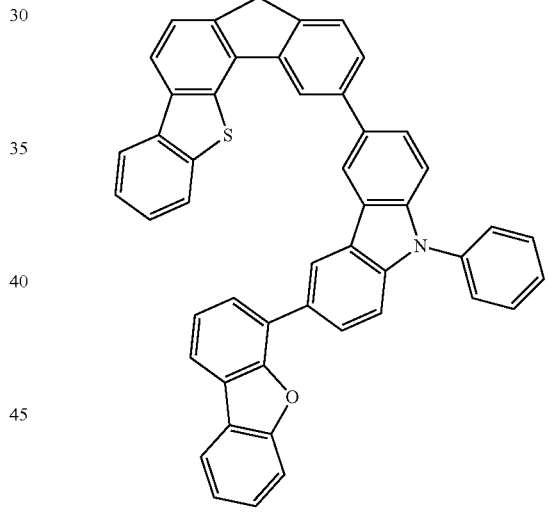
[Chemical Formula D-81]
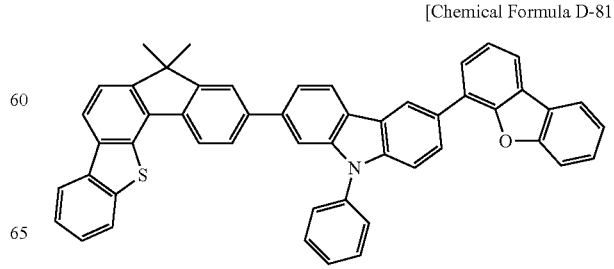

-continued
[Chemical Formula D-82]
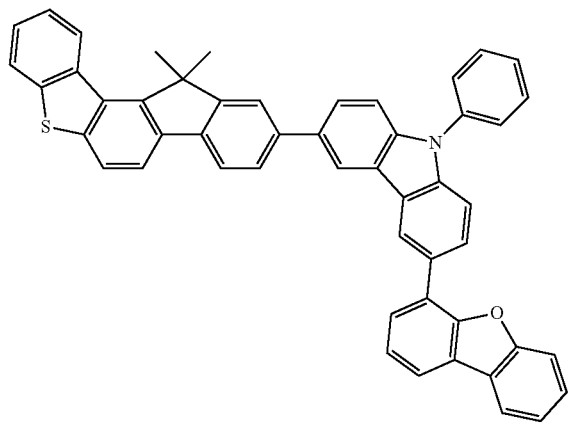
[Chemical Formula D-83]
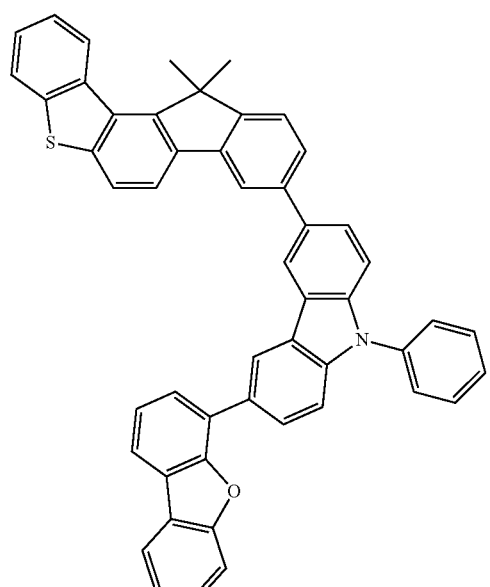
[Chemical Formula D-84]
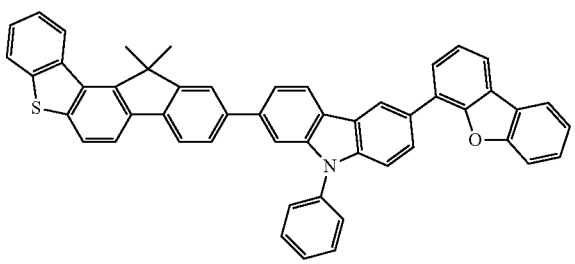
-continued
[Chemical Formula D-85]
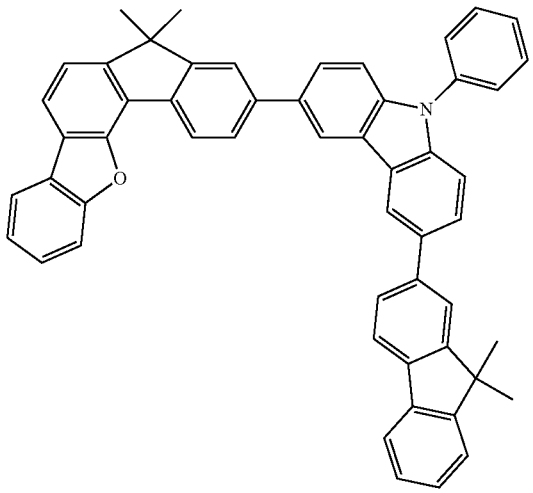
[Chemical Formula D-86]
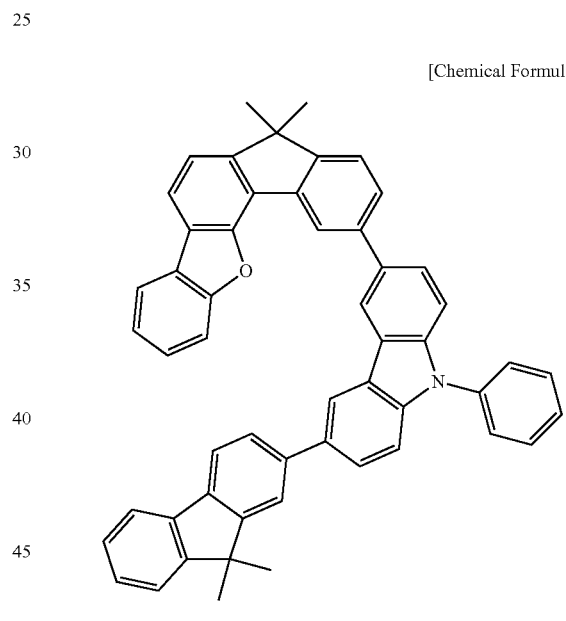
[Chemical Formula D-87]
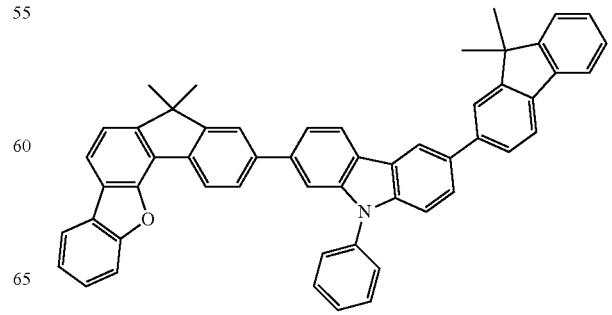

-continued
[Chemical Formula D-88]
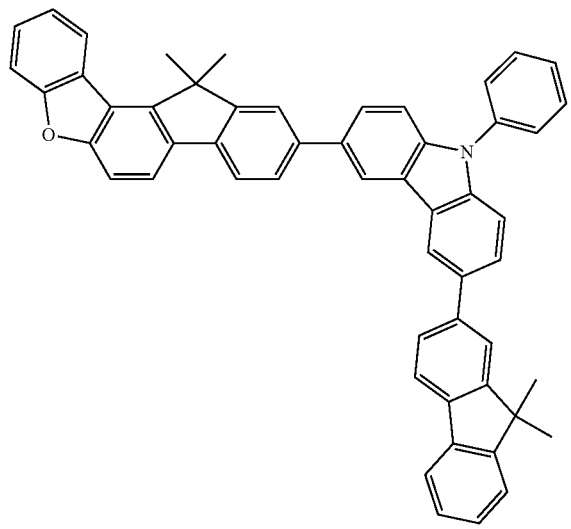
[Chemical Formula D-91]
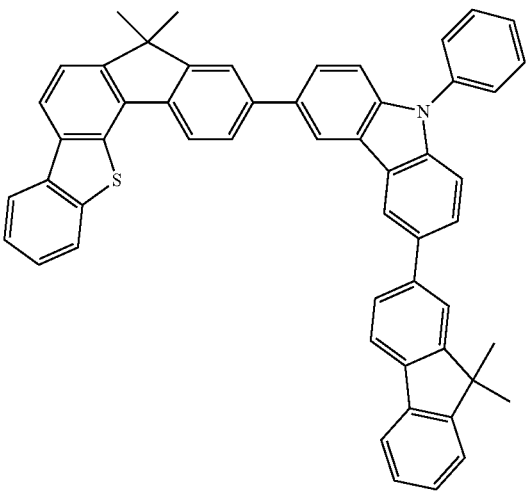
[Chemical Formula D-89]
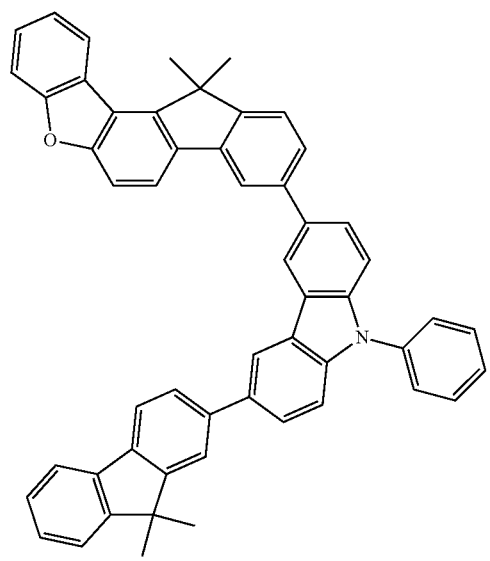
[Chemical Formula D-92]
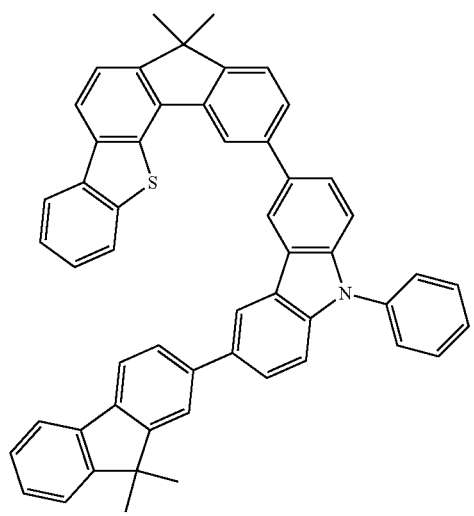
[Chemical Formula D-90]
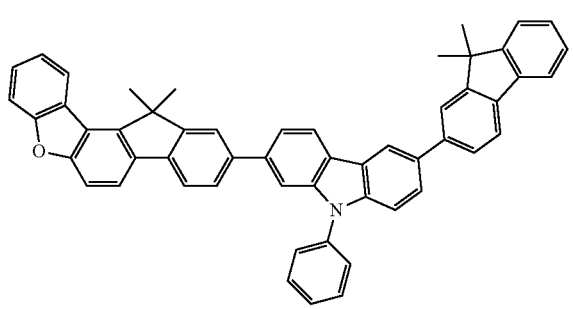
[Chemical Formula D-93]
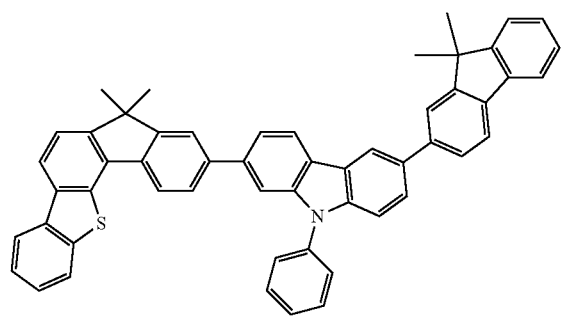

[Chemical Formula D-94]
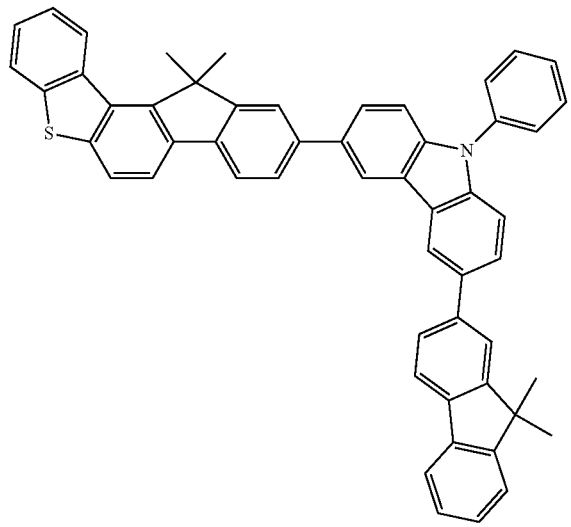
[Chemical Formula D-97]
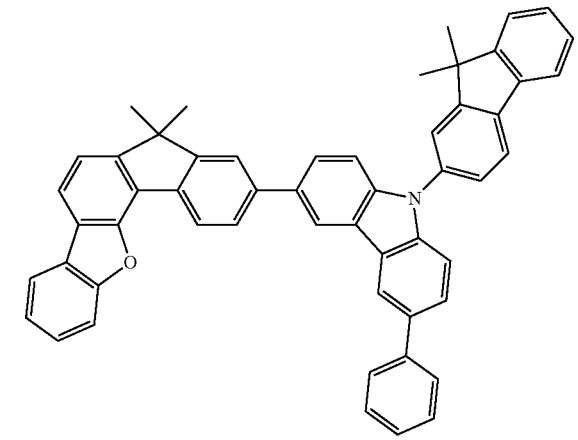
[Chemical Formula D-95]
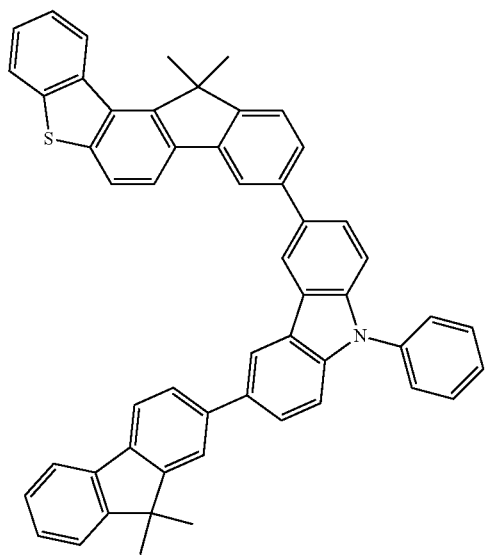
[Chemical Formula D-98]
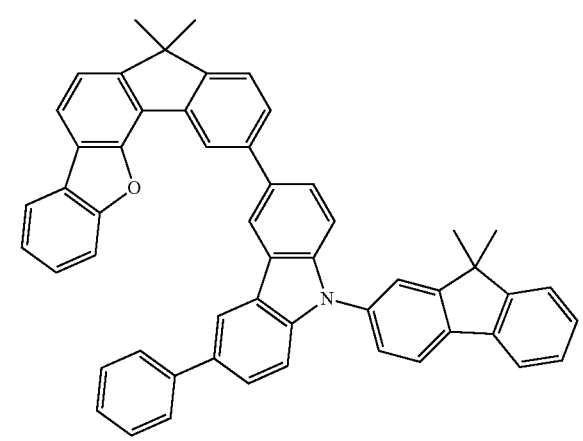
[Chemical Formula D-96]
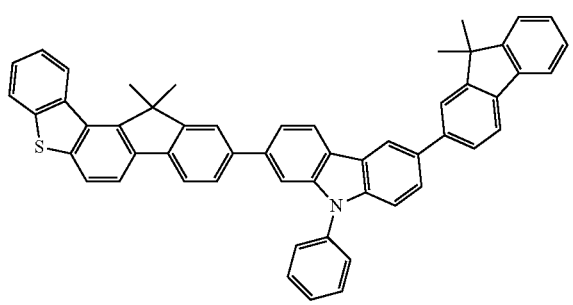
[Chemical Formula D-99]
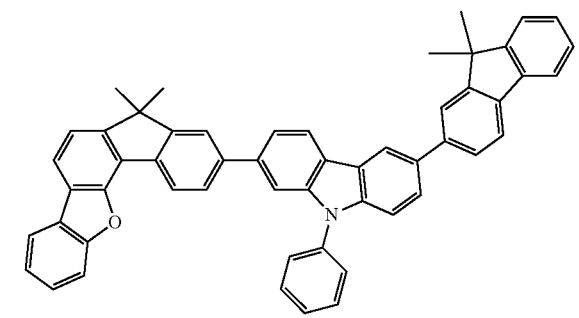

[Chemical Formula D-100]
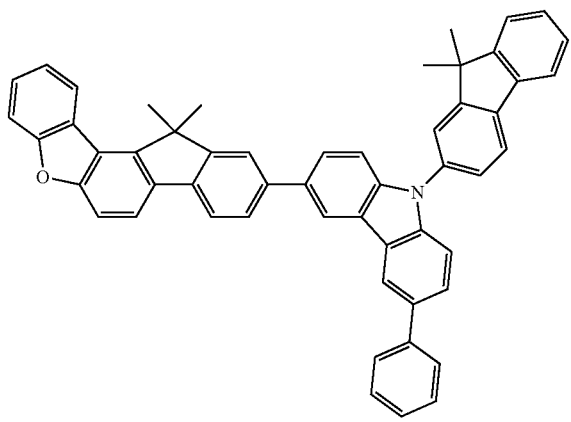
[Chemical Formula D-103]
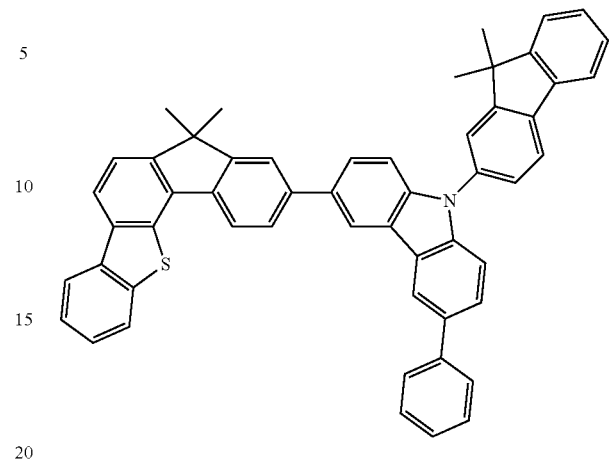
[Chemical Formula D-101]
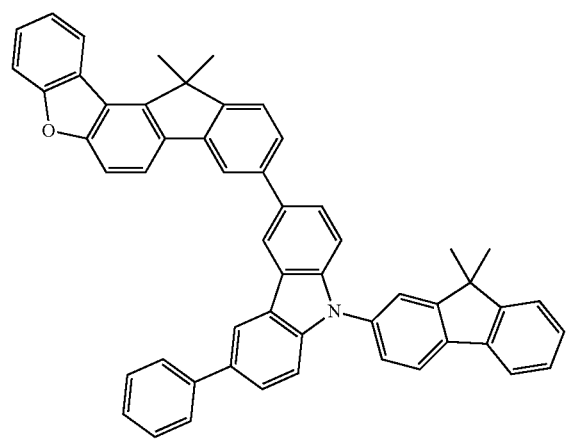
[Chemical Formula D-104]
[Chemical Formula D-102]
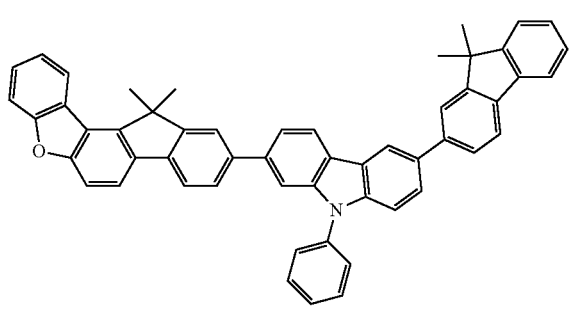
[Chemical Formula D-105]

[Chemical Formula D-106]
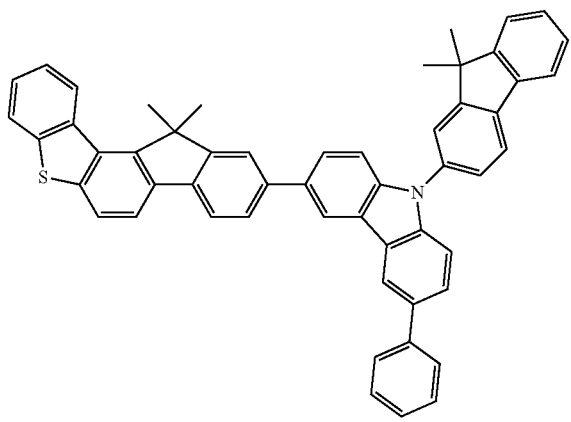
[Chemical Formula D-107]
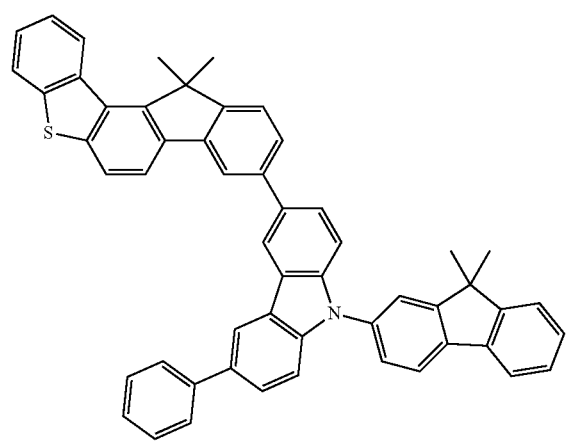
[Chemical Formula D-108]
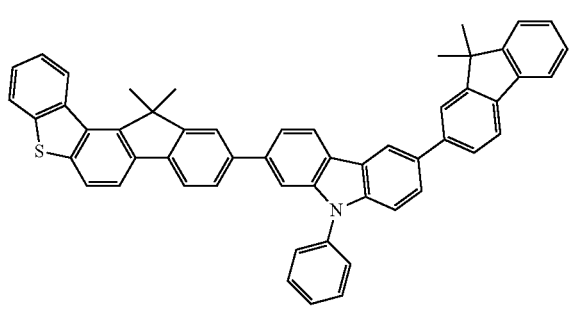
[Chemical Formula D-109]
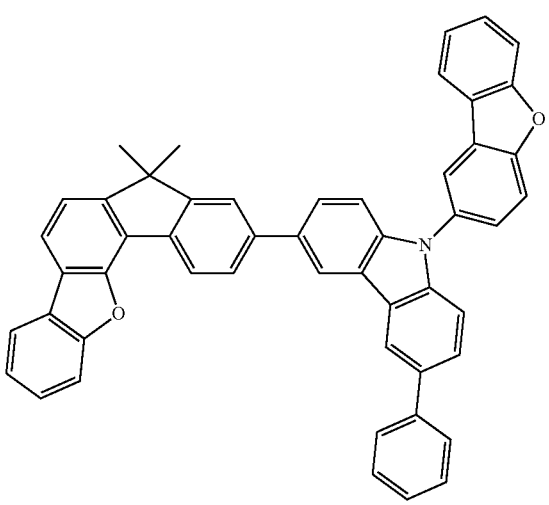
[Chemical Formula D-110]
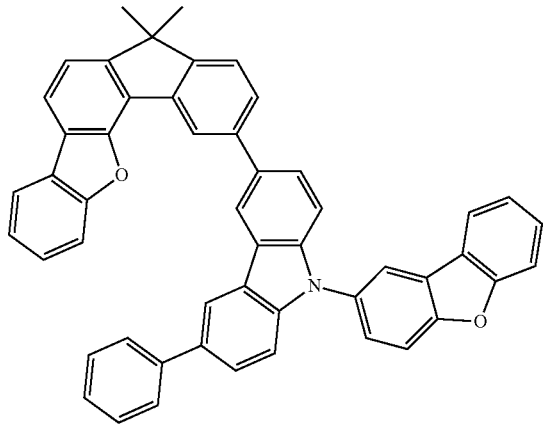
[Chemical Formula D-111]
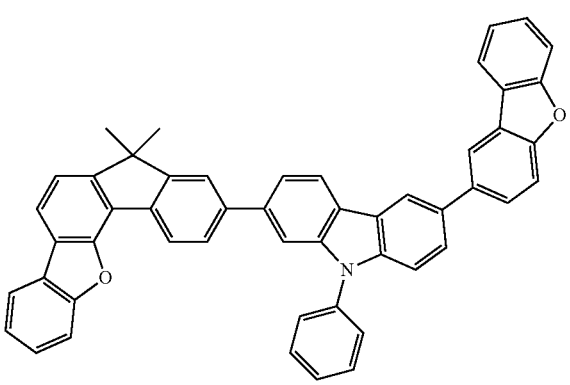

[Chemical Formula D-112]
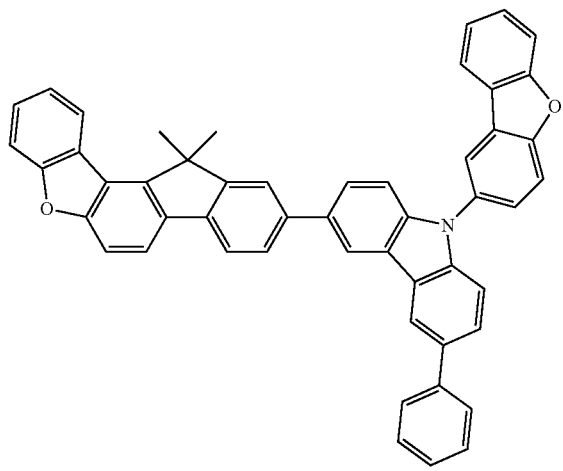
[Chemical Formula D-113]
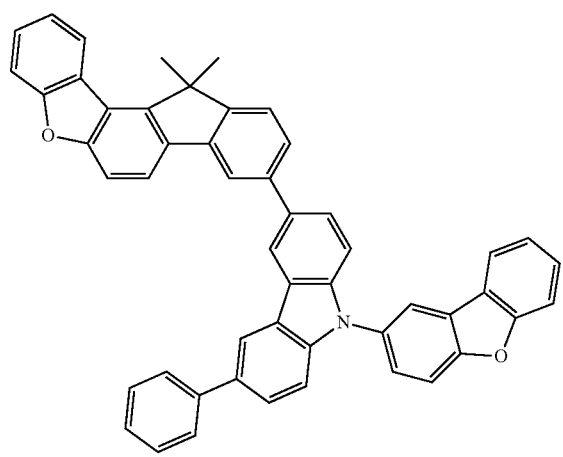
[Chemical Formula D-114]
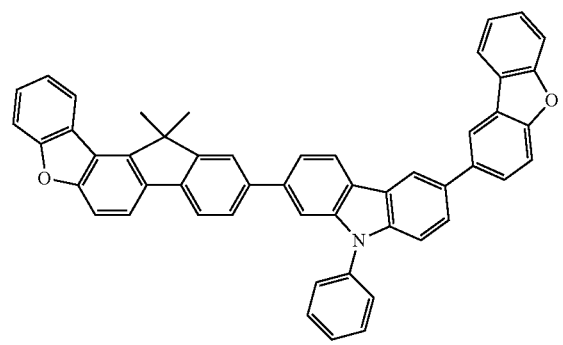
[Chemical Formula D-115]
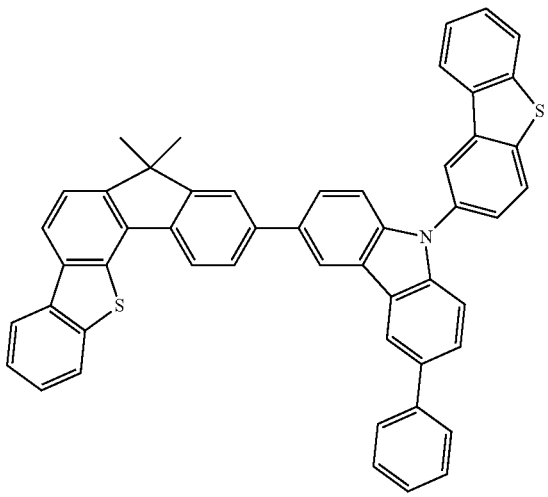
[Chemical Formula D-116]
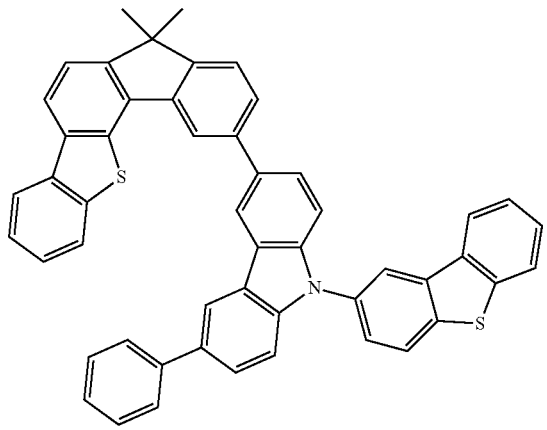
[Chemical Formula D-117]
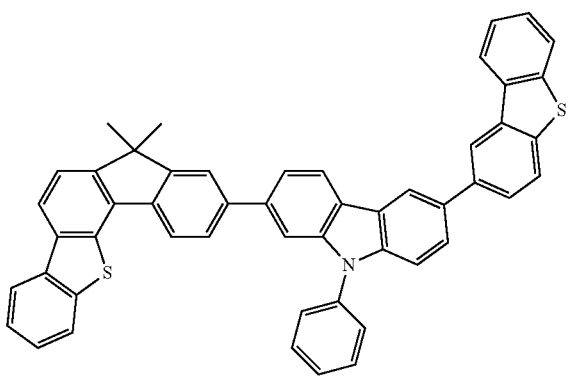

[Chemical Formula D-118]
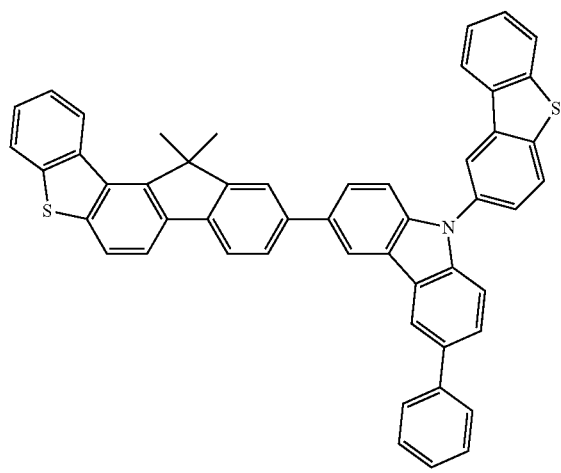
[Chemical Formula D-119]
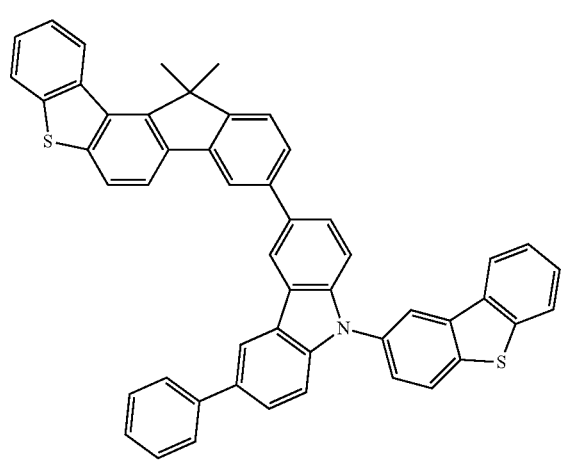
[Chemical Formula D-120]
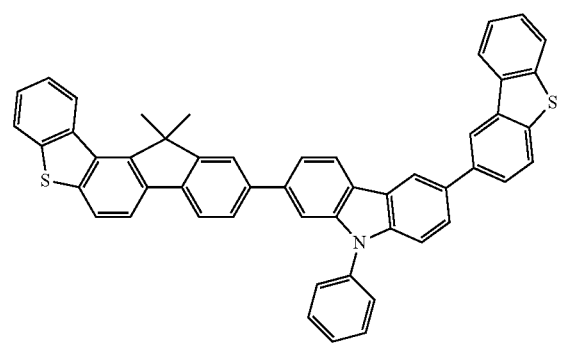
[Chemical Formula D-121]
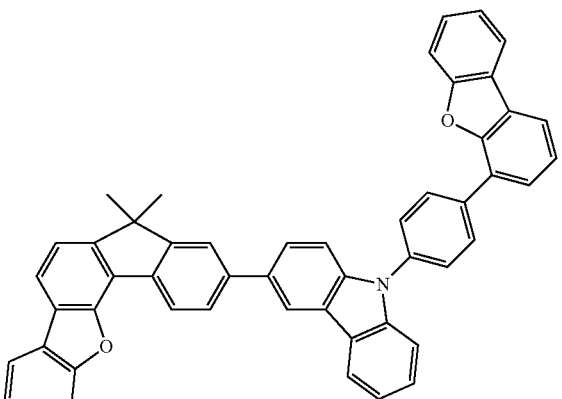
[Chemical Formula D-122]
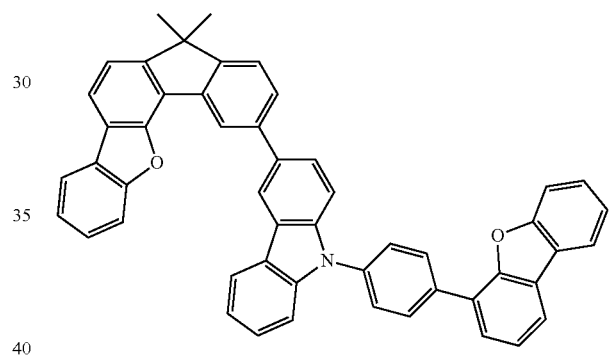
[Chemical Formula D-123]
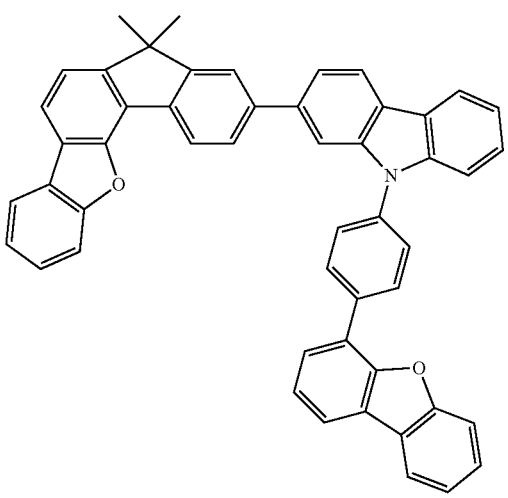

[Chemical Formula D-124]
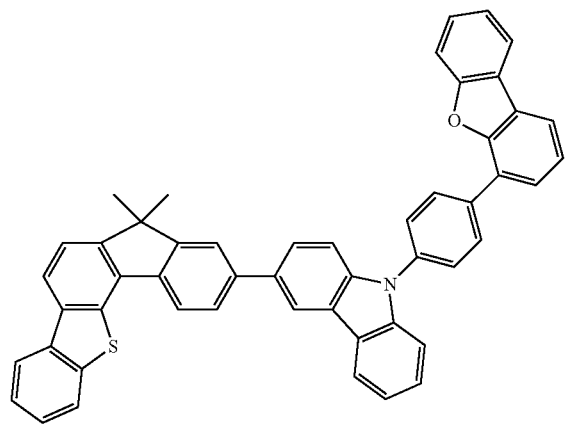
[Chemical Formula D-125]
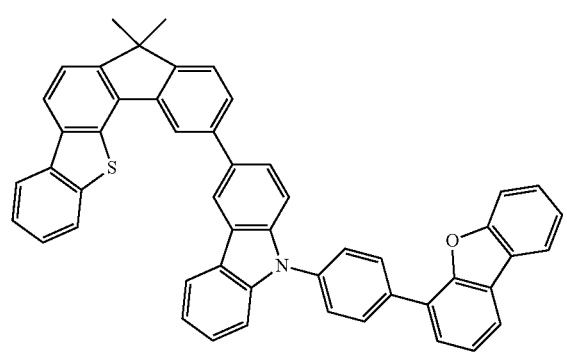
[Chemical Formula D-126]
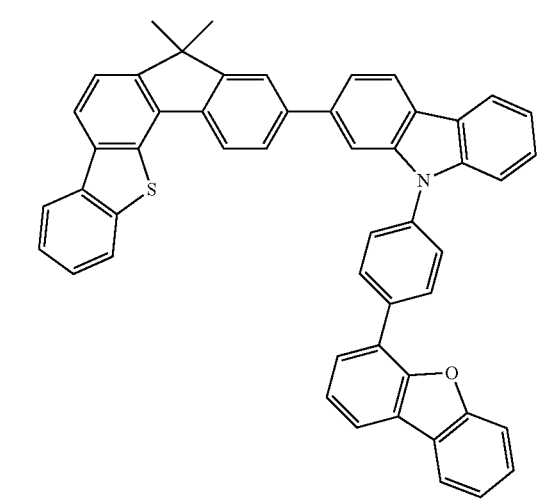
[Chemical Formula D-127]
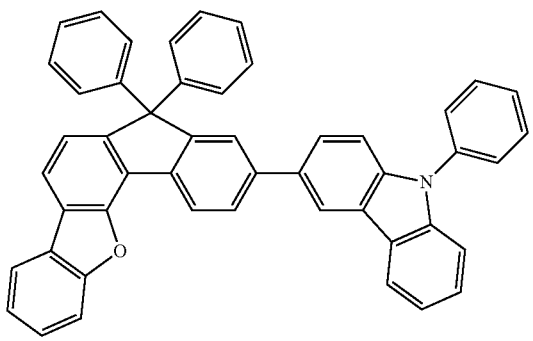
[Chemical Formula D-128]
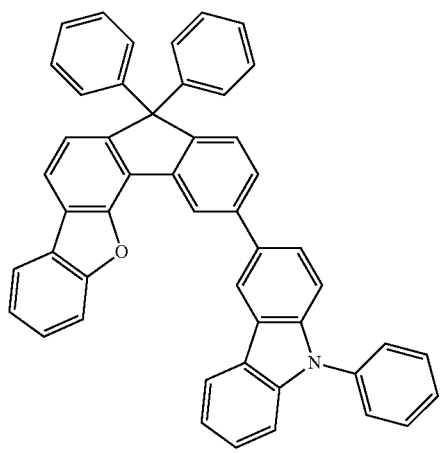
[Chemical Formula D-129]
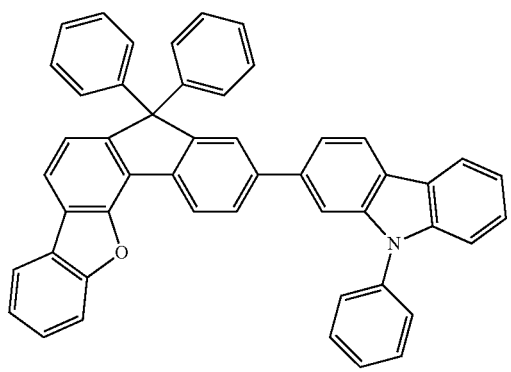
[Chemical Formula D-130]
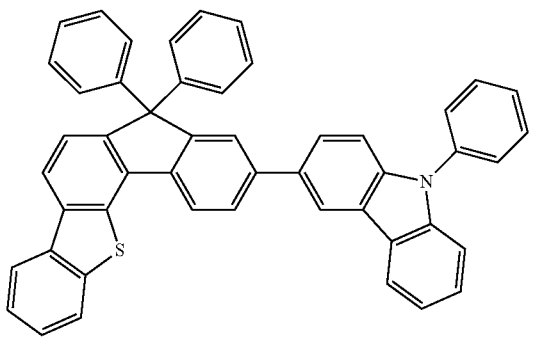

-continued
[Chemical Formula D-131]
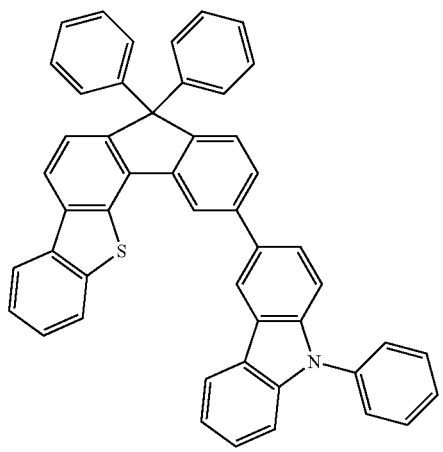
[Chemical Formula D-132]
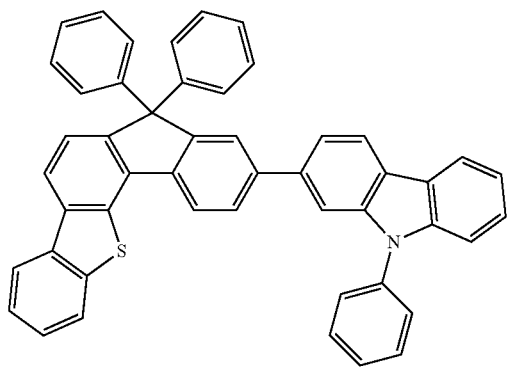
[Chemical Formula D-133]
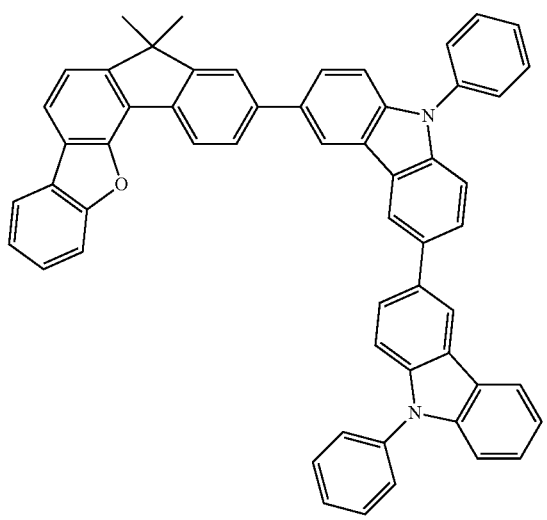
-continued
[Chemical Formula D-134]
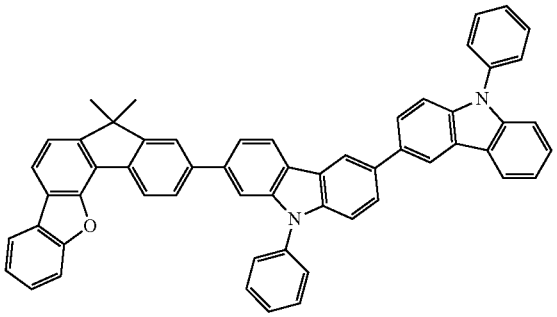
[Chemical Formula D-135]
[Chemical Formula D-136]
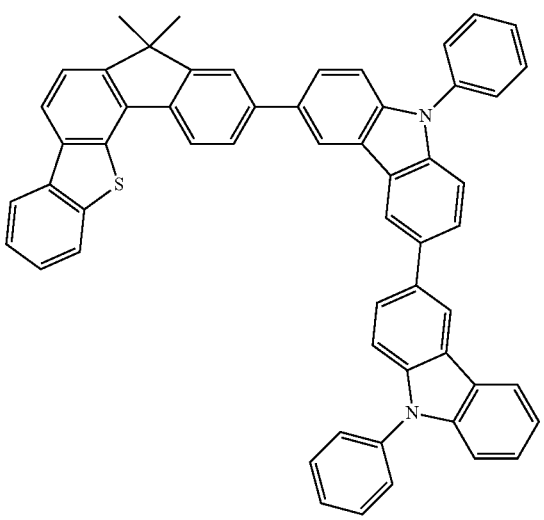

-continued
[Chemical Formula D-137]
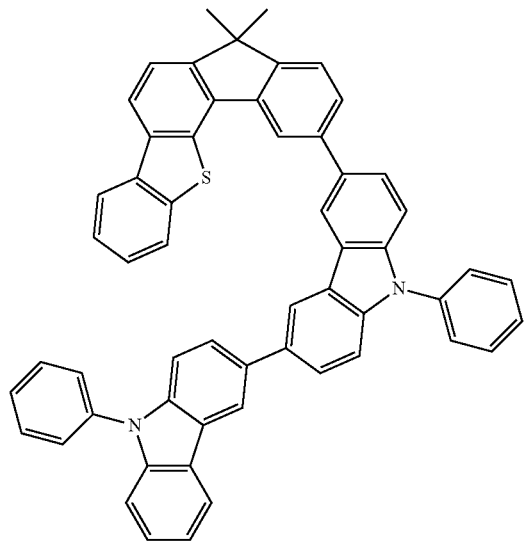
[Chemical Formula D-138]
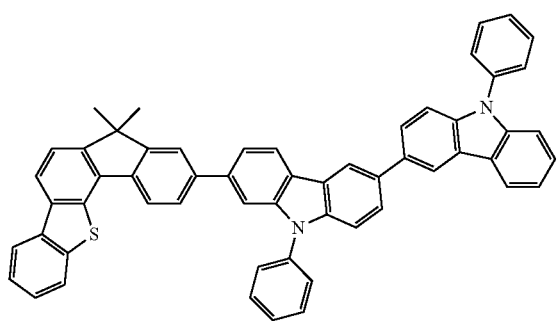
[Chemical Formula D-139]
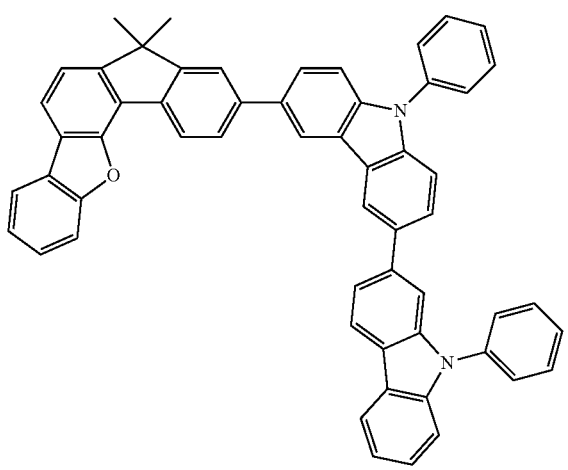
-continued
[Chemical Formula D-140]
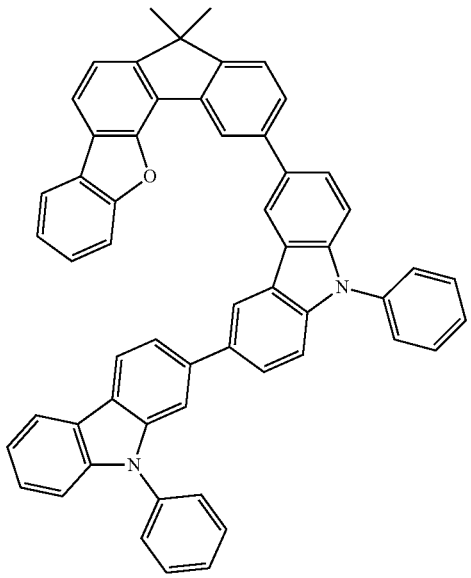
[Chemical Formula D-141]
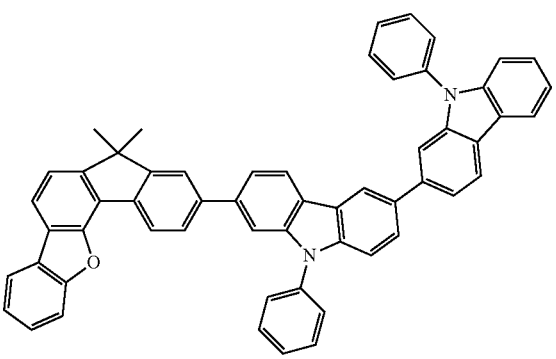
[Chemical Formula D-142]
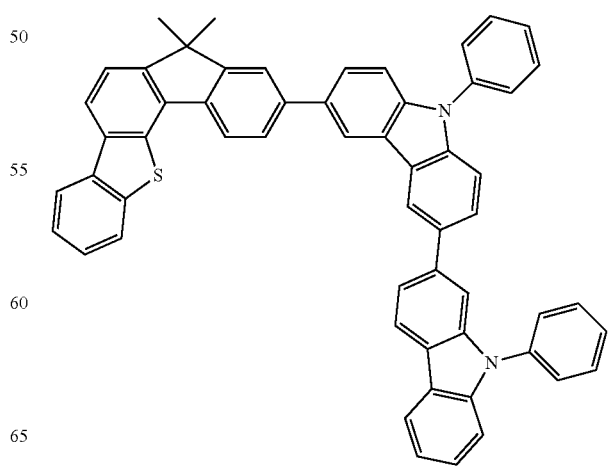

-continued
[Chemical Formula D-143]
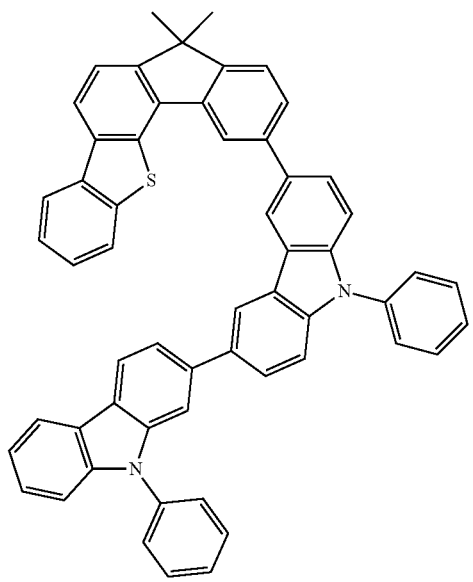
[Chemical Formula D-144]
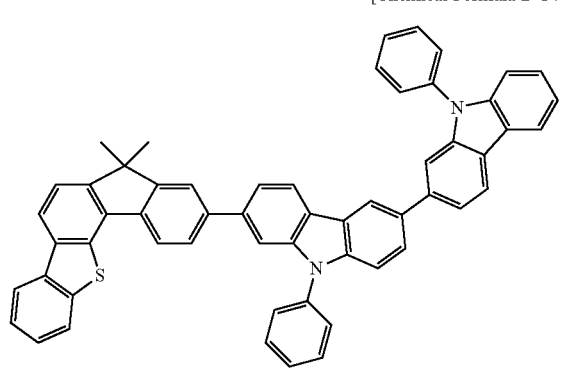
[Chemical Formula D-145]
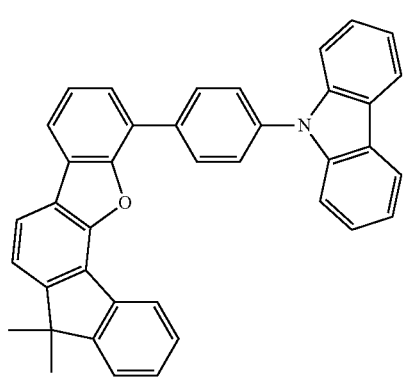
-continued
[Chemical Formula D-146]
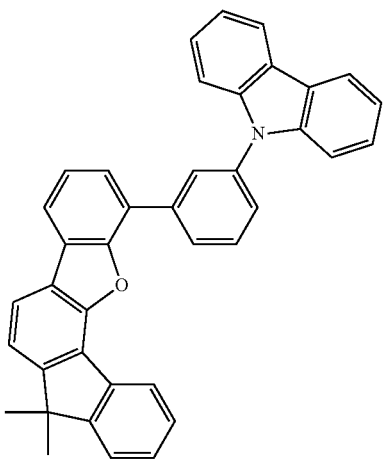
[Chemical Formula D-147]
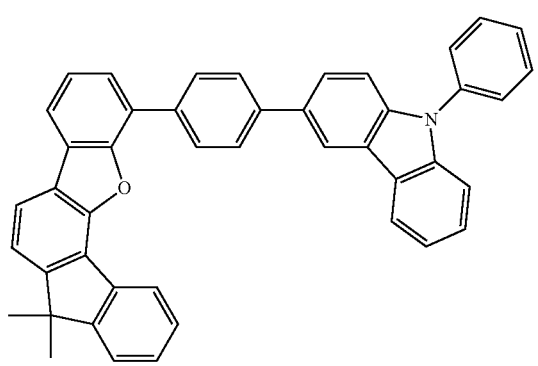
[Chemical Formula D-148]
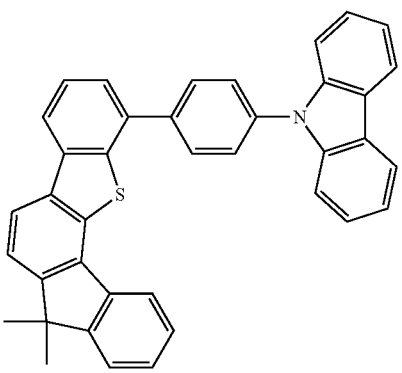

[Chemical Formula D-149]
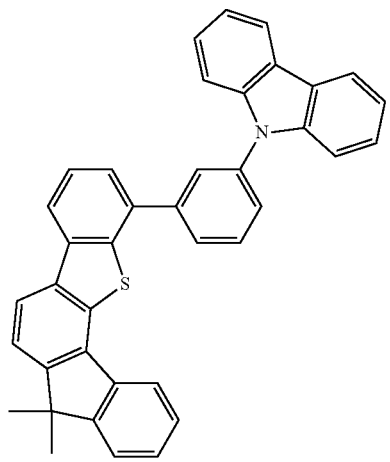
[Chemical Formula D-150]
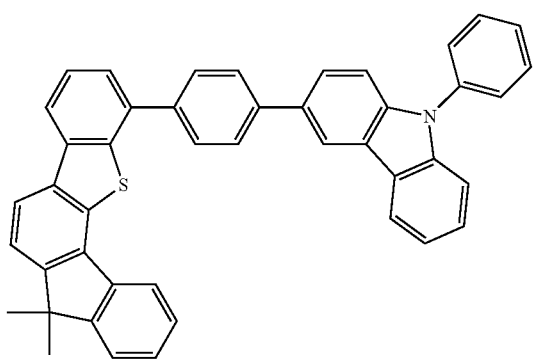
[Chemical Formula D-151]
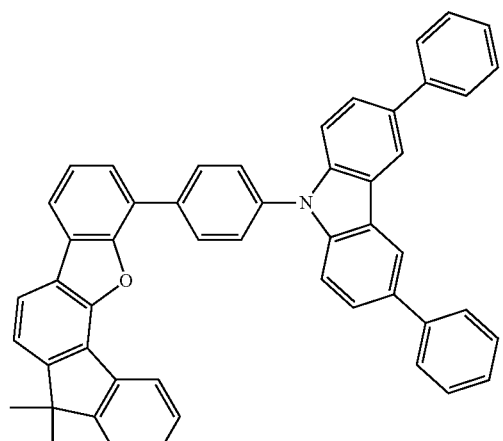
[Chemical Formula D-152]
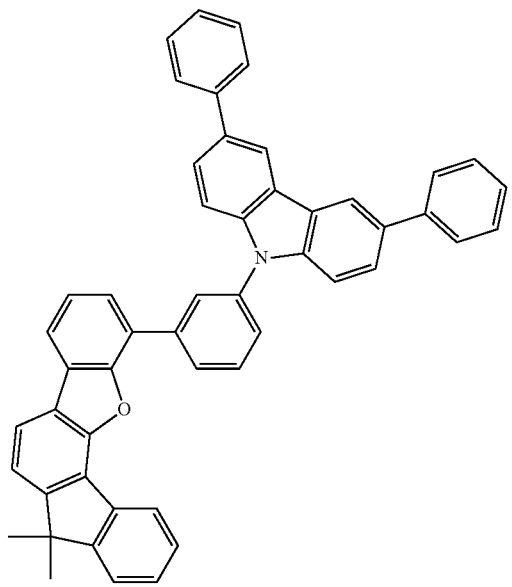
[Chemical Formula D-153]
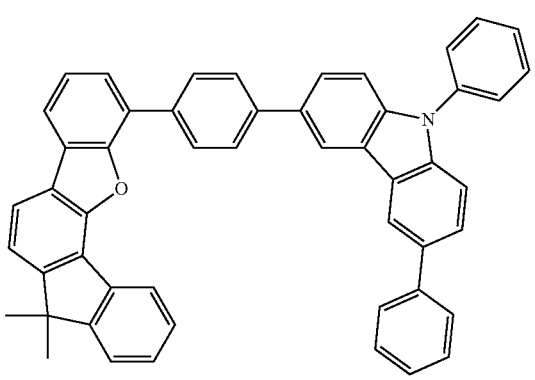
[Chemical Formula D-154]

[Chemical Formula D-155]
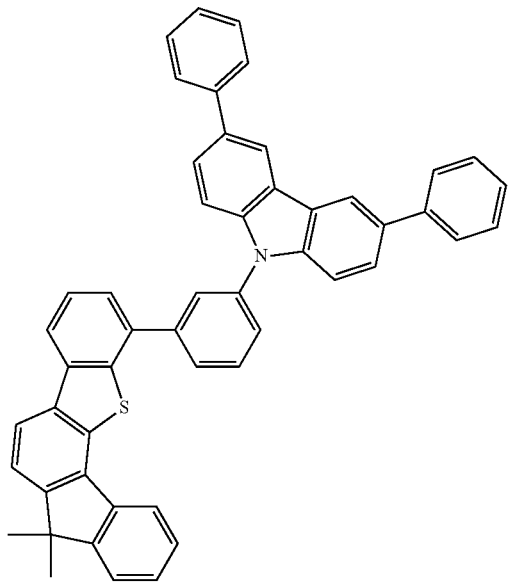
[Chemical Formula D-156]
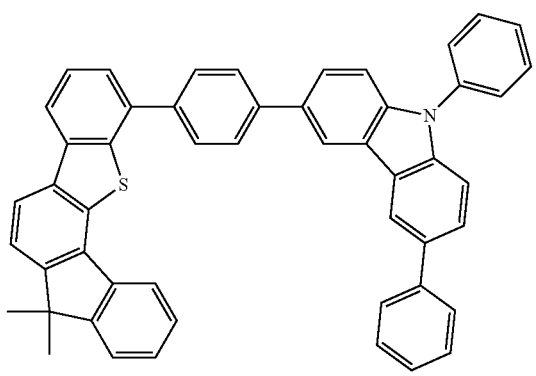
[Chemical Formula D-157]
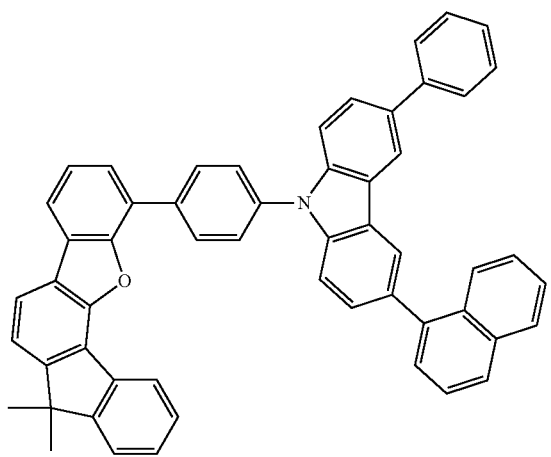
[Chemical Formula D-158]
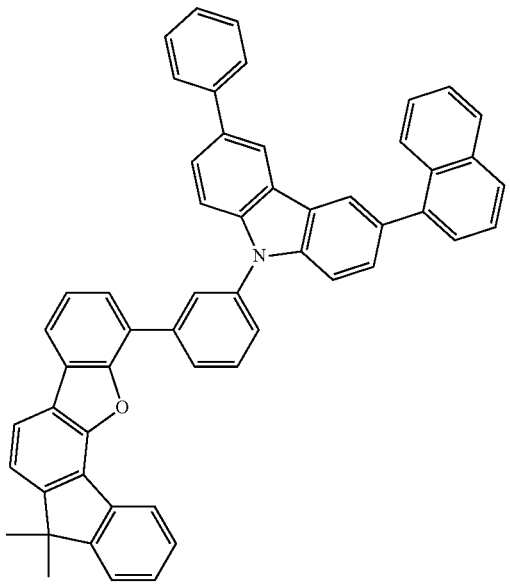
[Chemical Formula D-159]
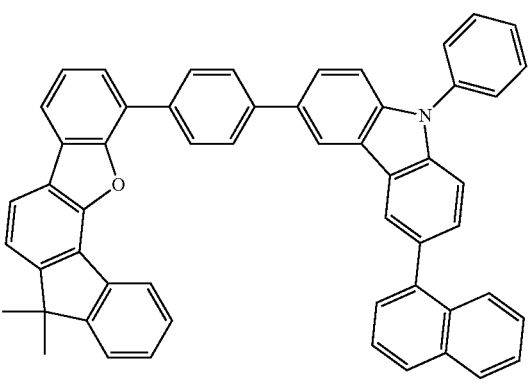
[Chemical Formula D-160]
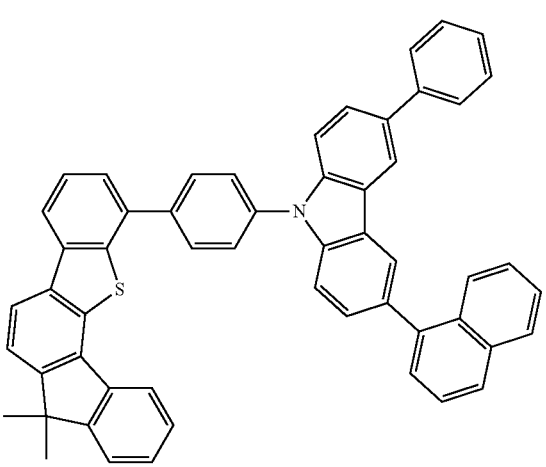

[Chemical Formula D-161]
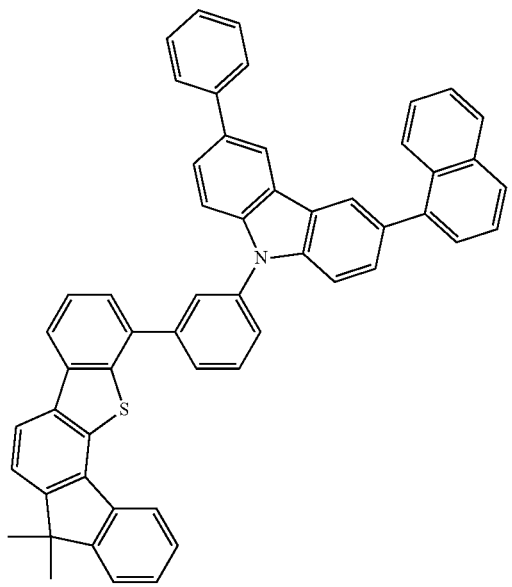
[Chemical Formula D-162]
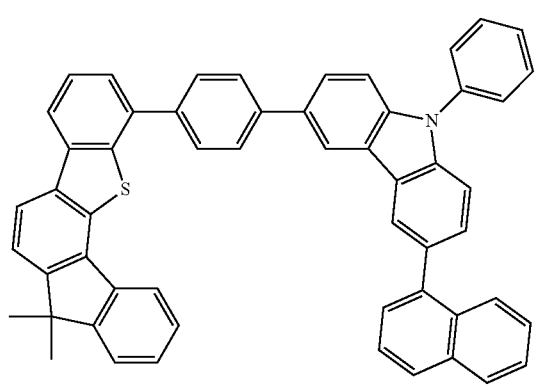
[Chemical Formula D-163]
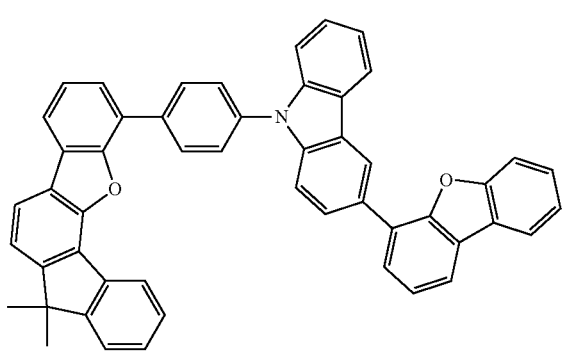
[Chemical Formula D-164]
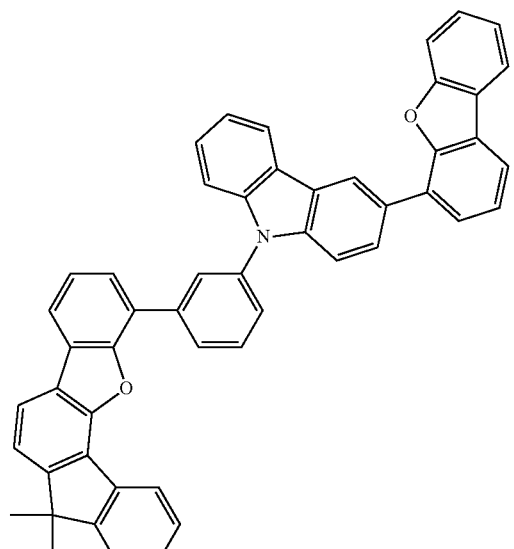
[Chemical Formula D-165]
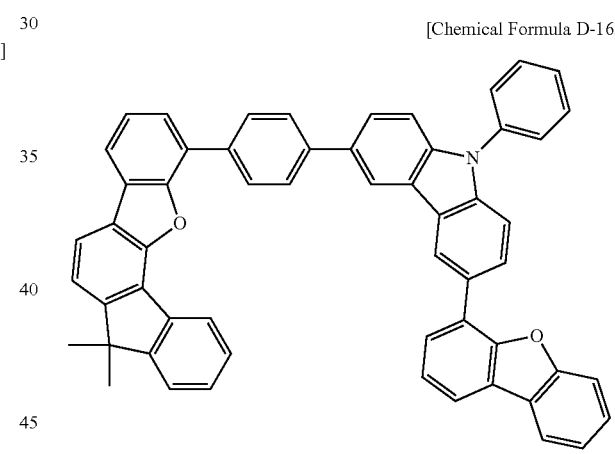
[Chemical Formula D-166]
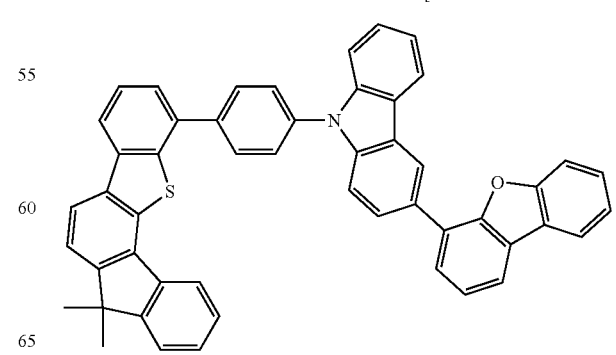

-continued
[Chemical Formula D-167]
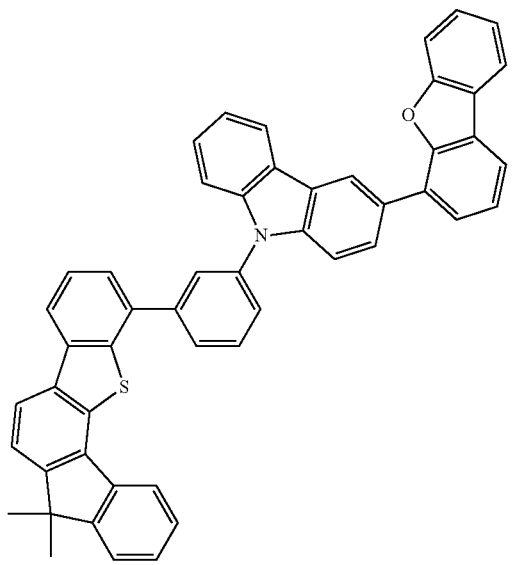
[Chemical Formula D-170]
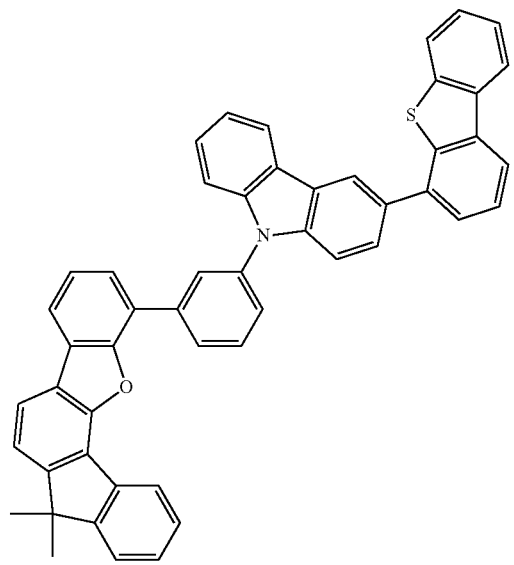
[Chemical Formula D-168]
[Chemical Formula D-171]
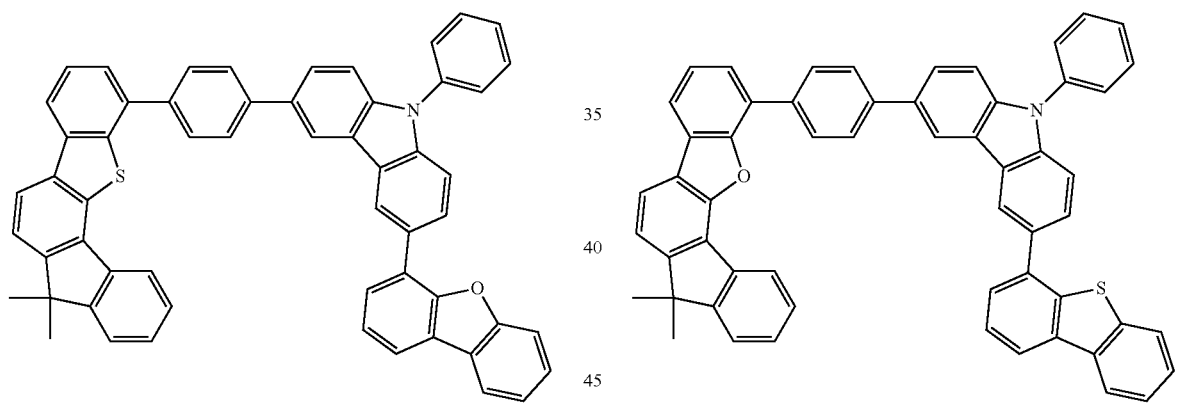
[Chemical Formula D-169]
[Chemical Formula D-172]
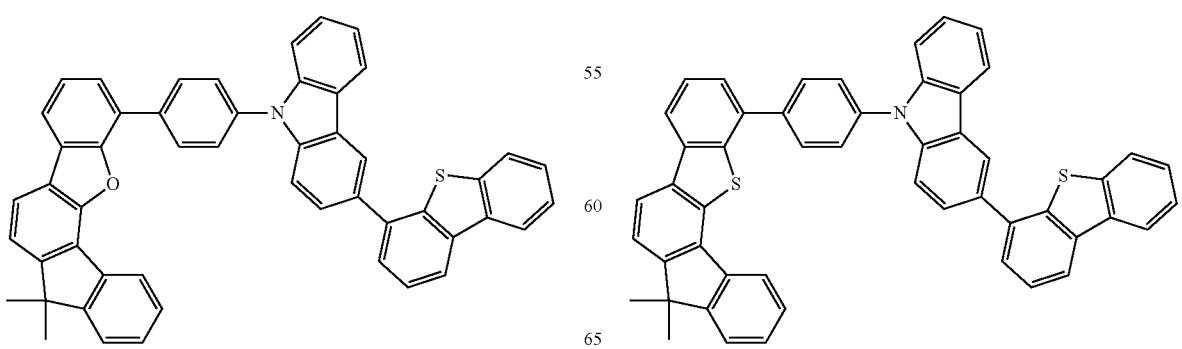

[Chemical Formula D-173]
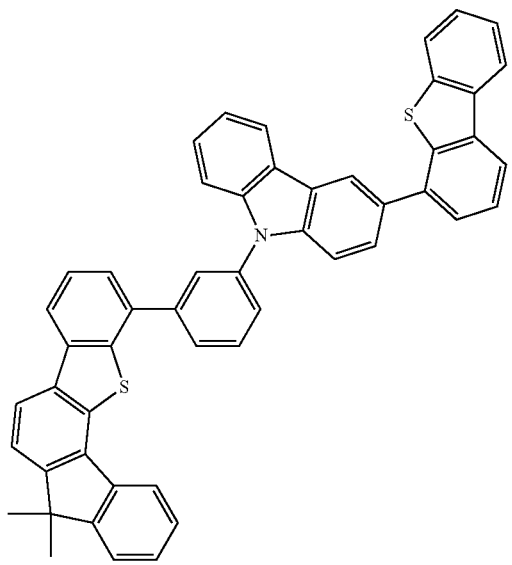
[Chemical Formula D-176]
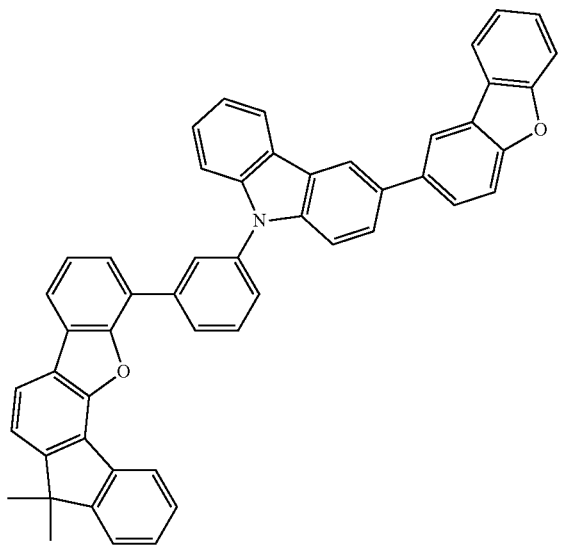
[Chemical Formula D-174]
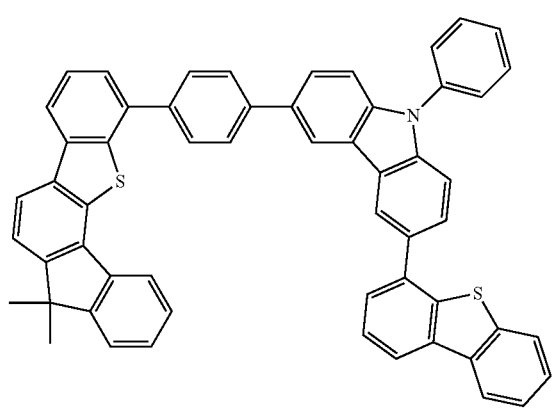
[Chemical Formula D-177]
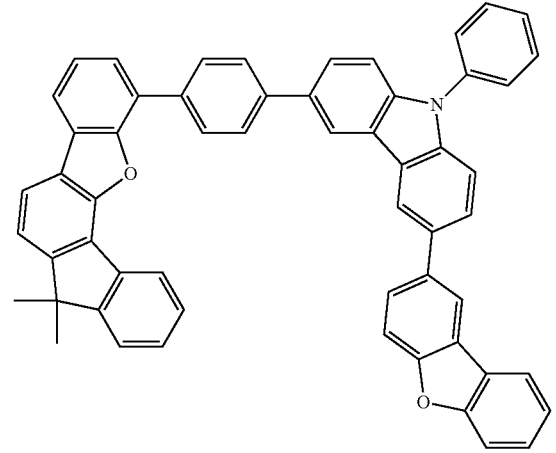
[Chemical Formula D-175]
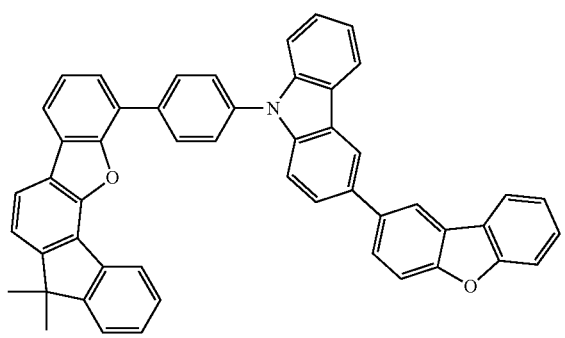
[Chemical Formula D-178]
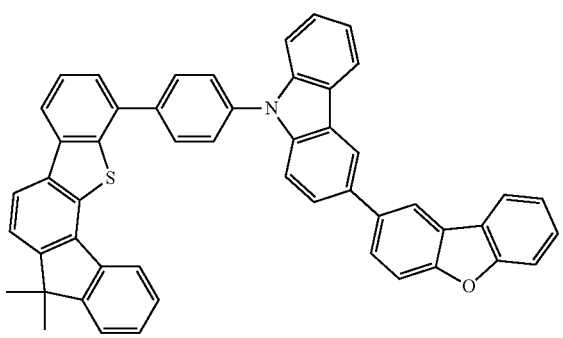

-continued
[Chemical Formula D-179]
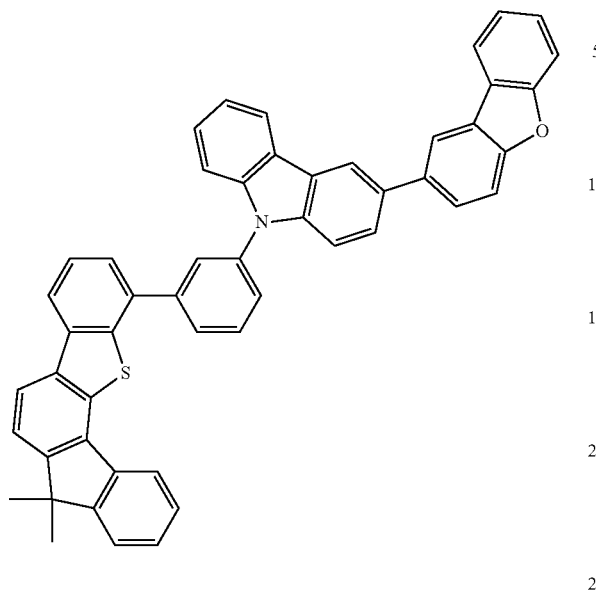
[Chemical Formula D-182]
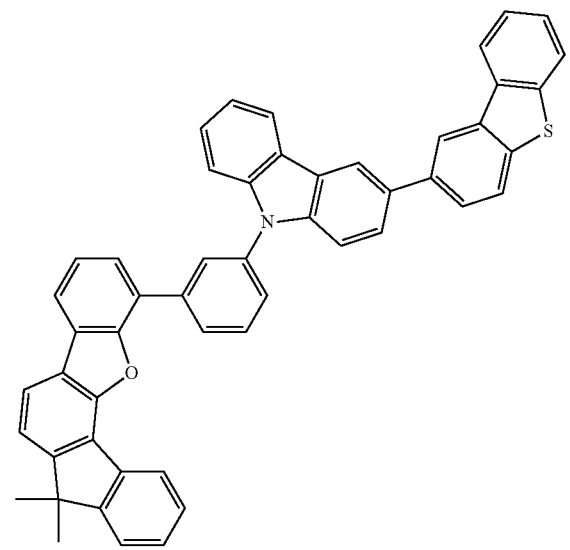
[Chemical Formula D-180]
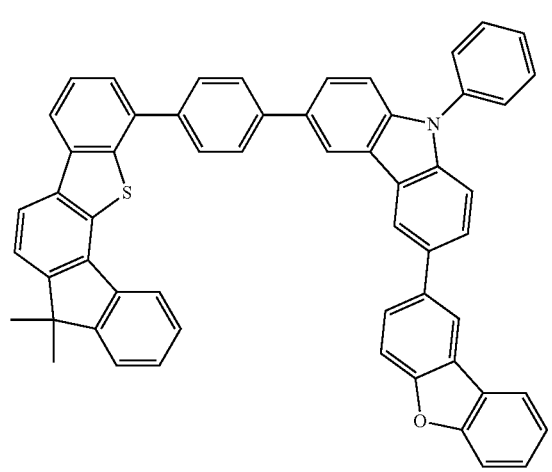
[Chemical Formula D-183]
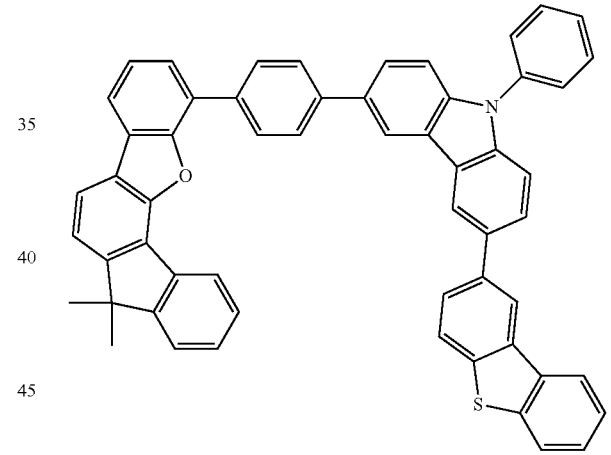
[Chemical Formula D-181]
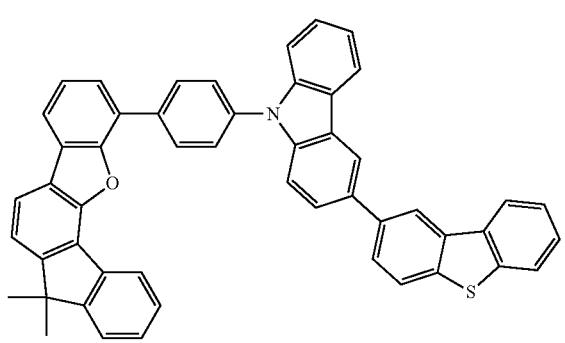
[Chemical Formula D-184]
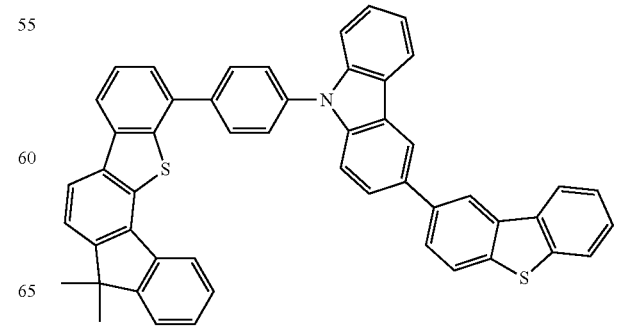

[Chemical Formula D-185]
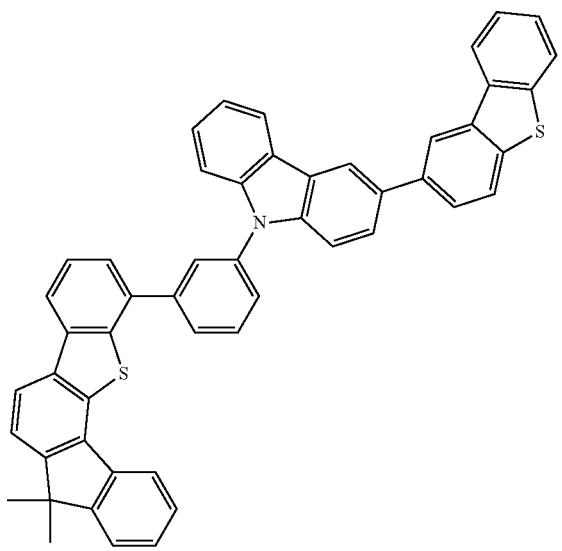
[Chemical Formula D-188]
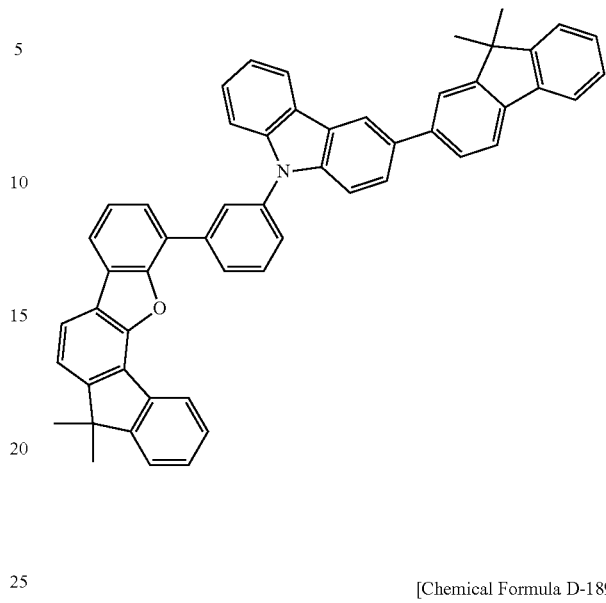
[Chemical Formula D-186]
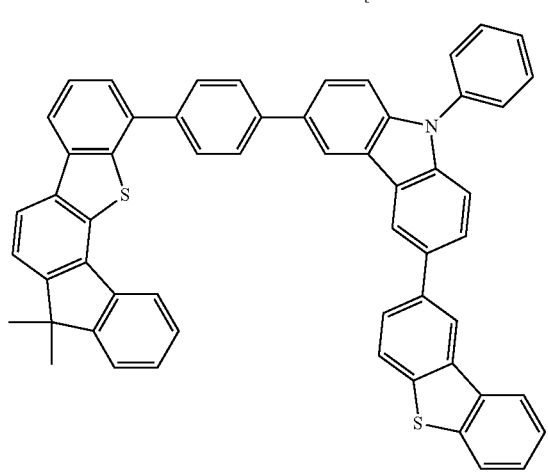
[Chemical Formula D-189]
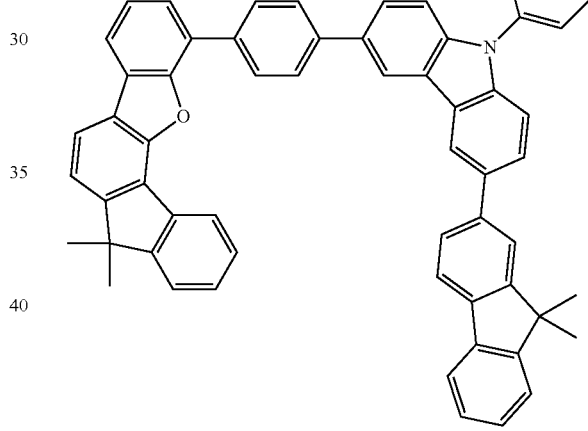
[Chemical Formula D-187]
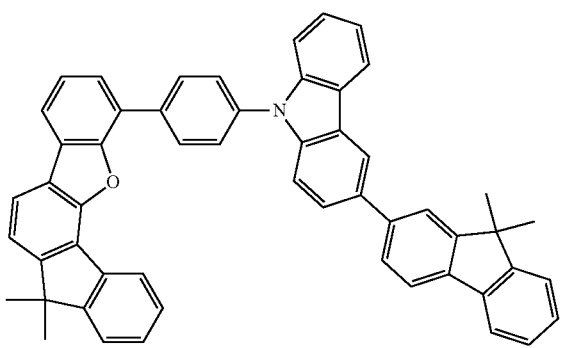
[Chemical Formula D-190]

[Chemical Formula D-191]
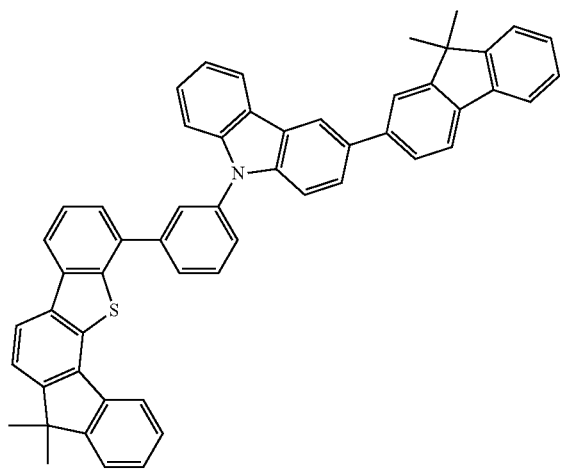
[Chemical Formula D-192]
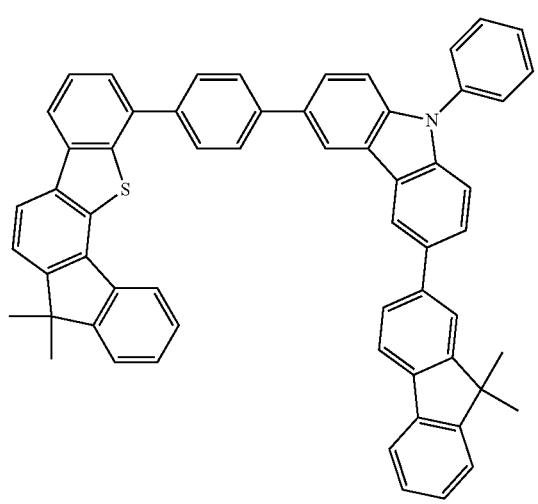
[Chemical Formula D-193]
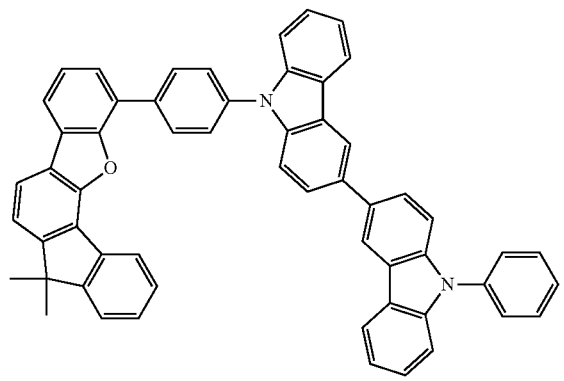
[Chemical Formula D-194]
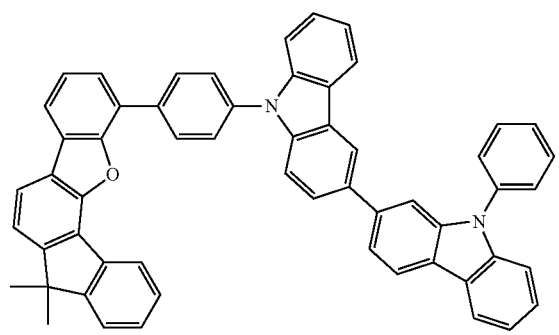
[Chemical Formula D-195]
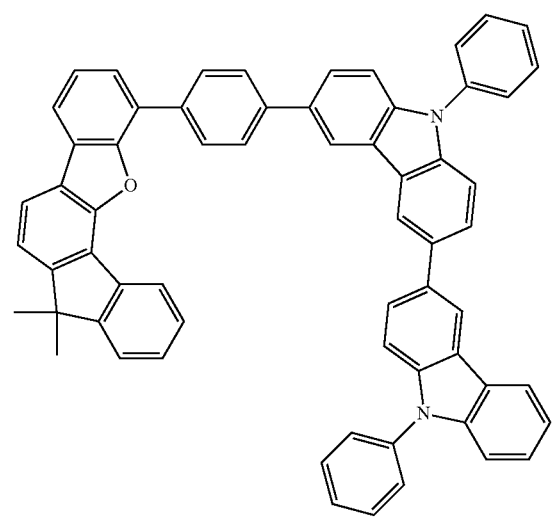
[Chemical Formula D-196]
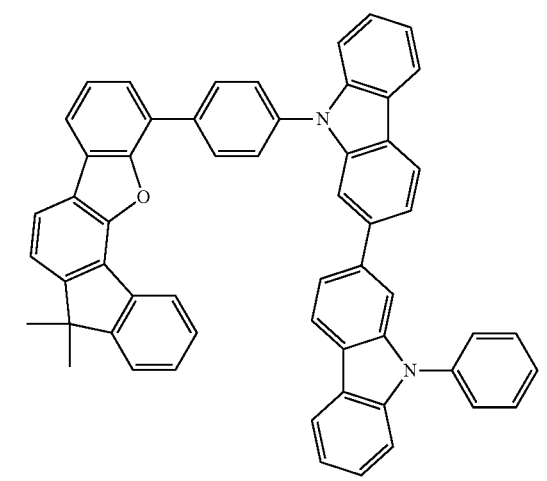

[Chemical Formula D-197]
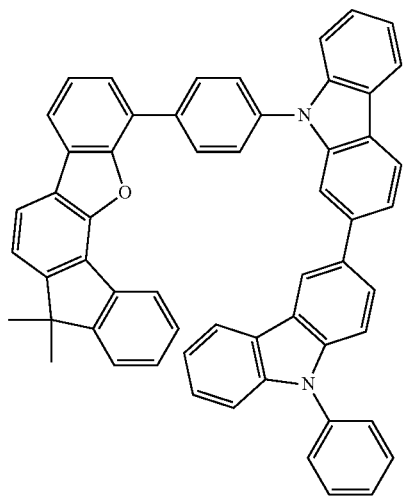
[Chemical Formula D-198]
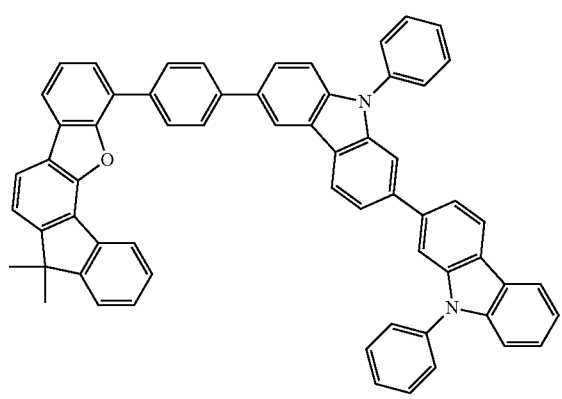
[Chemical Formula D-199]
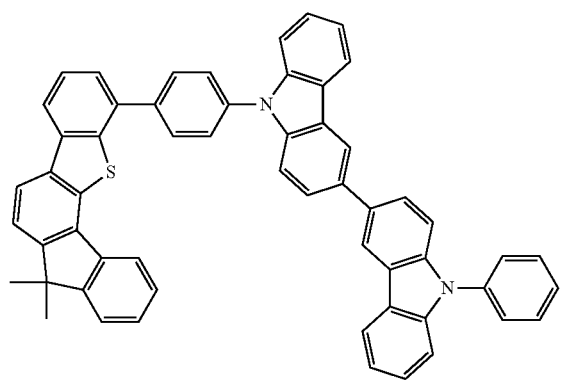
[Chemical Formula D-200]
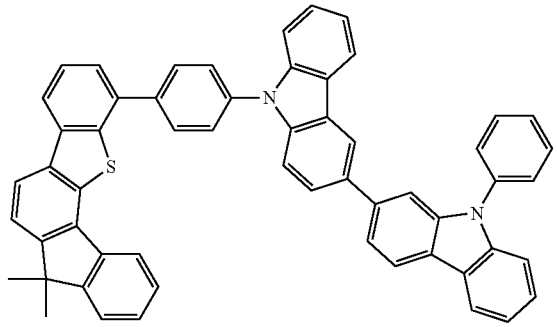
[Chemical Formula D-201]
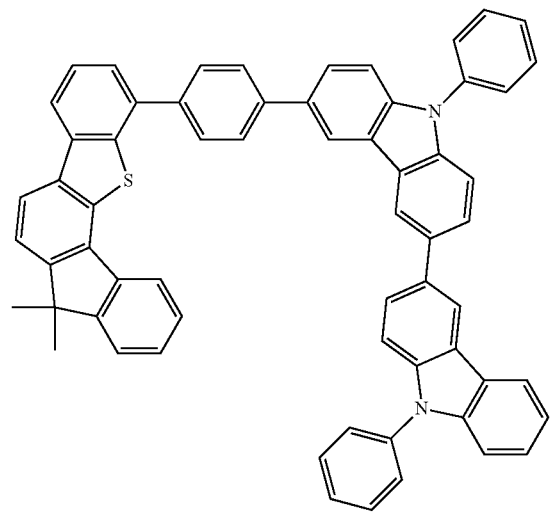
[Chemical Formula D-202]
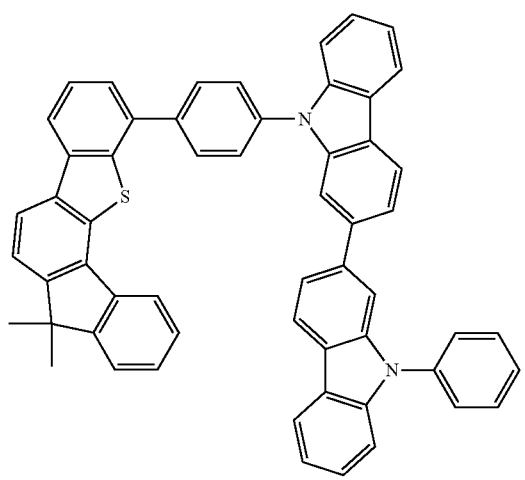

[Chemical Formula D-203]
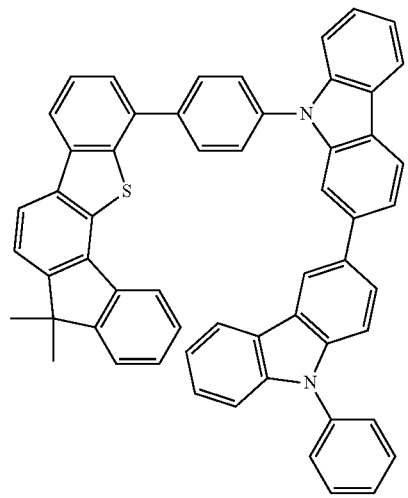
[Chemical Formula D-204]
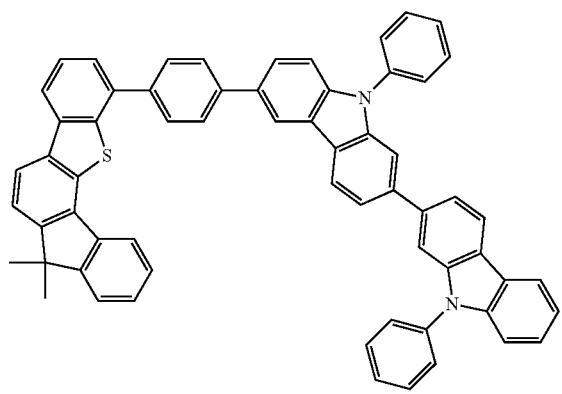
[Chemical Formula D-205]
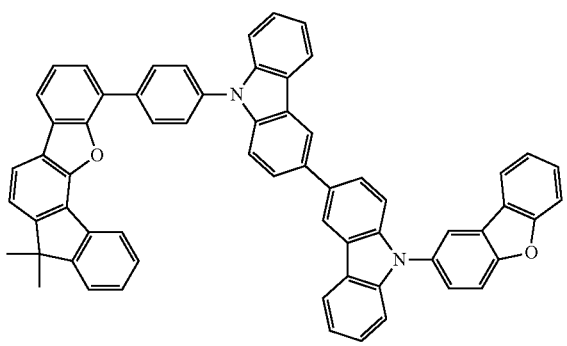
[Chemical Formula D-206]
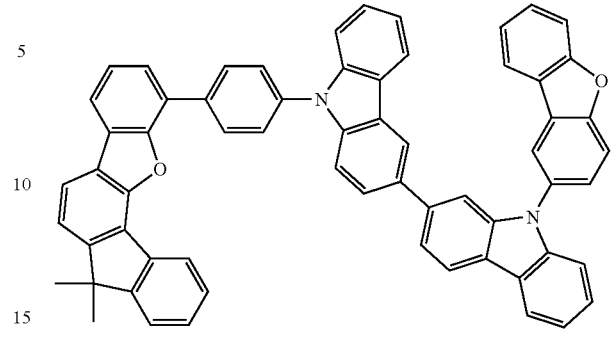
[Chemical Formula D-207]
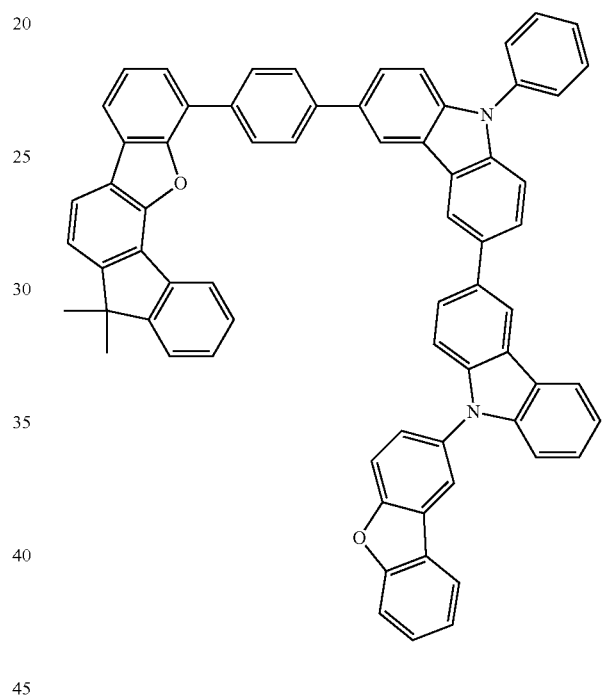
[Chemical Formula D-208]
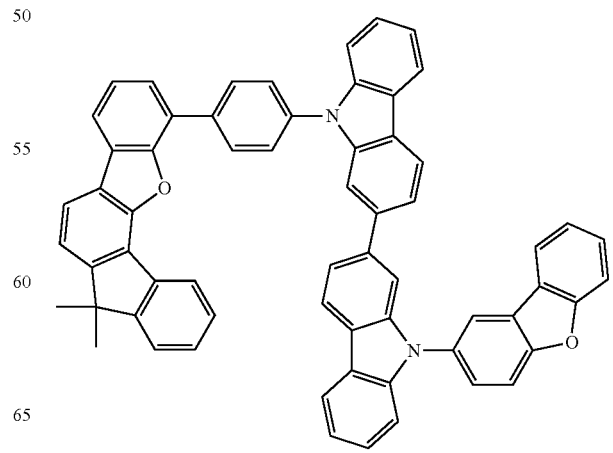

[Chemical Formula D-209]

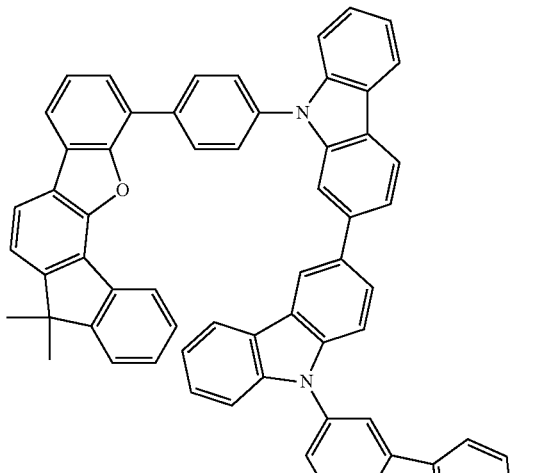

[Chemical Formula D-210]

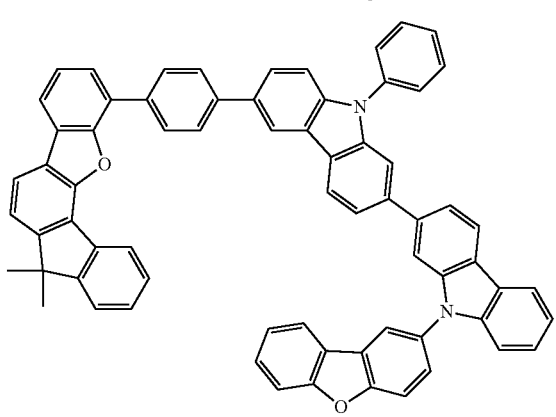

When the compound according to one embodiment of the present invention requires both electron and hole characteristics, the functional group having electron characteristics may be introduced to effectively improve life-span of an organic light emitting diode and decreasing its driving voltage.

The compound for an organic optoelectronic device according to one embodiment of the present invention shows a maximum light emitting wavelength in a range of about 320 to 500 nm, high triplet exciton energy (T1) of greater than equal to 2.0 eV and specifically, 2.0 to 4.0 eV and thus, has an advantage of increasing luminous efficiency of a dopant by well transporting charges of a host having high triplet exciton energy to the dopant and decreasing a driving voltage by freely adjusting HOMO and LUMO energy levels and accordingly, may be used as a host material or a charge transport material.

In addition, the compound for an organic optoelectronic device has optical and electrical activity and thus, may be used as a non-linear optical material, an electrode material, an electrochromic material, an optical switch, a sensor, a module, a wave guide, an organic transistor, a laser, an optical absorbing material, a dielectric material, and a material for a separation membrane and the like.

The compound for an organic optoelectronic device including the compounds has a glass transition temperature of greater than or equal to 90° C. and a thermal decomposition temperature of greater than or equal to 400° C., indicating improved thermal stability. Thereby, it is possible to produce an organic optoelectronic device having a high efficiency.

The compound for an organic optoelectronic device including the compounds may play a role for emitting light or injecting and/or transporting electrons, and also act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to one embodiment of the present invention is used for an organic thin layer, and it may improve the life-span characteristics, efficiency characteristics, electrochemical stability, and thermal stability of an organic optoelectronic device and decrease the driving voltage.

Therefore, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, and the like. For example, the compound for an organic optoelectronic device according to one embodiment may be included in an electrode or an electrode buffer layer in the organic solar cell to improve the quantum efficiency, and it may be used as an electrode material for a gate, a source-drain electrode, or the like in the organic transistor.

Hereinafter, an organic light emitting diode is specifically described.

An organic light emitting diode according to another embodiment of the present invention includes an anode, a cathode, and at least one or more organic thin layer between the anode and the cathode, and at least one of the organic thin layers may include the compound for an organic optoelectronic device according to one embodiment of the present invention.

The organic thin layer including the compound for an organic optoelectronic device may include a layer selected from the group consisting of an emission layer, a hole transport layer, a hole injection layer, an electron transport layer, an electron injection layer, a hole blocking layer, and a combination thereof, and the at least one layer includes the compound for an organic optoelectronic device according to one embodiment. Particularly, the compound for an organic optoelectronic device according to one embodiment may be included in an electron transport layer or electron injection layer. In addition, when the compound for an organic optoelectronic device is included in the emission layer, the compound for an organic optoelectronic device may be included as a phosphorescent or fluorescent host, and particularly, as a fluorescent blue dopant material.

Figure 2:
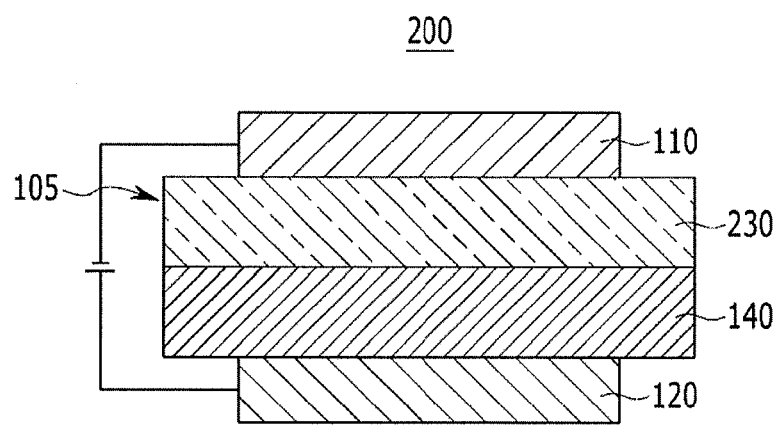

FIGS. 1 and 2 are cross-sectional views showing organic light emitting diodes including the compound for an organic optoelectronic device according to one embodiment of the present invention.

Referring to FIGS. 1 and 2, organic light emitting diodes 100 and 200, according to one embodiment include at least one organic thin layer 105 interposed between an anode 120 and a cathode 110.

The anode 120 includes an anode material, which is preferably a material having a large work function to help hole injection into an organic thin layer. Specific examples of the anode material include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as $ZnO:Al$ or $SnO_2:Sb$; or a conductive polymer such as poly(3-methylthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 includes a cathode material, which is a material having a small work function to help electron injection into an organic thin layer. Specific examples of the cathode material include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, LiF/Al, and BaF$_2$/Ca, but is not limited thereto. It is preferable to include a metal electrode including aluminum as a cathode.

First, referring to FIG. 1, the organic light emitting diode 100 includes the only emission layer 130 as an organic thin layer 105, and the organic thin layer 105 may be present as the only emission layer 130.

Referring to FIG. 2, a double-layered organic light emitting diode 200 includes an organic thin layer 105 including an emission layer 230 including an electron transport layer, and a hole transport layer 140 and as shown in FIG. 2, the organic thin layer 105 includes a double layer of the emission layer 230 and hole transport layer 140. The emission layer 230 also functions as an electron transport layer, and the hole transport layer 140 layer has an excellent binding property with a transparent electrode such as ITO or an excellent hole transport capability. In addition, as not shown in FIGS. 1 and 2, a device according to the present invention may be a multi-layered device additionally including a hole injection layer, an auxiliary hole transport layer, an auxiliary electron transport layer, an electron injection layer and the like, in the organic thin layer 105 of FIG. 1 or 2.

In FIGS. 1 and 2, at least one selected from the emission layers 130 and 230 and the hole transport layer 140 including the organic thin layer 105 and the hole injection layer, the auxiliary hole transport layer, the auxiliary electron transport layer, the electron injection layer and the like additionally included therein may include the compound for an organic optoelectronic device according to the present invention. Herein, the compound for an organic optoelectronic device may be used for the electron transport layer 150 or the electron transport layer 150 including an electron injection layer, and specifically when the compound for an organic optoelectronic device is used to form the electron transport layer 150, a hole blocking layer (not shown) does not need to be separately formed, and thus, an organic light emitting diode having a simplified structure may be provided.

Furthermore, when the compound for an organic optoelectronic device is included in the emission layers 130 and 230, the compound for an organic optoelectronic device may be included as a phosphorescent or fluorescent host or a fluorescent blue dopant.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

According to one embodiment of the present invention, a display device including the organic light emitting diode is provided.

Hereinafter, the embodiments are illustrated in more detail with reference to examples. These examples, however, should not in any sense be interpreted as limiting the scope of the present invention.

Preparation of Compound for Organic Optoelectronic Device

Synthesis Example 1: Preparation of Intermediate I-1

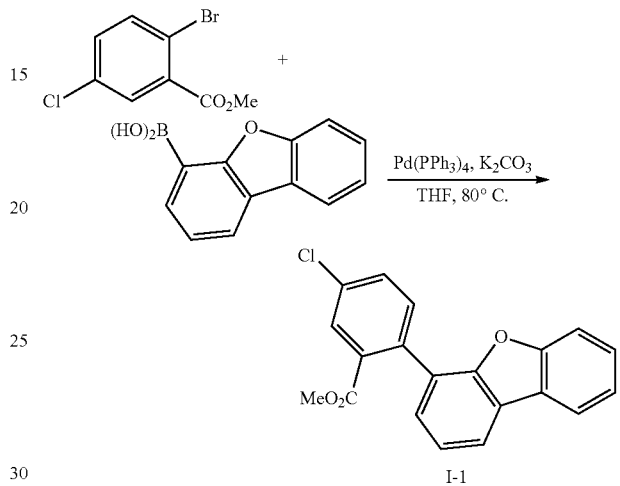

50 g (200 mmol) of methyl-2-bromo-5-chlorobenzoate was dissolved in of 0.5 L of tetrahydrofuran (THF) under a nitrogen environment, 51 g (241 mmol) of dibenzofuran-4-yl boronic acid and 7.0 g (6.0 mmol) of tetrakis(triphenylphosphine)palladium were added thereto, and the mixture was agitated. 59 g (401 mmol) of potassium carbonate saturated in water was added thereto, and the resulting mixture was heated and refluxed at 80° C. for 24 hours. When the reaction was terminated, water was added to the reaction solution, and the obtained mixture was extracted with dichloromethane (DCM), treated with anhydrous MgSO$_4$ to remove moisture and then, filtered and concentrated under a reduced pressure. The obtained residue was separated and purified through flash column chromatography, obtaining a compound I-1 (55 g, 81%).

HRMS (70 eV, EI+): m/z calcd for C20H13ClO3: 336.0553, found: 336.1.

Elemental Analysis: C, 71%; H, 4%

Synthesis Example 2: Preparation of Intermediate I-2

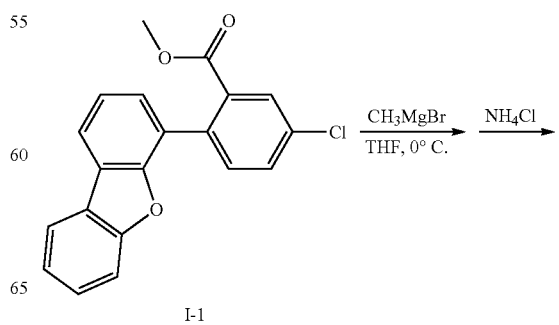

-continued

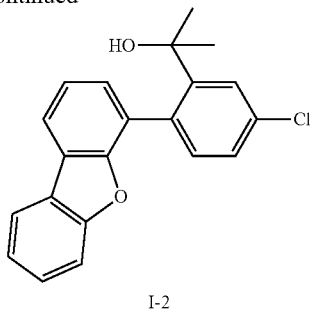

I-2

110 g (327 mmol) of the intermediate I-1 was dissolved in 1 L of tetrahydrofuran (THF) under a nitrogen environment, and the solution was cooled down to 0° C. Then, 0.27 L (817 mmol) of 3.0 M methylmagnesium bromide dissolved in diethyl ether was slowly added thereto in a dropwise fashion. The obtained mixture was agitated at room temperature for 29 hours. When the reaction was terminated, the reaction solution was neutralized by adding 52.4 g (980 mmol) of ammonium chloride dissolved in 0.25 L of water thereto. The resultant was extracted with dichloromethane (DCM), treated with anhydrous $MgSO_4$ to remove moisture and then, filtered and concentrated under a reduced pressure. An intermediate I-2 (113 g, 102%) was obtained.

HRMS (70 eV, EI+): m/z calcd for C21H17ClO2: 336.0917, found: 336.1.

Elemental Analysis: C, 75%; H, 5%

Synthesis Example 3: Preparation of Intermediate I-3

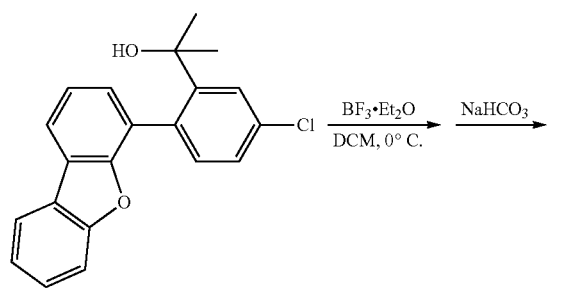

113 g (373 mmol) of the intermediate I-2 was dissolved in 0.6 L of dichloromethane (DCM) in a nitrogen environment, and the solution was cooled down to 0° C. Then, 52.9 g (373 mmol) of boron trifluoride dissolved in diethyl ether was slowly added thereto in a dropwise fashion. The mixture was agitated at room temperature for 12 hours. When the reaction was terminated, the reaction solution was neutralized by adding 31.3 g (373 mmol) of sodium bicarbonate dissolved in 0.25 L of water added thereto. The resultant was extracted with dichloromethan (DCM) and treated with anhydrous $MgSO_4$ to remove moisture, and the residue was separated and purified through flash column chromatography, obtaining a compound I-3 (67 g, 69%).

HRMS (70 eV, EI+): m/z calcd for C21H15ClO: 318.0811, found: 318.1.

Elemental Analysis: C, 79%; H, 5%

Synthesis Example 4: Preparation of Intermediate I-4

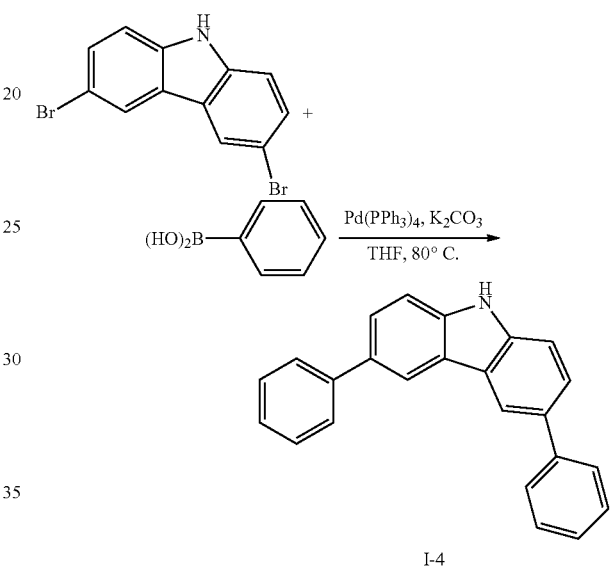

I-4

30 g (92.3 mmol) of 3,6-dibromo-9H-carbazole was dissolved in 0.3 L of tetrahydrofuran (THF) in a nitrogen environment, 28 g (231 mmol) of phenyl boronic acid and 3.2 g (2.8 mmol) of tetrakis(triphenylphosphine)palladium were added thereto, and the mixture was agitated. 40.8 g (277 mmol) of potassium carbonate saturated in water was added thereto, and the mixture was heated and refluxed at 80° C. for 10 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound I-4 (14.3 g, 48%).

HRMS (70 eV, EI+): m/z calcd for C24H17N: 319.1361, found: 319.1.

Elemental Analysis: C, 90%; H, 5%

Synthesis Example 5: Preparation of Intermediate I-5

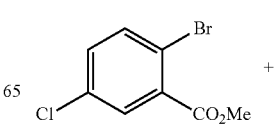

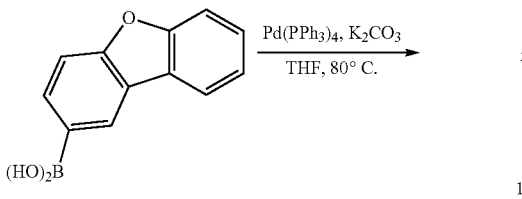

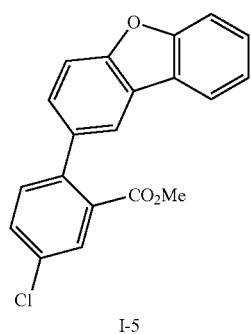

I-5

50 g (200 mmol) of methyl-2-bromo-5-chlorobenzoate was dissolved in 0.5 L of tetrahydrofuran (THF) in a nitrogen environment, 51 g (241 mmol) of dibenzofuran-2-yl boronic acid and 7.0 g (6.0 mmol) of tetrakis(triphenylphosphine)palladium were added thereto, and the mixture was agitated. 59 g (401 mmol) of potassium carbonate saturated in water was added thereto, and the mixture was heated and refluxed at 80° C. for 24 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound I-5 (63.4 g, 94%).

HRMS (70 eV, EI+): m/z calcd for C20H13ClO3: 336.0553, found: 336.1.

Elemental Analysis: C, 71%; H, 4%

Synthesis Example 6: Preparation of Intermediate I-6

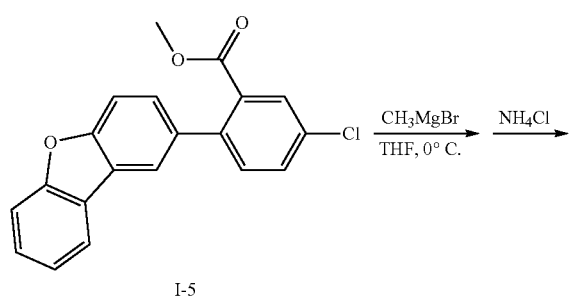

I-5

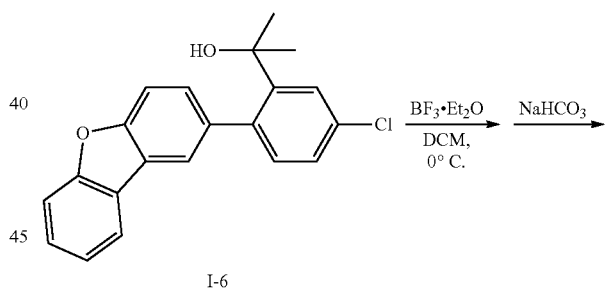

I-6

63.4 g (188 mmol) of the intermediate I-5 was dissolved in 0.6 L of tetrahydrofuran (THF) in a nitrogen environment, and the solution was cooled down to 0° C. 0.16 L (470 mmol) of 3.0 M methylmagnesiumbromide dissolved in diethyl ether was slowly added thereto over one hour in a dropwise fashion. The obtained mixture was agitated at room temperature for 25 hours. When the reaction was terminated, the reaction solution was neutralized by adding 30.2 g (564 mmol) of ammonium chloride dissolved in 0.15 L of water. The neutralized resultant was extracted with dichloromethane (DCM) was and treated with anhydrous MgSO₄ to remove moisture and then, filtered and concentrated under a reduced pressure. An intermediate I-6 (63.3 g, 100%) was obtained.

HRMS (70 eV, EI+): m/z calcd for C21H17ClO2: 336.0917, found: 336.1.

Elemental Analysis: C, 75%; H, 5%

Synthesis Example 7: Preparation of Intermediate I-7

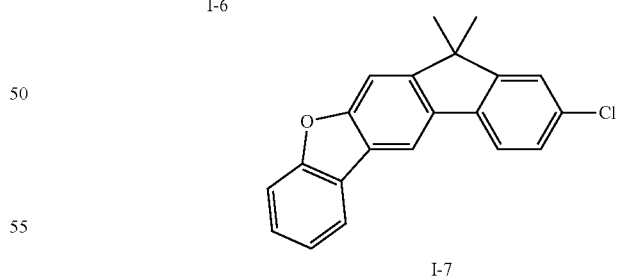

I-7

63.3 g (188 mmol) of the intermediate I-6 was dissolved in 0.3 L of dichloromethane (DCM) in a nitrogen environment, and the solution was cooled down to 0° C. 29.4 g (207 mmol) of boron trifluoride dissolved in diethyl ether was slowly added thereto over one hour in a dropwise fashion. The obtained mixture was agitated at room temperature for 10 hours. When the reaction was terminated, the reaction solution was neutralized by adding 17.4 g (207 mmol) of sodium bicarbonate dissolved in 0.25 L of water. The resultant was extracted with dichloromethane (DCM) and treated with anhydrous MgSO$_4$ to remove moisture, and the residue obtained therefrom was separated and purified through flash column chromatography, obtaining a compound I-7 (48.5 g, 81%).

HRMS (70 eV, EI+): m/z calcd for C21H15ClO: 318.0811, found: 318.1.

Elemental Analysis: C, 79%; H, 5%

Synthesis Example 8: Preparation of Intermediate I-8

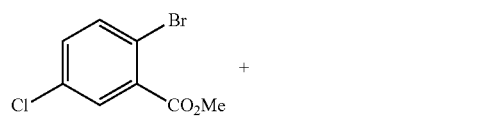

+

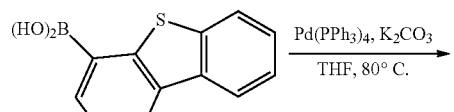

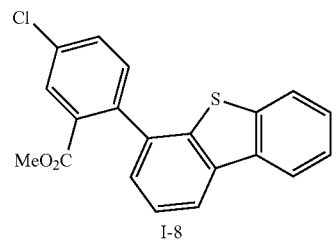

I-8

50 g (200 mmol) of methyl-2-bromo-5-chlorobenzoate was dissolved in 0.5 L of tetrahydrofuran (THF) in a nitrogen environment, 50.2 g (220 mmol) of dibenzothiophene-4-ylboronic acid and 4.62 g (4.0 mmol) of tetrakis(triphenylphosphine)palladium were added thereto, and the mixture was agitated. 58.9 g (400 mmol) of potassium carbonate saturated in water was added thereto, and the mixture was heated and refluxed at 80° C. for 21 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The residue obtained therefrom was separated and purified through flash column chromatography, obtaining a compound I-8 (60 g and 85%).

HRMS (70 eV, EI+): m/z calcd for C20H13ClO2S: 352.0325, found: 352.0.

Elemental Analysis: C, 68%; H, 4%

Synthesis Example 9: Preparation of Intermediate I-9

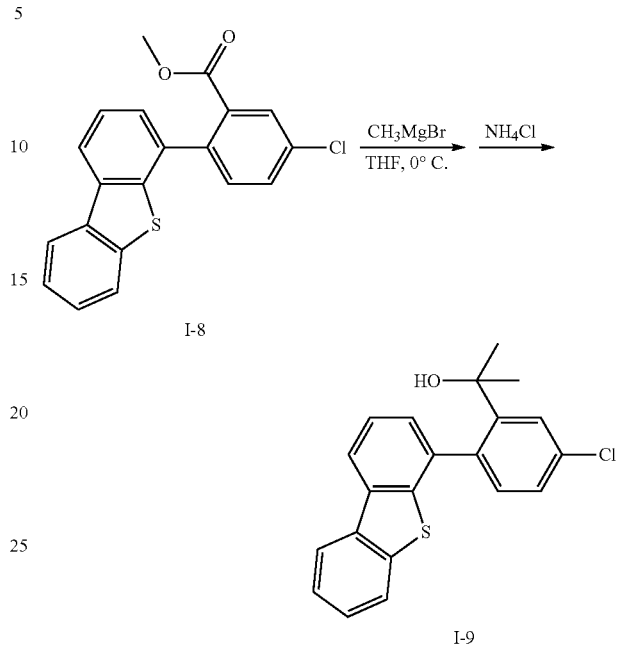

60 g (170 mmol) of the intermediate I-8 was dissolved in 0.6 L of tetrahydrofuran (THF) in a nitrogen environment, and the solution was cooled down to 0° C. 0.14 L (425 mmol) of 3.0 M methylmagnesiumbromide dissolved in diethyl ether was slowly added thereto over one hour in a dropwise fashion. The obtained mixture was agitated at room temperature for 10 hours. When the reaction was terminated, the reaction solution was neutralized by adding 27.3 g (510 mmol) of ammonium chloride dissolved in 0.14 L of water. The obtained resultant was extracted with dichloromethane (DCM) and treated with anhydrous MgSO$_4$ to remove moisture and then, filtered and concentrated under a reduced pressure. An intermediate I-9 was obtained (60 g, 100%).

HRMS (70 eV, EI+): m/z calcd for C21H17ClOS: 352.0689, found: 352.1.

Elemental Analysis: C, 71%; H, 5%

Synthesis Example 10: Preparation of Intermediate I-10

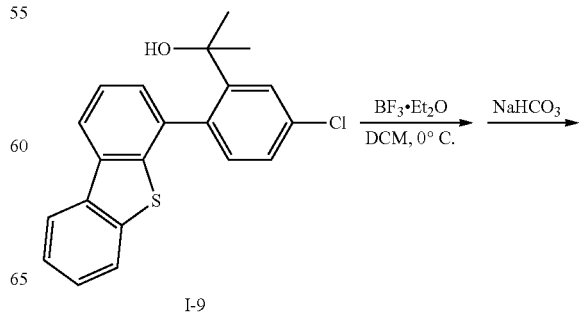

I-9

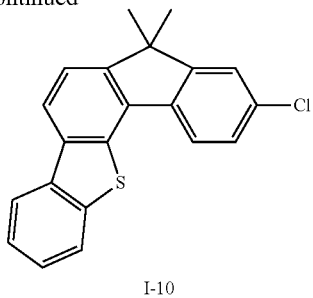

I-10

60 g (170 mmol) of the intermediate I-9 was dissolved in 0.85 L of dichloromethane (DCM) in a nitrogen environment, and the solution was cooled down to 0° C. 26.5 g (187 mmol) of boron trifluoride dissolved in diethyl ether was slowly added thereto over one hour in a dropwise fashion. The obtained mixture was agitated at room temperature for 6 hours. When the reaction was terminated, the reaction solution was neutralized by adding 15.7 g (187 mmol) of sodium bicarbonate dissolved in 0.16 L of water. The resultant was extracted with dichloromethane (DCM) and treated with anhydrous MgSO₄ to remove moisture and then, filtered and concentrated through flash colummatography, obtaining a compound I-10 (43.8 g, 77%).

HRMS (70 eV, EI+): m/z calcd for C21H15ClS: 334.0583, found: 334.1.

Elemental Analysis: C, 75%; H, 5%

Synthesis Example 11: Preparation of Intermediate I-11

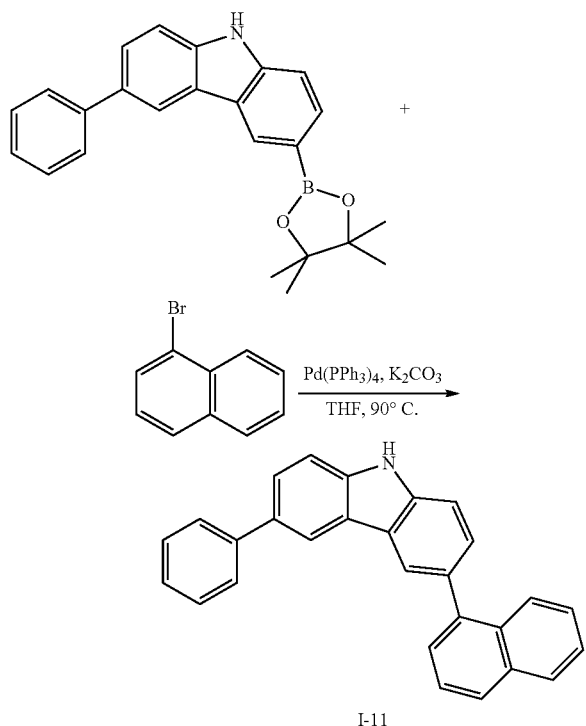

I-11

15 g (72.4 mmol) of 1-bromonaphthalene was dissolved in 0.2 L of tetrahydrofuran (THF) in a nitrogen environment, 29.4 g (79.7 mmol) of 3-phenyl-6-(4,4,5,5-tetramethyl-1,3, 2-dioxaborolan-2-yl)-9H-carbazole and 0.84 g (0.72 mmol) of tetrakis(triphenylphosphine)palladium were added thereto, and the mixture was agitated. 21.3 g (155 mmol) of potassium carbonate saturated in water was added thereto, and the mixture was heated and refluxed at 90° C. for 50 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound I-11 (7 g, 26%).

HRMS (70 eV, EI+): m/z calcd for C28H19N: 369.1517, found: 369.5.

Elemental Analysis: C, 91%; H, 5%

Synthesis Example 12: Preparation of Intermediate I-12

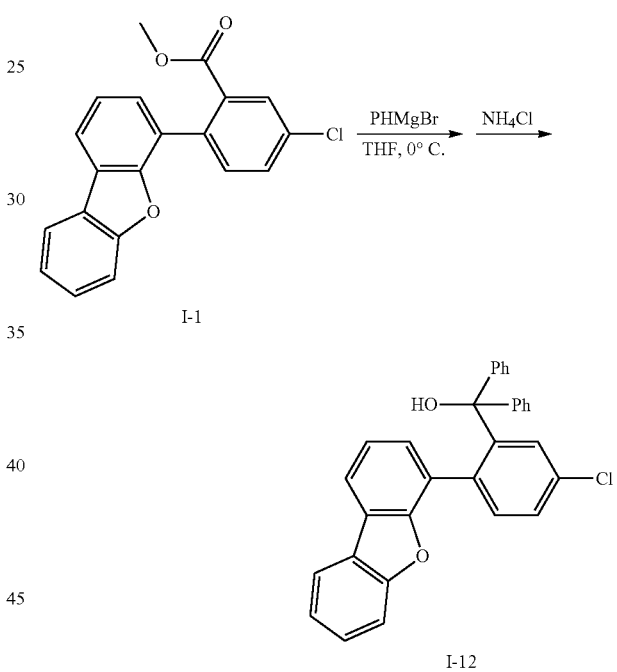

I-12

50 g (148 mmol) of the intermediate I-1 was dissolved in 0.5 L of tetrahydrofuran (THF) in a nitrogen environment, and the solution was cooled down to 0° C. 0.12 L (370 mmol) of 3.0 M phenylmagnesium bromide dissolved in diethyl ether was slowly added thereto over one hour in a dropwise fashion. The obtained mixture was agitated at room temperature for 30 hours. When the reaction was terminated, the reaction solution was neutralized by adding 23.7 g (444 mmol) of ammonium chloride dissolved in 0.12 L of water. The resultant was extracted with dichloromethane (DCM) and treated with anhydrous MgSO₄ to remove moisture and then, filtered and concentrated under a reduced pressure. An intermediate I-12 was obtained (68.2 g, 100%).

HRMS (70 eV, EI+): m/z calcd for C31H21ClO2: 460.1230, found: 460.1.

Elemental Analysis: C, 81%; H, 5%

Synthesis Example 13: Preparation of Intermediate I-13

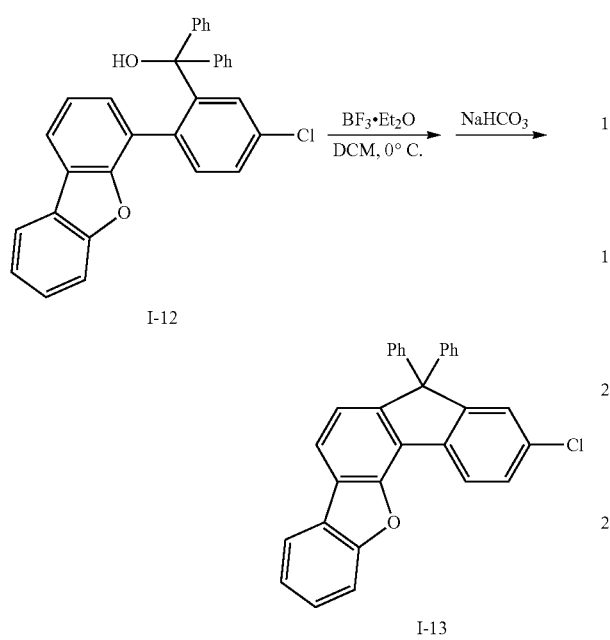

I-12

I-13

68.2 g (148 mmol) of the intermediate I-12 was dissolved in 0.34 L of dichloromethane (DCM) in a nitrogen environment, and the solution was cooled down to 0° C. 23.1 g (163 mmol) of boron trifluoride dissolved in diethyl ether was slowly added thereto over one hour in a dropwise fashion. The obtained mixture was agitated at room temperature for 6 hours. When the reaction was terminated, the reaction solution was neutralized by adding 13.7 g (163 mmol) of ammonium chloride dissolved in 0.14 L of water. The resultant was extracted with dichloromethane (DCM) and treated with anhydrous $MgSO_4$ to remove moisture, and then, the residue was separated and purified through flash column chromatography, obtaining a compound I-13 (60.3 g, 92%).

HRMS (70 eV, EI+): m/z calcd for C31H19ClO: 442.1124, found: 442.1.

Elemental Analysis: C, 84%; H, 4%

Synthesis Example 14: Preparation of Intermediate I-14

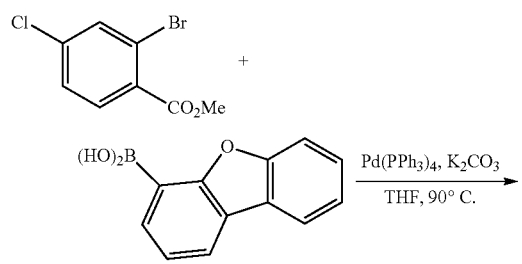

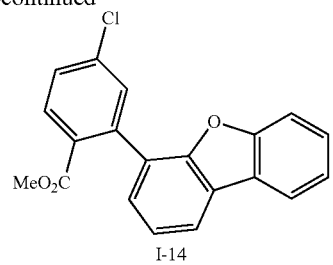

I-14

50 g (200 mmol) of methyl-2-bromo-5-chlorobenzoate was dissolved in 0.5 L of tetrahydrofuran (THF) in a nitrogen environment, 46.7 g (220 mmol) of dibenzofuran-4-yl boronic acid and 4.63 g (4.01 mmol) of tetrakis(triphenylphosphine)palladium were added thereto, and the mixture was agitated. 59 g (401 mmol) of potassium carbonate saturated in water was added thereto, and the mixture was heated and refluxed at 90° C. for 21 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound I-14 (47.7 g, 71%).

HRMS (70 eV, EI+): m/z calcd for C20H13ClO3: 336.0553, found: 336.1.

Elemental Analysis: C, 71%; H, 4%

Synthesis Example 15: Preparation of Intermediate I-15

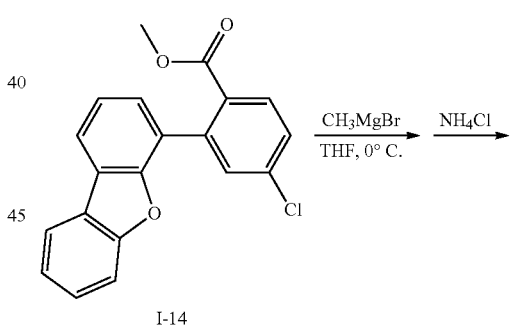

I-14

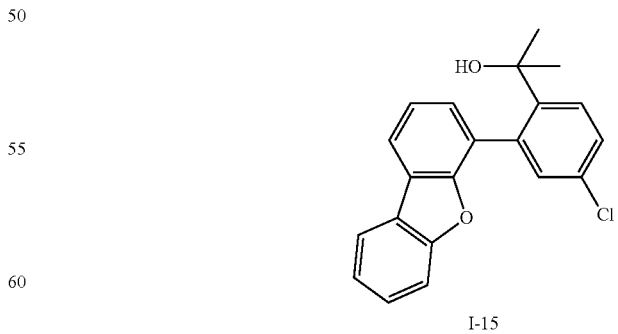

I-15

47.7 g (142 mmol) of the intermediate I-14 was dissolved in 0.5 L of tetrahydrofuran (THF) in a nitrogen environment, and the solution was cooled down to 0° C. 0.12 L (354 mmol) of 3.0 M methylmagnesium bromide dissolved in diethyl ether was slowly added thereto over one hour in a dropwise fashion. The obtained mixture was agitated at room temperature for 19 hours. When the reaction was terminated, the reaction solution was neutralized by adding 22.7 g (425 mmol) of ammonium chloride dissolved in 0.12 L of water. The resultant was extracted with dichloromethane (DCM) and treated with anhydrous MgSO₄ to remove moisture and then, filtered and concentrated under a reduced pressure. An intermediate I-15 was obtained (49.4 g, 104%).

HRMS (70 eV, EI+): m/z calcd for C21H17ClO2: 336.0917, found: 336.1.

Elemental Analysis: C, 75%; H, 5%

Synthesis Example 16: Preparation of Intermediate I-16

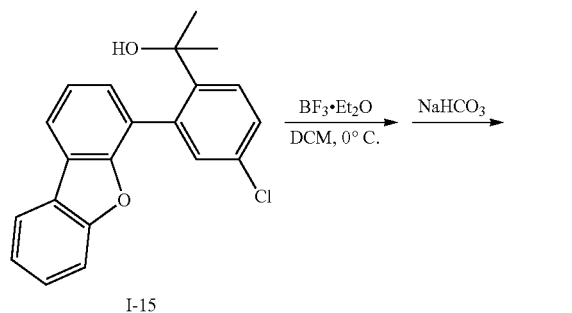

I-15

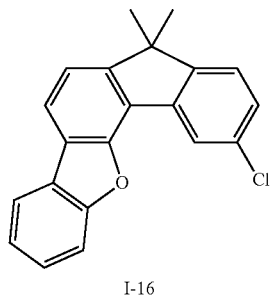

I-16

49.4 g (147 mmol) of the intermediate I-15 was dissolved in 0.25 L of dichloromethane (DCM) in a nitrogen environment, and the solution was cooled down to 0° C. 22.9 g (161 mmol) of boron trifluoride dissolved in diethyl ether was slowly added thereto over one hour in a dropwise fashion. The obtained mixture was agitated at room temperature for 6 hours. When the reaction was terminated, the reaction solution was neutralized by adding 13.6 g (161 mmol) of sodium bicarbonate dissolved in 0.14 L of water. The resultant was extracted with dichloromethane (DCM) and treated with anhydrous MgSO₄ to remove moisture, and then, the residue was separated and purified through flash column chromatography, obtaining a compound I-16 (34 g, 73%).

HRMS (70 eV, EI+): m/z calcd for C21H15ClO: 318.0811, found: 318.1.

Elemental Analysis: C, 79%; H, 5%

Synthesis Example 17: Preparation of Intermediate I-17

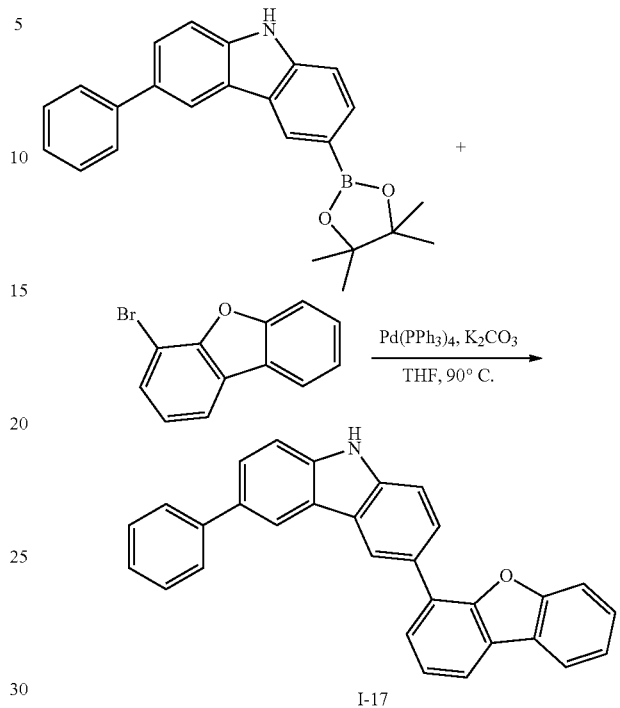

I-17

15 g (60.7 mmol) of 4-bromodibenzofuran was dissolved in 0.2 L of tetrahydrofuran (THF) in a nitrogen environment, 24.7 g (66.8 mmol) of 3-phenyl-6-(4,4,5,5-tetramethyl-1,3,2-dioxaborolan-2-yl)-9H-carbazole and 0.70 g (0.61 mmol) of tetrakis(triphenylphosphine)palladium were added thereto, and the mixture was agitated. 17.9 g (121 mmol) of potassium carbonate saturated in water was added thereto, and the mixture was heated and refluxed at 90° C. for 26 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound I-17 (22.6 g, 91%).

HRMS (70 eV, EI+): m/z calcd for C30H19NO: 409.1467, found: 409.1.

Elemental Analysis: C, 88%; H, 5%

Synthesis Example 18: Preparation of Intermediate I-18

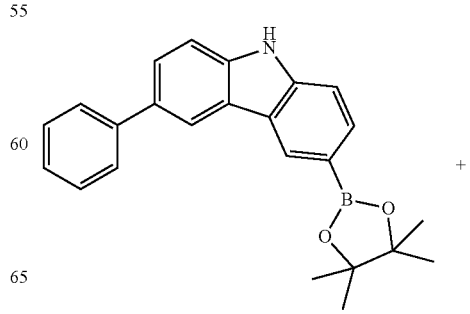

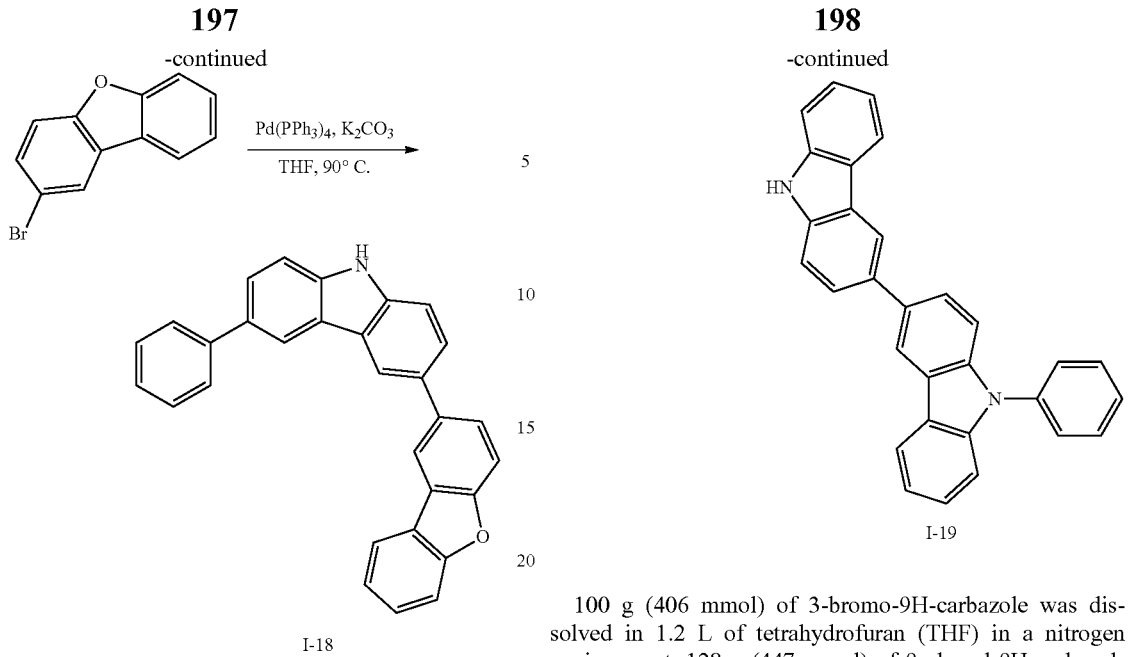

15 g (60.7 mmol) of 2-bromodibenzofuran was dissolved in 0.2 L of tetrahydrofuran (THF) in a nitrogen environment, 24.7 g (66.8 mmol) of 3-phenyl-6-(4,4,5,5-tetramethyl-1,3,2-dioxaborolan-2-yl)-9H-carbazole and 0.70 g (0.61 mmol) of tetrakis(triphenylphosphine)palladium were added thereto, and the mixture was agitated. 17.9 g (121 mmol) of potassium carbonate saturated in water was added thereto, and the mixture was heated and refluxed at 90° C. for 24 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound I-18 (22.4 g, 90%).

HRMS (70 eV, EI+): m/z calcd for C30H19NO: 409.1467, found: 409.1.

Elemental Analysis: C, 88%; H, 5%

Synthesis Example 19: Preparation of Intermediate I-19

100 g (406 mmol) of 3-bromo-9H-carbazole was dissolved in 1.2 L of tetrahydrofuran (THF) in a nitrogen environment, 128 g (447 mmol) of 9-phenyl-9H-carbazol-3-ylboronic acid and 4.69 g (4.06 mmol) of tetrakis(triphenylphosphine)palladium were added thereto, and the mixture was agitated. 120 g (812 mmol)) of potassium carbonate saturated in water was added thereto, and the mixture was heated and refluxed at 80° C. for 24 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound I-19 (74.6 g, 45%).

HRMS (70 eV, EI+): m/z calcd for C30H20N2: 408.1626, found: 408.2.

Elemental Analysis: C, 88%; H, 5%

Synthesis Example 20: Preparation of Intermediate I-20

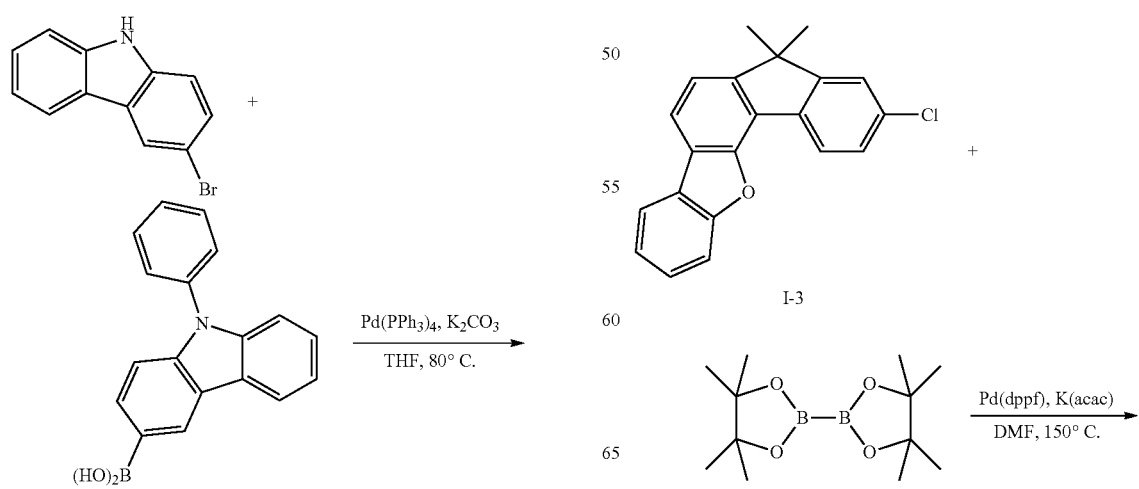

-continued

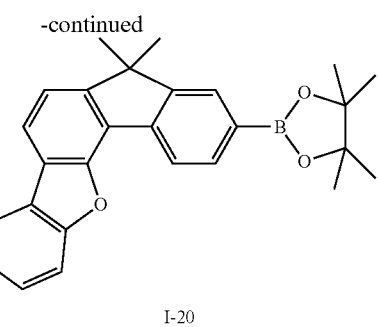

I-20

20 g (62.7 mmol) of the intermediate I-3 was dissolved in 0.2 L of dimethylformamide (DMF) in a nitrogen environment, 23.9 g (94.1 mmol) of bis(pinacolato)diboron and 1.54 g (1.88 mmol) of 1,1'-bis(diphenylphosphine)ferrocene)dichloropalladium (II) were added thereto, and the mixture was agitated at 150° C. for 24 hours. When the reaction was terminated, water was added to the reaction solution, and the mixture was filtered and dried in a vacuum oven. The obtained residue was separated and purified through flash column chromatography, obtaining a compound I-20 (14.1 g, 55%).

HRMS (70 eV, EI+): m/z calcd for C27H27BO3: 410.2053, found: 410.2.

Elemental Analysis: C, 79%; H, 7%

Synthesis Example 21: Preparation of Intermediate I-21

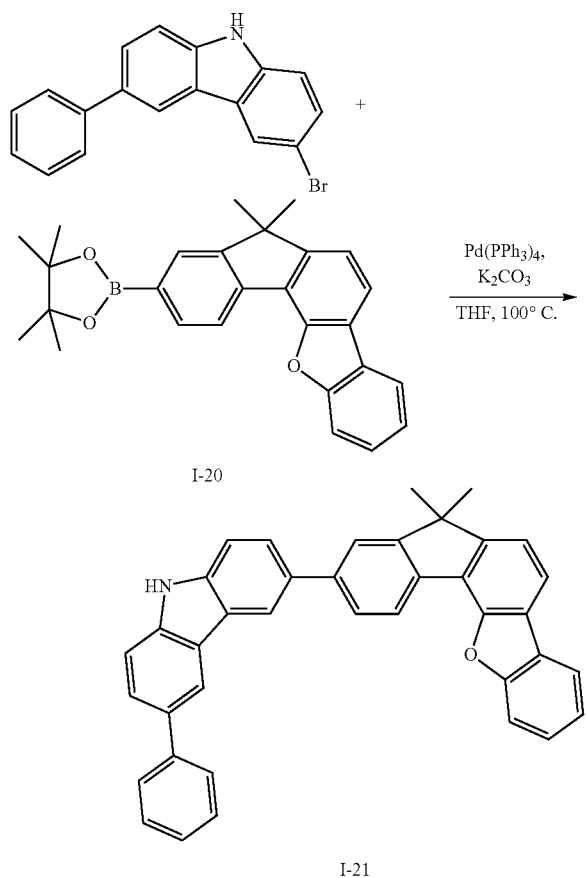

15 g (46.6 mmol) of 3-bromo-6-phenyl-9H-carbazole was dissolved in 0.2 L of tetrahydrofuran (THF) in a nitrogen environment, 21.0 g (51.3 mmol) of the intermediate I-20 and 0.54 g (0.47 mmol) of tetrakis(triphenylphosphine)palladium were added thereto, and the mixture was agitated. 13.7 g (93.2 mmol) of potassium carbonate saturated in water was added thereto, and the mixture was heated and refluxed at 100° C. for 94 hours. When the reaction was terminated, water was added to the reaction solution, and the mixture was extracted with dichloromethane (DCM) and treated with anhydrous MgSO4 to remove moisture and then, filtered and concentrated under a reduced pressure. The obtained residue was separated and purified through flash column chromatography, obtaining a compound I-21 (13.5 g, 55%).

HRMS (70 eV, EI+): m/z calcd for C39H27NO3: 525.2093, found: 525.2.

Elemental Analysis: C, 89%; H, 5%

Synthesis Example 22: Preparation of Intermediate I-22

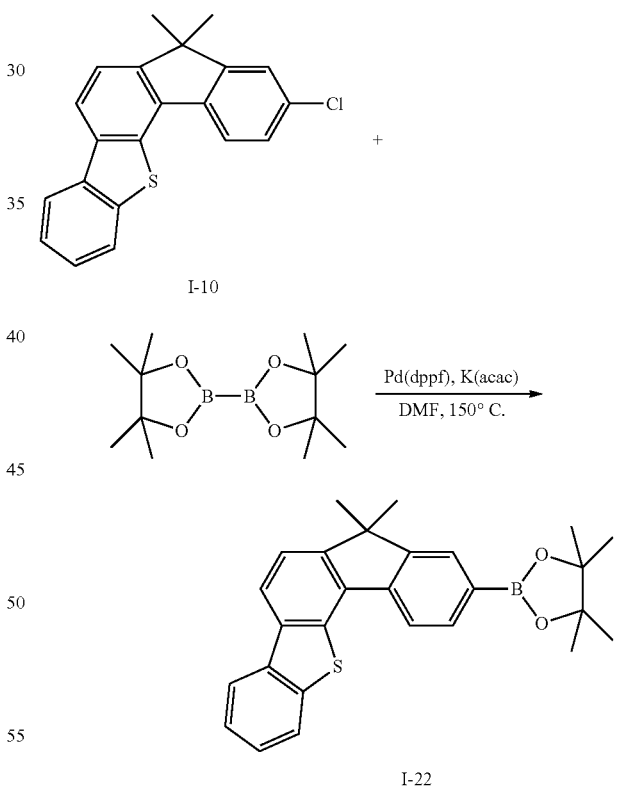

50 g (149 mmol) of the intermediate I-10 was dissolved in 0.5 L of dimethyl formamide (DMF) in a nitrogen environment, 56.9 g (224 mmol) of bis(pinacolato)diboron, 3.65 g (4.47 mmol) of 1,1'-bis(diphenylphosphine)ferrocene)dichloropalladium (II), and 29.2 g, 298 mmol of potassium acetate were added thereto, and the mixture was agitated at 150° C. for 22 hours. When the reaction was terminated, water was added to the reaction solution, and the mixture was filtered and dried in a vacuum oven. The obtained residue was separated and purified through flash column chromatography, obtaining a compound I-22 (34.3 g, 54%).

HRMS (70 eV, EI+): m/z calcd for C27H27BO2S: 426.1825, found: 426.2.

Elemental Analysis: C, 76%; H, 6%

Synthesis Example 23: Preparation of Intermediate I-23

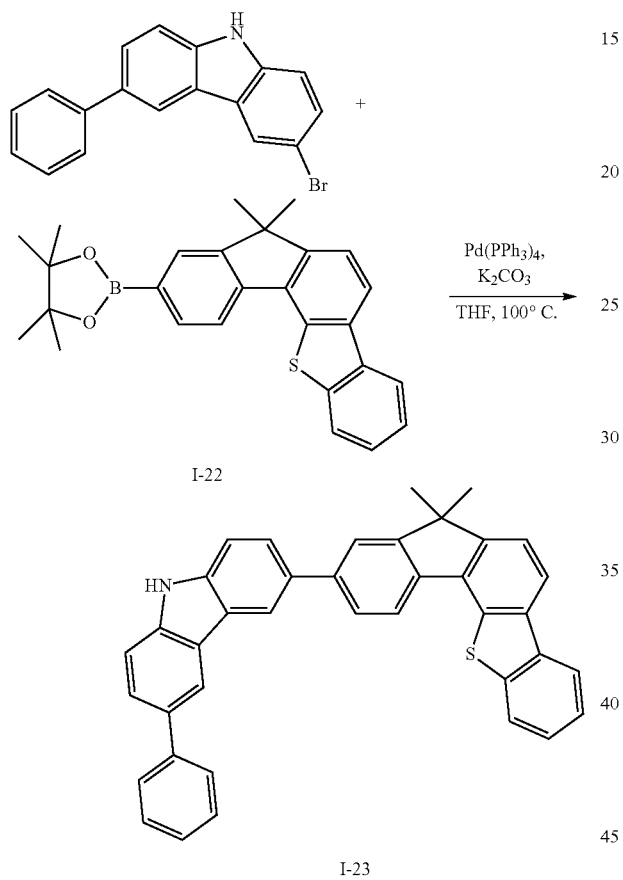

I-22

I-23

Synthesis Example 24: Preparation of Intermediate I-24

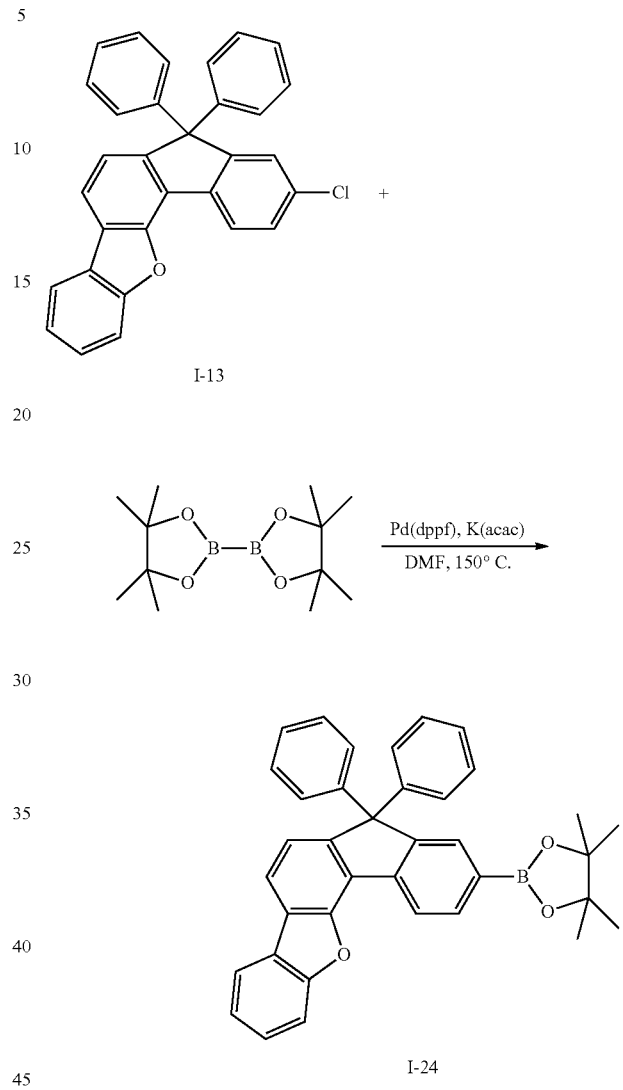

I-13

I-24

15 g (46.6 mmol) of 3-bromo-6-phenyl-9H-carbazole was dissolved in 0.2 L of tetrahydrofuran (THF) in a nitrogen environment, 21.9 g (51.3 mmol) of the intermediate I-22 and 0.54 g (0.47 mmol) of tetrakis(triphenylphosphine) palladium were added thereto, and the mixture was agitated. 13.7 g (93.2 mmol) of potassium carbonate saturated in water was added thereto, and the mixture was heated and refluxed at 100° C. for 82 hours. When the reaction was terminated, water was added to the reaction solution, and the mixture was extracted with dichloromethane (DCM) and treated with anhydrous MgSO4 to remove moisture and then, filtered and concentrated under a reduced pressure. The obtained residue was separated and purified through flash column chromatography, obtaining a compound I-23 (12.1 g, 48%).

HRMS (70 eV, EI+): m/z calcd for C39H27NS: 541.1864, found: 541.2.

Elemental Analysis: C, 86%; H, 5%

20 g (45.2 mmol) of the intermediate I-13 was dissolved in 0.2 L of dimethyl formamide (DMF) in a nitrogen environment, 17.2 g of 67.7 mmol of bis(pinacolato)diboron, 1.11 g of 1.36 mmol) of 1,1'-bis(diphenylphosphine) ferrocene)dichloropalladium (II), and 8.87 g (90.4 mmol) of potassium acetate were added thereto, and the mixture was hated and refluxed at 150° C. for 29 hours. When the reaction was terminated, water was added to the reaction solution, and the mixture was filtered and then, dried in a vacuum oven. The obtained residue was separated and purified through flash column chromatography, obtaining a compound I-24 (12.8 g, 53%).

HRMS (70 eV, EI+): m/z calcd for C37H31BO3: 534.2366, found: 534.2.

Elemental Analysis: C, 83%; H, 6%

Synthesis Example 25: Preparation of Intermediate I-25

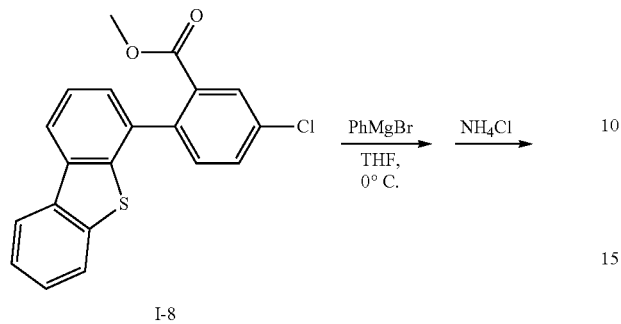

I-8

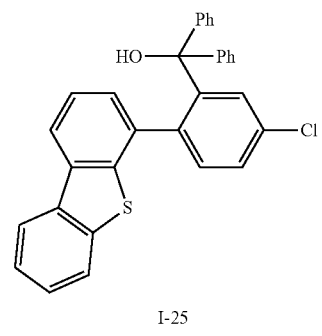

I-25

50 g (142 mmol) of the intermediate I-8 was dissolved in 0.5 L of tetrahydrofuran (THF) in a nitrogen environment, and the solution was cooled down to 0° C. 0.12 L (355 mmol) of 3.0 M phenylmagnesium bromide dissolved in diethyl ether was slowly added thereto over one hour in a dropwise fashion. The obtained mixture was agitated at room temperature for 12 hours. When the reaction was terminated, the reaction solution was neutralized by adding 22.8 g (426 mmol) of ammonium chloride dissolved in 0.14 L of water. The resultant was extracted with dichloromethane (DCM) and treated with anhydrous MgSO$_4$ to remove moisture and then, filtered and concentrated under a reduced pressure. An intermediate I-25 was obtained (67.7 g, 100%).

HRMS (70 eV, EI+): m/z calcd for C31H21ClSO: 476.1002, found: 476.1.

Elemental Analysis: C, 78%; H, 4%

Synthesis Example 26: Preparation of Intermediate I-26

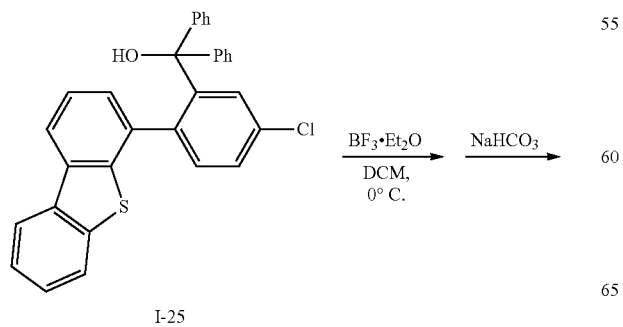

I-25

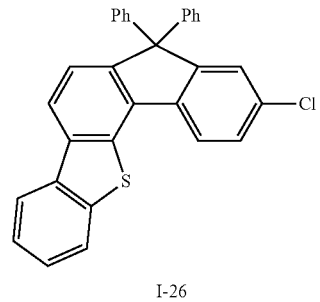

I-26

67.7 g (142 mmol) of the intermediate I-25 was dissolved in 0.3 L of tetrahydrofuran (THF) in a nitrogen environment, and the solution was cooled down to 0° C. 22.2 g (156 mmol) of boron trifluoride dissolved in diethyl ether was slowly added thereto over one hour in a dropwise fashion. The obtained mixture was agitated at room temperature for 6 hours. When the reaction was terminated, the reaction solution was neutralized by adding 13.1 g (156 mmol) of sodium bicarbonate dissolved in 0.14 L of water. The resultant was extracted with dichloromethane (DCM) and treated with anhydrous MgSO$_4$ to remove moisture, and then, the residue was separated and purified through flash colummatography, obtaining a compound I-26 (53.4 g, 82%).

HRMS (70 eV, EI+): m/z calcd for C31H19ClS: 458.0896, found: 458.1.

Elemental Analysis: C, 81%; H, 4%

Synthesis Example 27: Preparation of Intermediate I-27

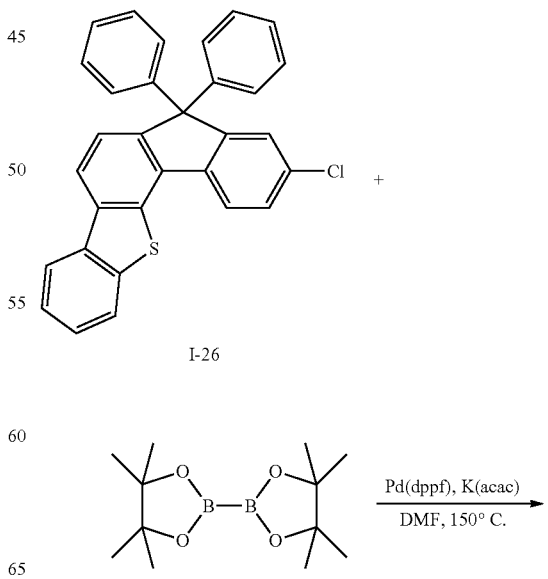

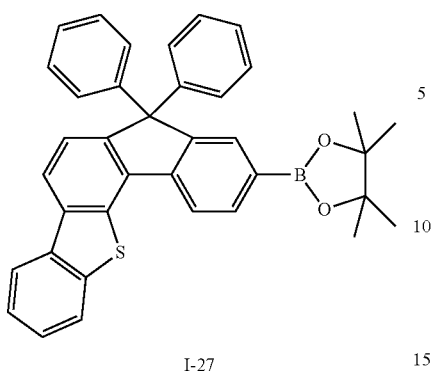

I-27

51 g (109 mmol) of the intermediate I-26 was dissolved in 0.5 L of dimethyl formamide (DMF) in a nitrogen environment, 41.5 g (163 mmol) of bis(pinacolato)diboron, 2.67 g (3.27 mmol) of 1,1'-bis(diphenylphosphine)ferrocene)dichloropalladium (II) and 21.4 g (218 mmol) of potassium acetate were added thereto, and the mixture was heated and refluxed at 150° C. for 23 hours. When the reaction was terminated, water was added to the reaction solution, and the mixture was filtered and then, dried in an vacuum oven 0-||에서-|. The obtained residue was separated and purified through flash column chromatography, obtaining a compound I-27 (31.2 g, 52%).

HRMS (70 eV, EI+): m/z calcd for C37H31BO2S: 550.2138, found: 550.2.

Elemental Analysis: C, 81%; H, 6%

Synthesis Example 28: Preparation of Intermediate I-28

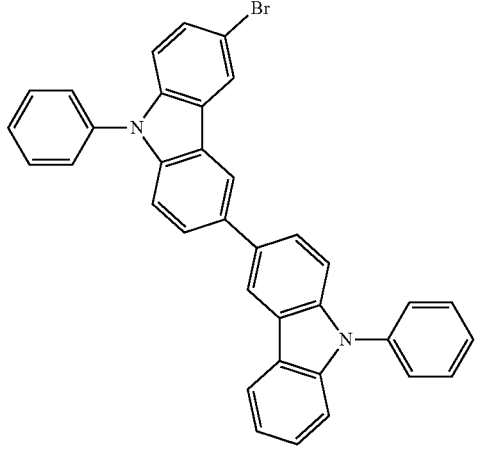

I-28

100 g (348 mmol) of 9-phenyl-9H-carbazol-3-ylboronic acid was dissolved in 1.3 L of tetrahydrofuran (THF) in a nitrogen environment, 168 g (418 mmol) of 3,6-dibromo-9-phenyl-9H-carbazole and 4.02 g, 3.48 mmol) of tetrakis (triphenylphosphine)palladium were added thereto, and the mixture was agitated. 102 g (696 mmol) of potassium carbonate saturated in water was added thereto, and the mixture was heated and refluxed at 80° C. for 16 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound I-28 (62.8 g, 32%).

HRMS (70 eV, EI+): m/z calcd for C36H23BrN2: 562.1045, found: 562.1.

Elemental Analysis: C, 77%; H, 4%

Synthesis Example 29: Preparation of Intermediate I-29

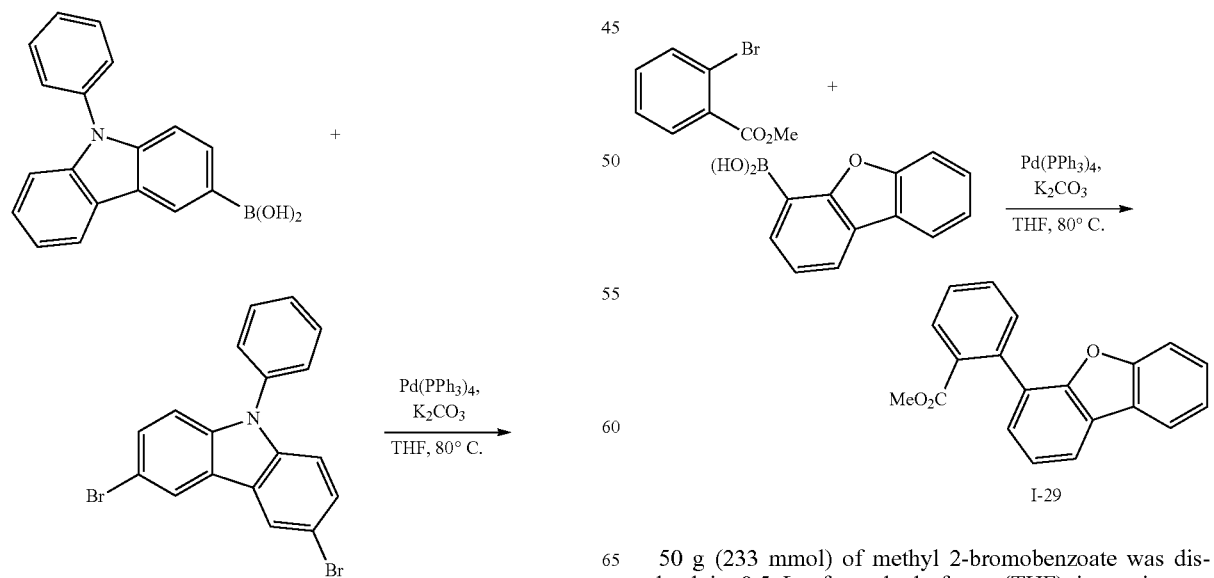

I-29

50 g (233 mmol) of methyl 2-bromobenzoate was dissolved in 0.5 L of tetrahydrofuran (THF) in a nitrogen environment, 54.3 g (256 mmol) of dibenzofuran-4-ylboronic acid and 2.69 g (2.33 mmol) of tetrakis(triphenylphosphine)palladium were added thereto, and the mixture was agitated. 59 g (401 mmol) of potassium carbonate saturated in water was added thereto, and the mixture was heated and refluxed at 80° C. for 27 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound I-29 (54.9 g, 78%).

HRMS (70 eV, EI+): m/z calcd for C20H14O3: 302.0943, found: 302.1.

Elemental Analysis: C, 79%; H, 5%

Synthesis Example 30: Preparation of Intermediate I-30

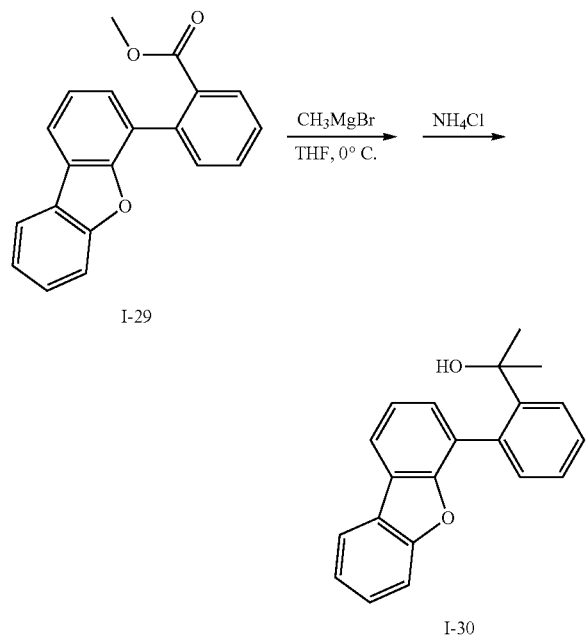

54.9 g (182 mmol) of the intermediate I-29 was dissolved in 0.5 L of tetrahydrofuran (THF) in a nitrogen environment, and the solution was cooled down to 0° C. 0.15 L (454 mmol) of 3.0 M methymagnesium bromide dissolved in diethyl ether was slowly added thereto over one hour in a dropwise fashion. The obtained mixture was agitated at room temperature for 17 hours. When the reaction was terminated, the reaction solution was neutralized by adding 29.2 g (546 mmol) of ammonium chloride dissolved in 0.15 L of water. The resultant was extracted with dichloromethane (DCM) and treated with anhydrous $MgSO_4$ to remove moisture and then, filtered and concentrated under a reduced pressure. An intermediate I-30 was obtained (55.6 g, 101%).

HRMS (70 eV, EI+): m/z calcd for C21H18O2: 302.1307, found: 302.1.

Elemental Analysis: C, 83%; H, 6%

Synthesis Example 31: Preparation of Intermediate I-31

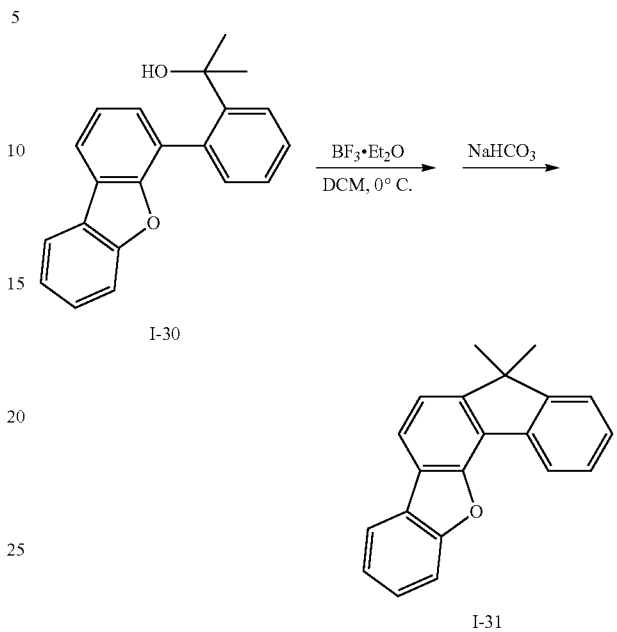

55.6 g (184 mmol) of the intermediate I-30 was dissolved in 0.3 L of dichloromethane (DCM) in a nitrogen environment, and the solution was cooled down to 0° C. 28.7 g (202 mmol) of boron trifluoride dissolved in diethyl ether was slowly added thereto over one hour in a dropwise fashion. The obtained mixture was agitated at room temperature for 5 hours. When the reaction was terminated, the reaction solution was neutralized by adding 17.0 g (202 mmol) of sodium bicarbonate dissolved in 0.1 L of water. The resultant was extracted with dichloromethane (DCM) and treated with anhydrous $MgSO_4$ to remove moisture, and then, the residue was separated and purified through flash column chromatography, obtaining a compound I-31 (37.7 g, 72%).

HRMS (70 eV, EI+): m/z calcd for C21H16O: 284.1201, found: 284.1.

Elemental Analysis: C, 89%; H, 6%

Synthesis Example 32: Preparation of Intermediate I-32

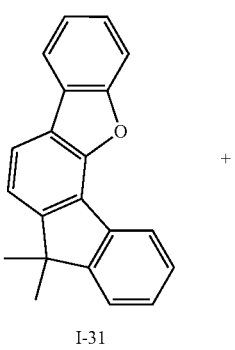

+

-continued

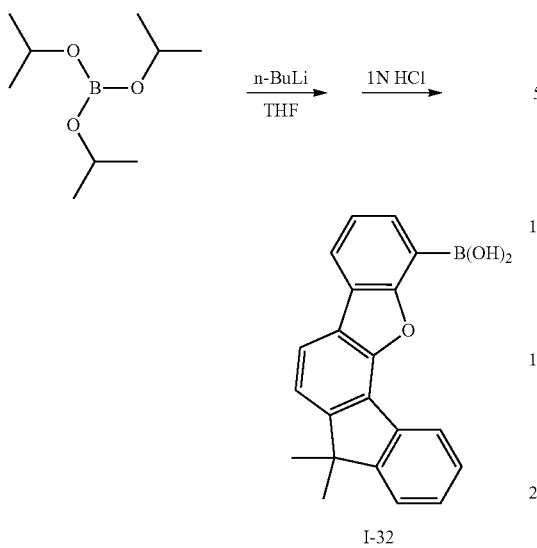

I-32

37.7 g (133 mmol) of the intermediate I-31 was dissolved in 0.3 L of tetrahydrofuran (THF) in a nitrogen environment, and the solution was cooled down to −78° C. 80 mL (200 mmol) of 2.5 M n-BuLi dissolved in hexane ether was slowly added thereto over 10 minutes in a dropwise fashion. The obtained mixture was agitated at room temperature for 16 hours. When the reaction was terminated, the reaction solution was neutralized by adding 200 mL (200 mmol) of was 1N HCl thereto. The resultant was extracted with ethylacetate (EA) and treated with anhydrous MgSO$_4$ to remove moisture, and then, the residue was washed with hexane and dichloromethane (DCM) to remove impurities, obtaining a compound I-32 (34.5 g, 79%).

HRMS (70 eV, EI+): m/z calcd for C21H17BO3: 328.1271, found: 328.1.

Elemental Analysis: C, 77%; H, 5%

Synthesis Example 33: Preparation of Intermediate I-33

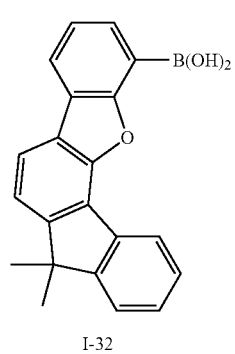

I-32

+

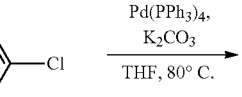

Pd(PPh$_3$)$_4$,
K$_2$CO$_3$
―――――→
THF, 80° C.

-continued

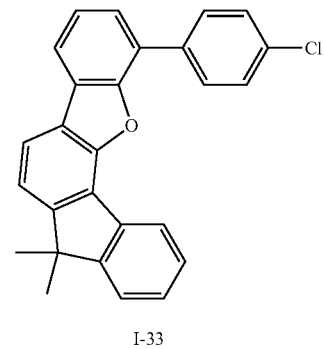

I-33

34.5 g (105 mmol) of the intermediate I-32 was dissolved in 0.3 L of tetrahydrofuran (THF) in a nitrogen environment, 20.1 g (105 mmol) of 1-bromo-4-chlorobenzene and 1.21 g (1.05 mmol) of tetrakis(triphenylphosphine)palladium were added thereto, and the mixture was agitated. 30.9 g (210 mmol) of potassium carbonate saturated in water was added thereto, and the mixture was heated and refluxed at 80° C. for 23 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound I-33 (33.2 g, 80%).

HRMS (70 eV, EI+): m/z calcd for C27H19ClO: 394.1124, found: 394.1.

Elemental Analysis: C, 82%; H, 5%

Synthesis Example 34: Preparation of Intermediate I-34

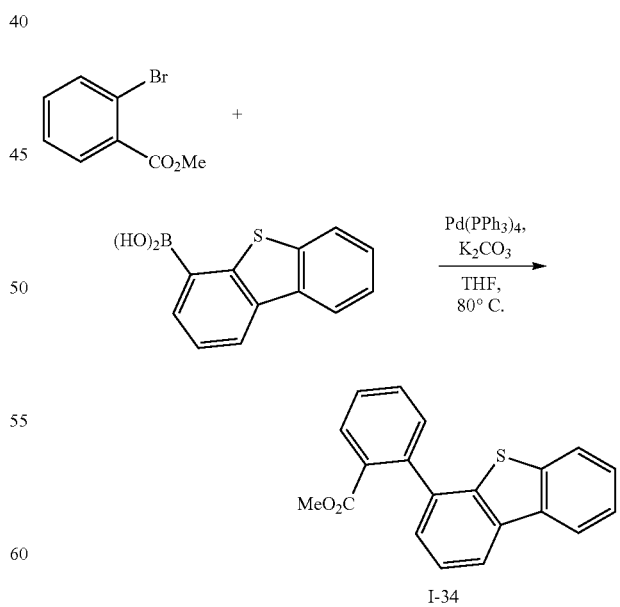

I-34

50 g (233 mmol) of methyl 2-bromobenzoate was dissolved in 0.3 L of tetrahydrofuran (THF) in a nitrogen environment, 58.4 g (256 mmol) of dibenzothiophene-4-ylboronic acid and 2.69 g (2.33 mmol) of tetrakis(triphenylphosphine)palladium were added thereto, and the mixture was agitated. 68.6 g (466 mmol) of potassium carbonate saturated in water was added thereto, and the mixture was heated and refluxed at 80° C. for 23 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound I-34 (69.7 g, 94%).

HRMS (70 eV, EI+): m/z calcd for C20H14O2S: 318.0715, found: 318.1.

Elemental Analysis: C, 75%; H, 4%

Synthesis Example 35: Preparation of Intermediate I-35

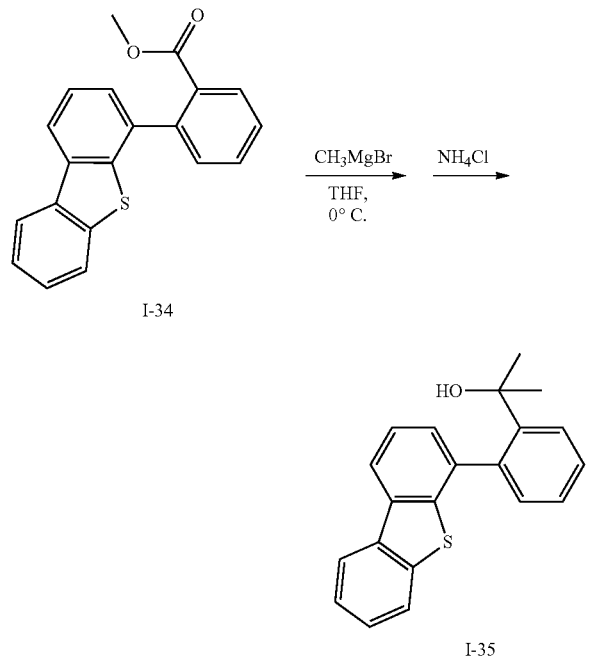

69.7 g (219 mmol) of the intermediate I-34 was dissolved in 0.7 L of tetrahydrofuran (THF) in a nitrogen environment, and the solution was cooled down to 0° C. 0.18 L (547 mmol) of 3.0 M methymagnesium bromide dissolved in diethyl ether was slowly added thereto over one hour in a dropwise fashion. The obtained mixture was agitated at room temperature for 8 hours. When the reaction was terminated, the reaction solution was neutralized by adding 35.1 g (657 mmol) of ammonium chloride dissolved in 0.18 L of water thereto. The resultant was extracted with dichloromethane (DCM) and treated with anhydrous MgSO₄ to remove moisture and then, filtered and concentrated under a reduced pressure. An intermediate I-35 was obtained (69.7 g, 100%).

HRMS (70 eV, EI+): m/z calcd for C21H18OS: 318.1078, found: 318.1.

Elemental Analysis: C, 79%; H, 6%

Synthesis Example 36: Preparation of Intermediate I-36

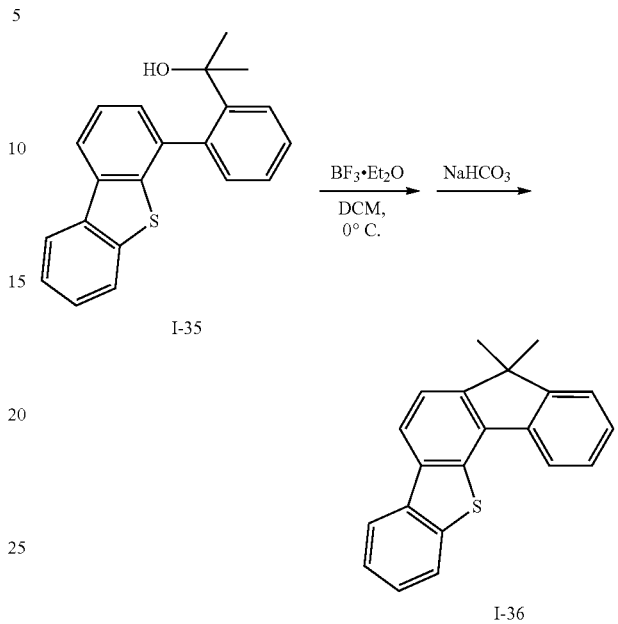

69.7 g (219 mmol) of the intermediate I-35 was dissolved in 0.35 L of dichloromethane (DCM) in a nitrogen environment, and the solution was cooled down to 0° C. 34.2 g (241 mmol) of boron trifluoride dissolved in diethyl ether was slowly added thereto over one hour in a dropwise fashion. The obtained mixture was agitated at room temperature for 6 hours. When the reaction was terminated, the reaction solution was neutralized by adding 20.2 g (241 mmol) of sodium bicarbonate dissolved in 0.1 L of water thereto. The resultant was extracted with dichloromethane (DCM) and treated with anhydrous MgSO₄ to remove moisture, and then, the residue was separated and purified through flash column chromatography, obtaining a compound I-36 (52.6 g, 80%).

HRMS (70 eV, EI+): m/z calcd for C21H16S: 300.0973, found: 300.1.

Elemental Analysis: C, 84%; H, 5%

Synthesis Example 37: Preparation of Intermediate I-37

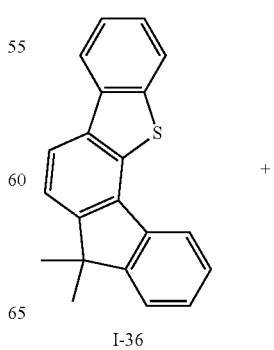

213
-continued

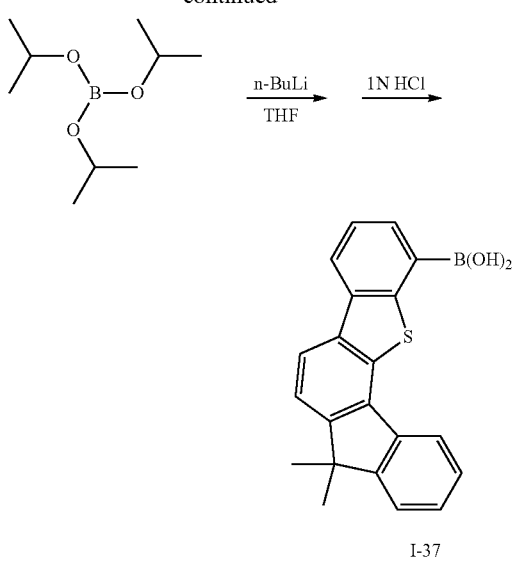

I-37

52.6 g (175 mmol) of the intermediate I-36 was dissolved in 0.5 L of tetrahydrofuran (THF) in a nitrogen environment, and the solution was cooled down to −78° C. 105 mL (263 mmol) of 2.5 M n-BuLi dissolved in hexane was slowly added thereto over 10 minutes in a dropwise fashion. The obtained mixture was agitated at room temperature for 12 hours. When the reaction was terminated, the reaction solution was neutralized by adding 263 mL (263 mmol) of water 1N HCl thereto. The resultant was extracted with ethylacetate (EA) and treated with anhydrous MgSO$_4$ to remove moisture, and then, the residue was washed with hexane and dichloromethane (DCM) to remove impurities, obtaining a compound I-37 (53.6 g, 89%)

HRMS (70 eV, EI+): m/z calcd for C21H17BO2S: 344.1042, found: 300.1.

Elemental Analysis: C, 73%; H, 5%

Synthesis Example 38: Preparation of Intermediate I-38

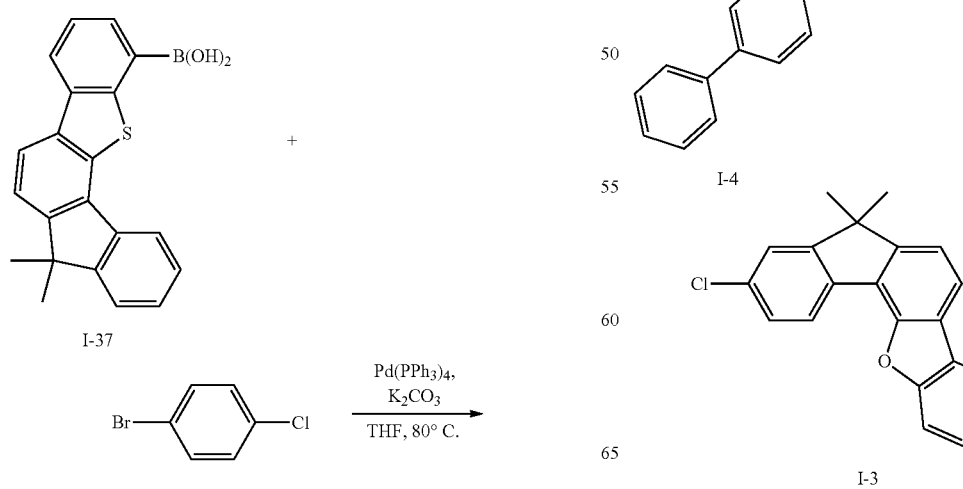

214
-continued

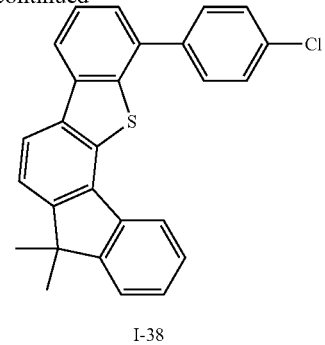

I-38

53.6 g (156 mmol) of the intermediate I-37 was dissolved in 0.3 L of tetrahydrofuran (THF) in a nitrogen environment, 29.8 g (156 mmol) of 1-bromo-4-chlorobenzene and 1.80 g (1.56 mmol) of tetrakis(triphenylphosphine)palladium were added thereto, and the mixture was agitated. 45.9 g (312 mmol) of potassium carbonate saturated in water was added thereto, and the mixture was heated and refluxed at 80° C. for 21 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound I-38 (58.3 g, 91%).

HRMS (70 eV, EI+): m/z calcd for C27H19ClS: 410.0896, found: 410.1.

Elemental Analysis: C, 79%; H, 5%

Example 1: Preparation of Compound A-1

215
-continued

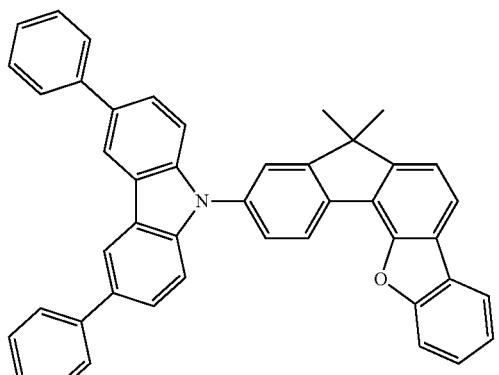

A-1

11 g (34.4 mmol) of the intermediate I-4 was dissolved in 0.11 L of toluene in a nitrogen environment, intermediate I-3 (11.5 g, 36.2 mmol), 0.95 g (1.03 mmol) of tris(dibenzylideneacetone)dipalladium (0), 0.83 g (4.12 mmol) of tris-tert butylphosphine and 3.97 g (41.3 mmol) of sodium tertiarybutoxide were sequentially added thereto, and the mixture was heated and refluxed at 100° C. for 16 hours. When the reaction was terminated, water was added to the reaction solution, and the mixture was extracted with dichloromethane (DCM) and treated with anhydrous MgSO₄ to remove moisture and then, filtered and concentrated under a reduced pressure.

The obtained residue was separated and purified through flash column chromatography, obtaining a compound A-1 (14.5 g, 70%).

HRMS (70 eV, EI+): m/z calcd for C45H31NO: 601.2406, found: 602.2.

Elemental Analysis: C, 90%; H, 5%

Example 2: Preparation of Compound A-5

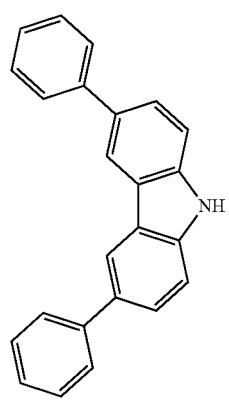

I-4

216
-continued

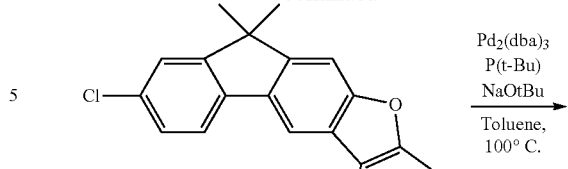

I-7

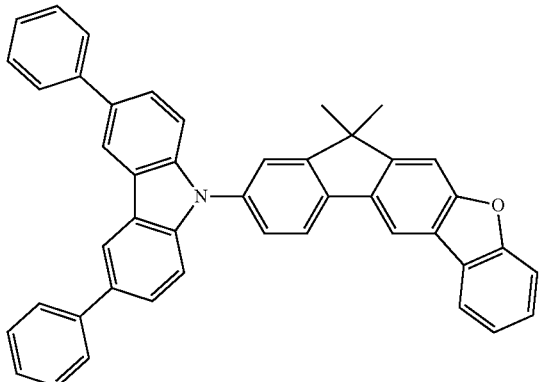

A-5

10 g (31.3 mmol) of the intermediate I-4 was dissolved in 0.1 L of toluene in a nitrogen environment, 10.5 g (32.9 mmol) of the intermediate I-7, 0.86 g (0.94 mmol) of tris(dibenzylideneacetone)dipalladium (0), 0.76 g (3.76 mmol) of tris-tertiarybutylphosphine, and 3.61 g (37.6 mmol) of sodium tertiarybutoxide were sequentially added thereto, and the mixture was heated and refluxed at 100° C. for 12 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound A-5 (16.6 g, 88%).

HRMS (70 eV, EI+): m/z calcd for C45H31NO: 601.2406, found: 601.2.

Elemental Analysis: C, 90%; H, 5%

Example 3: Preparation of Compound A-7

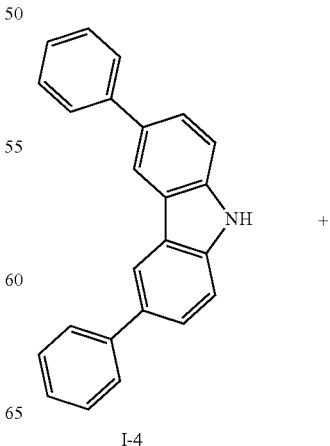

I-4

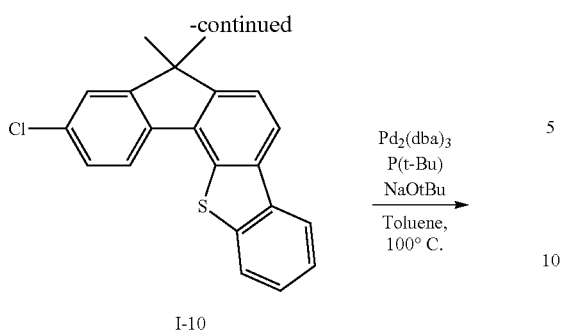

I-10

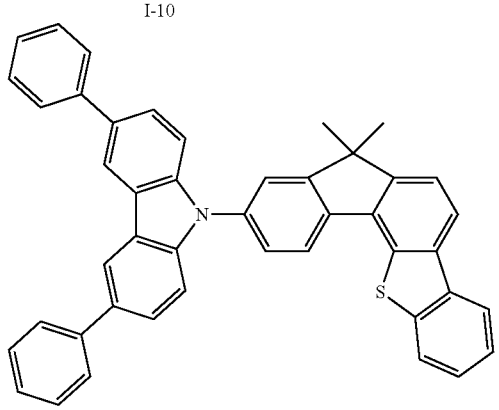

A-7

10 g (31.3 mmol) of the intermediate I-4 was dissolved in 0.1 L of toluene in a nitrogen environment, 0.86 g (0.94 mmol) of tris(dibenzylideneacetone)dipalladium (0), 0.76 g (3.76 mmol) of tris-tertiarybutylphosphine, and 3.61 g (37.6 mmol) of sodium tertiarybutoxide were sequentially added thereto, and the mixture was heated and refluxed at 100° C. for 6 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound A-7 (15.9 g, 82%).

HRMS (70 eV, EI+): m/z calcd for C45H31NS: 617.2177, found: 617.2.

Elemental Analysis: C, 87%; H, 5%

Example 4: Preparation of Compound A-13

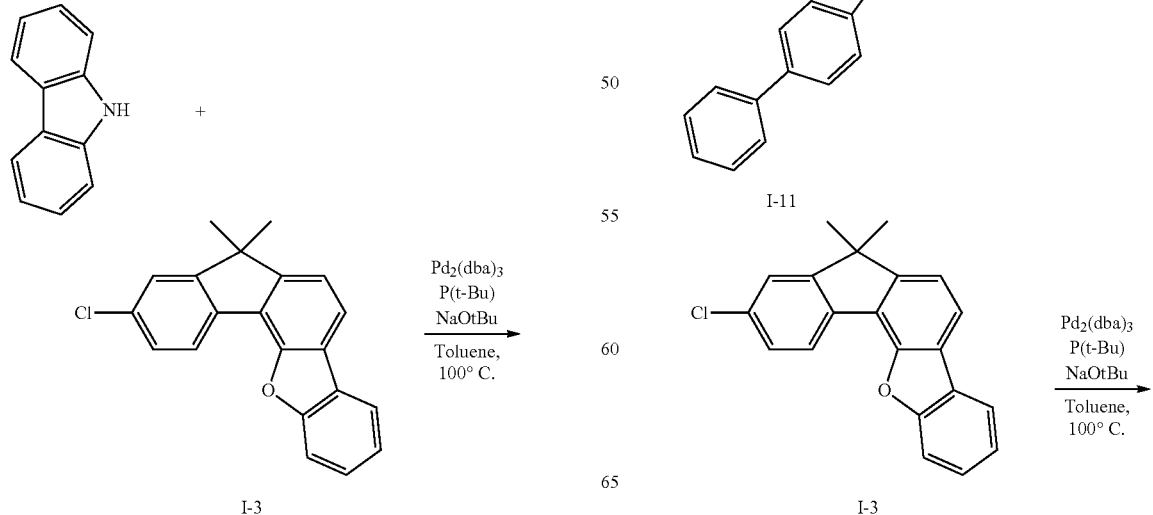

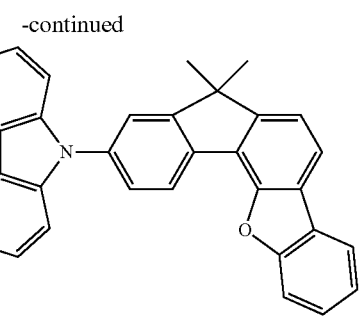

A-13

10 g (59.8 mmol) of the intermediate 9H-carbazole was dissolved in 0.15 L of toluene in a nitrogen environment, 20.0 g (62.8 mmol) of the intermediate I-3, 1.64 g (1.79 mmol) of tris(dibenzylideneacetone)dipalladium (0), 1.45 g (7.18 mmol) of tris-tertiarybutylphosphine, and 6.90 g (71.8 mmol) of sodium tertiarybutoxide were sequentially added thereto, and the mixture was heated and refluxed at 100° C. for 15 hours. When the reaction was terminated, water was added to the reaction solution, and the mixture was extracted with dichloromethane (DCM) and treated with anhydrous MgSO₄ to remove moisture and then, filtered and concentrated under a reduced pressure.

The obtained residue was separated and purified through flash column chromatography, obtaining a compound A-13 (22.6 g, 85%).

HRMS (70 eV, EI+): m/z calcd for C33H23NO: 449.1780, found: 449.2.

Elemental Analysis: C, 88%; H, 5%

Example 5: Preparation of Compound A-73

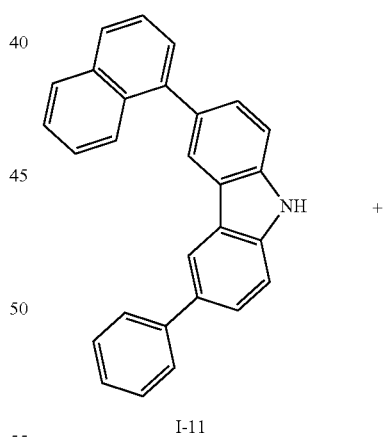

I-11

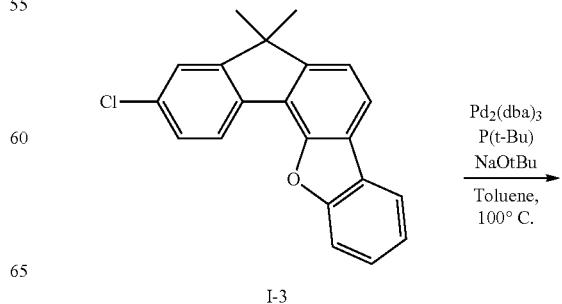

I-3

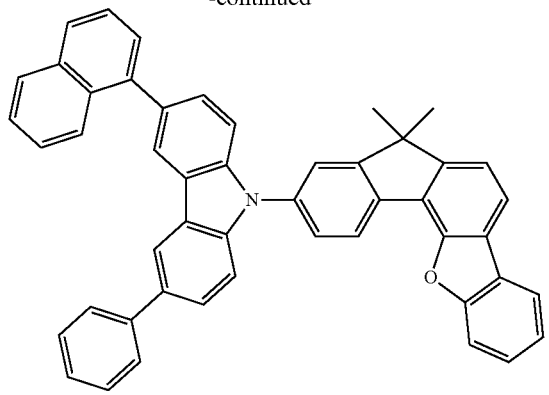

A-73

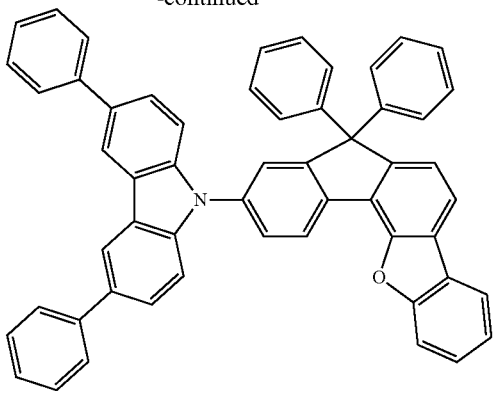

A-88

7 g (19.0 mmol) of the intermediate I-11 was dissolved in 0.07 L of toluene in a nitrogen environment, 6.32 g (19.9 mmol) of the intermediate I-3, 0.52 g (0.57 mmol) of tris(dibenzylideneacetone)dipalladium (0), 0.46 g (2.27 mmol) of tris-tertiarybutylphosphine, and 2.18 g (22.7 mmol) of sodium tertiarybutoxide were sequentially added thereto, and the mixture was heated and refluxed at 100° C. for 90 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound A-73 (9.5 g, 77%).

HRMS (70 eV, EI+): m/z calcd for C49H33NO: 651.2562, found: 651.3.

Elemental Analysis: C, 90%; H, 5%

10 g (31.3 mmol) of the intermediate I-4 was dissolved in 0.1 L of toluene in a nitrogen environment, 14.6 g (32.9 mmol) of the intermediate I-13, 0.86 g (0.94 mmol) of tris(dibenzylideneacetone)dipalladium (0), 0.76 g (3.76 mmol) of tris-tertiarybutylphosphine and 3.61 g (37.6 mmol) of sodium tertiarybutoxide were sequentially added thereto, and the mixture was heated and refluxed at 100° C. for 12 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound A-88 (21.6 g, 95%).

HRMS (70 eV, EI+): m/z calcd for C55H35NO: 725.2719, found: 725.3.

Elemental Analysis: C, 91%; H, 5%

Example 6: Preparation of Compound A-88

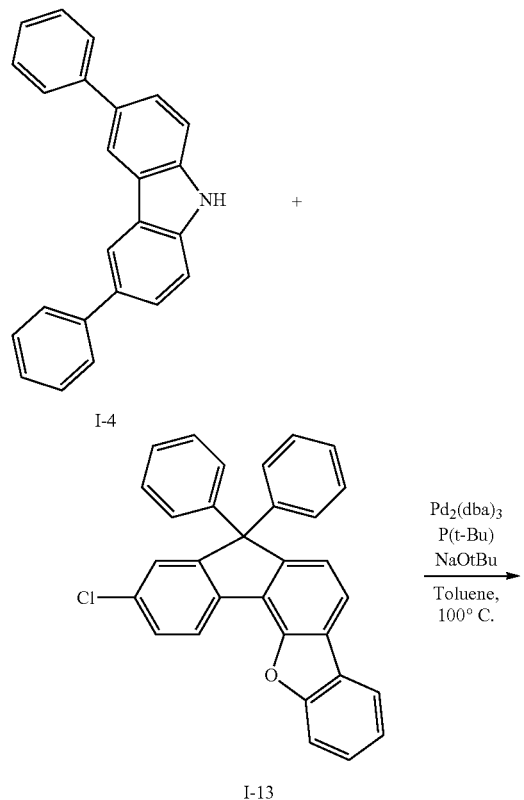

Example 7: Preparation of Compound A-124

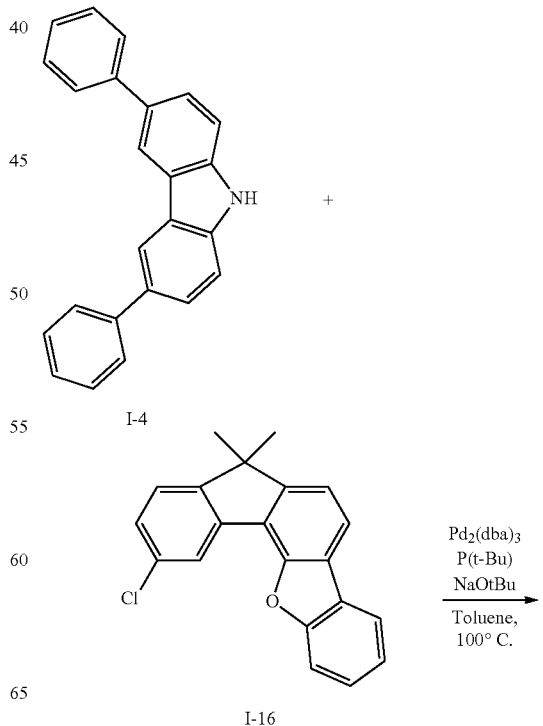

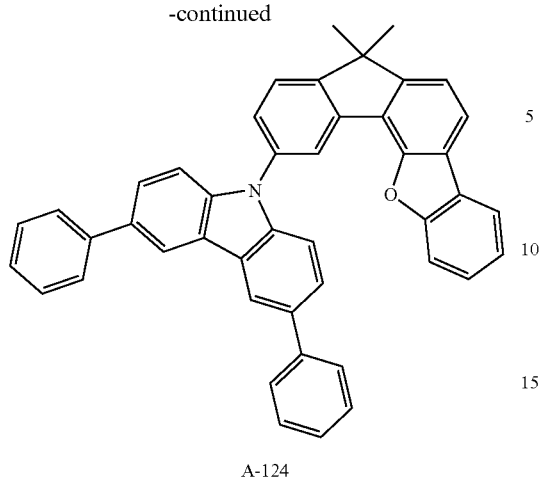

A-124

10 g (31.3 mmol) of the intermediate I-4 was dissolved in 0.1 L of toluene in a nitrogen environment, 10.5 g (32.9 mmol) of the intermediate I-16, 0.86 g (0.94 mmol) of tris(dibenzylideneacetone)dipalladium (0), 0.76 g (3.76 mmol) of tris-tertiarybutylphosphine, and 3.61 g (37.6 mmol) of sodium tertiarybutoxide were sequentially added thereto, and the mixture was heated and refluxed at 100° C. for 24 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound A-124 (17.0 g, 90%).

HRMS (70 eV, EI+): m/z calcd for C45H31NO: 601.2406, found: 601.2.

Elemental Analysis: C, 90%; H, 5%

Example 8: Preparation of Compound B-14

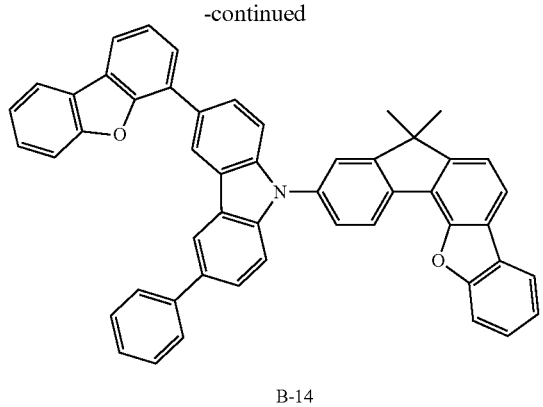

B-14

10 g (24.4 mmol) of the intermediate I-17 was dissolved in 0.09 L of toluene in a nitrogen environment, 8.17 g (25.6 mmol) of the intermediate I-3, 0.67 g (0.73 mmol) of tris(dibenzylideneacetone)dipalladium (0), 0.59 g (2.93 mmol) of tris-tertiarybutylphosphine, and 2.81 g (29.3 mmol) of sodium tertiarybutoxide were sequentially added thereto, and the mixture was heated and refluxed at 100° C. for 48 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound B-14 (16.9 g, 81%).

HRMS (70 eV, EI+): m/z calcd for C51H33NO2: 691.2511, found: 691.3.

Elemental Analysis: C, 89%; H, 5%

Example 9: Preparation of Compound B-20

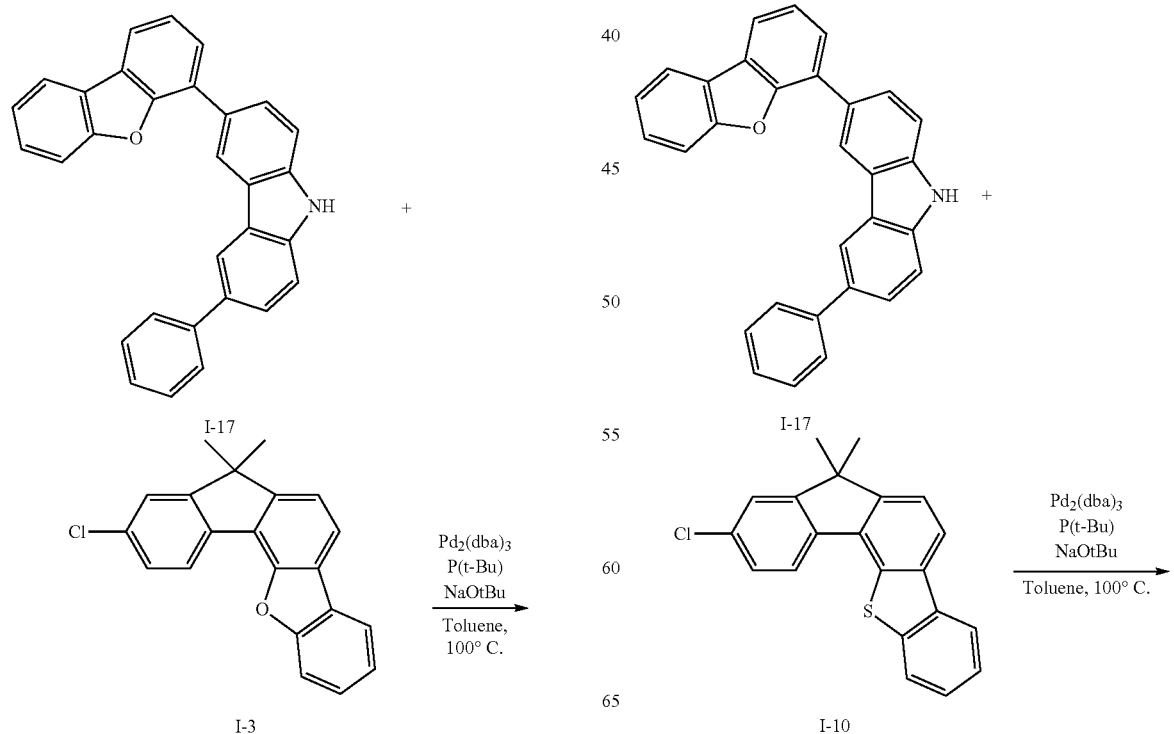

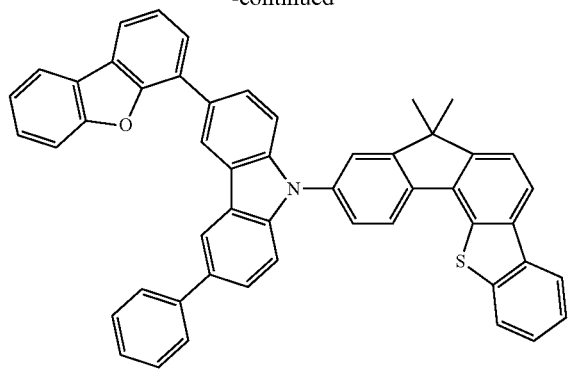

B-20

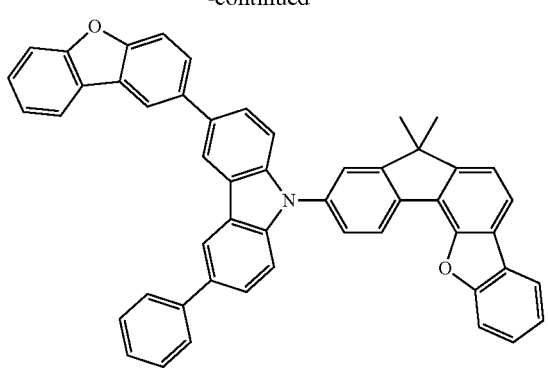

B-26

10 g (24.4 mmol) of the intermediate I-17 was dissolved in 0.09 L of toluene in a nitrogen environment, 8.57 g (25.6 mmol) of the intermediate I-10, 0.67 g (0.73 mmol) of tris(dibenzylideneacetone)dipalladium (0), 0.59 g (2.93 mmol) of tris-tertiarybutylphosphine, and 2.81 g (29.3 mmol) of sodium tertiarybutoxide were sequentially added thereto, and the mixture was heated and refluxed at 100° C. for 35 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound B-20 (17.3 g, 96%).

HRMS (70 eV, EI+): m/z calcd for C51H33NOS: 707.2283, found: 707.2.

Elemental Analysis: C, 87%; H, 5%

Example 10: Preparation of Compound B-26

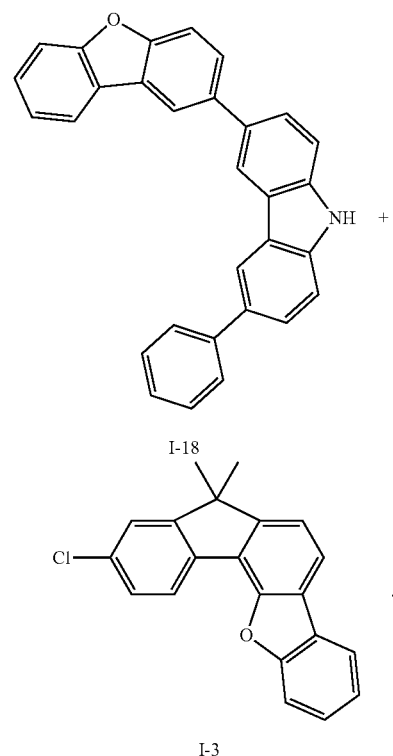

10 g (24.4 mmol) of the intermediate I-18 was dissolved in 0.09 L of toluene in a nitrogen environment, 8.17 g (25.6 mmol) of the intermediate I-3, 0.67 g (0.73 mmol) of tris(dibenzylideneacetone)dipalladium (0), 0.59 g (2.93 mmol) of tris-tertiarybutylphosphine, and 2.81 g (29.3 mmol) of sodium tertiarybutoxide were sequentially added thereto, and the mixture was heated and refluxed at 100° C. for 35 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound B-26 (13.2 g, 78%).

HRMS (70 eV, EI+): m/z calcd for C51H33NO2: 691.2511, found: 691.3.

Elemental Analysis: C, 89%; H, 5%

Example 11: Preparation of Compound B-32

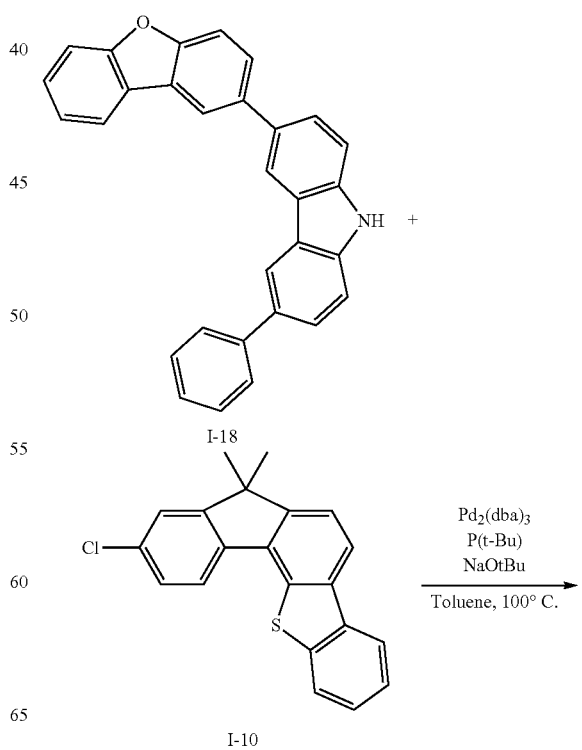

-continued

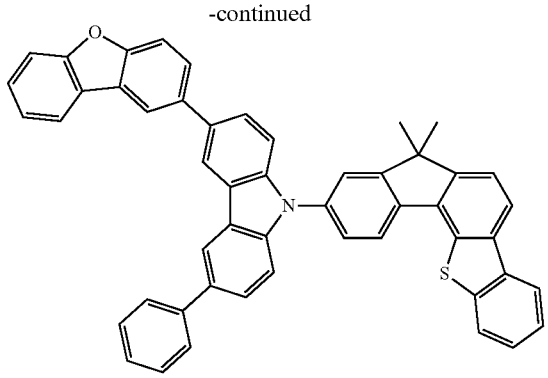

B-32

10 g (24.4 mmol) of the intermediate I-17 was dissolved in 0.09 L of toluene in a nitrogen environment, 8.17 g (25.6 mmol) of the intermediate I-10, 0.67 g (0.73 mmol) of tris(dibenzylideneacetone)dipalladium (0), 0.59 g (2.93 mmol) of tris-tertiarybutylphosphine, and 2.81 g (29.3 mmol) of sodium tertiarybutoxide were sequentially added thereto, and the mixture was heated and refluxed at 100° C. for 38 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound B-32 (15.7 g, 91%).

HRMS (70 eV, EI+): m/z calcd for C51H33NOS: 707.2283, found: 707.2.

Elemental Analysis: C, 87%; H, 5%

Example 12: Preparation of Compound C-1

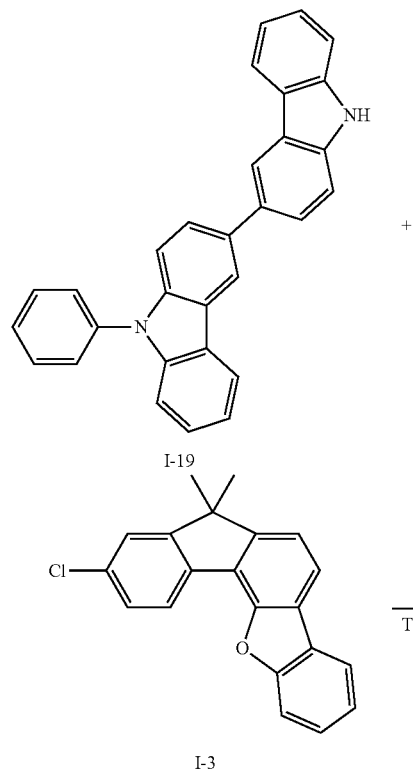

-continued

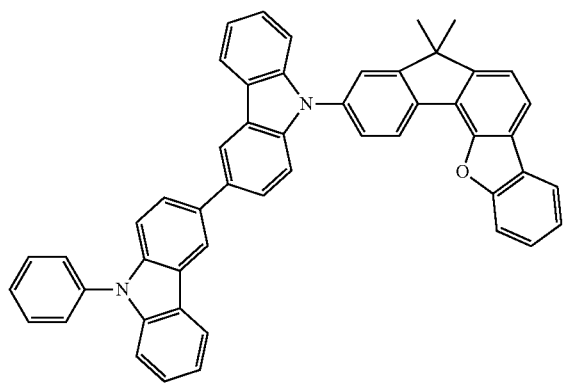

C-1

10 g (24.5 mmol) of the intermediate I-19 was dissolved in 0.1 L of toluene in a nitrogen environment, 8.19 g (25.7 mmol) of the intermediate I-3, 0.67 g (0.74 mmol) of tris(dibenzylideneacetone)dipalladium (0), 0.59 g (2.94 mmol) of tris-tertiarybutylphosphine, and 2.81 g (29.3 mmol) of sodium tertiarybutoxide were sequentially added thereto, and the mixture was heated and refluxed at 100° C. for 24 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound C-1 (11.3 g, 67%).

HRMS (70 eV, EI+): m/z calcd for C51H34N2O: 690.2671, found: 690.3.

Elemental Analysis: C, 89%; H, 5%

Example 13: Preparation of Compound C-7

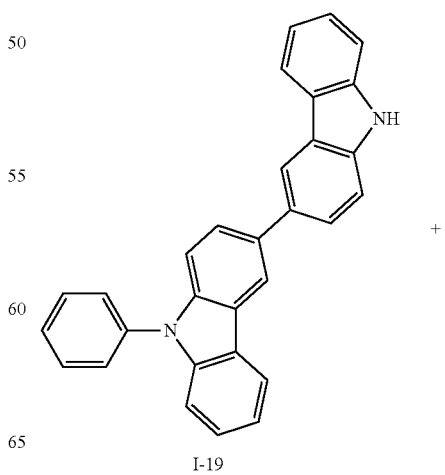

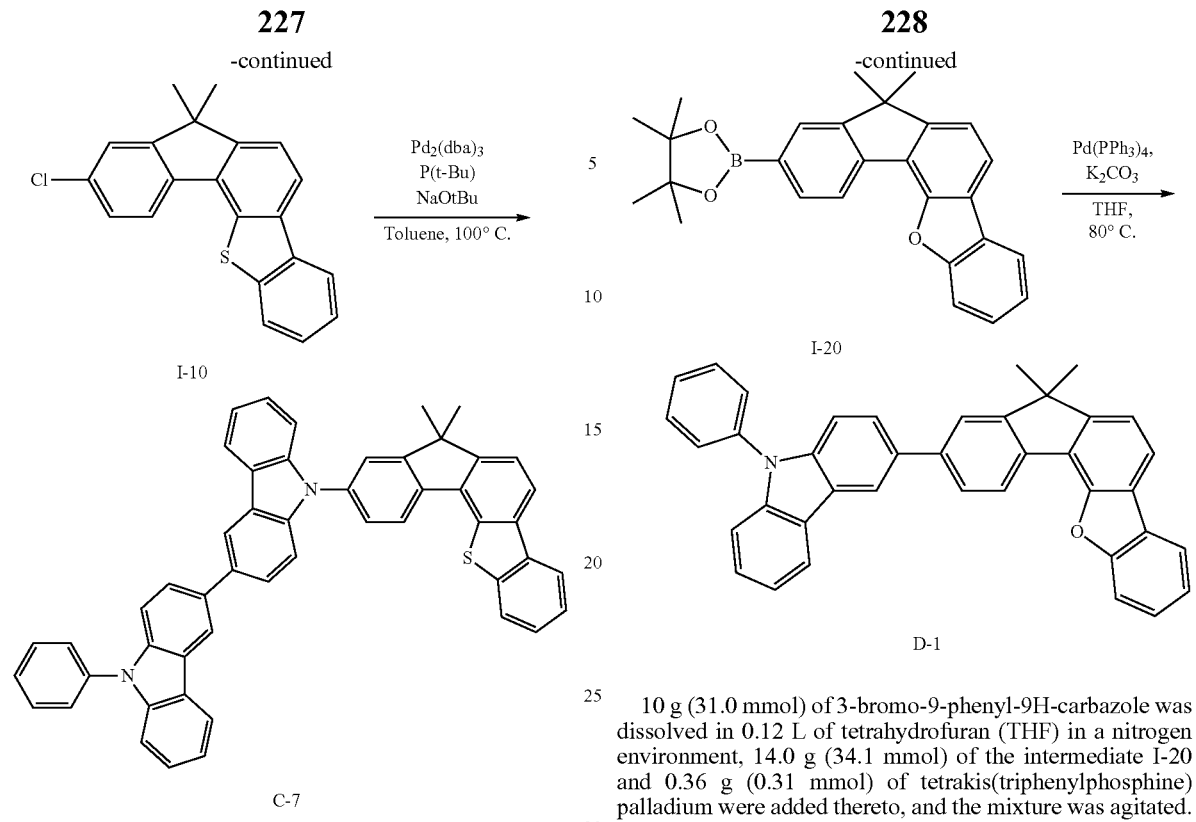

10 g (24.5 mmol) of the intermediate I-19 was dissolved in 0.1 L of toluene in a nitrogen environment, 8.61 g (25.7 mmol) of the intermediate I-10, 0.67 g (0.74 mmol) of tris(dibenzylideneacetone)dipalladium (0), 0.59 g (2.94 mmol) of tris-tertiarybutylphosphine, and 2.83 g (29.4 mmol) of sodium tertiarybutoxide were sequentially added thereto, and the mixture was heated and refluxed at 100° C. for 19 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound C-7 (13.0 g, 75%).

HRMS (70 eV, EI+): m/z calcd for C51H34N2S: 706.2443, found: 706.2.

Elemental Analysis: C, 87%; H, 5%

Example 14: Preparation of Compound D-1

10 g (31.0 mmol) of 3-bromo-9-phenyl-9H-carbazole was dissolved in 0.12 L of tetrahydrofuran (THF) in a nitrogen environment, 14.0 g (34.1 mmol) of the intermediate I-20 and 0.36 g (0.31 mmol) of tetrakis(triphenylphosphine) palladium were added thereto, and the mixture was agitated. 5.48 g (37.2 mmol) of potassium carbonate saturated in water was added thereto, and the mixture was heated and refluxed at 80° C. for 26 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound D-1 (15.0 g, 92%).

HRMS (70 eV, EI+): m/z calcd for C39H27NO: 525.2093, found: 525.2.

Elemental Analysis: C, 89%; H, 5%

Example 15: Preparation of Compound D-7

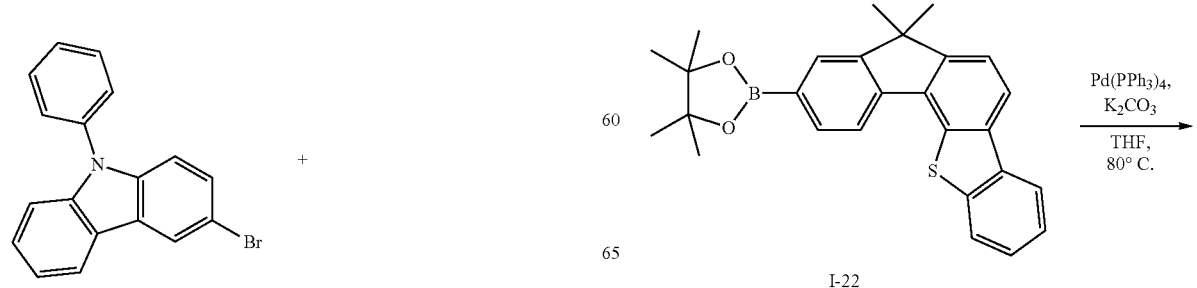

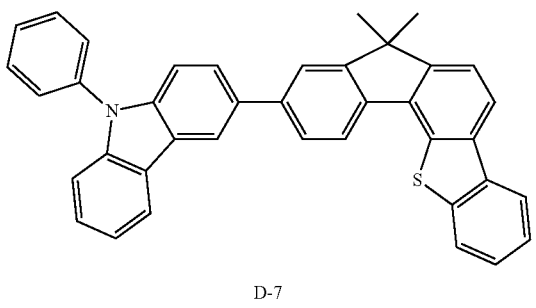

D-7

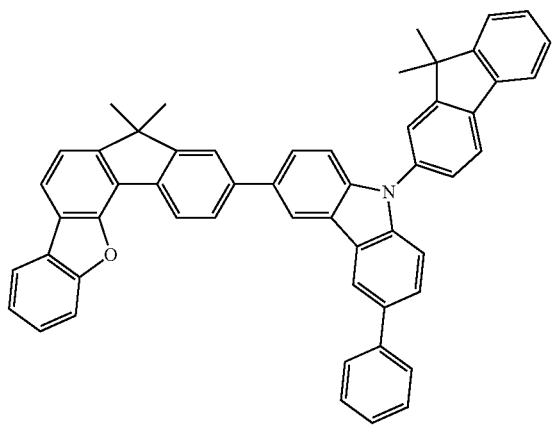

D-97

10 g (31.0 mmol) of 3-bromo-9-phenyl-9H-carbazole was dissolved in 0.12 L of tetrahydrofuran (THF) in a nitrogen environment, 14.5 g (34.1 mmol) of the intermediate I-22 and 0.36 g (0.31 mmol) of tetrakis(triphenylphosphine) palladium were added thereto, and the mixture was agitated. 5.48 g (37.2 mmol) of potassium carbonate saturated in water was added thereto, and the mixture was heated and refluxed at 80° C. for 24 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound D-7 (16.0 g, 95%).

HRMS (70 eV, EI+): m/z calcd for C39H27NS: 541.1864, found: 541.2.

Elemental Analysis: C, 86%; H, 5%

Example 16: Preparation of Compound D-97

10 g (19.0 mmol) of the intermediate I-21 was dissolved in 0.1 L of toluene in a nitrogen environment, 5.71 g (20.9 mmol) of 2-bromo-9,9-dimethylfluorene, 0.67 g (0.57 mmol) of tris(dibenzylideneacetone)dipalladium (0), 0.46 g (2.28 mmol) of tris-tertiarybutylphosphine and 2.19 g (22.8 mmol) of sodium tertiarybutoxide were sequentially added thereto, and the mixture was heated and refluxed at 100° C. for 25 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound D-97 (12.7 g, 93%).

HRMS (70 eV, EI+): m/z calcd for C54H39NO: 717.3032, found: 717.3.

Elemental Analysis: C, 90%; H, 5%

Example 17: Preparation of Compound D-103

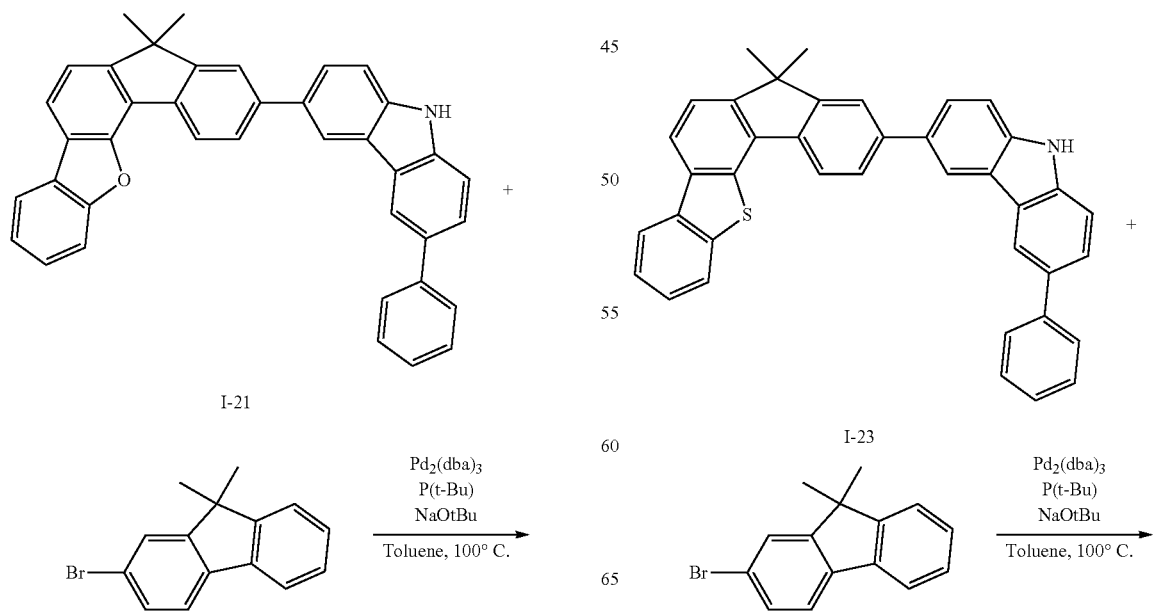

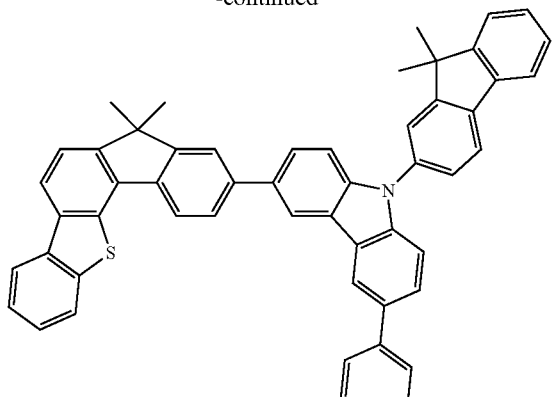

D-103

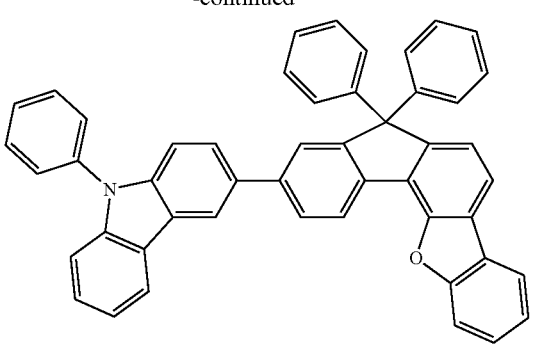

D-127

10 g (18.5 mmol) of the intermediate I-21 was dissolved in 0.1 L of toluene in a nitrogen environment, 5.55 g (20.3 mmol) of 2-bromo-9,9-dimethylfluorene, 0.51 g (0.56 mmol) of tris(dibenzylideneacetone)dipalladium (0), 0.45 g (2.22 mmol) of tris-tertiarybutylphosphine and 2.13 g (22.2 mmol) of sodium tertiarybutoxide were sequentially added thereto, and the mixture was heated and refluxed at 100° C. for 23 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound D-103 (12.4 g, 91%).

HRMS (70 eV, EI+): m/z calcd for C54H39NS: 733.2803, found: 733.3.

Elemental Analysis: C, 88%; H, 5%

Example 18: Preparation of Compound D-127

10 g (31.0 mmol) of 3-bromo-9-phenyl-9H-carbazole was dissolved in 0.14 L of tetrahydrofuran (THF) in a nitrogen environment, 18.2 g (34.1 mmol) of the intermediate I-24 and 0.36 g (0.31 mmol) of tetrakis(triphenylphosphine)palladium were added thereto, and the mixture was agitated. 5.48 g (37.2 mmol) of potassium carbonate saturated in water was added thereto, and the mixture was heated and refluxed at 80° C. for 24 hours. When the reaction was terminated, water was added to the reaction solution, and the mixture was extracted with dichloromethane (DCM) and treated with anhydrous $MgSO_4$ to remove moisture and then, filtered and concentrated under a reduced pressure. The obtained residue was separated and purified through flash column chromatography, obtaining a compound D-127 (17.9 g, 89%).

HRMS (70 eV, EI+): m/z calcd for C49H31NO: 649.2406, found: 649.2.

Elemental Analysis: C, 91%; H, 5%

Example 19: Preparation of Compound D-130

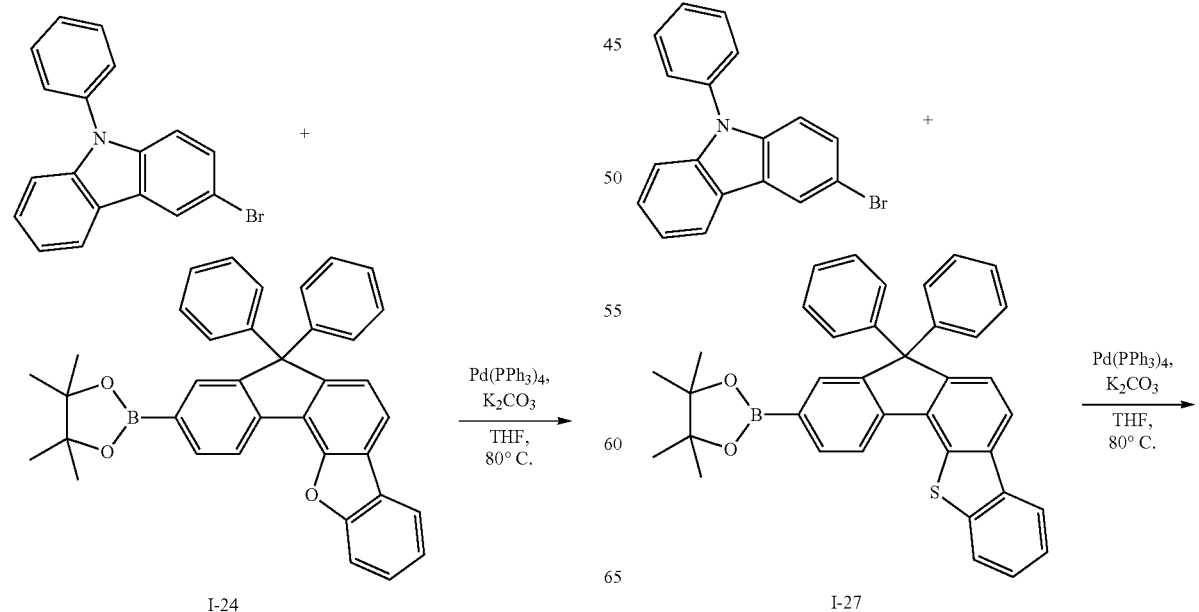

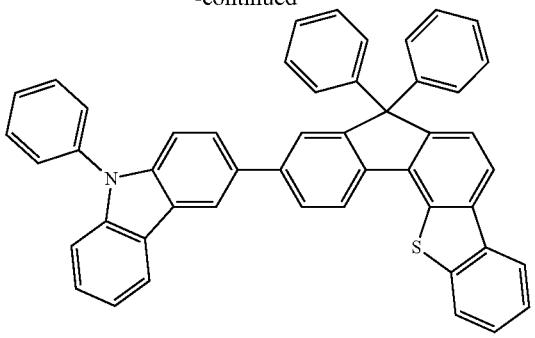

D-130

10 g (31.0 mmol) of 3-bromo-9-phenyl-9H-carbazole was dissolved in 0.14 L of tetrahydrofuran (THF) in a nitrogen environment, 18.8 g (34.1 mmol) of the intermediate I-27 and 0.36 g (0.31 mmol) of tetrakis(triphenylphosphine) palladium were added thereto, and the mixture was agitated. 5.48 g (37.2 mmol) of potassium carbonate saturated in water was added thereto, and the mixture was heated and refluxed at 80° C. for 22 hours. When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound D-130 (16.7 g, 81%).

HRMS (70 eV, EI+): m/z calcd for C49H31NS: 665.2177, found: 665.2.

Elemental Analysis: C, 88%; H, 5%

Example 20: Preparation of Compound D-133

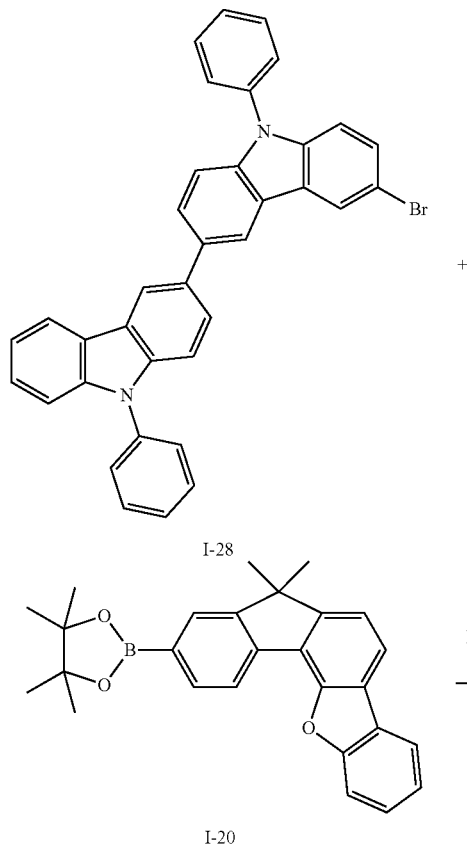

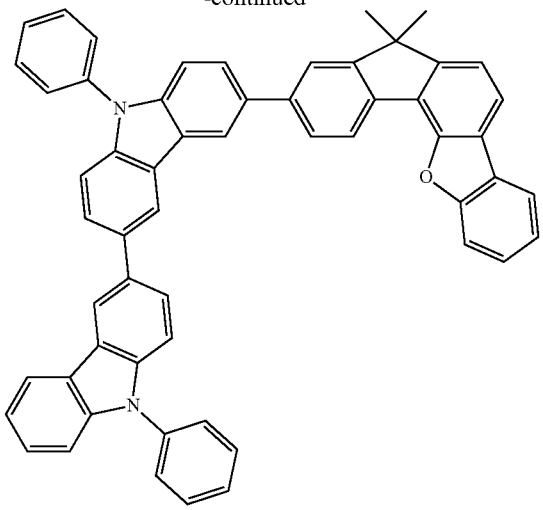

D-133

20 g (35.5 mmol) of the intermediate I-28 was dissolved in 0.2 L of tetrahydrofuran (THF) in a nitrogen environment, 16.0 g (39.0 mmol) of the intermediate I-20 and 0.41 g (0.36 mmol) of tetrakis(triphenylphosphine)palladium were added thereto, and the mixture was agitated. 10.5 g (71.0 mmol) of potassium carbonate saturated in water was added thereto, and the mixture was heated and refluxed at 80° C. for 13 hours When the reaction was terminated, water was added to the reaction solution, and the mixture was extracted with dichloromethane (DCM) and treated with anhydrous MgSO₄ to remove moisture and then, filtered and concentrated under a reduced pressure. The obtained residue was separated and purified through flash column chromatography, obtaining a compound D-133 (23.6 g, 88%).

HRMS (70 eV, EI+): m/z calcd for C57H38N2O: 766.2984, found: 766.3.

Elemental Analysis: C, 89%; H, 5%

Example 21: Preparation of Compound D-136

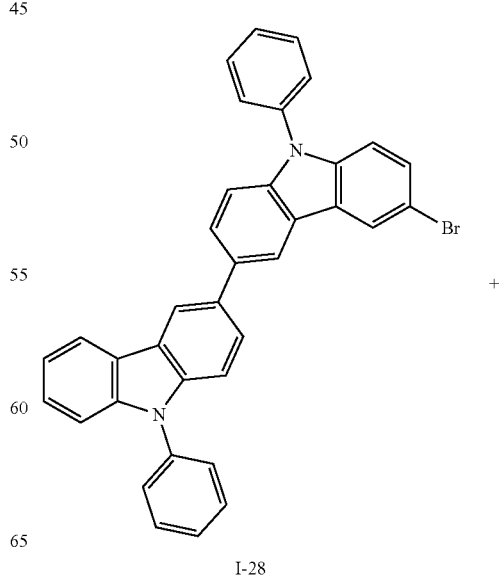

Example 22: Preparation of Compound D-151

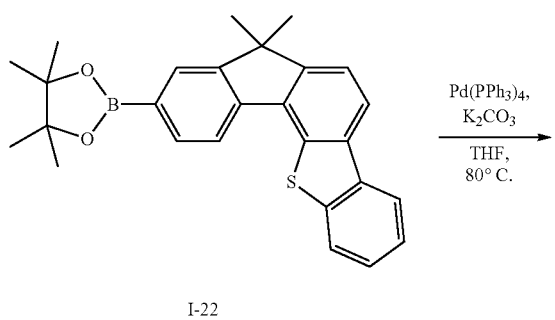

I-22

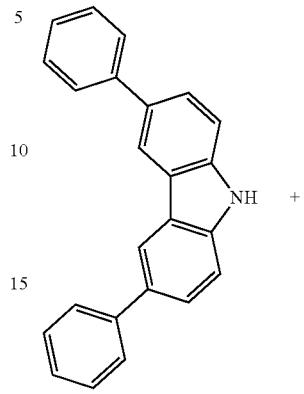

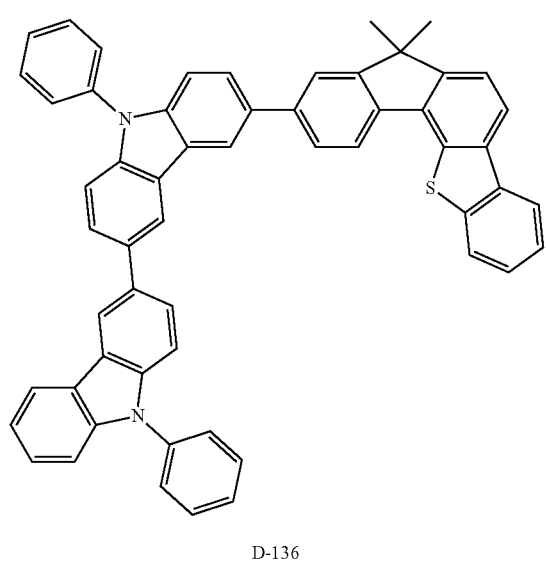

D-136

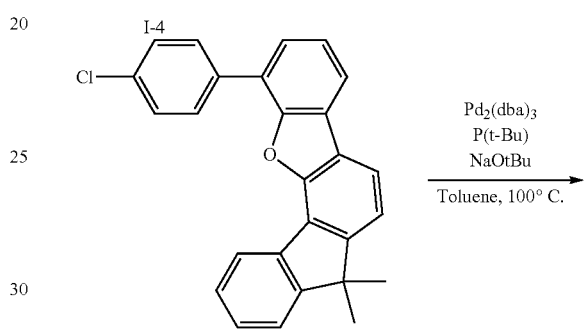

I-33

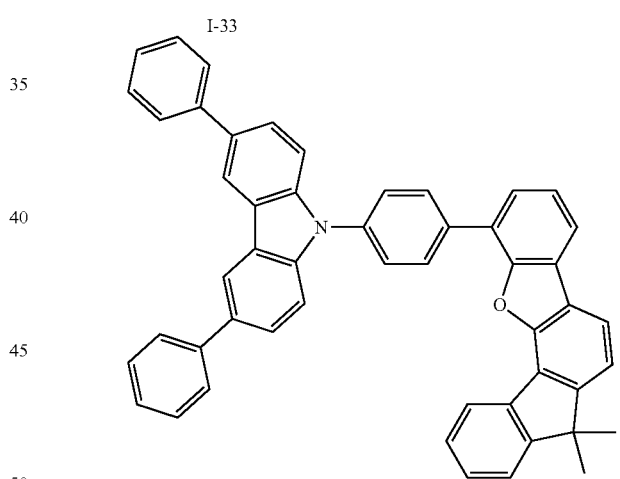

B-151

20 g (35.5 mmol) of the intermediate I-28 was dissolved in 0.2 L of tetrahydrofuran (THF) in a nitrogen environment, 16.0 g (39.0 mmol) of the intermediate I-22 and 0.41 g (0.36 mmol) of tetrakis(triphenylphosphine)palladium were added thereto, and the mixture was agitated. 10.5 g (71.0 mmol) of potassium carbonate saturated in water was added thereto, and the mixture was heated and refluxed at 80° C. for 15 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound D-136 (25.0 g, 90%).

HRMS (70 eV, EI+): m/z calcd for C57H38N2S: 782.2756, found: 782.3.

Elemental Analysis: C, 87%; H, 5%

10 g (31.3 mmol) of the intermediate I-4 was dissolved in 0.12 L of toluene in a nitrogen environment, 13.0 g (32.9 mmol) of the intermediate I-33, 0.86 g (0.94 mmol) of tris(dibenzylideneacetone)dipalladium (0), 0.76 g (3.76 mmol) of tris-tert butylphosphine and 3.61 g (37.6 mmol) of sodium tertiarybutoxide were sequentially added thereto, and the mixture was heated and refluxed at 100° C. for 48 hours. When the reaction was terminated, water was added to the reaction solution, and the mixture was extracted with dichloromethane (DCM) and treated with anhydrous MgSO$_4$ to remove moisture and then, filtered and concentrated under a reduced pressure. The obtained residue was separated and purified through flash column chromatography, obtaining a compound D-151 (18.0 g, 85%).

HRMS (70 eV, EI+): m/z calcd for C51H35NO: 677.2719, found: 677.3.
Elemental Analysis: C, 90%; H, 5%

Example 23: Preparation of Compound D-154

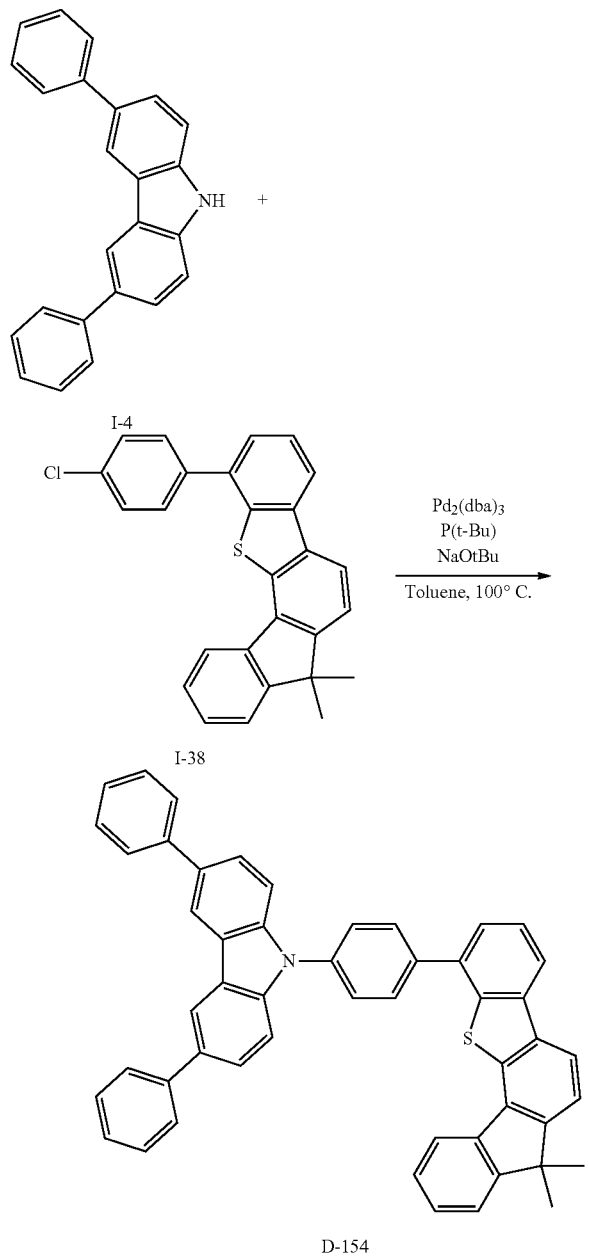

10 g (31.3 mmol) of the intermediate I-4 was dissolved in 0.12 L of toluene in a nitrogen environment, 13.5 g (32.9 mmol) of the intermediate I-38, 0.86 g (0.94 mmol) of tris(dibenzylideneacetone)dipalladium (0), 0.76 g (3.76 mmol) of tris-tert butylphosphine and 3.61 g (37.6 mmol) of sodium tertiarybutoxide were sequentially added thereto, and the mixture was heated and refluxed at 100° C. for 37 hours. When the reaction was terminated, water was added to the reaction solution, and the mixture was extracted with dichloromethane (DCM) and treated with anhydrous MgSO4 to remove moisture and then, filtered and concentrated under a reduced pressure. The obtained residue was separated and purified through flash column chromatography, obtaining a compound D-154 (19.3 g, 89%).
HRMS (70 eV, EI+): m/z calcd for C51H35NS: 693.2490, found: 693.2.
Elemental Analysis: C, 88%; H, 5%

Manufacture of Organic Light Emitting Diode

Example 24: Manufacture of Organic Light Emitting Diode (Blue)

A glass substrate was coated with a 1500 Å-thick ITO (Indium tinoxide) thin film and then, ultrasonic wave-cleaned with distilled water. After cleaning with distilled water, the glass substrate was ultrasonic wave-cleaned with a solvent such as isopropyl alcohol, acetone, methanol and the like and dried and then, transported to a plasma cleaner, cleaned with oxygen plasma for 5 minutes, and transported to a vacuum depositor. This obtained ITO transparent electrode was used as an anode, and a 600 Å-thick hole injection layer was formed thereon by vacuum depositing 4,4'-bis[N-[4-{N,N-bis(3-methylphenyl)amino}-phenyl]-N-phenylamino]biphenyl (DNTPD). Subsequently, a 300 Å-thick hole transport layer was formed by vacuum-depositing the compound A-1 according to Example 1. On the hole transport layer, a 250 Å-thick emission layer was formed by vacuum-depositing 9,10-di-(2-naphthyl)anthracene (AND) as a host and 3 wt % of 2,5,8,11-tetra(tert-butyl)perylene (TBPe) as a dopant. Then, a 250 Å-thick electron transport layer was formed by vacuum-depositing Alq3 on the emission layer. On the electron transport layer, a cathode was formed by sequentially vacuum-depositing LiF to be 10 Å thick and Al to be 1000 Å thick, manufacturing an organic light emitting diode.

The organic light emitting diode had a structure of 5 organic thin layers and specifically, a structure of Al (1000 Å)/LiF 10 Å/Alq3 250 Å/EML [AND:TBPe=97:3] 250 Å/HTL 300 Å/DNTPD 600 Å/ITO (1500 Å).

Example 25

An organic light emitting diode was manufactured according to the same method as Example 24 except for using the compound of Example 2 instead of the compound of Example 1.

Example 26

An organic light emitting diode was manufactured according to the same method as Example 24 except for using the compound of Example 3 instead of the compound of Example 1.

Example 27

An organic light emitting diode was manufactured according to the same method as Example 24 except for using the compound of Example 4 instead of the compound of Example 1.

Example 28

An organic light emitting diode was manufactured according to the same method as Example 24 except for using the compound of Example 5 instead of the compound of Example 1.

Example 29

An organic light emitting diode was manufactured according to the same method as Example 24 except for using the compound of Example 6 instead of the compound of Example 1.

Example 30

An organic light emitting diode was manufactured according to the same method as Example 24 except for using the compound of Example 7 instead of the compound of Example 1.

Example 31

An organic light emitting diode was manufactured according to the same method as Example 24 except for using the compound of Example 8 instead of the compound of Example 1.

Example 32

An organic light emitting diode was manufactured according to the same method as Example 24 except for using the compound of Example 9 instead of the compound of Example 1.

Example 33

An organic light emitting diode was manufactured according to the same method as Example 24 except for using the compound of Example 10 instead of the compound of Example 1.

Example 34

An organic light emitting diode was manufactured according to the same method as Example 24 except for using the compound of Example 11 instead of the compound of Example 1.

Example 35

An organic light emitting diode was manufactured according to the same method as Example 24 except for using the compound of Example 22 instead of the compound of Example 1.

Example 36

An organic light emitting diode was manufactured according to the same method as Example 24 except for using the compound of Example 23 instead of the compound of Example 1.

Comparative Example 1

An organic light emitting diode was manufactured according to the same method as Example 24 except for using NPB instead of the compound of Example 1. The NPB has a following structure.

Comparative Example 2

An organic light emitting diode was manufactured according to the same method as Example 24 except for using HT1 instead of the compound of Example 1. The HT1 has a following structure.

Comparative Example 3

An organic light emitting diode was manufactured according to the same method as Example 24 except for using HT2 instead of the compound of Example 1. The HT2 has a following structure.

DNTPD, AND, TBPe, NPB, HT1 and HT2 used to manufacture the organic light emitting diode have following structures.

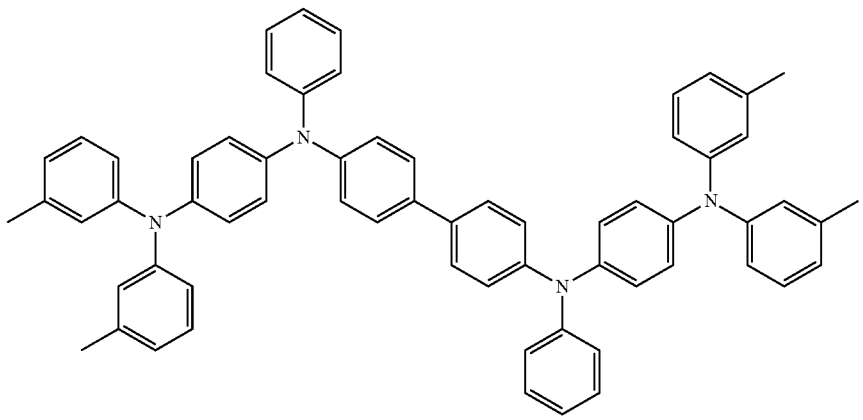

[DNTPD]

-continued

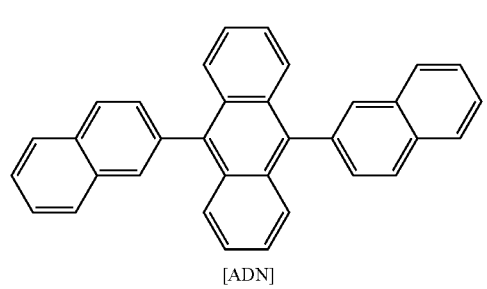

[ADN]

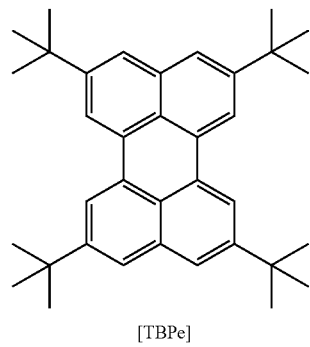

[TBPe]

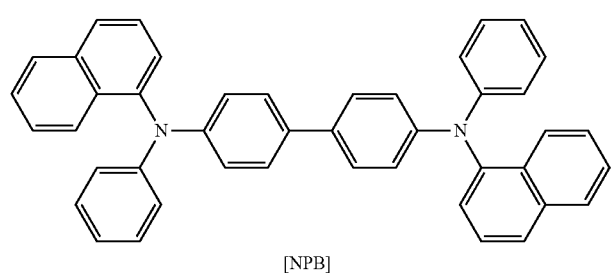

[NPB]

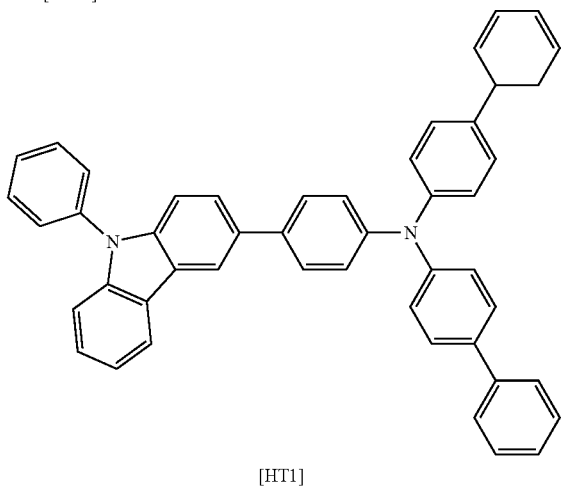

[HT1]

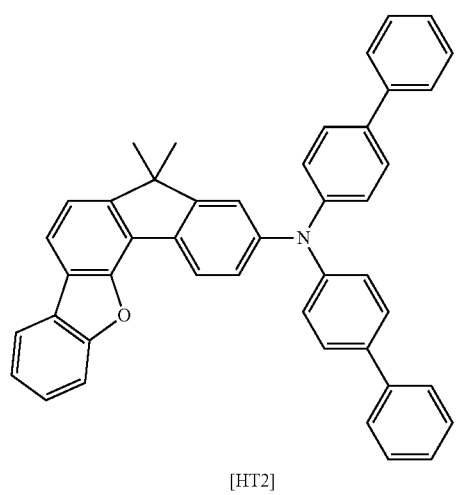

[HT2]

(Performance Measurement of Organic Light Emitting Diode)

Current density and luminance changes depending on a voltage and luminous efficiency of each organic light emitting diode according to Examples 24 to 36 and Comparative Examples 1 to 3 were measured. The measurements were specifically performed in the following method, and the results were provided in the following Table 1.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0V to 10V using a luminance meter (Minolta Cs-1000A).

(3) Measurement of Luminous Efficiency

Current efficiency (cd/A) at the same current density (10 mA/cm$^2$) were calculated by using the luminance, current density, and voltages (V) from the items (1) and (2).

TABLE 1

| Device | Compound of hole transport layer (HTL) | Voltage (V) | Color (EL color) | Efficiency (cd/A) | Half-life life-span (h) At 1000 cd/m$^2$ |
|---|---|---|---|---|---|
| Example 24 | A-1 | 6.3 | Blue | 6.5 | 1,550 |
| Example 25 | A-5 | 5.8 | Blue | 7.0 | 1,400 |
| Example 26 | A-7 | 5.8 | Blue | 6.9 | 1,400 |
| Example 27 | A-13 | 6.7 | Blue | 5.0 | 1,350 |
| Example 28 | A-73 | 6.5 | Blue | 6.0 | 1,600 |
| Example 29 | A-88 | 6.5 | Blue | 6.6 | 1,550 |
| Example 30 | A-124 | 5.0 | Blue | 7.0 | 1,450 |
| Example 31 | B-14 | 5.7 | Blue | 7.2 | 1,200 |
| Example 32 | B-20 | 5.6 | Blue | 7.4 | 1,100 |
| Example 33 | B-26 | 5.7 | Blue | 7.2 | 1,150 |
| Example 34 | B-32 | 5.6 | Blue | 7.0 | 1,000 |
| Example 35 | D-151 | 6.7 | Blue | 6.9 | 1,650 |
| Example 36 | D-154 | 6.5 | Blue | 7.0 | 1,550 |
| Comparative Example 1 | NPB | 7.1 | Blue | 4.9 | 1,250 |
| Comparative Example 2 | HT1 | 6.6 | Blue | 5.7 | 1,340 |
| Comparative Example 3 | HT2 | 6.0 | Blue | 6.9 | 830 |

Referring to Table 1, the materials for a hole transport layer (HTL) according to Examples 24 to 30 showed remarkably improved life-span compared with the material for a hole transport layer according to Comparative Example 3. In addition, the organic light emitting diodes manufactured by materials for a hole transport layer (HTL) according to Examples 24 to 30 showed remarkably improved life-span compared with widely-used Comparative Examples 1 and 2.

The Example showed a lower driving voltage and a little increased efficiency compared with Comparative Example.

Specifically, Examples 35 and 36 showed excellent efficiency, voltage, and life-span and particularly, excellent life-span compared with Comparative Examples 1 to 3.

Based on the results, organic light emitting diode of a low voltage, high efficiency, high luminance, and a long life-span having excellent hole injection and hole transportation capability may be manufactured.

Example 37: Manufacture of Organic Light Emitting Diode (Green Phosphorescence)

An organic light emitting diode is manufactured by using 4,4'-di(9H-carbazol-9-yl)biphenyl (CBP) as a host and Ir(PPy)$_3$ as a dopant. As for an anode, a 1000 Å-thick ITO was used, and as for a cathode, a 1000 Å-thick aluminum (Al) was used. Specifically, illustrating a method of manufacturing the organic light emitting diode, an anode was prepared by cutting an ITO glass substrate having sheet resistance of 15 Ω/cm$^2$ into a size of 50 mm×50 mm×0.7 mm ◯| size, ultrasonic wave-cleaning it in acetone, isopropyl-alcohol and pure water for 15 minutes respectively, and UV ozone-cleaning it for 30 minutes. On the substrate upper, an 800 Å hole transport layer was formed by depositing N4,N4'-di(naphthalen-1-yl)-N4,N4'-diphenylbiphenyl-4,4'-diamine (NPB) (70 nm) and the compound C-1 synthesized in Example 12 (10 nm) under a vacuum degree of 650×10$^{-7}$ Pa at a deposit speed of 0.1 to 0.3 nm/s. Subsequently, a 300 Å-thick emission layer was formed by depositing 4,4'-di(9H-carbazol-9-yl)biphenyl (CBP) and simultaneously Ir(PPy)$_3$ as a phosphorescent dopant under the same vacuum deposit condition. Herein, the phosphorescent dopant was deposited in an amount of 7 wt % based on 100 wt % of the entire amount of the emission layer by adjusting the deposit speed of the phosphorescent dopant. On the emission layer, a 50 Å-thick hole blocking layer was formed by vacuum-depositing bis(2-methyl-8-quinolinolate)-4-(phenylphenolato)aluminium (BAlq) under the same vacuum deposit condition. Subsequently, a 20 Å-thick electron transport layer was formed by depositing Alq$_3$ under the same vacuum deposit condition. On the electron transport layer, a cathode was formed by sequentially depositing LiF and Al, manufacturing an organic photoelectric device. The organic photoelectric device had a structure of ITO/NPB (70 nm)/Example 12 (10 nm)/EML (CBP (93 wt %)+Ir(PPy)3 (7 wt %), 30 nm)/Balq (5 nm)/Alq$_3$ (20 nm)/LiF (1 nm)/Al (100 nm).

Example 38

An organic light emitting diode was manufactured according to the same method as Example 37 except for using Example 13 instead of Example 12.

Example 39

An organic light emitting diode was manufactured according to the same method as Example 37 except for using Example 14 instead of Example 12.

Example 40

An organic light emitting diode was manufactured according to the same method as Example 37 except for using Example 15 instead of Example 12.

Example 41

An organic light emitting diode was manufactured according to the same method as Example 37 except for using Example 16 instead of Example 12.

Example 42

An organic light emitting diode was manufactured according to the same method as Example 37 except for using Example 17 instead of Example 12.

Example 43

An organic light emitting diode was manufactured according to the same method as Example 37 except for using Example 18 instead of Example 12.

Example 44

An organic light emitting diode was manufactured according to the same method as Example 37 except for using Example 19 instead of Example 12.

Example 45

An organic light emitting diode was manufactured according to the same method as Example 37 except for using Example 20 instead of Example 12.

Example 46

An organic light emitting diode was manufactured according to the same method as Example 37 except for using Example 21 instead of Example 12.

Comparative Example 4

An organic light emitting diode was manufactured according to the same method as Example 37 except for using NPB instead of Example 12. The NPB had a structure provided in the following.

NPB, BAlq, CBP and Ir(PPy)3 used to manufacture the organic light emitting diodes had structures provided in the following.

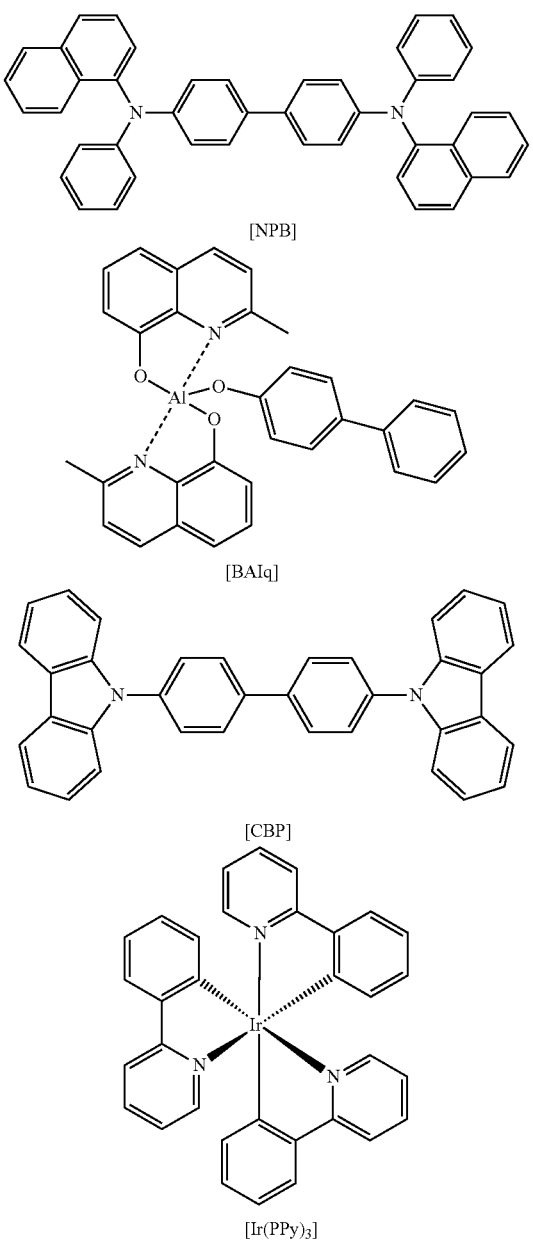

[NPB]

[BAlq]

[CBP]

[Ir(PPy)3]

(Performance Measurement of Organic Light Emitting Diode)

Current density and luminance changes depending on a voltage and luminous efficiency of each organic light emitting diode according to Examples 37 to 46 and Comparative Example 4 were measured. The measurements were specifically performed in the following method, and the results were provided in the following Table 2.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0V to 10V using a luminance meter (Minolta Cs-1000A).

(3) Measurement of Luminous Efficiency

Current efficiency (cd/A) at the same current density (10 mA/cm$^2$) were calculated by using the luminance, current density, and voltages (V) from the items (1) and (2).

TABLE 2

| Device | Compound of hole transport layer (HTL) | Voltage (V) | Color (EL color) | Efficiency (cd/A) | Half-life life-span (h) at 5000 cd/m$^2$ |
| --- | --- | --- | --- | --- | --- |
| Example 37 | NPB/C-1 | 4.2 | Green | 40.8 | 11,000 |
| Example 38 | NPB/C-7 | 4.1 | Green | 41.0 | 9,500 |
| Example 39 | NPB/D-1 | 4.9 | Green | 35.2 | 9,000 |
| Example 40 | NPB/D-7 | 4.8 | Green | 37.2 | 8,800 |
| Example 41 | NPB/D-97 | 4.5 | Green | 38.1 | 8,500 |
| Example 42 | NPB/D-103 | 4.3 | Green | 38.0 | 8,800 |
| Example 43 | NPB/D-127 | 5.0 | Green | 34.5 | 9,100 |
| Example 44 | NPB/D-130 | 4.9 | Green | 35.0 | 8,500 |
| Example 45 | NPB/D-133 | 4.1 | Green | 39.8 | 11,500 |
| Example 46 | NPB/D-136 | 4.2 | Green | 40.0 | 10,000 |
| Comparative Example 4 | NPB | 4.8 | Green | 31.4 | 10,000 |

Referring to Table 2 the materials used as an auxiliary layer of a hole transport layer (HTL) in Examples 37 to 46 showed remarkably increased luminous efficiency compared with the material in Comparative Example 4. In addition, most of the materials turned out to deteriorate a driving voltage.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

DESCRIPTION OF SYMBOLS

100: organic light emitting diode 110: cathode
120: anode 105: organic thin layer
130: emission layer 140: hole transport layer (HTL)
150: electron transport layer (ETL) 160: electron injection layer (EIL)
170: hole injection layer (HIL) 230: emission layer+ electron transport layer (ETL)

What is claimed is:

1. A compound for an organic optoelectronic device, the compound being represented by a combination of the following Chemical Formulae 1 and 5:

[Chemical Formula 1]

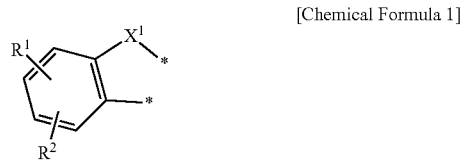

[Chemical Formula 5]

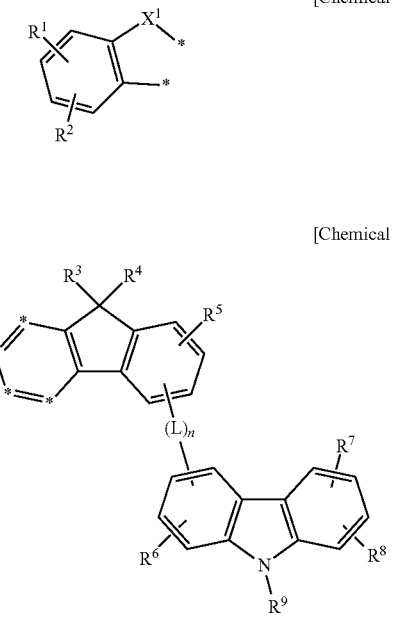

wherein, in Chemical Formulae 1 and 5,

X¹ is —O—, —S—, —S(O)— or —S(O)₂—,

R¹ to R⁹ are each independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and the two *s of Chemical Formula 1 are bonded with two adjacent *s of Chemical Formula 5 to form a fused ring, and the remaining two *s of Chemical Formula 5 are CH.

2. The compound for an organic optoelectronic device as claimed in claim 1, wherein the compound is represented by a combination of the following Chemical Formulae 1 and 6:

[Chemical Formula 1]

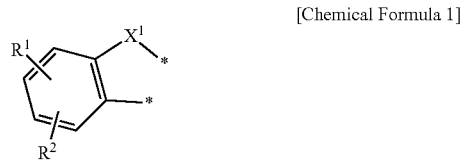

-continued

[Chemical Formula 6]

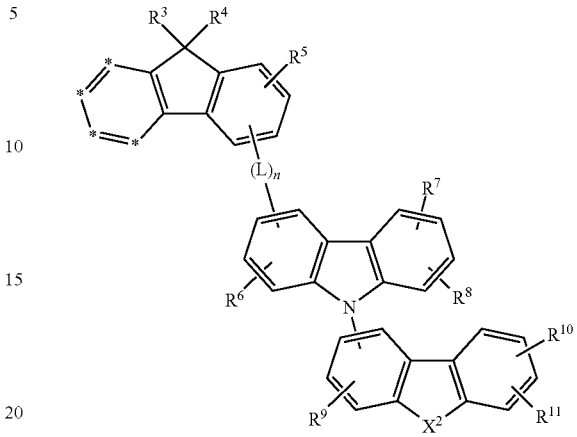

wherein, in Chemical Formulae 1 and 6,

X¹ is —O—, —S—, —S(O)— or —S(O)₂—,

X² is —O—, —S—, —S(O)—, —CR'R"—, —S(O)₂— or —NR'—, in which R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, R¹ to R¹¹ are each independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and the two *s of Chemical Formula 1 are bonded with two adjacent *s of Chemical Formula 6 to form a fused ring, and the remaining two *s of Chemical Formula 6 are CH.

3. The compound for an organic optoelectronic device as claimed in claim 1, wherein the compound is represented by a combination of the following Chemical Formulae 1 and 7:

[Chemical Formula 1]

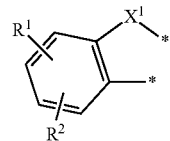

[Chemical Formula 7]

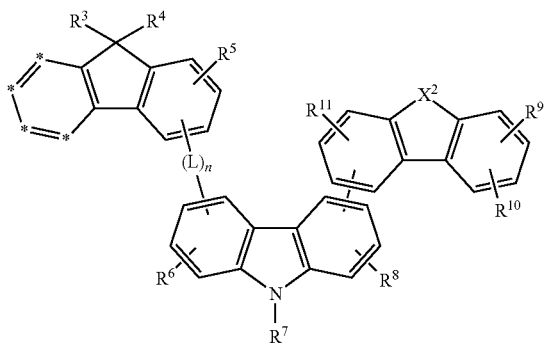

wherein, in Chemical Formulae 1 and 7, $X^1$ is —O—, —S—, —S(O)— or —S(O)$_2$—, $X^2$ is —O—, —S—, —S(O)—, —S(O)$_2$—, —CR'R"— or —NR'—, in which R' and R" are each independently hydrogen, deuterium, a substituted or unsubstituted C1 to C10 alkyl group, a substituted or unsubstituted C6 to C30 aryl group or a substituted or unsubstituted C2 to C30 heteroaryl group, $R^1$ to $R^{11}$ are each independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and the two *s of Chemical Formula 1 are bonded with two adjacent *s of Chemical Formula 7 to form a fused ring, and the remaining two *s of Chemical Formula 7 are CH.

4. The compound for an organic optoelectronic device as claimed in claim 1, wherein $R^1$ to $R^9$ are each independently hydrogen, a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

5. The compound for an organic optoelectronic device as claimed in claim 1, wherein the compound is represented by one of the following Chemical Formulae D-1 to D-144:

[Chemical Formula D-1]

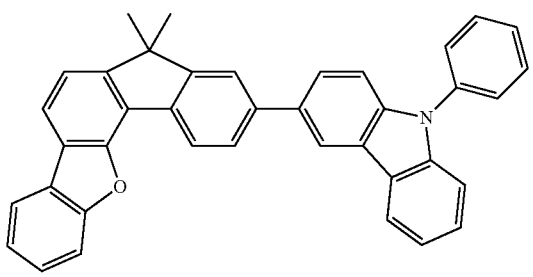

[Chemical Formula D-2]

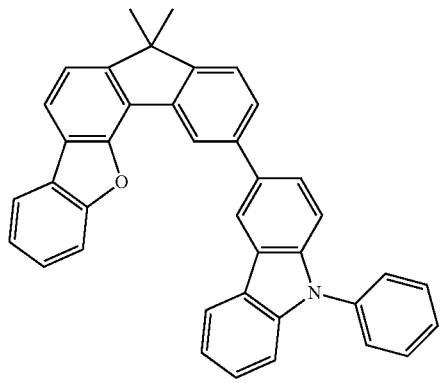

[Chemical Formula D-3]

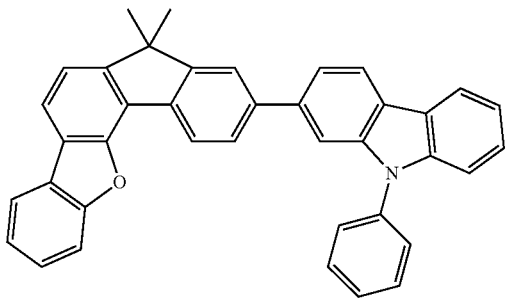

[Chemical Formula D-4]
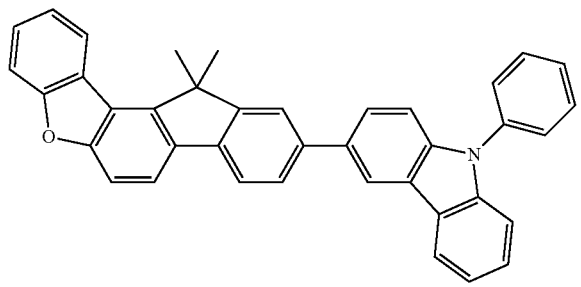
[Chemical Formula D-5]
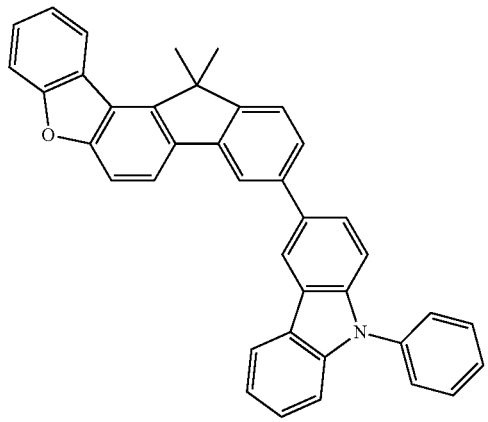
[Chemical Formula D-6]
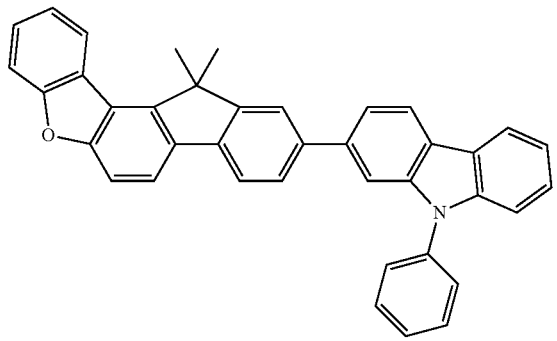
[Chemical Formula D-7]
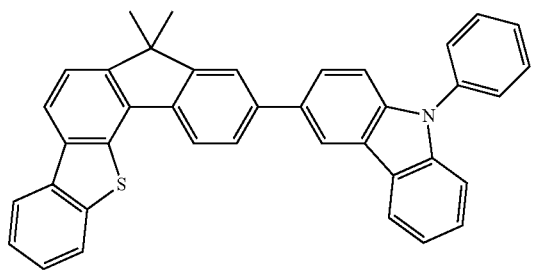
[Chemical Formula D-8]
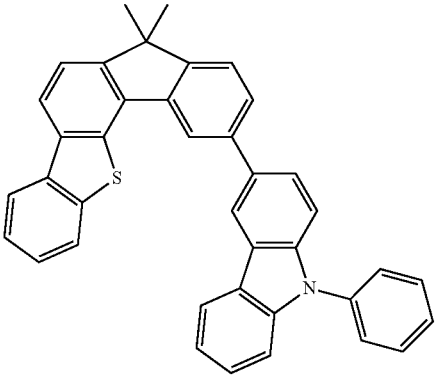
[Chemical Formula D-9]
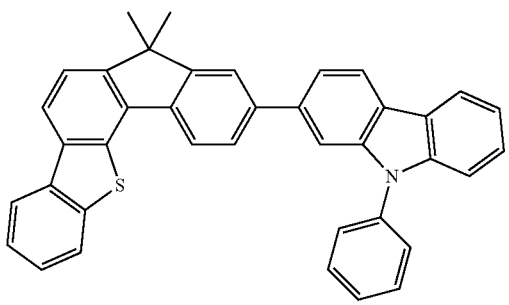
[Chemical Formula D-10]
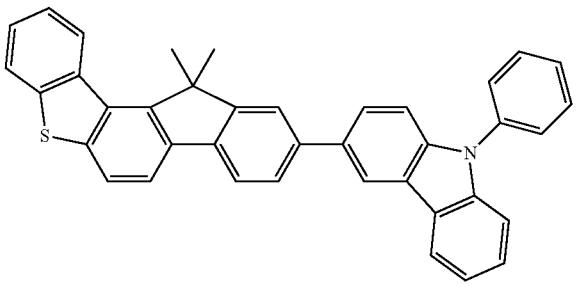
[Chemical Formula D-11]
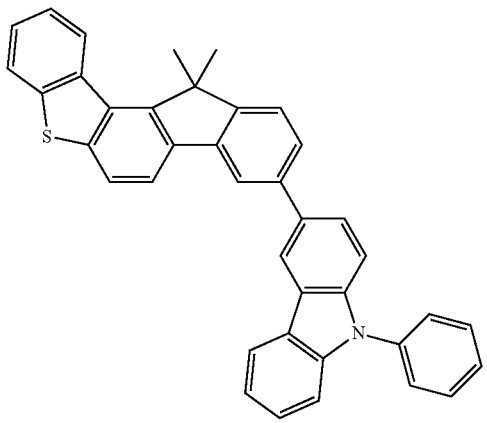

[Chemical Formula D-12]
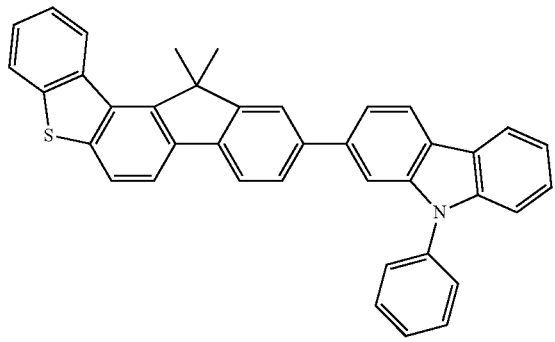
[Chemical Formula D-13]
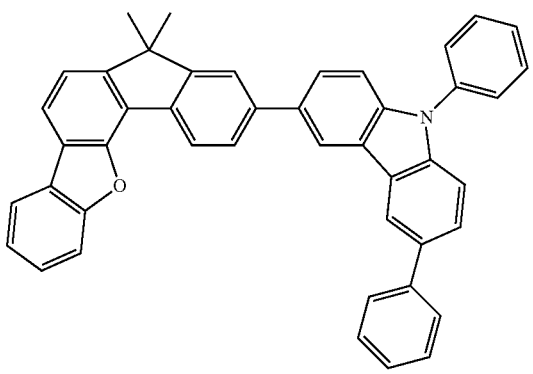
[Chemical Formula D-14]
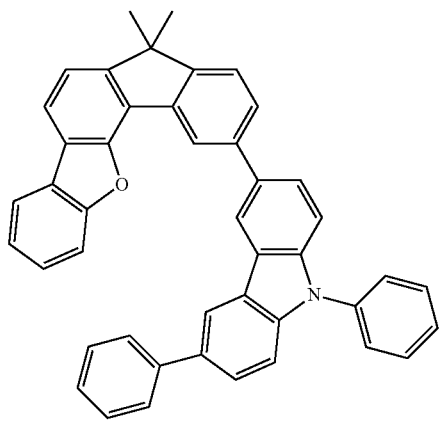
[Chemical Formula D-15]
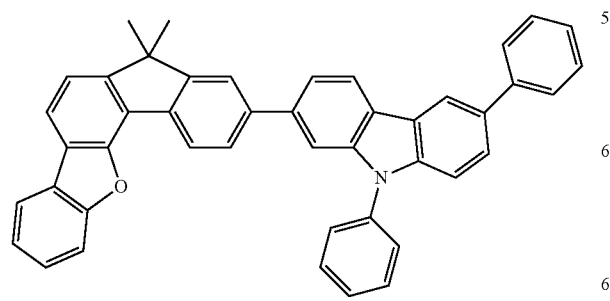
[Chemical Formula D-16]
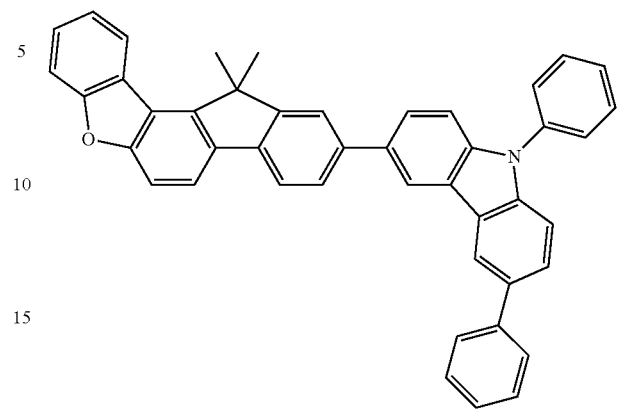
[Chemical Formula D-17]
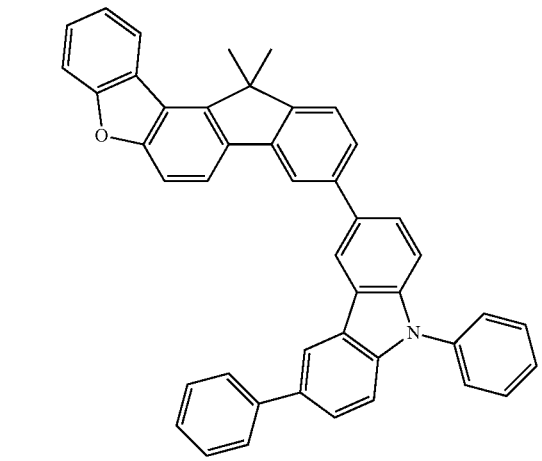
[Chemical Formula D-18]
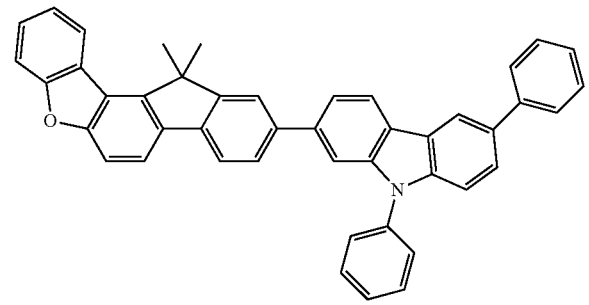
[Chemical Formula D-19]
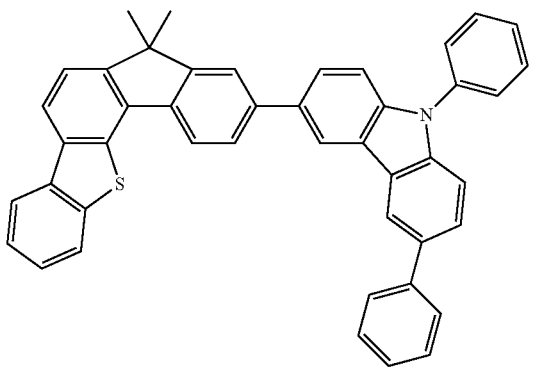

[Chemical Formula D-20]
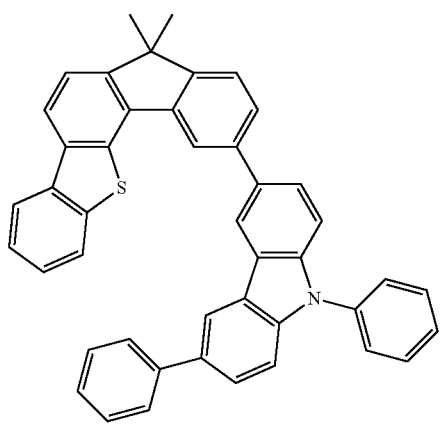
[Chemical Formula D-23]
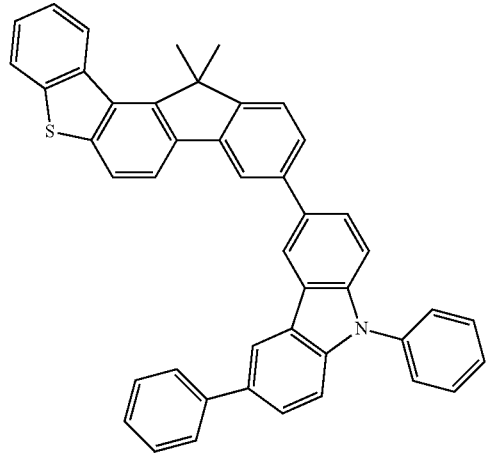
[Chemical Formula D-21]
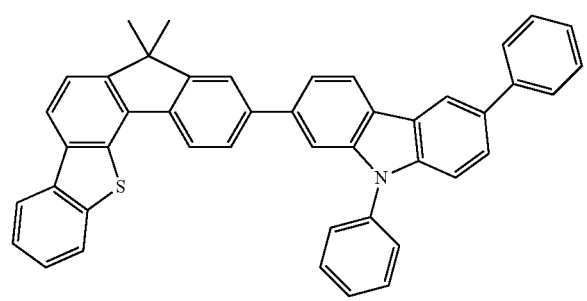
[Chemical Formula D-24]
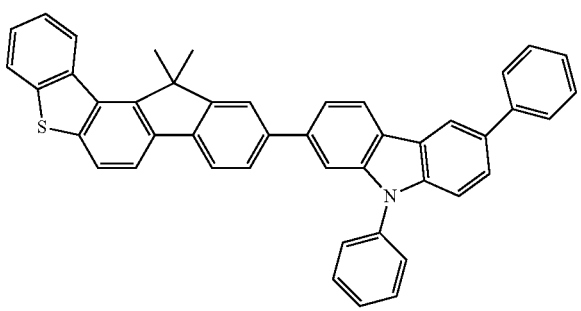
[Chemical Formula D-22]
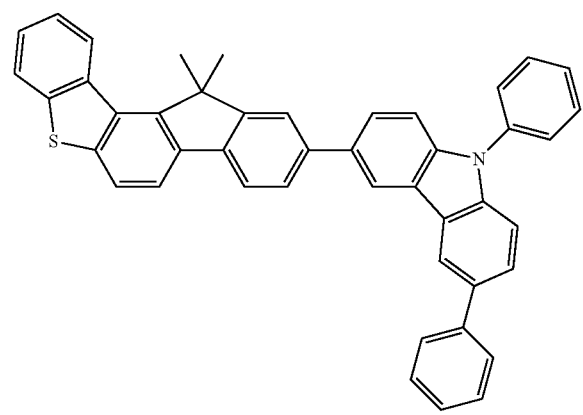
[Chemical Formula D-25]
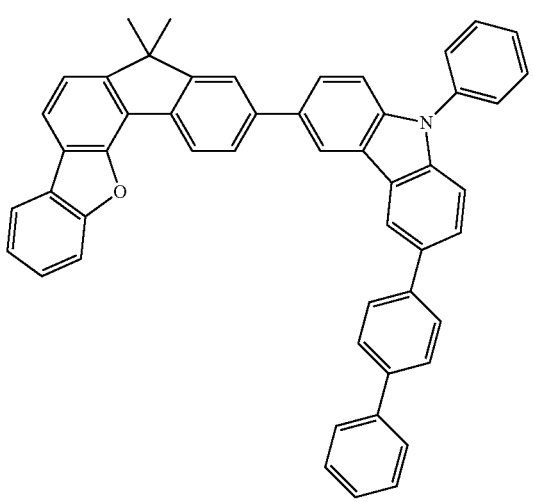

[Chemical Formula D-26]
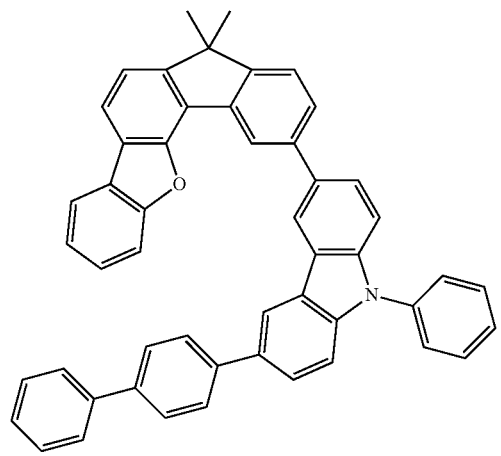
[Chemical Formula D-29]
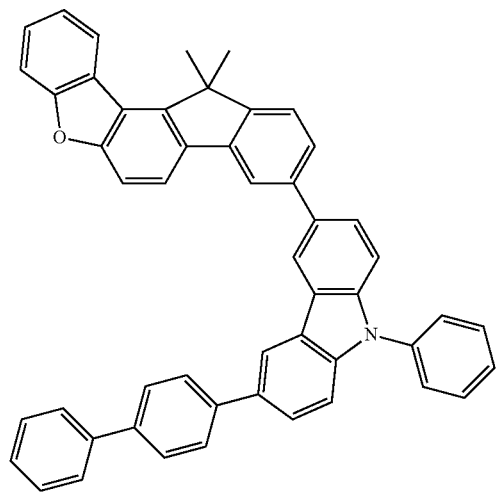
[Chemical Formula D-27]
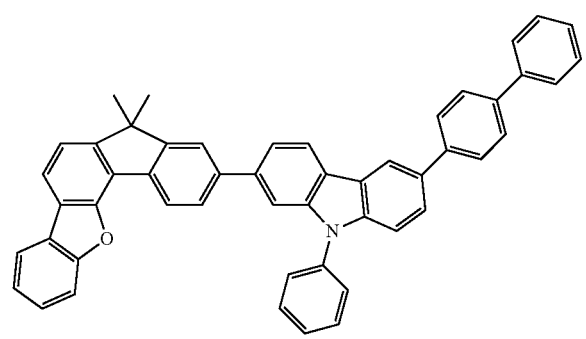
[Chemical Formula D-30]
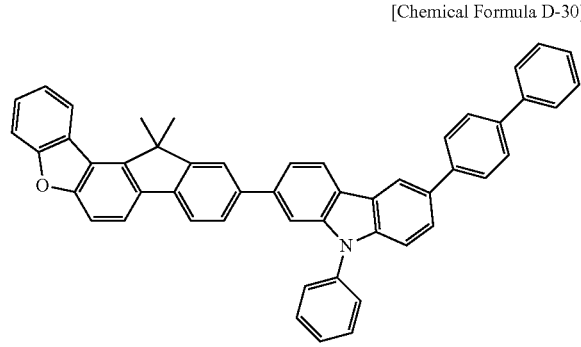
[Chemical Formula D-28]
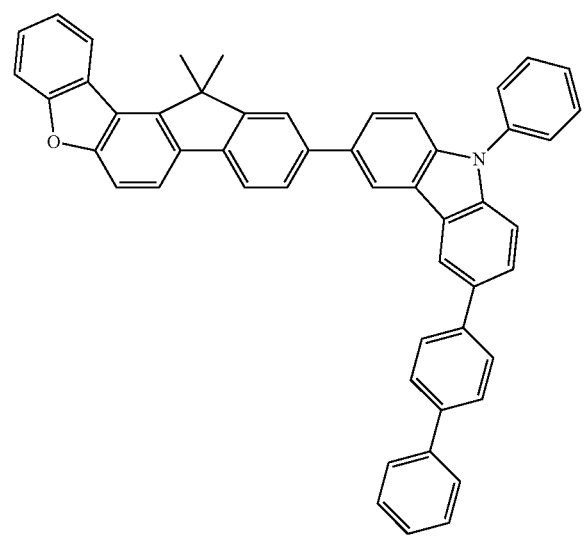
[Chemical Formula D-31]
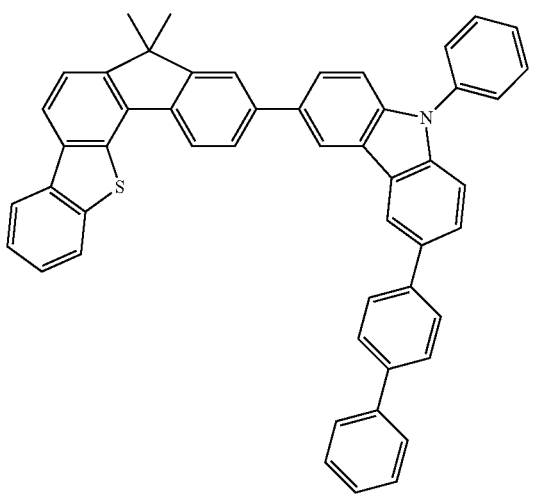

[Chemical Formula D-32]
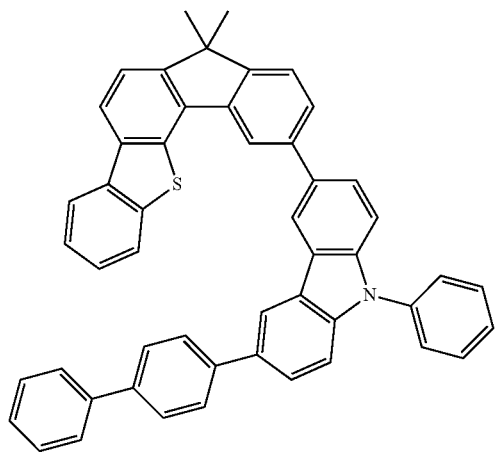
[Chemical Formula D-33]
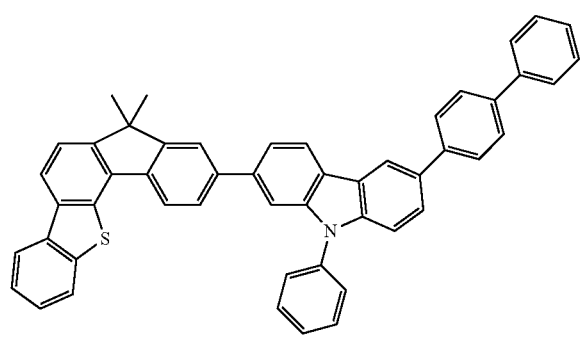
[Chemical Formula D-34]
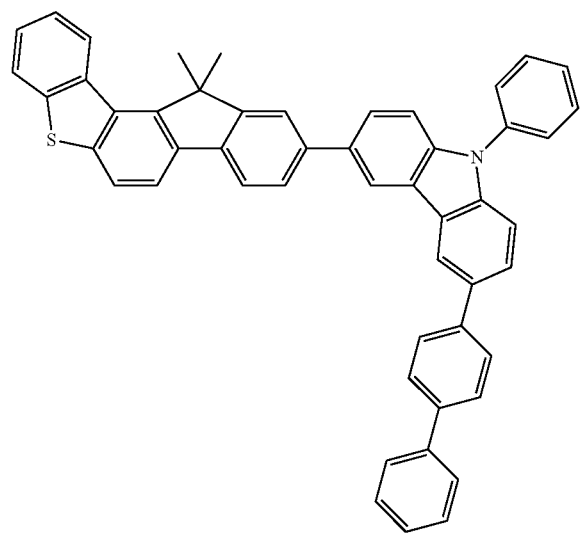
[Chemical Formula D-35]
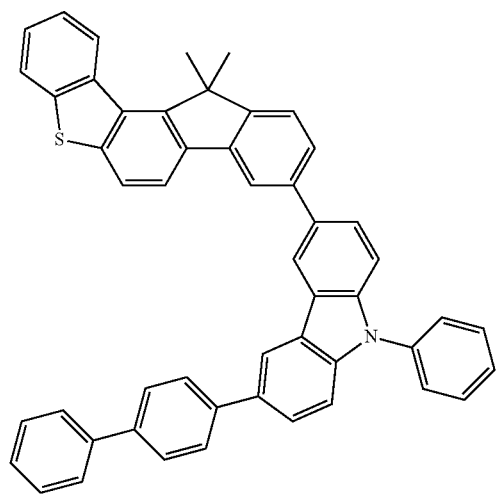
[Chemical Formula D-36]
[Chemical Formula D-37]
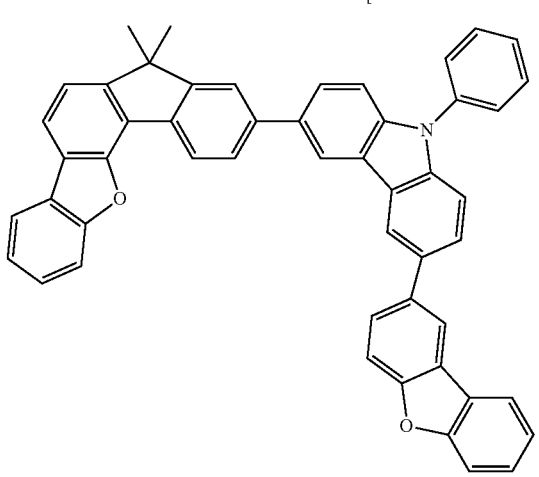

[Chemical Formula D-38]
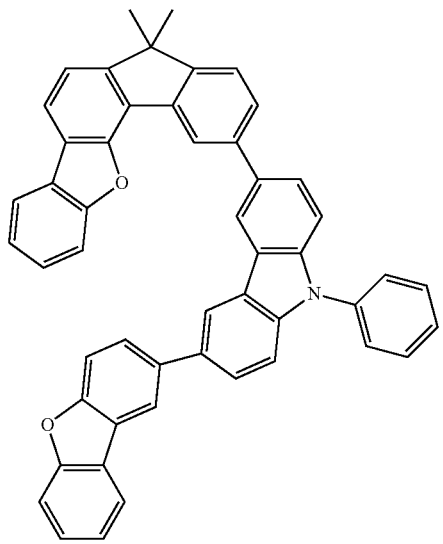
[Chemical Formula D-41]
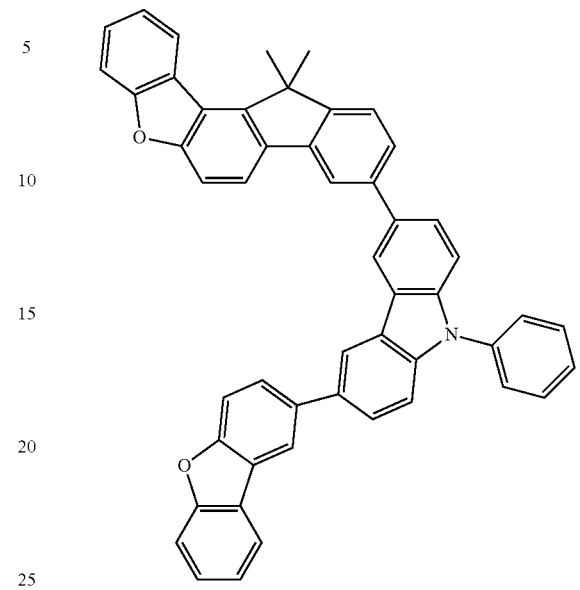
[Chemical Formula D-39]
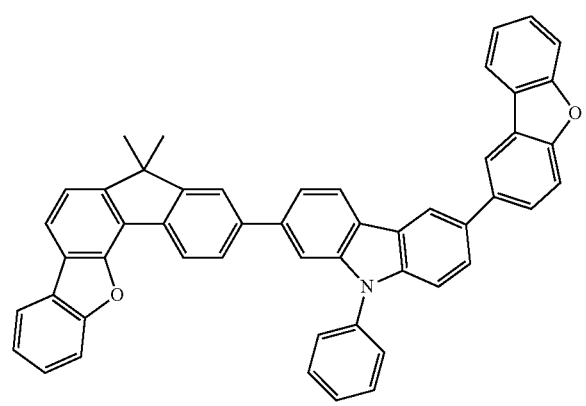
[Chemical Formula D-42]
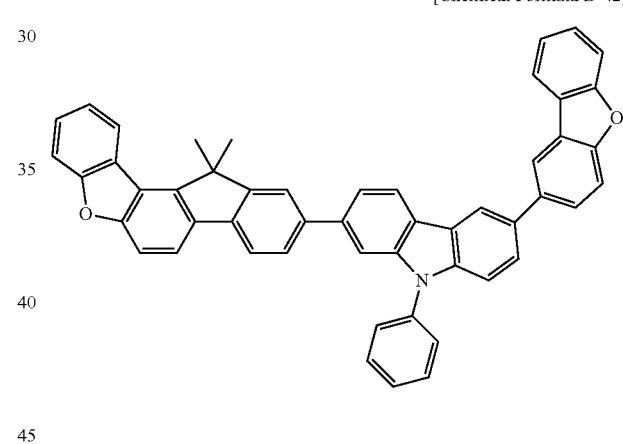
[Chemical Formula D-40]
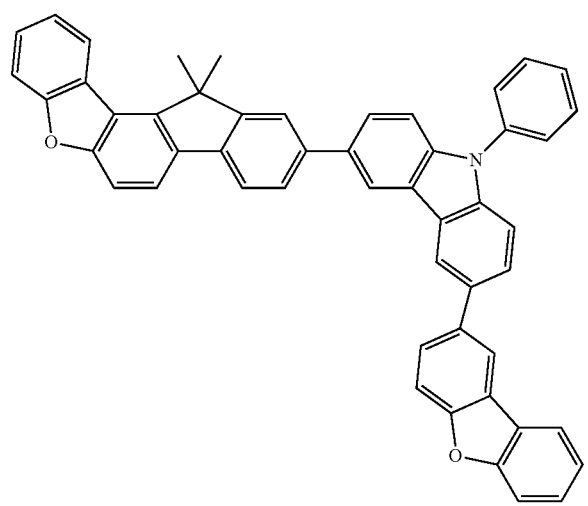
[Chemical Formula D-43]
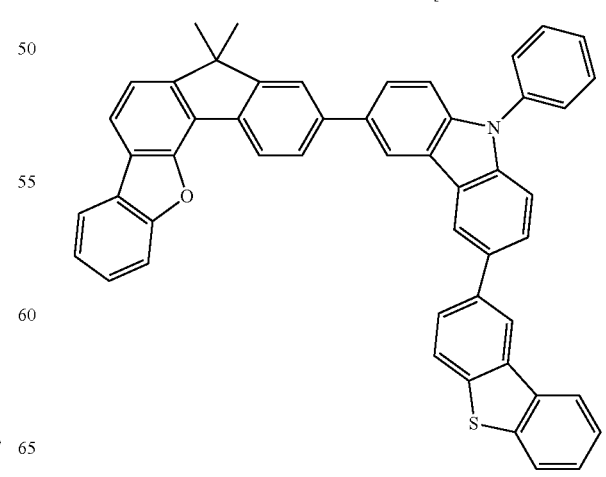

[Chemical Formula D-44]
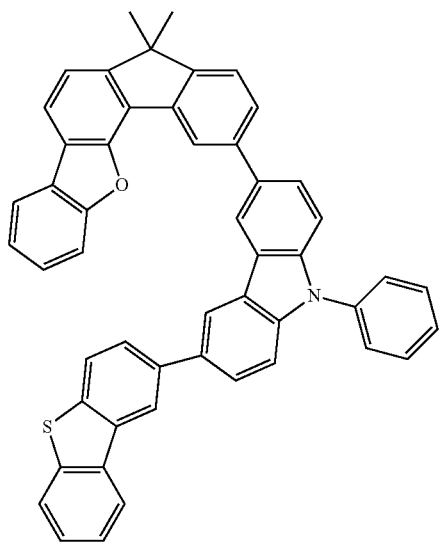
[Chemical Formula D-47]
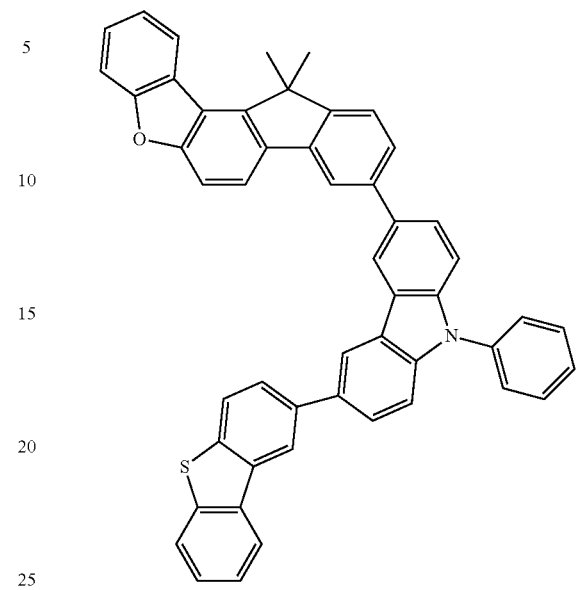
[Chemical Formula D-45]
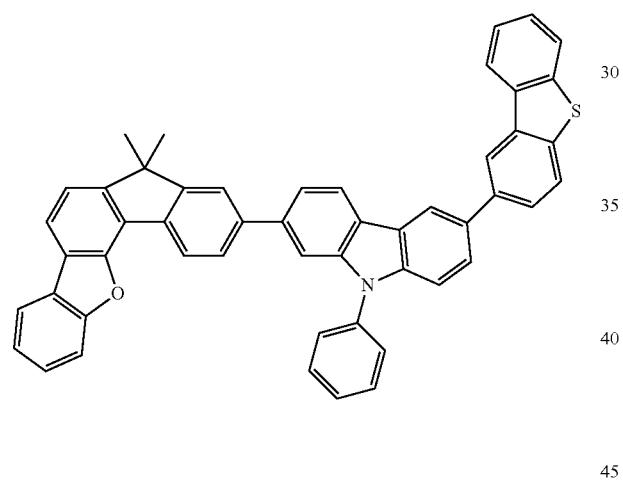
[Chemical Formula D-48]
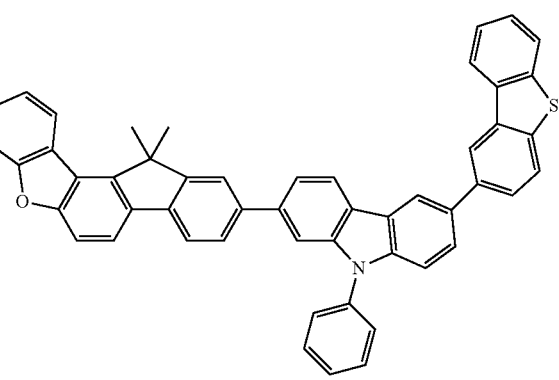
[Chemical Formula D-46]
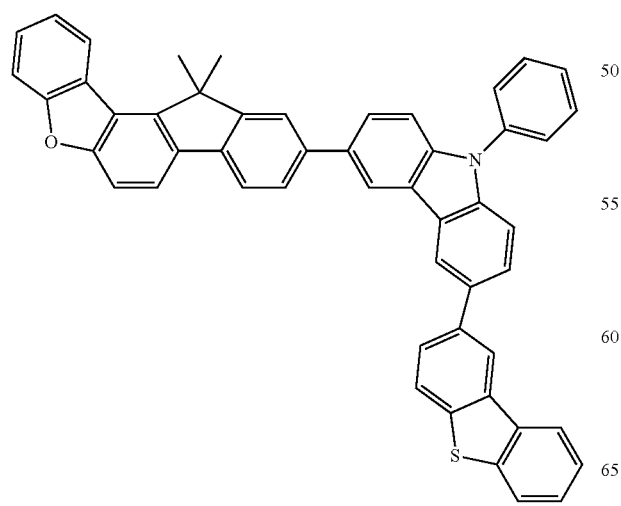
[Chemical Formula D-49]
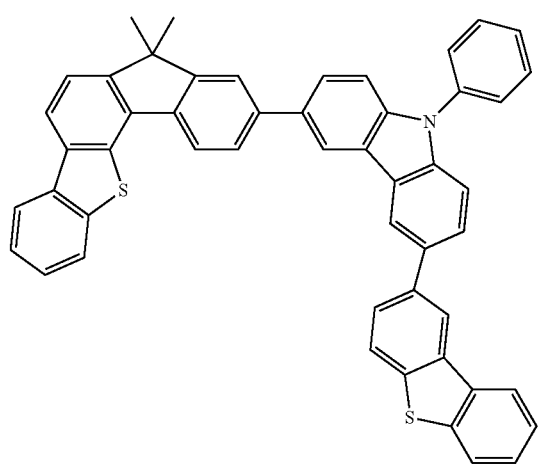

[Chemical Formula D-50]
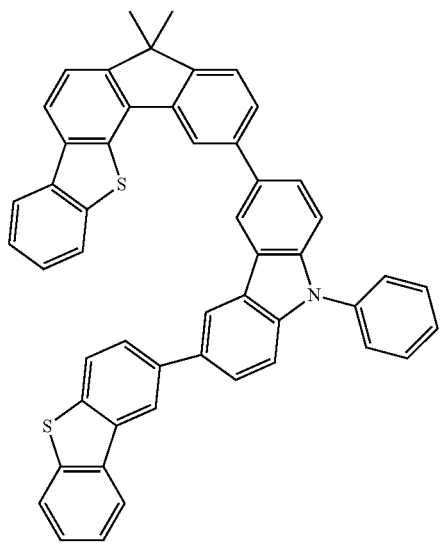
[Chemical Formula D-51]
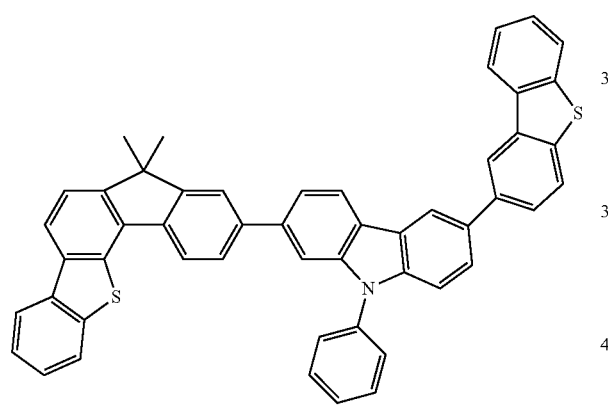
[Chemical Formula D-52]
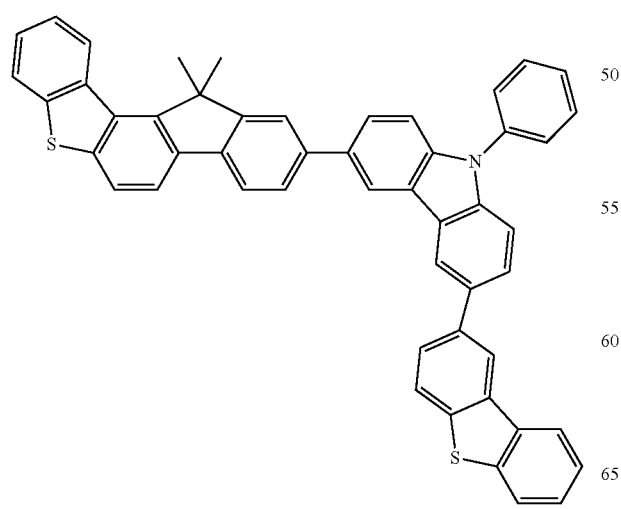
[Chemical Formula D-53]
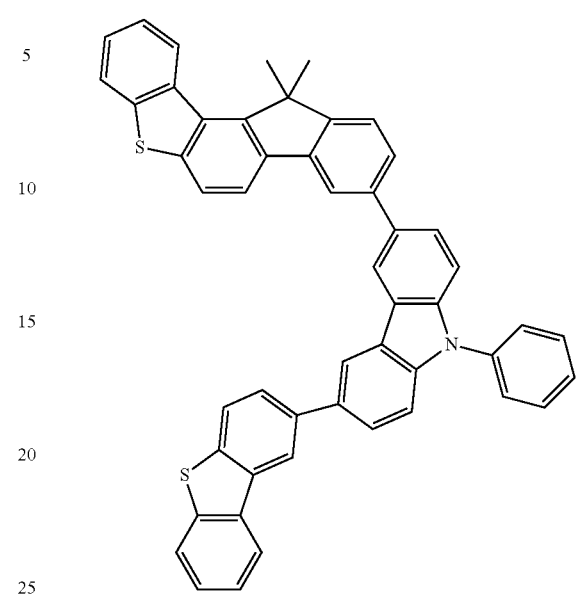
[Chemical Formula D-54]
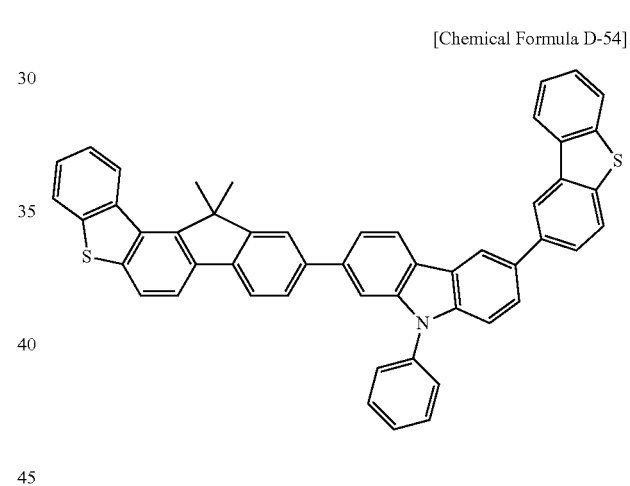
[Chemical Formula D-55]
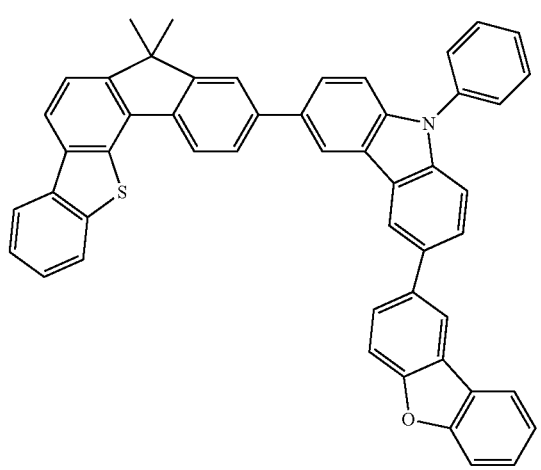

[Chemical Formula D-56]
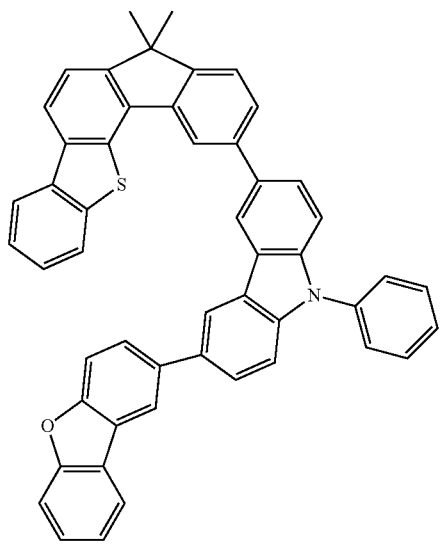
[Chemical Formula D-57]
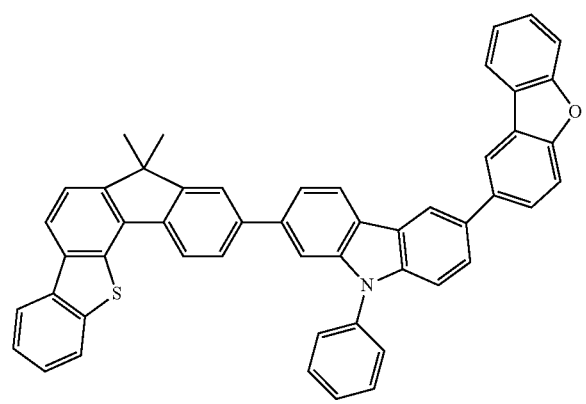
[Chemical Formula D-58]
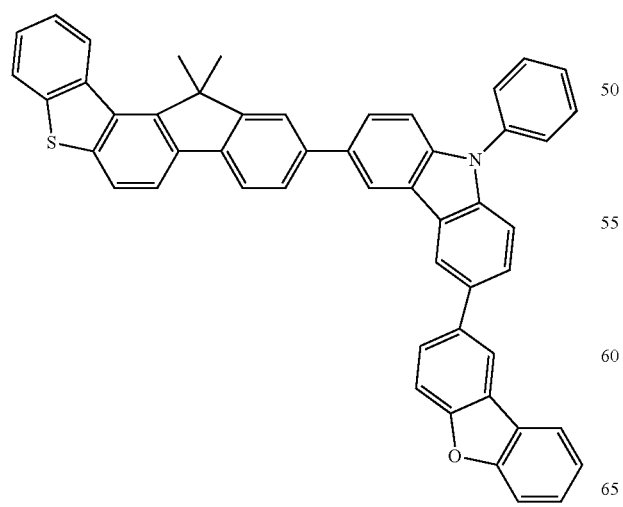
[Chemical Formula D-59]
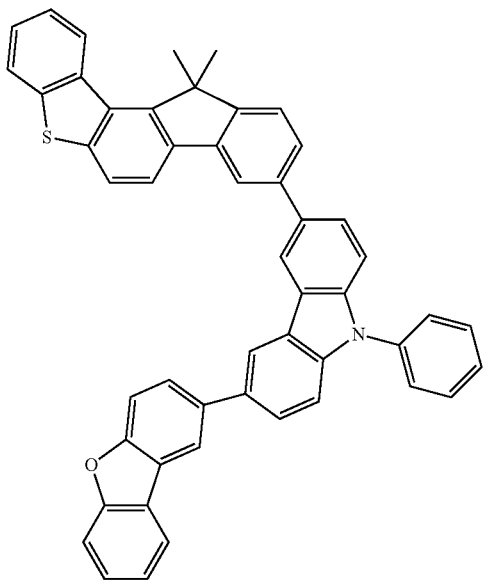
[Chemical Formula D-60]
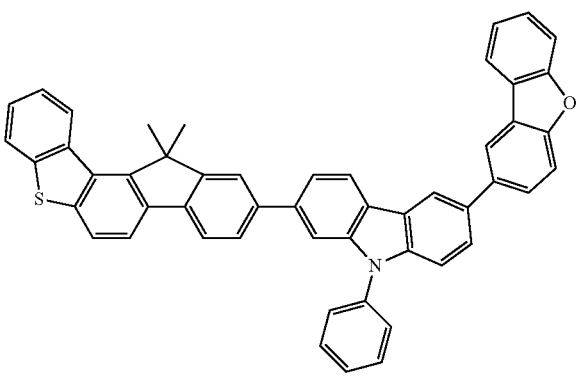
[Chemical Formula D-61]
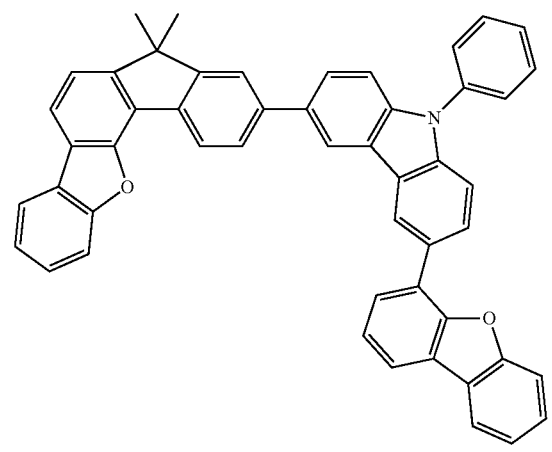

[Chemical Formula D-62]
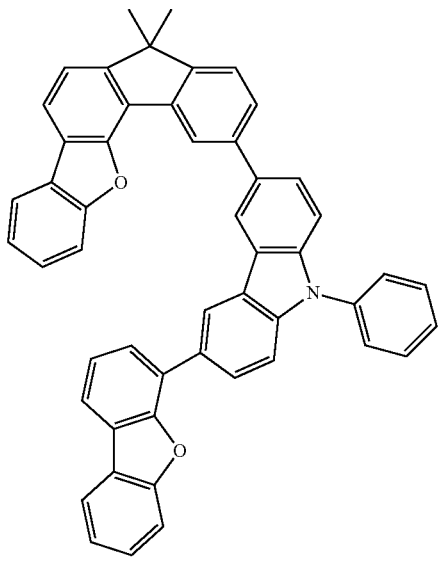
[Chemical Formula D-65]
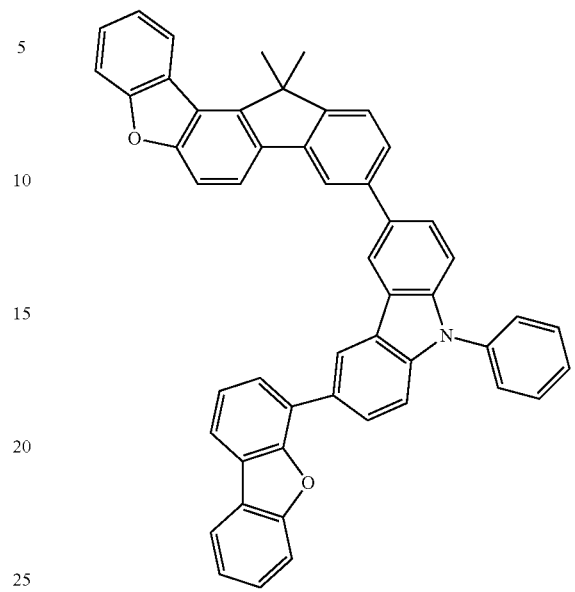
[Chemical Formula D-63]
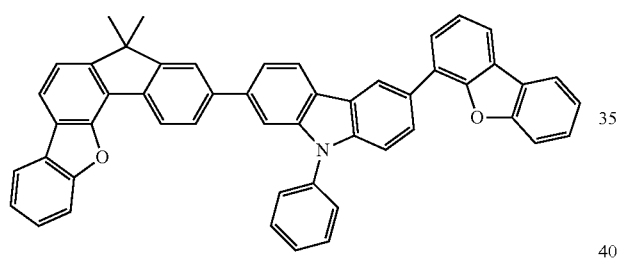
[Chemical Formula D-66]
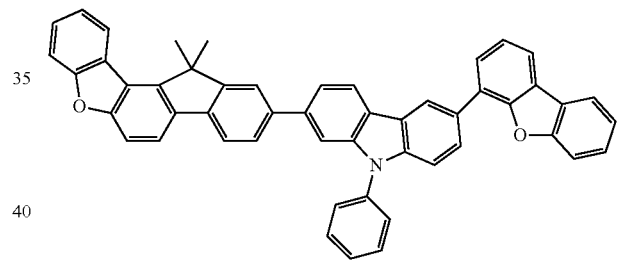
[Chemical Formula D-64]
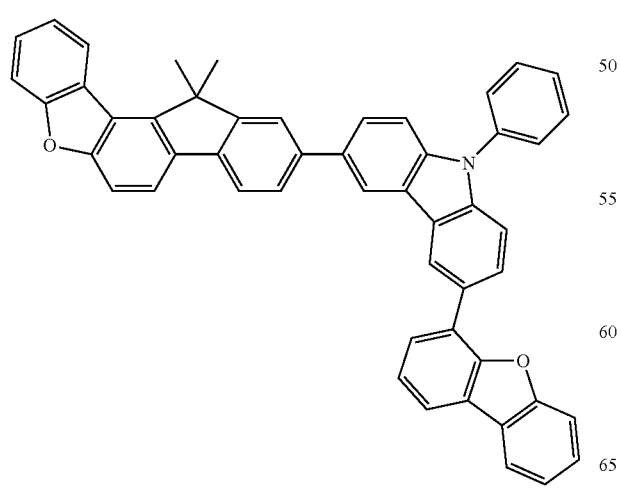
[Chemical Formula D-67]
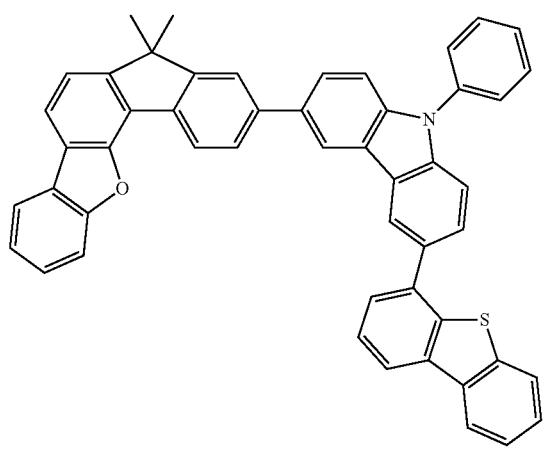

[Chemical Formula D-68]
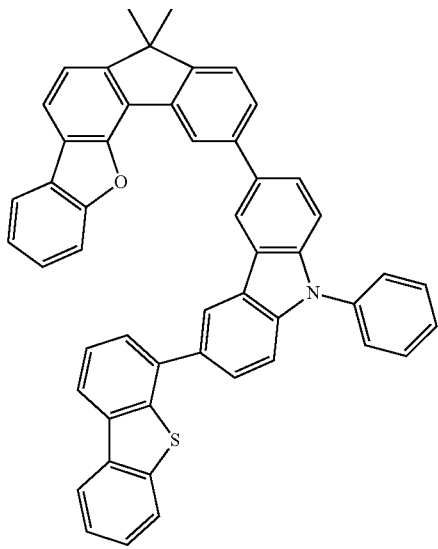
[Chemical Formula D-69]
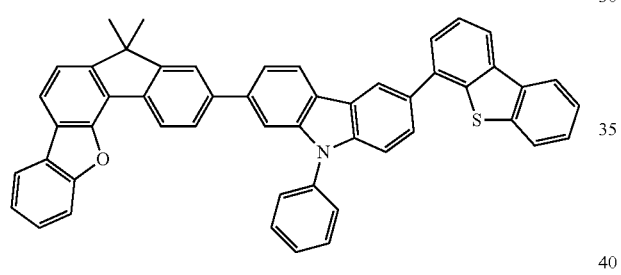
[Chemical Formula D-70]
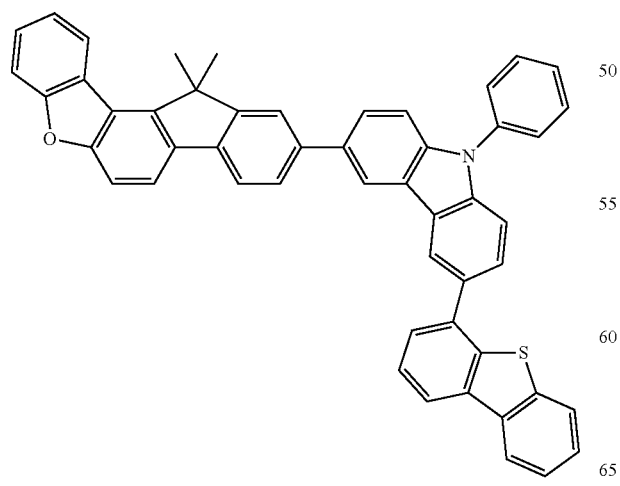
[Chemical Formula D-71]
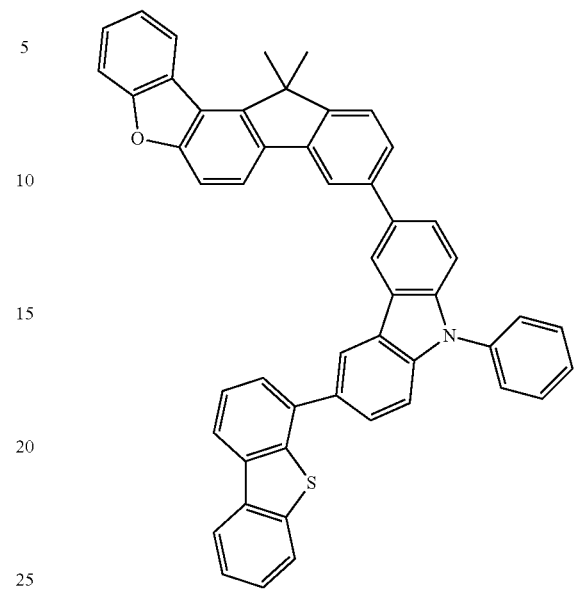
[Chemical Formula D-72]
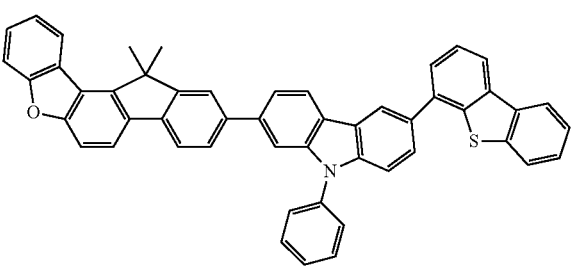
[Chemical Formula D-73]
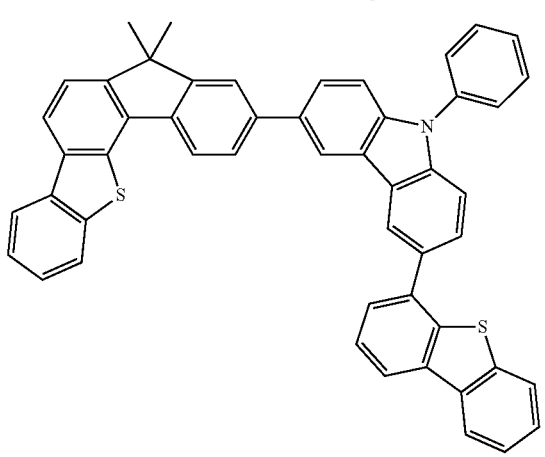

[Chemical Formula D-74]
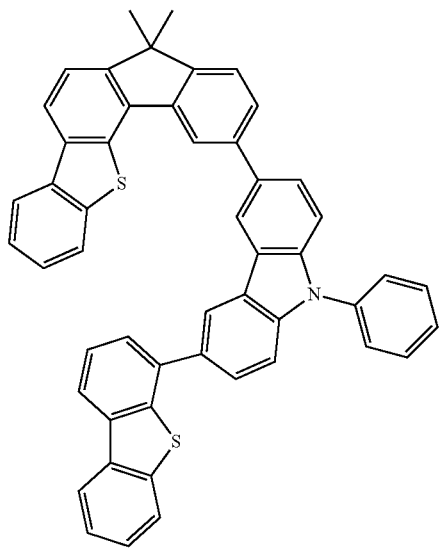
[Chemical Formula D-75]
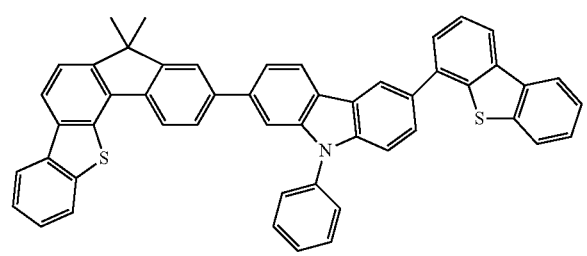
[Chemical Formula D-76]
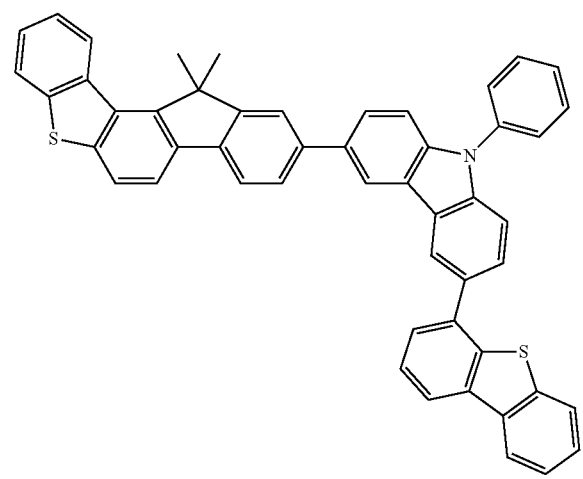
[Chemical Formula D-77]
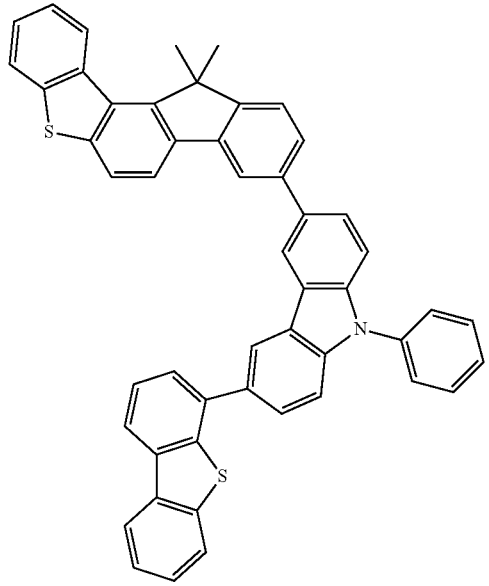
[Chemical Formula D-78]
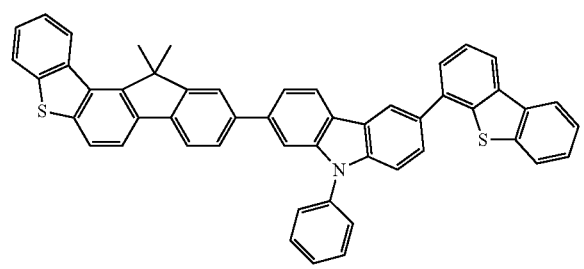
[Chemical Formula D-79]
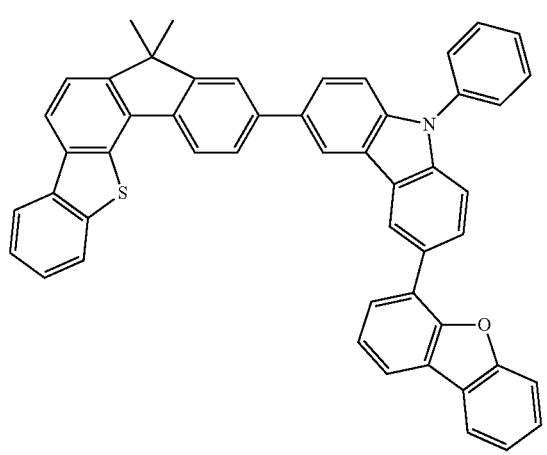

[Chemical Formula D-80]
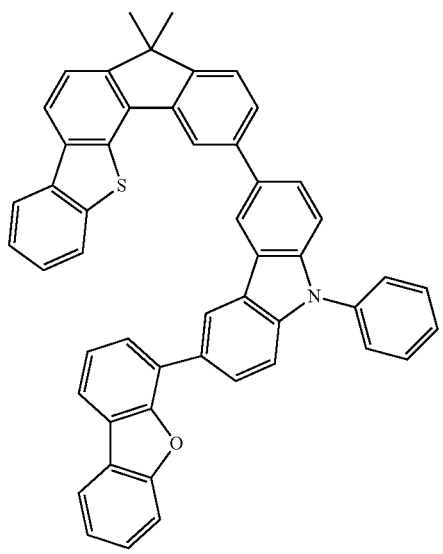
[Chemical Formula D-81]
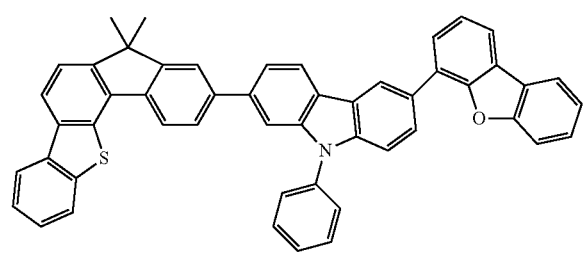
[Chemical Formula D-82]
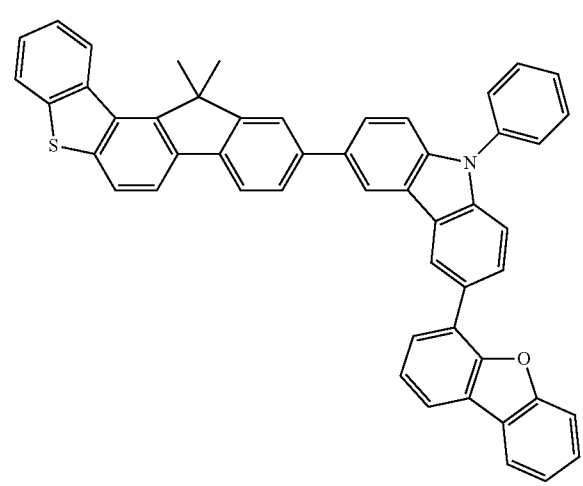
[Chemical Formula D-83]
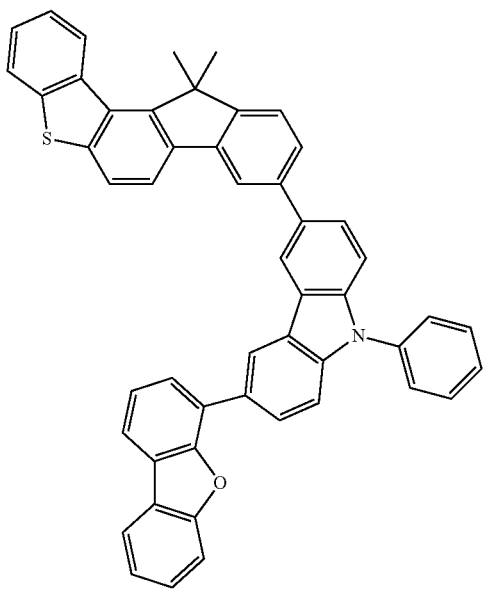
[Chemical Formula D-84]
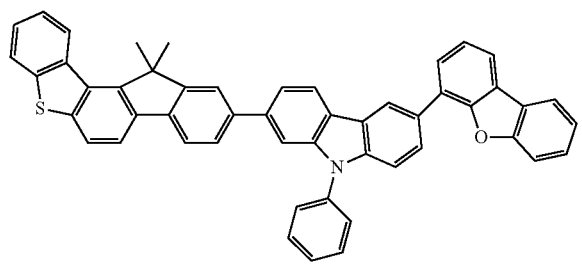
[Chemical Formula D-85]
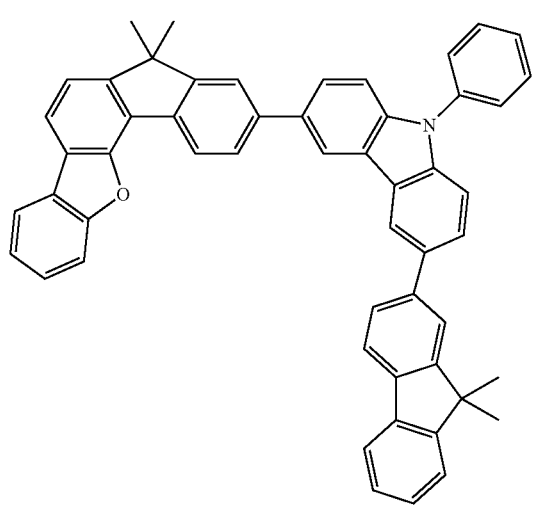

[Chemical Formula D-86]
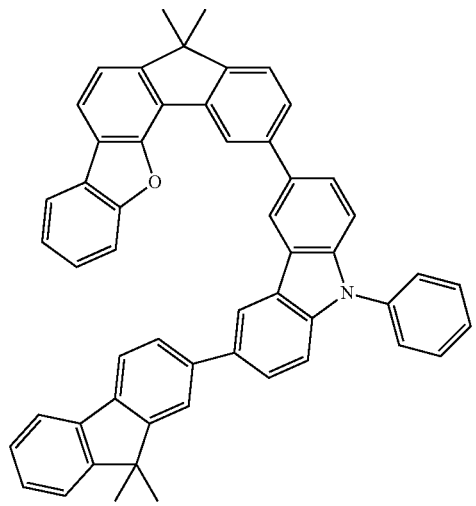
[Chemical Formula D-89]
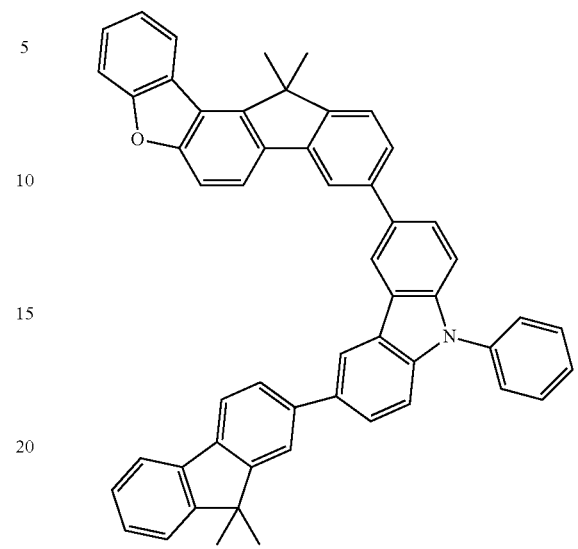
[Chemical Formula D-87]
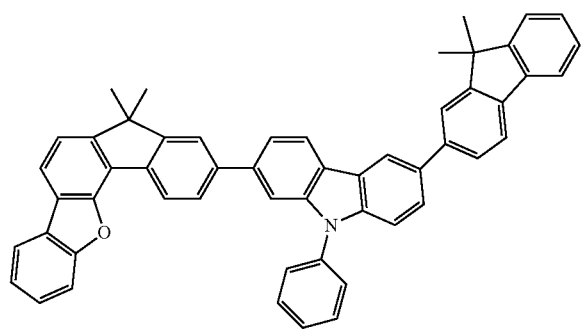
[Chemical Formula D-90]
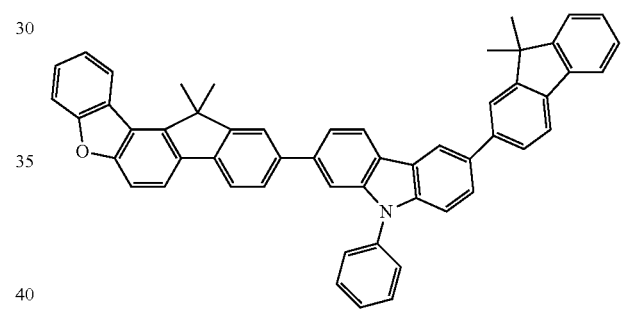
[Chemical Formula D-88]
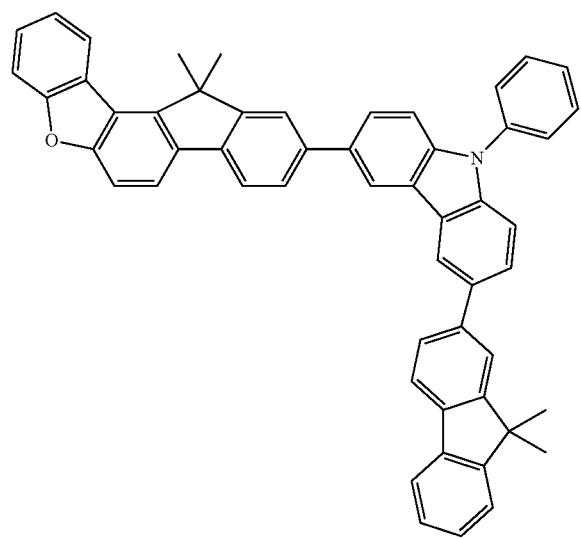
[Chemical Formula D-91]
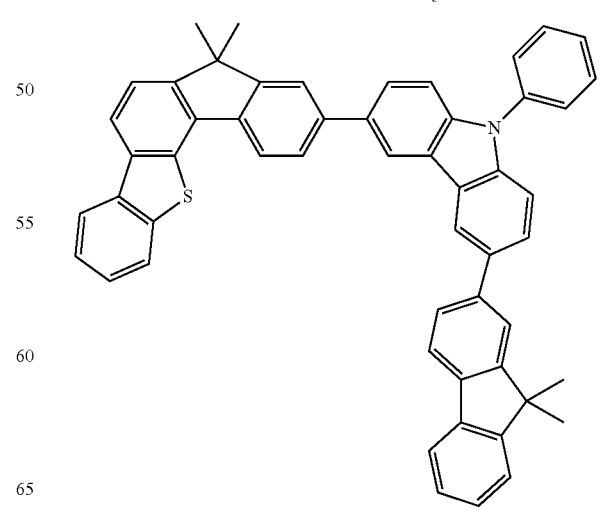

[Chemical Formula D-92]
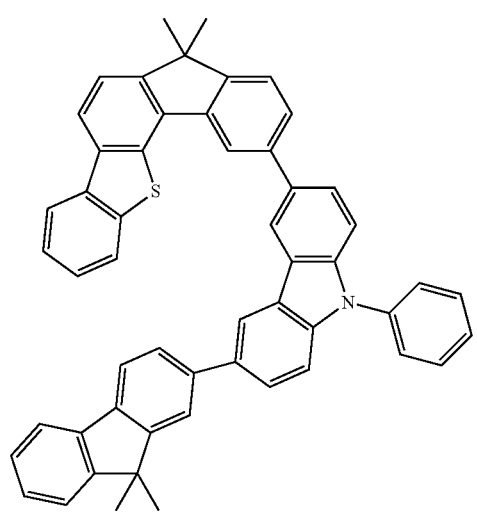
[Chemical Formula D-93]
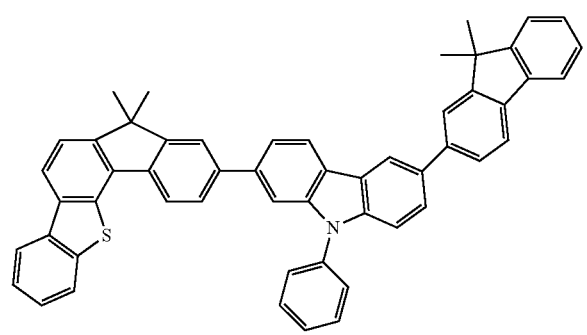
[Chemical Formula D-94]
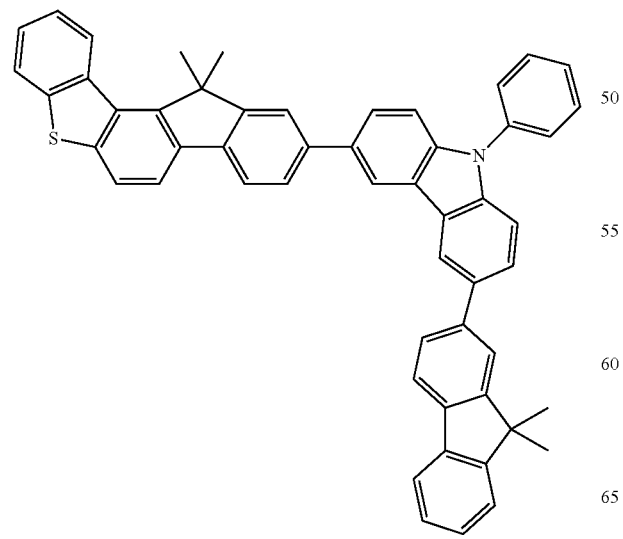
[Chemical Formula D-95]
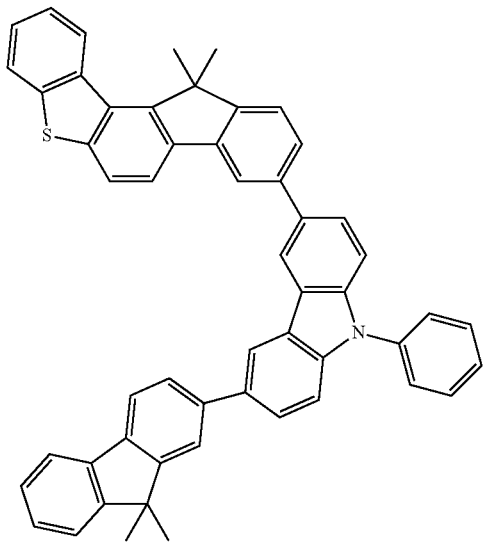
[Chemical Formula D-96]
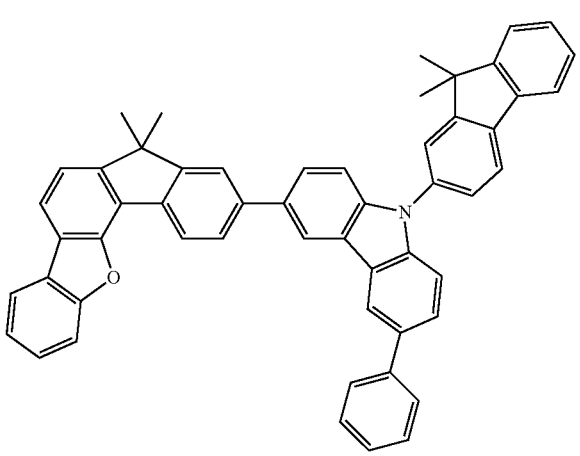
[Chemical Formula D-97]

[Chemical Formula D-98]
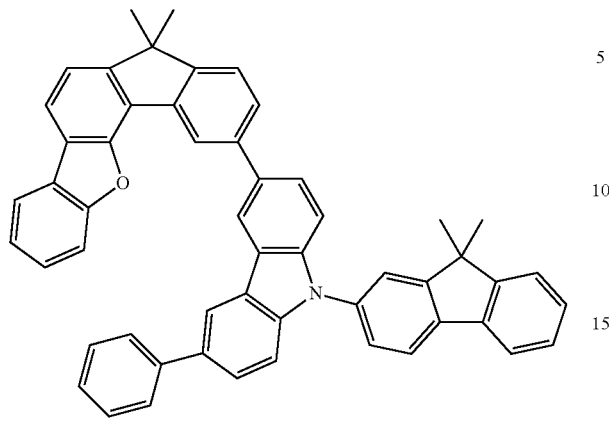
[Chemical Formula D-99]
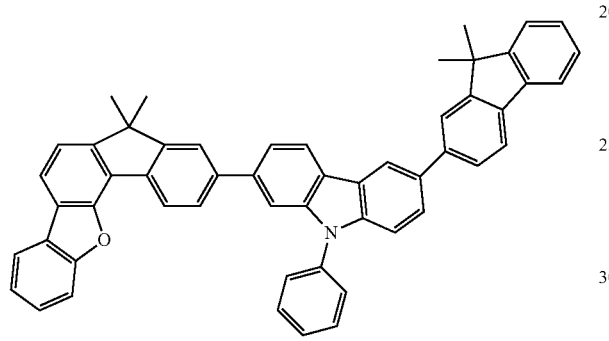
[Chemical Formula D-100]
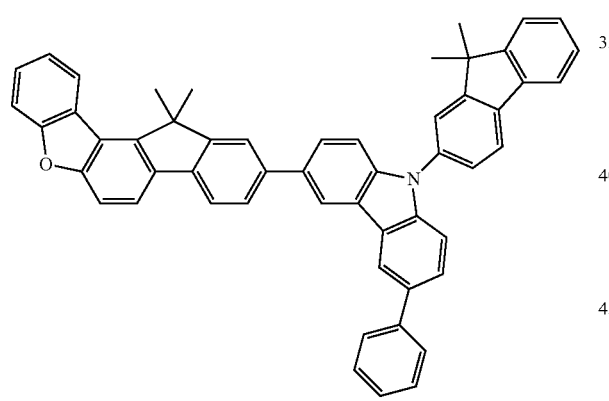
[Chemical Formula D-101]
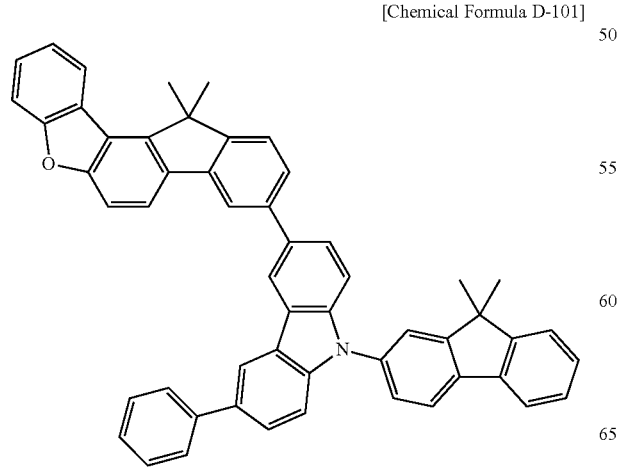
[Chemical Formula D-102]
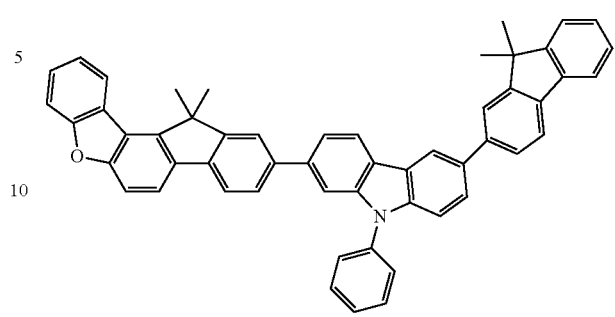
[Chemical Formula D-103]
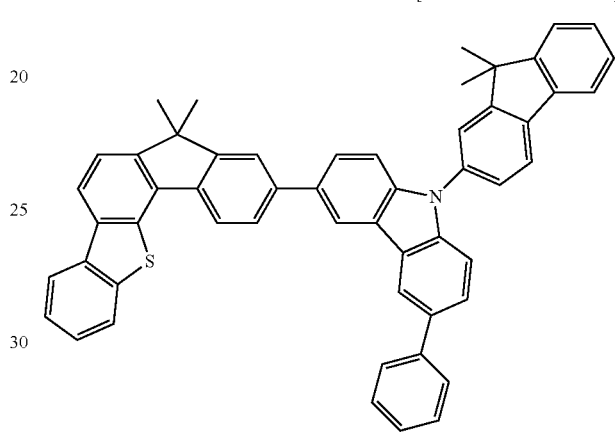
[Chemical Formula D-104]
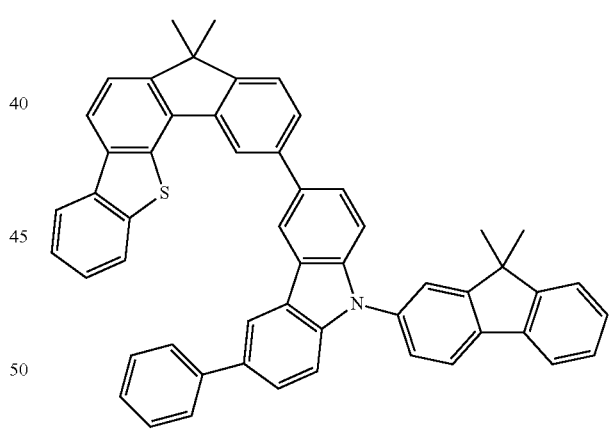
[Chemical Formula D-105]
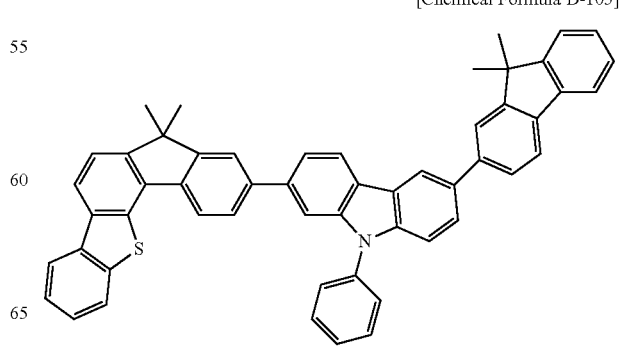

[Chemical Formula D-106]
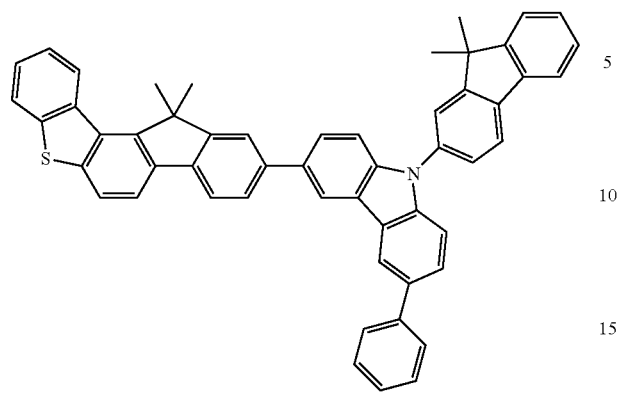
[Chemical Formula D-109]
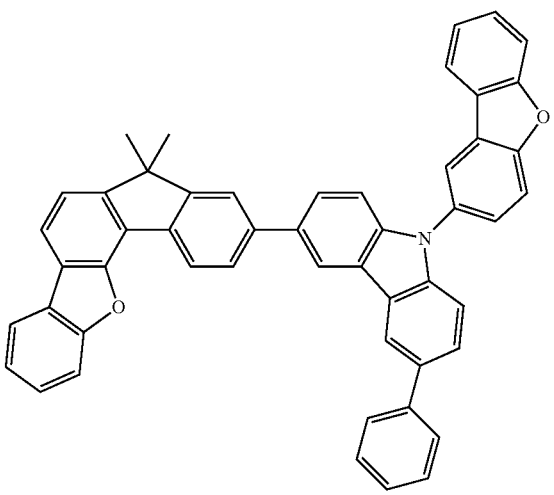
[Chemical Formula D-107]
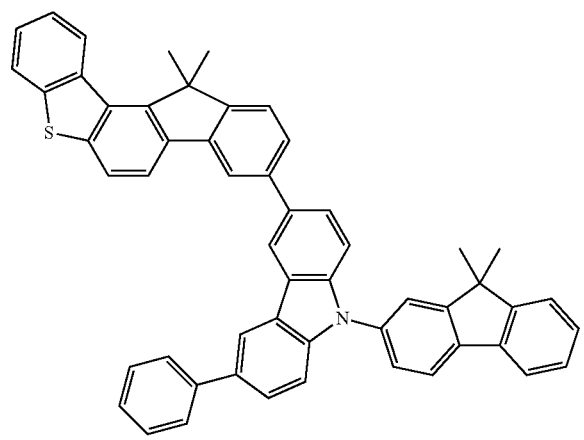
[Chemical Formula D-110]
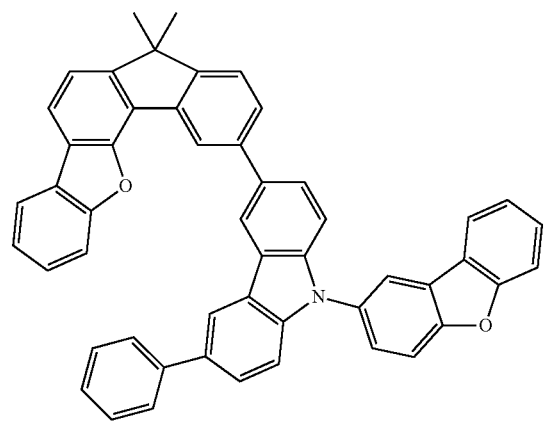
[Chemical Formula D-108]
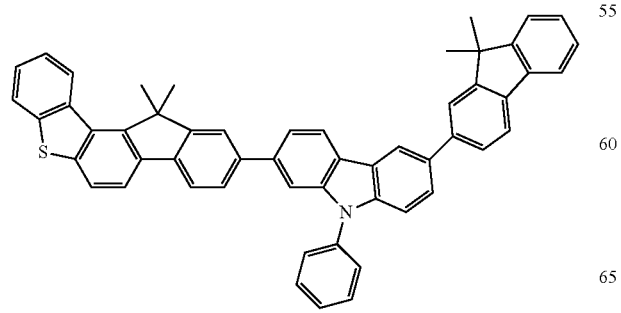
[Chemical Formula D-111]
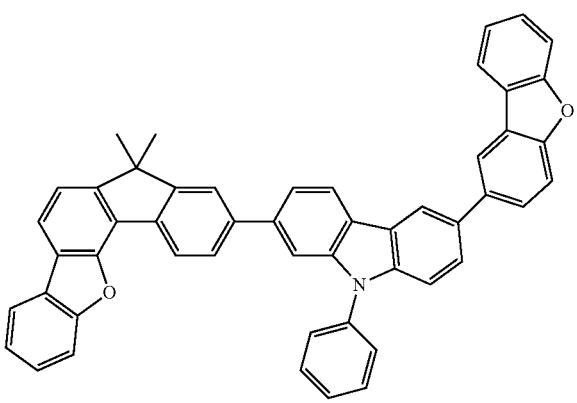

[Chemical Formula D-112]
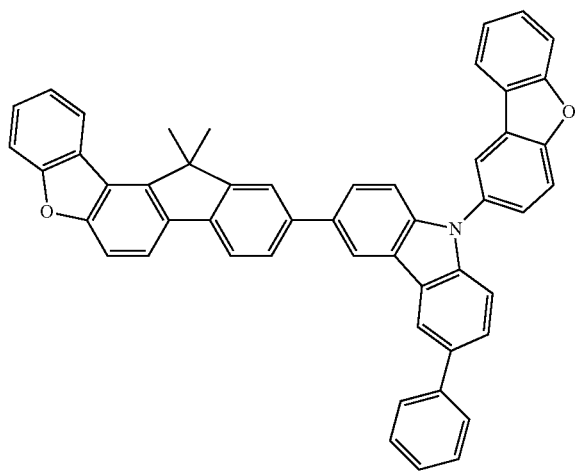
[Chemical Formula D-113]
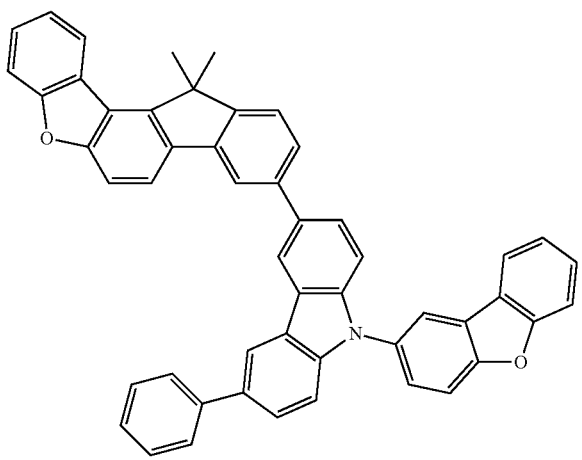
[Chemical Formula D-114]
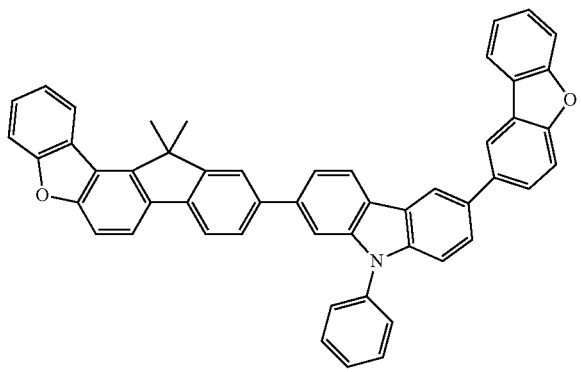
[Chemical Formula D-115]
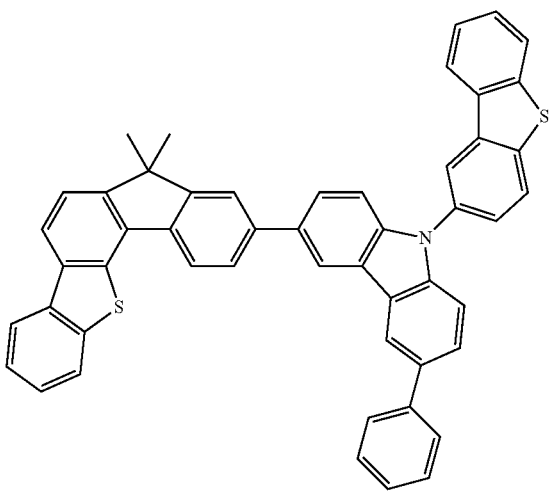
[Chemical Formula D-116]
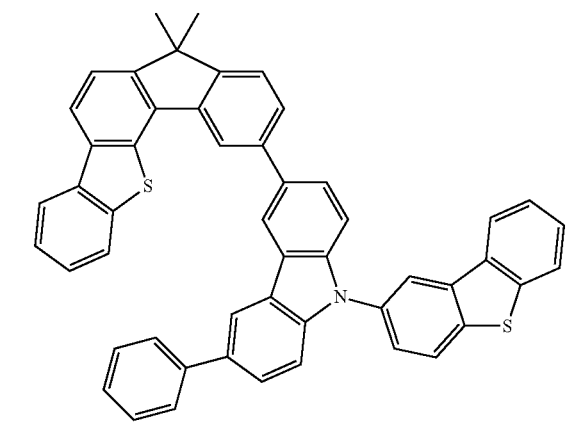
[Chemical Formula D-117]
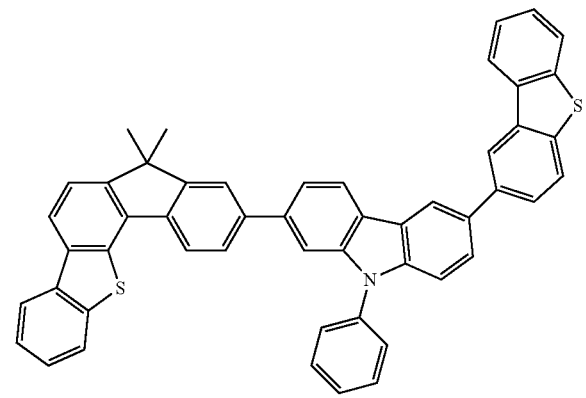

[Chemical Formula D-118]
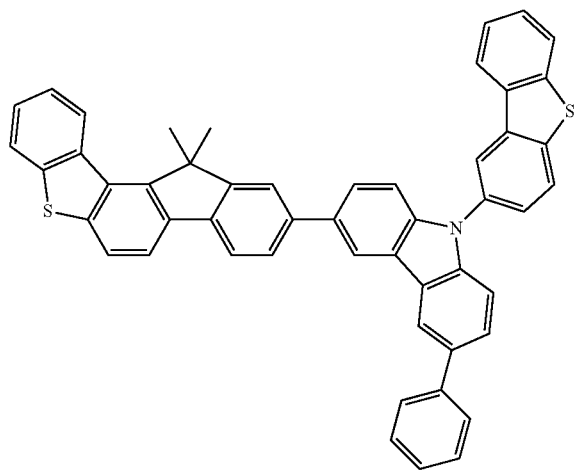
[Chemical Formula D-119]
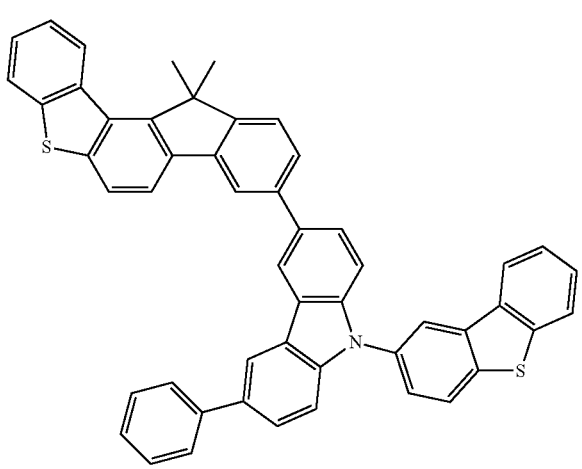
[Chemical Formula D-120]
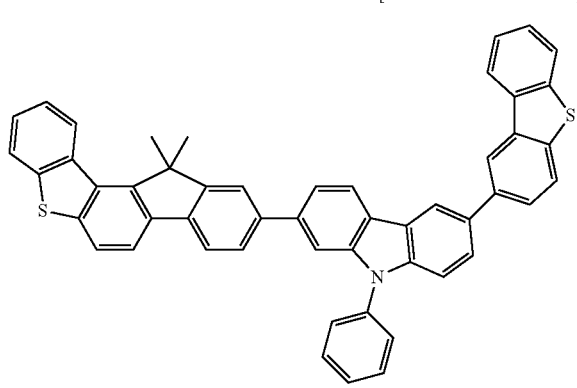
[Chemical Formula D-121]
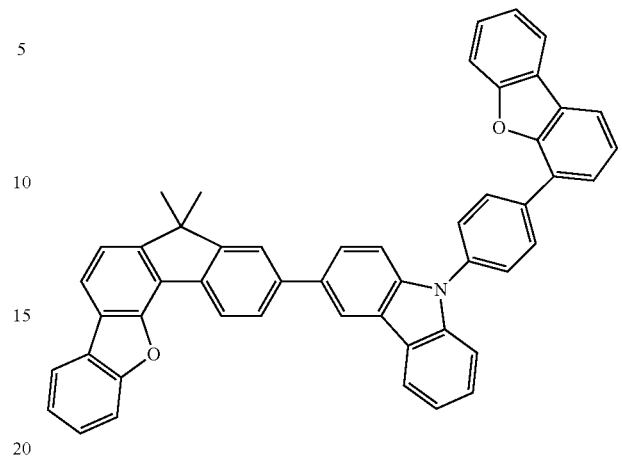
[Chemical Formula D-122]
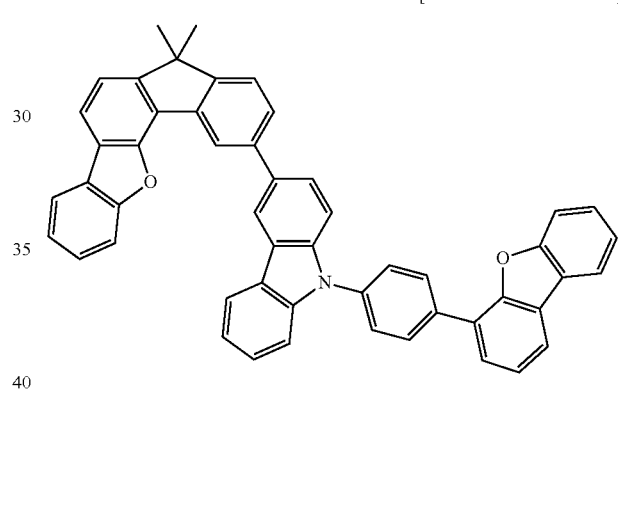
[Chemical Formula D-123]
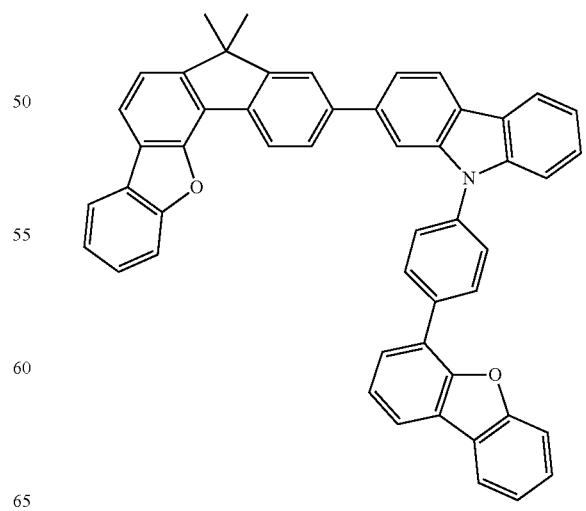

[Chemical Formula D-124]
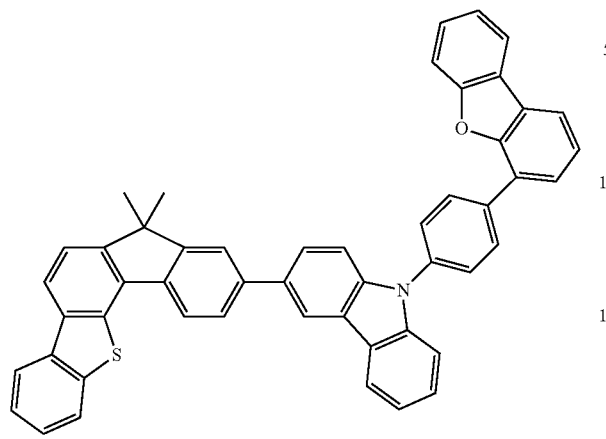
[Chemical Formula D-125]
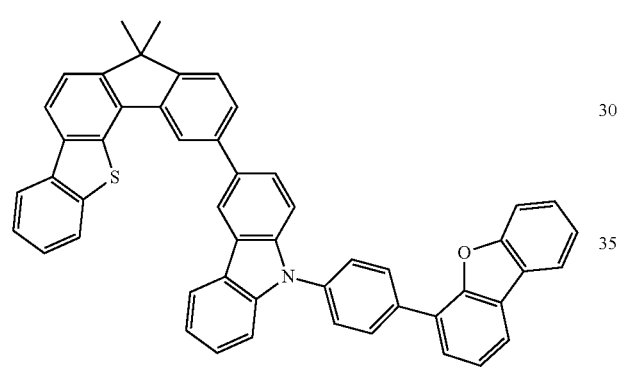
[Chemical Formula D-126]
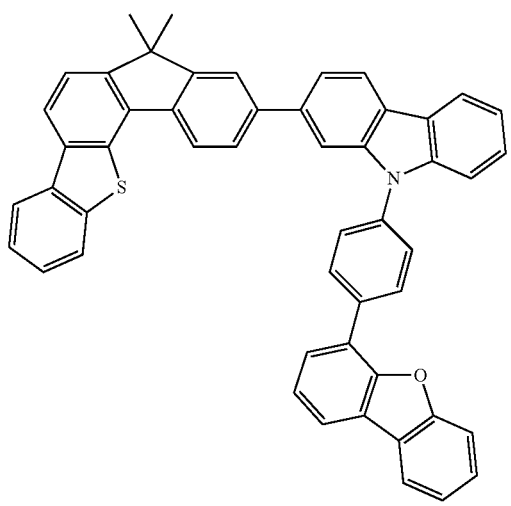
[Chemical Formula D-127]
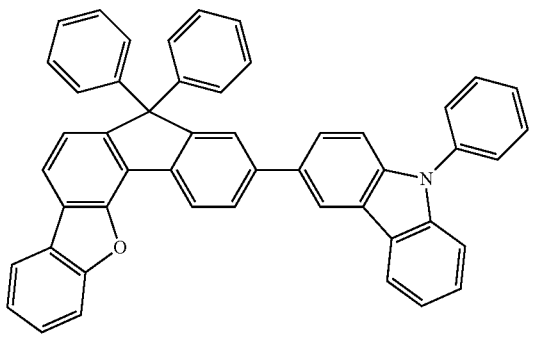
[Chemical Formula D-128]
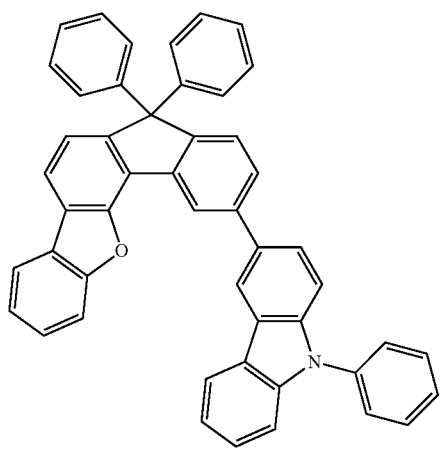
[Chemical Formula D-129]
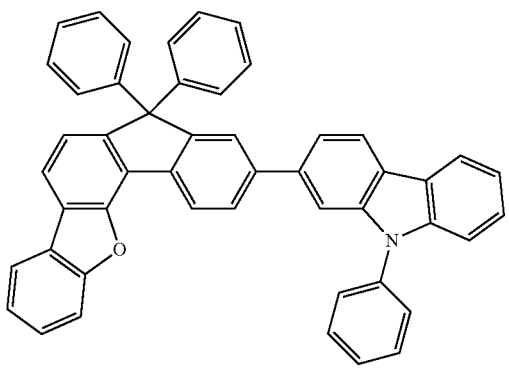
[Chemical Formula D-130]
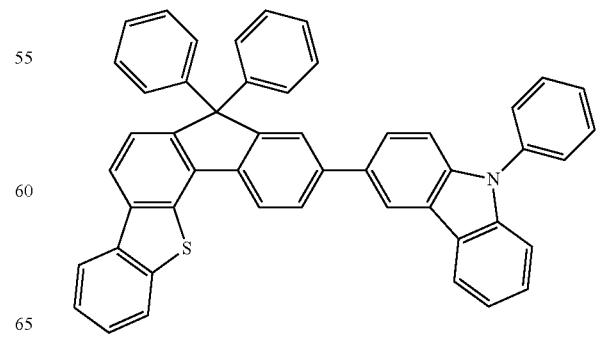

[Chemical Formula D-131]
[Chemical Formula D-134]
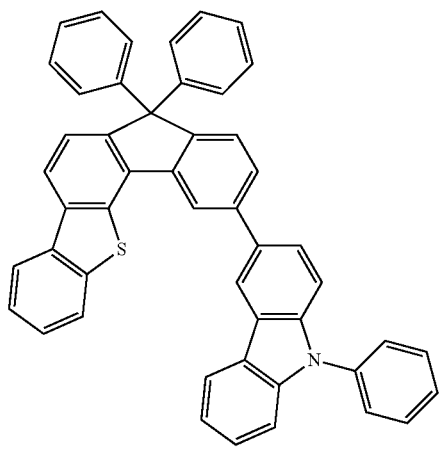
[Chemical Formula D-132]
[Chemical Formula D-135]
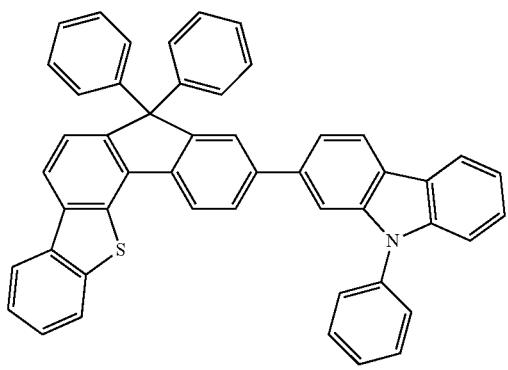
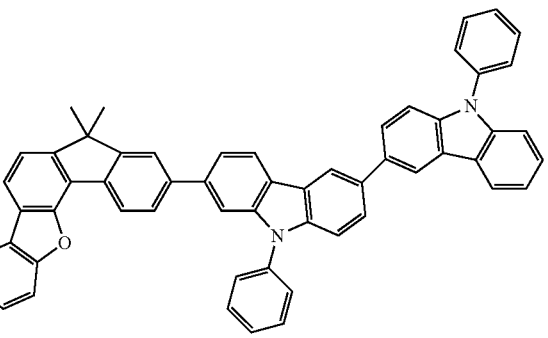
[Chemical Formula D-133]
[Chemical Formula D-136]
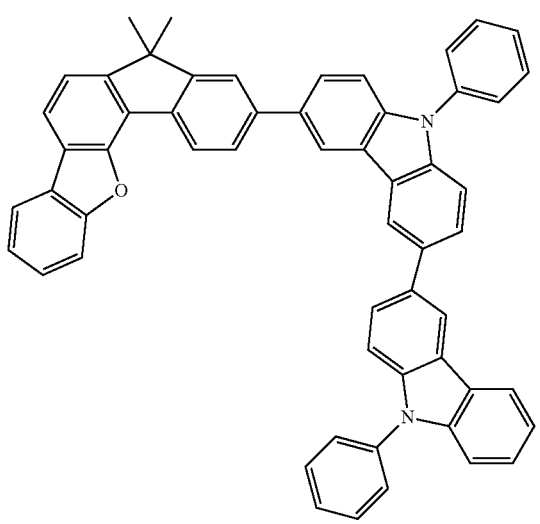
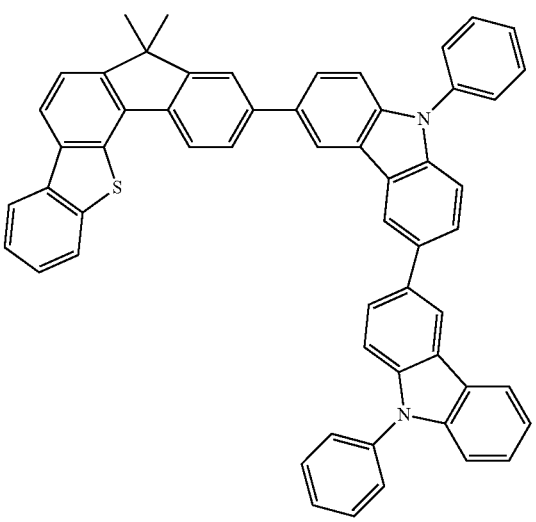

[Chemical Formula D-137]
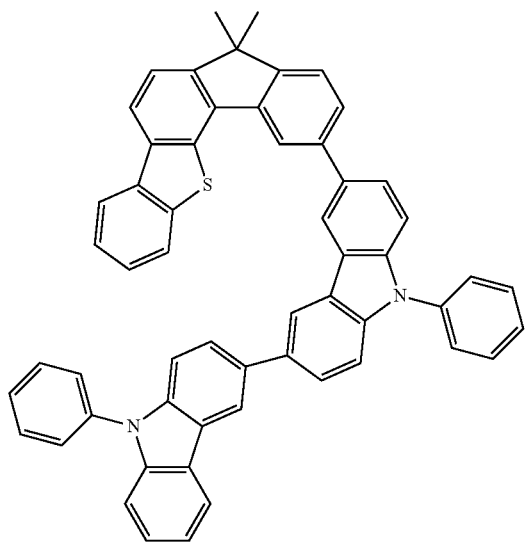
[Chemical Formula D-138]
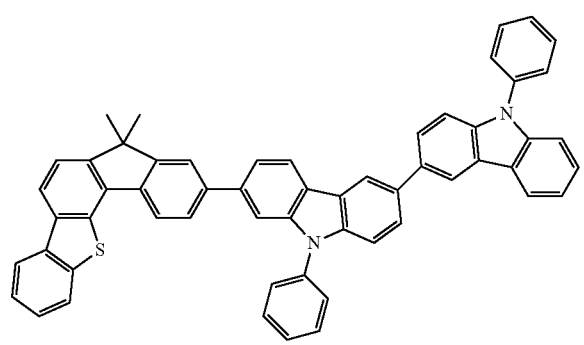
[Chemical Formula D-139]
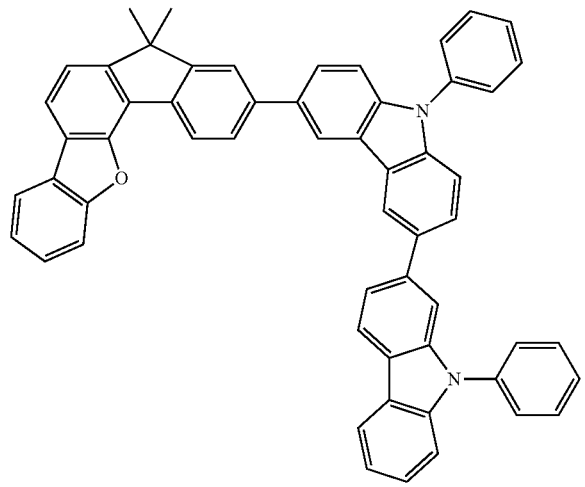
[Chemical Formula D-140]
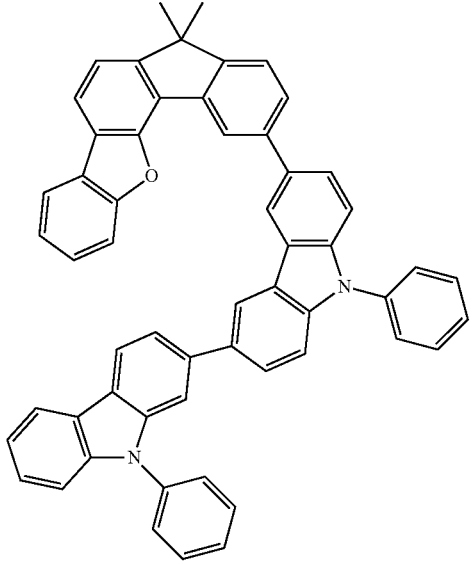
[Chemical Formula D-141]
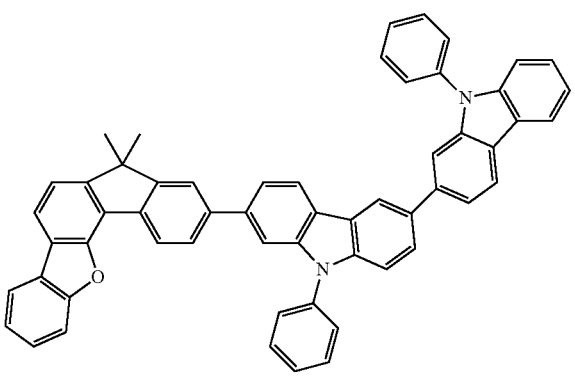
[Chemical Formula D-142]
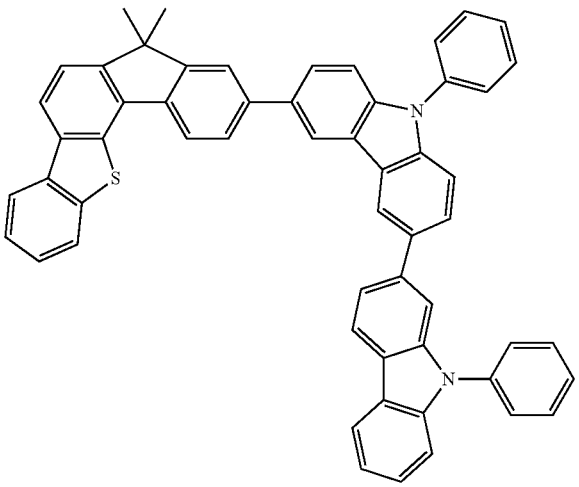

[Chemical Formula D-143]

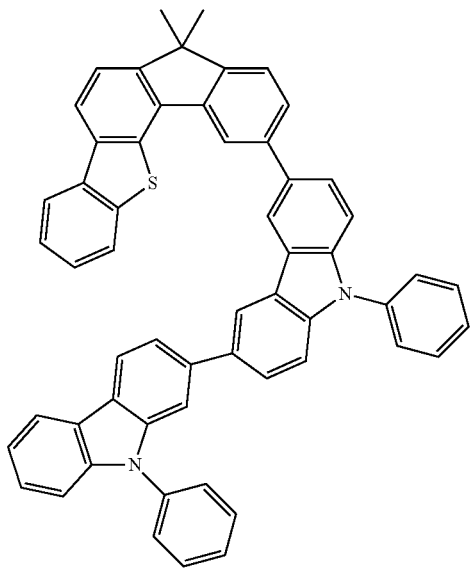

[Chemical Formula D-144]

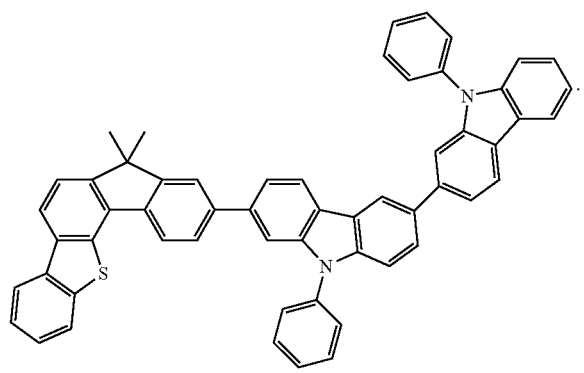

6. The compound for an organic optoelectronic device as claimed in claim 1, wherein the compound has a triplet exciton energy of greater than or equal to 2.0 eV.

7. An organic light emitting diode, comprising:
an anode;
a cathode;
and at least one organic thin layer between the anode and cathode,
wherein the at least one organic thin layer includes the compound for an organic optoelectronic device as claimed in claim 1.

8. The organic light emitting diode as claimed in claim 7, wherein the at least one organic thin layer includes an emission layer, a hole transport layer, a hole injection layer, an electron transport layer, an electron injection layer, a hole blocking layer, or a combination thereof.

9. The organic light emitting diode as claimed in claim 8, wherein:
the at least one organic thin layer includes a hole transport layer (HTL) or a hole injection layer (HIL), and
the compound is included in the hole transport layer (HTL) or the hole injection layer (HIL).

10. The organic light emitting diode as claimed in claim 8, wherein:
the at least one organic thin layer includes an emission layer, and
the compound is included in the emission layer.

11. A display device comprising the organic light emitting diode as claimed in claim 7.

12. A compound for an organic optoelectronic device, the compound being represented by a combination of the following Chemical Formulae AD-5 and AD-2:

[Chemical Formula AD-5]

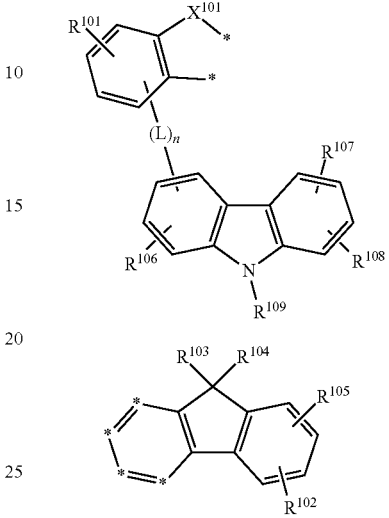

[Chemical Formula AD-2]

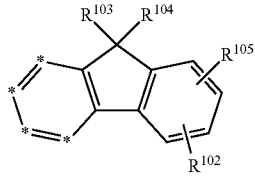

wherein, in Chemical Formulae AD-5 and AD-2,
$X^{101}$ is —O—, —S—, —S(O)— or —S(O)$_2$—,
$R^{101}$ to $R^{109}$ are each independently hydrogen, deuterium, a substituted or unsubstituted C1 to C10 alkyl group, a substituted or unsubstituted C6 to C30 aryl group or a substituted or unsubstituted C2 to C30 heteroaryl group,
L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group,
n is an integer of 0 to 3, and
the two *s of Chemical Formula AD-5 are bonded with two adjacent *s of Chemical Formula AD-2 to form a fused ring, and the remaining two *s of Chemical Formula AD-2 are CH.

13. The compound for an organic optoelectronic device as claimed in claim 12, wherein the compound for an organic optoelectronic device is represented by a combination of the following Chemical Formulae AD-6 and AD-2:

[Chemical Formula AD-6]

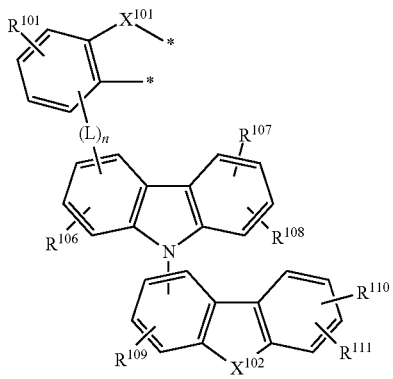

[Chemical Formula AD-2]

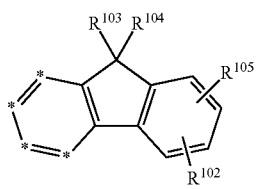

wherein, in Chemical Formulae AD-6 and AD-2,

X$^{101}$ is —O—, —S—, —S(O)— or —S(O)$_2$—,

X$^{102}$ is —O—, —S—, —S(O)—, —CR'R"—, —S(O)$_2$— or —NR'—, in which R' and R" are each independently hydrogen, deuterium, a substituted or unsubstituted C1 to C10 alkyl group, a substituted or unsubstituted C6 to C30 aryl group or a substituted or unsubstituted C2 to C30 heteroaryl group, R$^{101}$ to R$^{111}$ are each independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and the two *s of Chemical Formula AD-6 are bonded with two adjacent *s of Chemical Formula AD-2 to form a fused ring, and the remaining two *s of Chemical Formula AD-2 are CH.

14. The compound for an organic optoelectronic device as claimed in claim 12, wherein the compound is represented by a combination of the following Chemical Formulae:

[Chemical Formula AD-7]

[Chemical Formula AD-2]

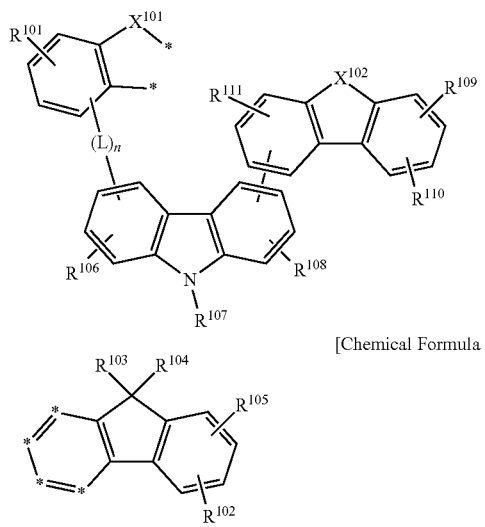

wherein, in Chemical Formulae AD-7 and AD-2,

X$^{101}$ is —O—, —S—, —S(O)— or —S(O)$_2$—,

X$^{102}$ is —O—, —S—, —S(O)—, —S(O)$_2$—, —CR'R"— or —NR'—, in which R' and R" are each independently hydrogen, deuterium, a substituted or unsubstituted C1 to C10 alkyl group, a substituted or unsubstituted C6 to C30 aryl group or a substituted or unsubstituted C2 to C30 heteroaryl group, R$^{101}$ to R$^{111}$ are each independently hydrogen, deuterium, a substituted or unsubstituted C1 to C10 alkyl group, a substituted or unsubstituted C6 to C30 aryl group or a substituted or unsubstituted C2 to C30 heteroaryl group, L is a single bond, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n is an integer of 0 to 3, and the two *s of Chemical Formula AD-7 are bonded with two adjacent *s of Chemical Formula AD-2 to form a fused ring, and the remaining two *s of Chemical Formula AD-2 are CH.

15. The compound for an organic optoelectronic device as claimed in claim 12, wherein R$^{101}$ to R$^{109}$ are each independently hydrogen, a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

16. The compound for an organic optoelectronic device as claimed in claim 12, wherein the compound is represented by one of the following Chemical Formulae D-147, D-150, D-153, D-156, D-159, D-162, D-165, D-168, D-171, D-174, D-177, D-180, D-183, D-186, D-189, D-192, D-195, D-198, D-201, D-204, D-207, and D-210:

[Chemical Formula D-147]
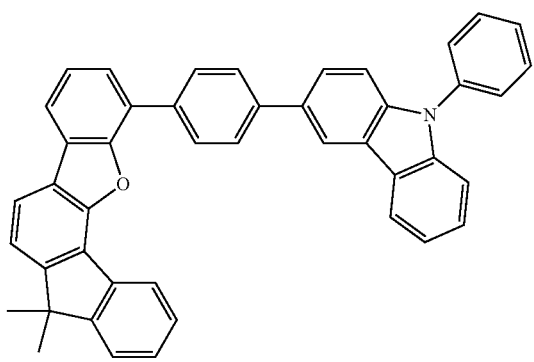
[Chemical Formula D-150]
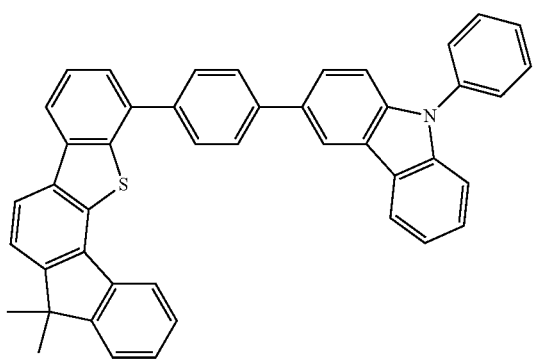
[Chemical Formula D-153]
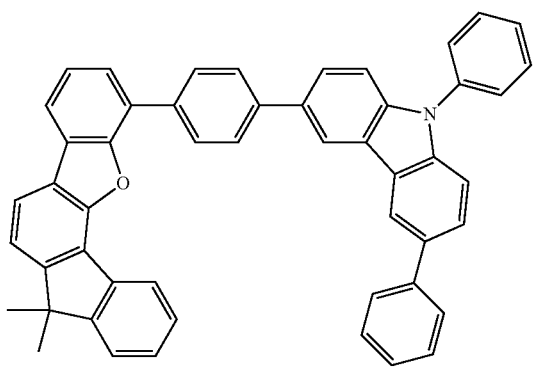
[Chemical Formula D-156]
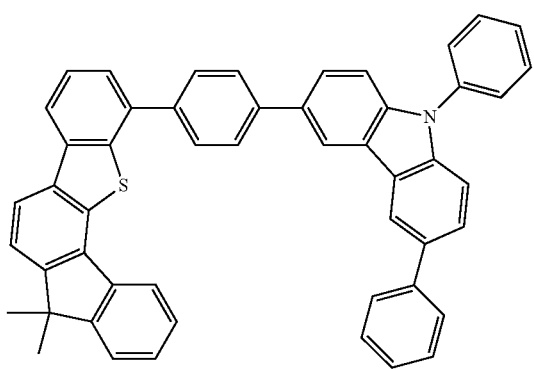
[Chemical Formula D-159]
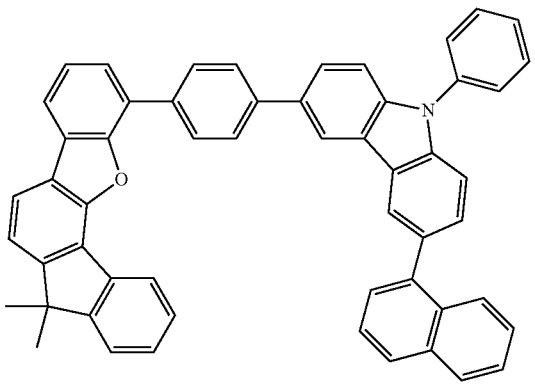
[Chemical Formula D-162]
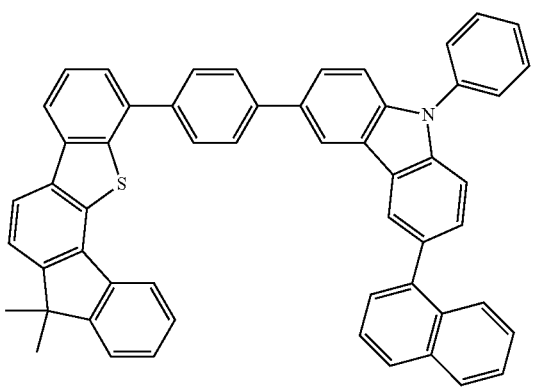
[Chemical Formula D-165]
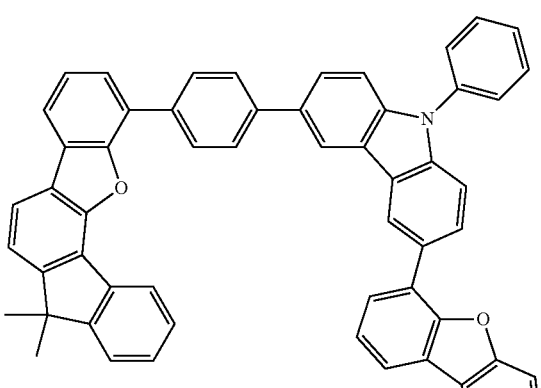

[Chemical Formula D-168]
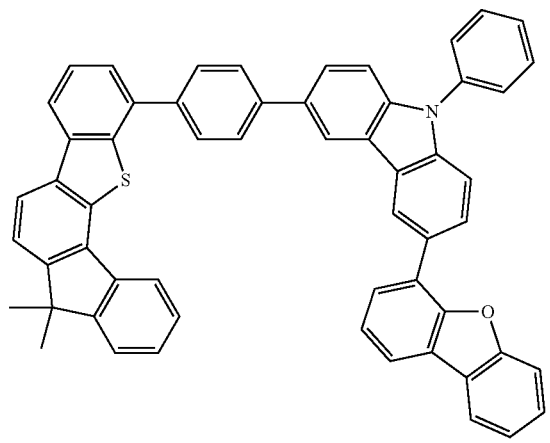
[Chemical Formula D-177]
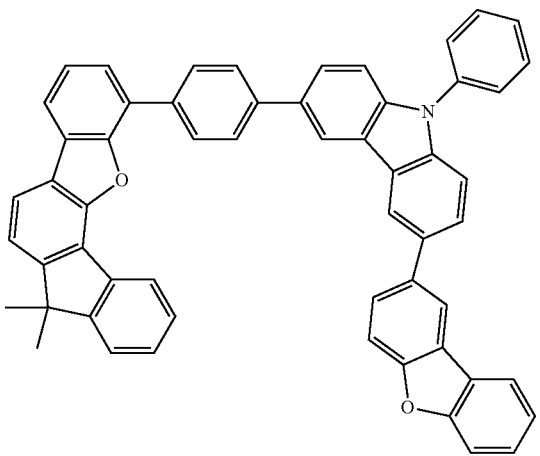
[Chemical Formula D-171]
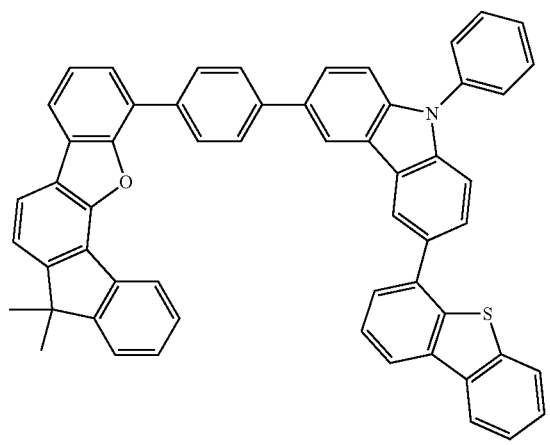
[Chemical Formula D-180]
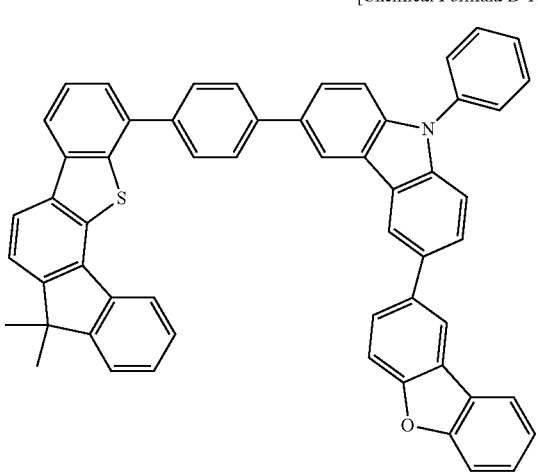
[Chemical Formula D-174]
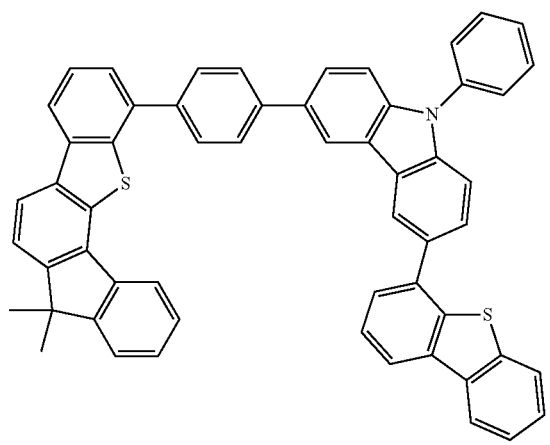
[Chemical Formula D-183]
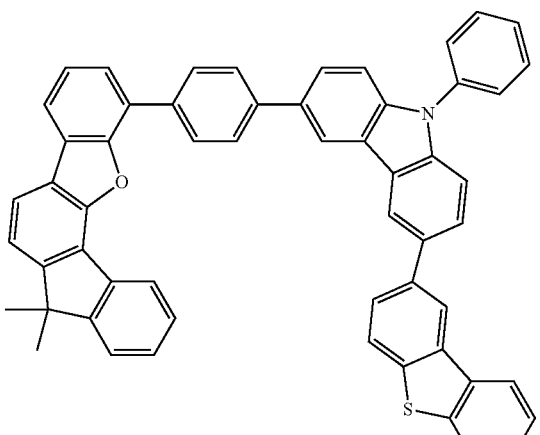

[Chemical Formula D-186]
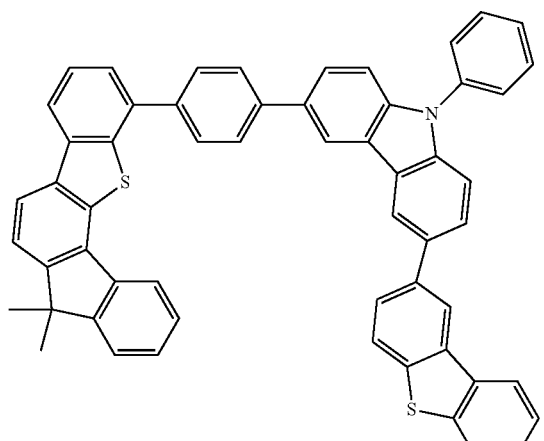
[Chemical Formula D-189]
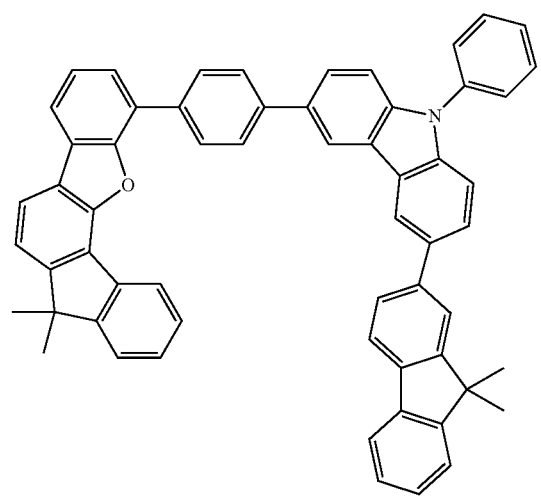
[Chemical Formula D-192]
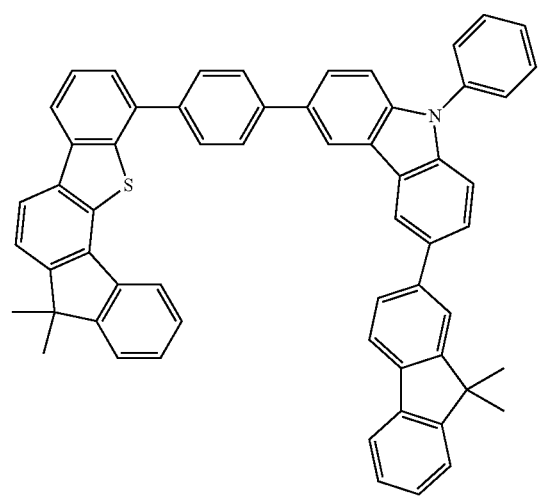
[Chemical Formula D-195]
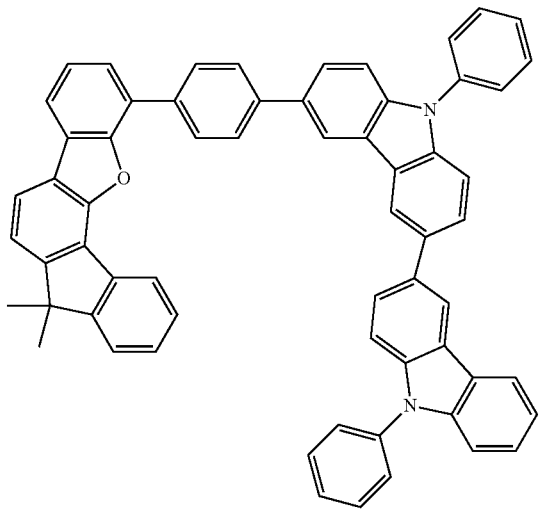
[Chemical Formula D-198]
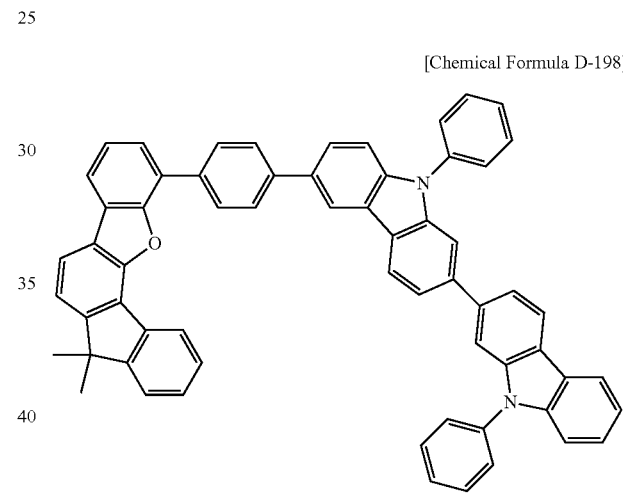
[Chemical Formula D-201]
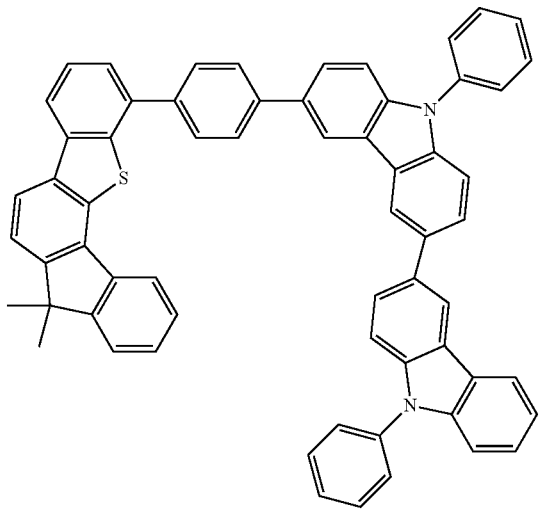

-continued
[Chemical Formula D-204]
[Chemical Formula D-207]
[Chemical Formula D-210]
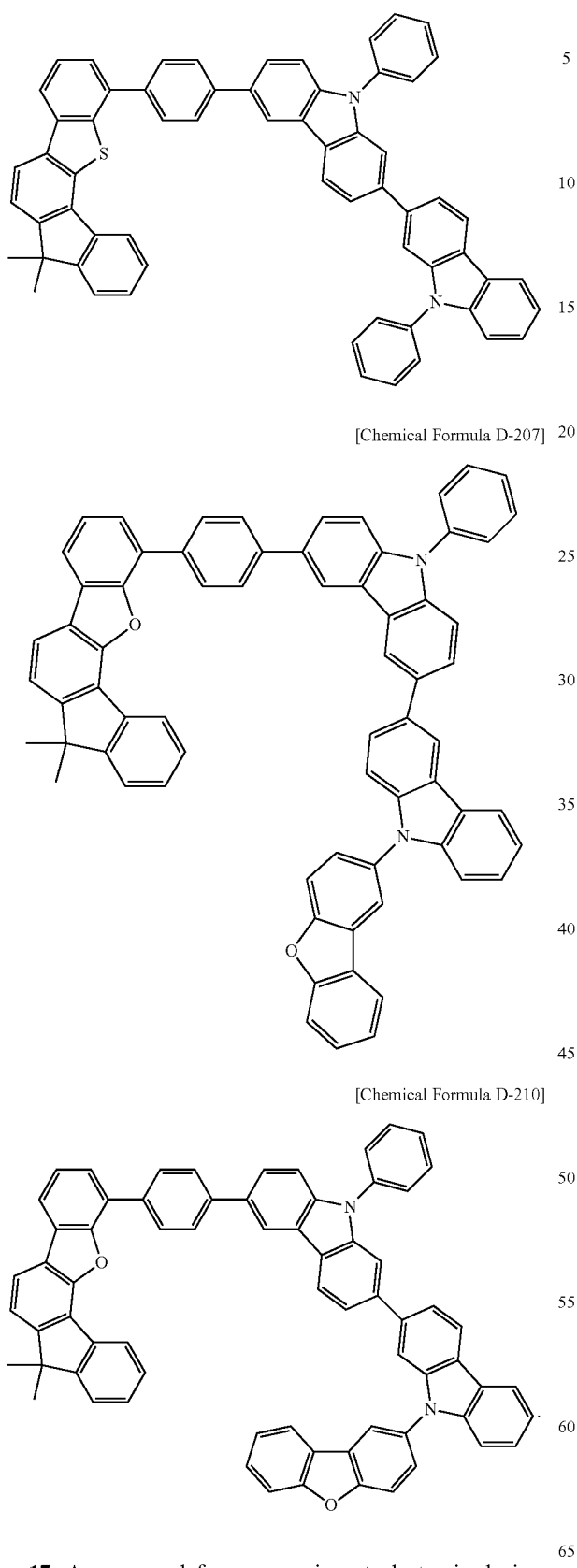
ing Chemical Formulae D-145, D-146, D-148, D-149, D-151, D-152, D-154, D-155, D-157, D-158, D-160, D-161, D-163, D-164, D-166, D-167, D-169, D-170, D-172, D-173, D-175, D-176, D-178, D-179, D-181, D-182, D-184, D-185, D-187, D-188, D-190, D-191, D-193, D-194, D-196, D-197, D-199, D-200, D-202, D-203, D-205, D-206, D-208, and D-209:
[Chemical Formula D-145]
[Chemical Formula D-146]
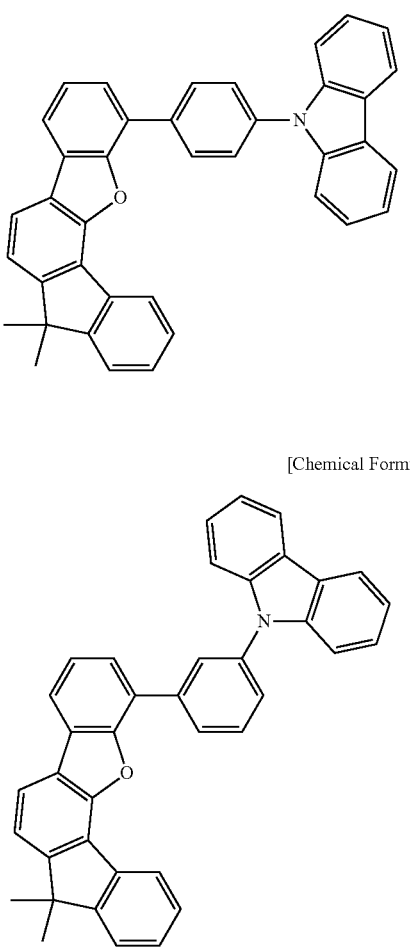
[Chemical Formula D-148]
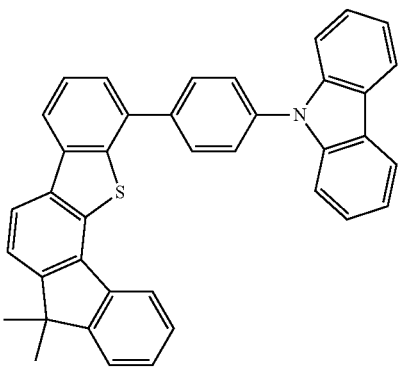
17. A compound for an organic optoelectronic device, wherein the compound is represented by one of the follow-

[Chemical Formula D-149]
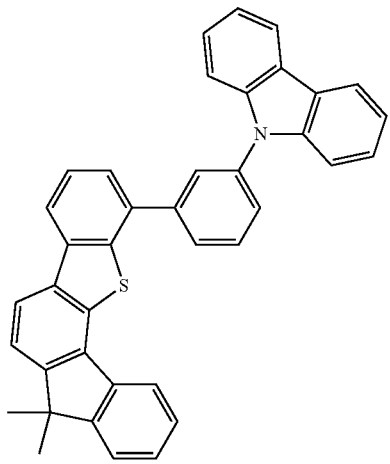
[Chemical Formula D-151]
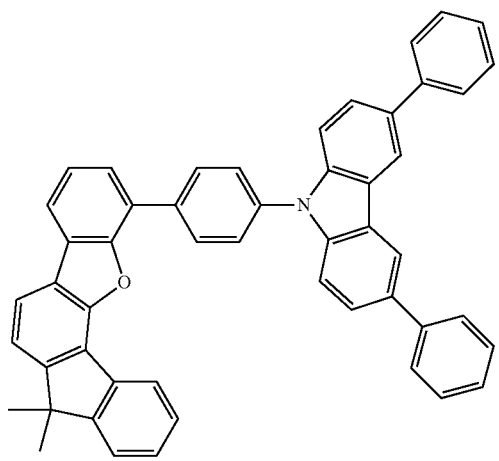
[Chemical Formula D-152]
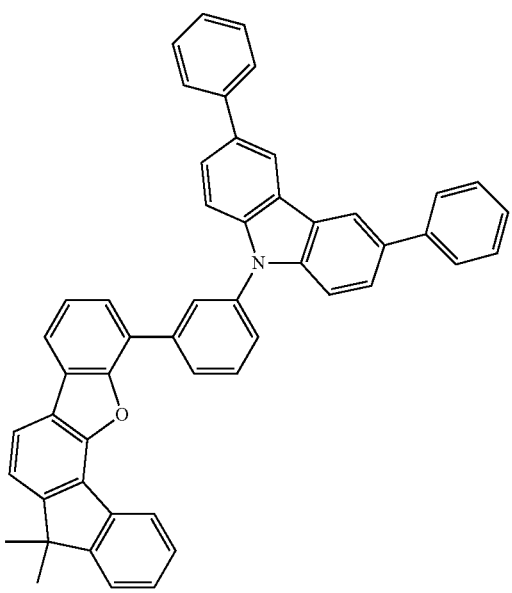
[Chemical Formula D-154]
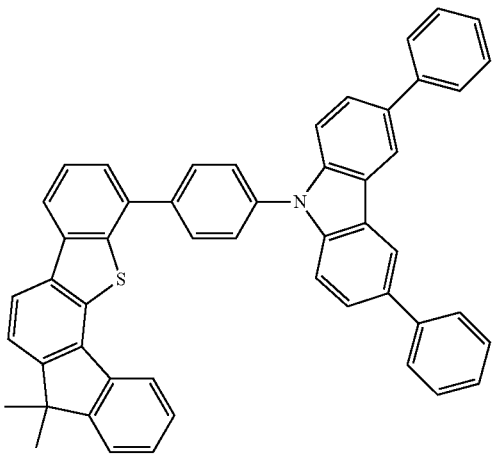
[Chemical Formula D-155]
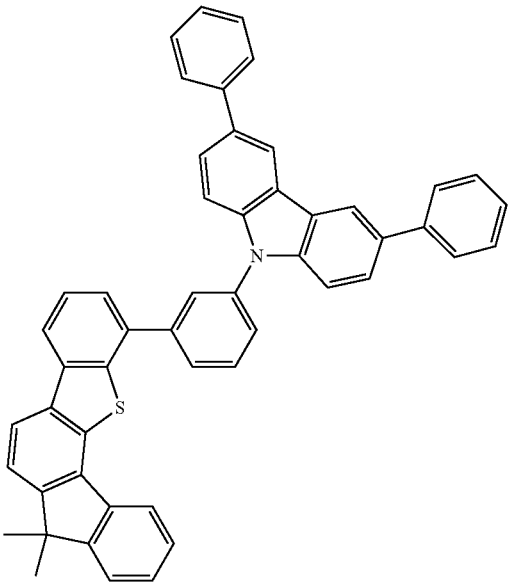
[Chemical Formula D-157]
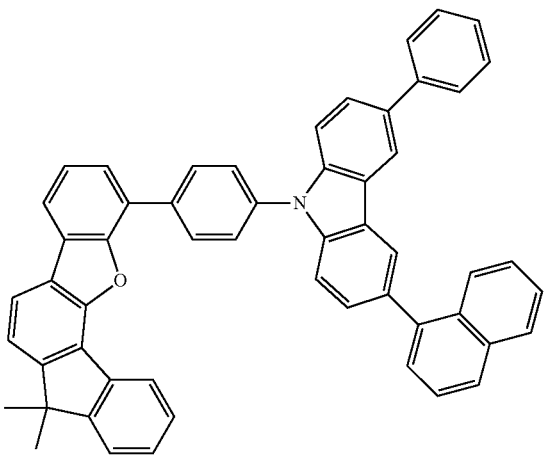

[Chemical Formula D-158]
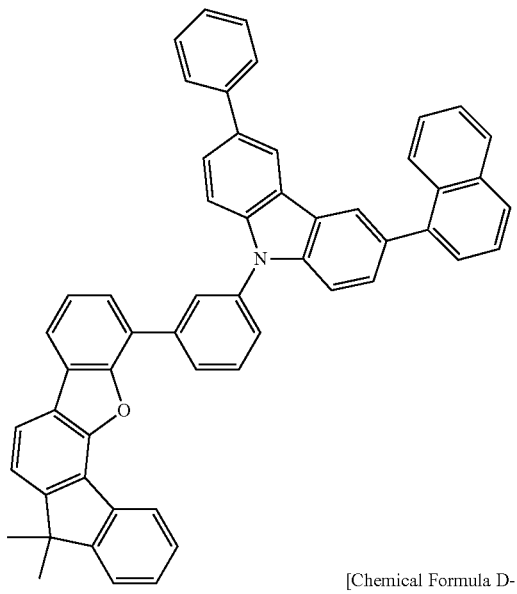
[Chemical Formula D-160]
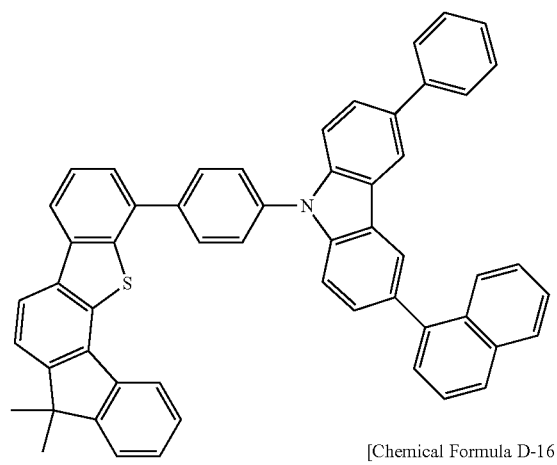
[Chemical Formula D-161]
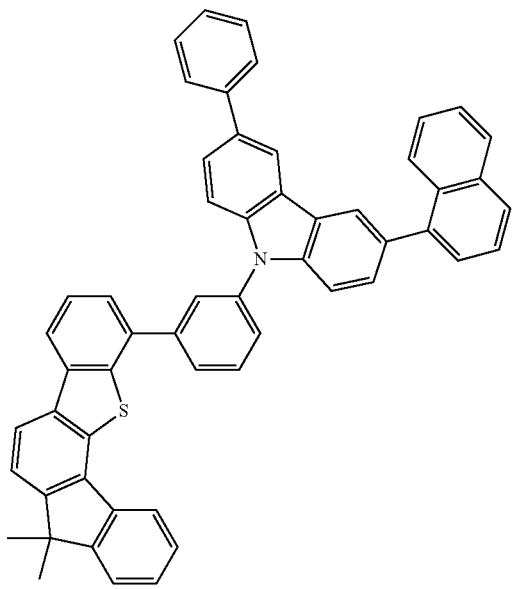
[Chemical Formula D-163]
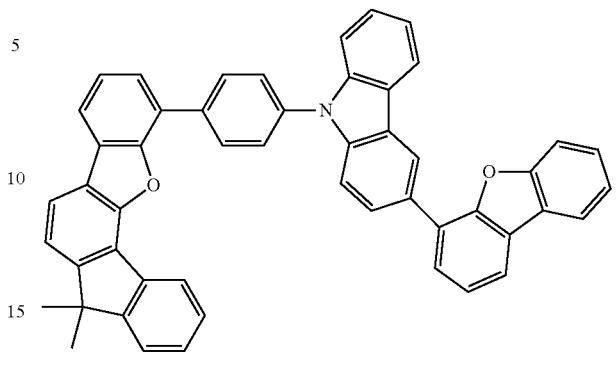
[Chemical Formula D-164]
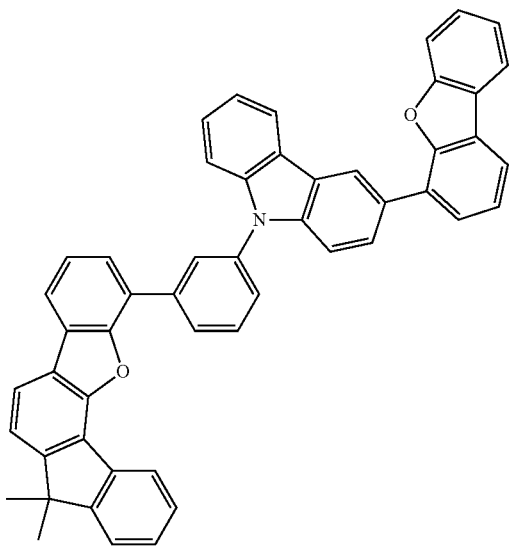
[Chemical Formula D-166]
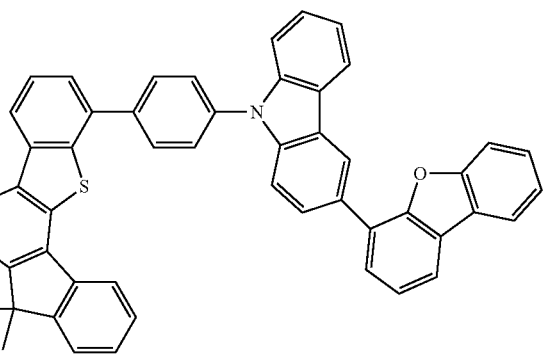

[Chemical Formula D-167]
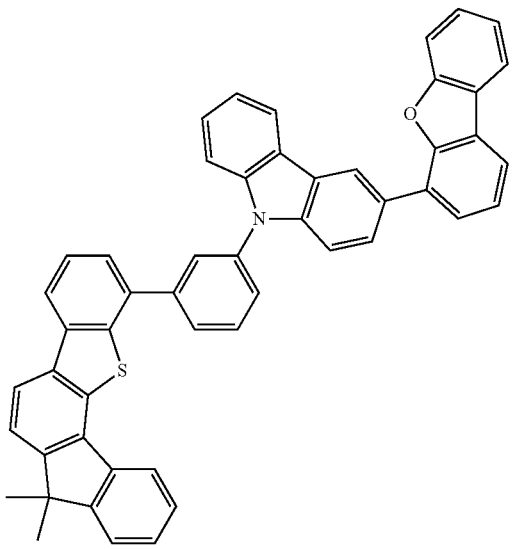
[Chemical Formula D-169]
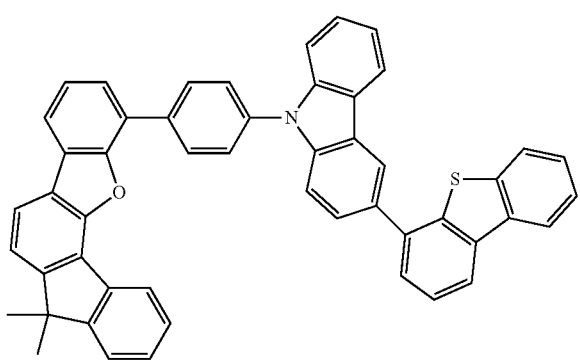
[Chemical Formula D-170]
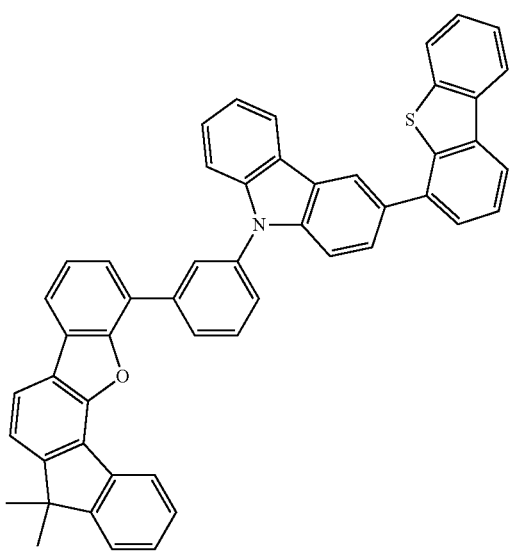
[Chemical Formula D-172]
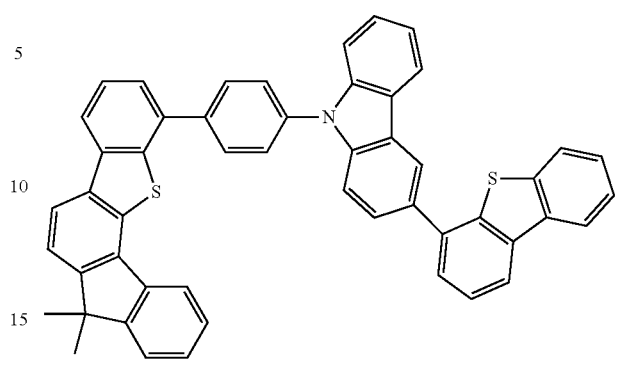
[Chemical Formula D-173]
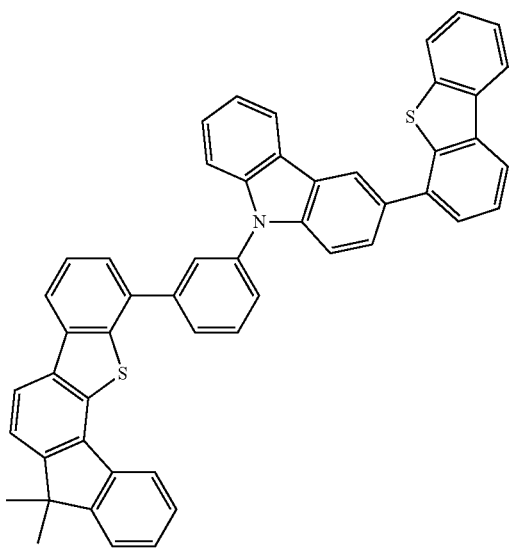
[Chemical Formula D-175]
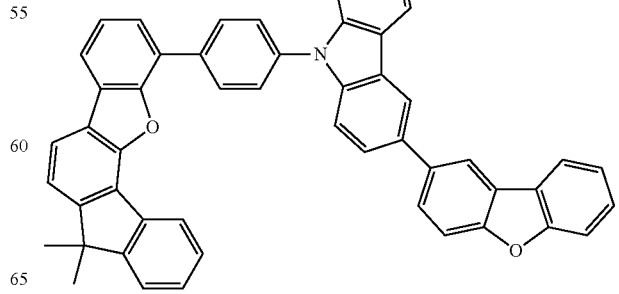

[Chemical Formula D-176]
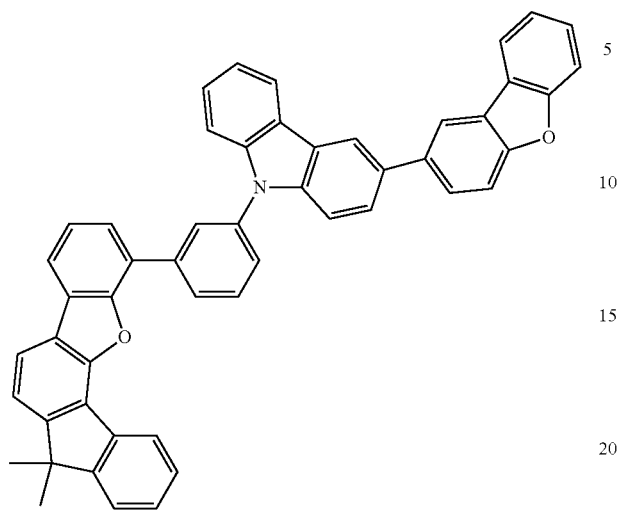
[Chemical Formula D-178]
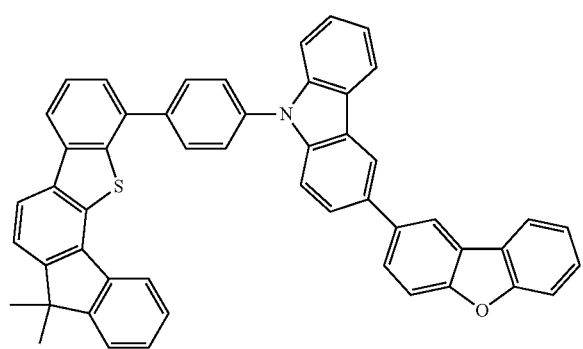
[Chemical Formula D-179]
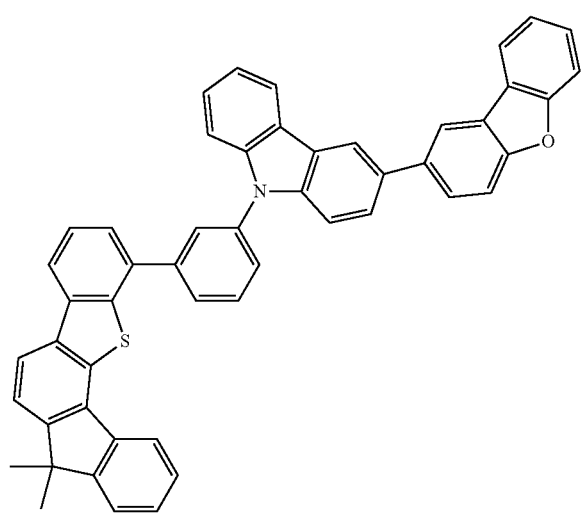
[Chemical Formula D-181]
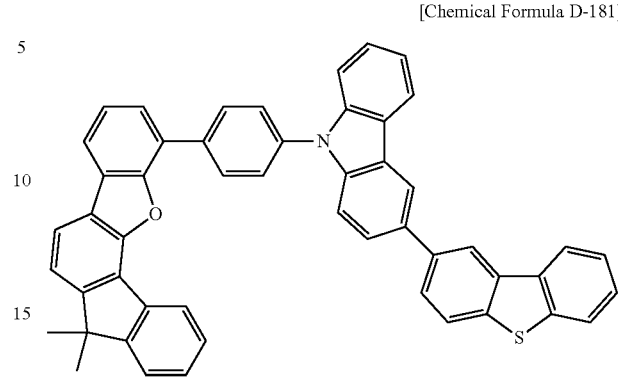
[Chemical Formula D-182]
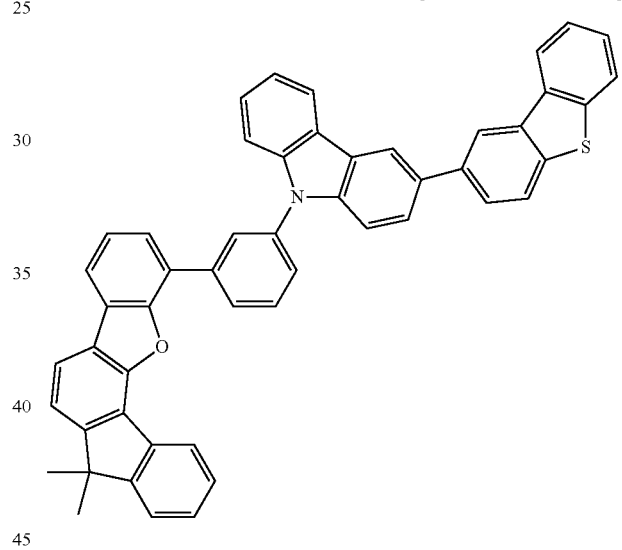
[Chemical Formula D-184]
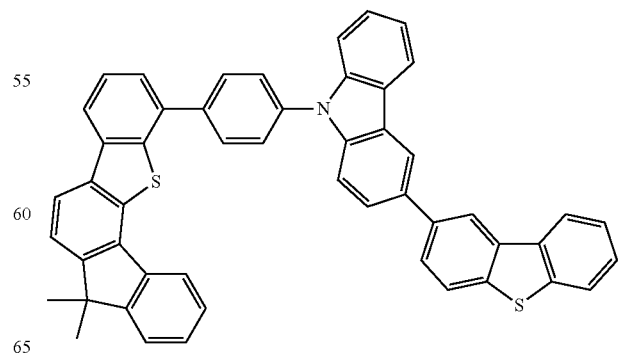

[Chemical Formula D-185]
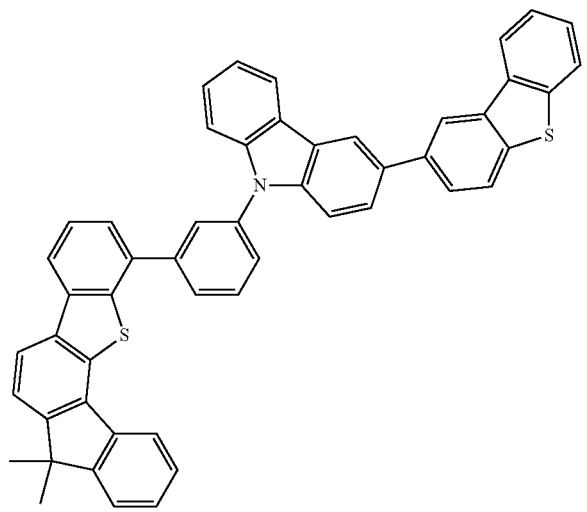
[Chemical Formula D-187]
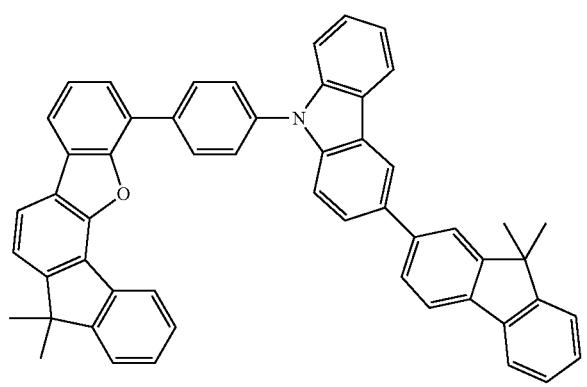
[Chemical Formula D-188]
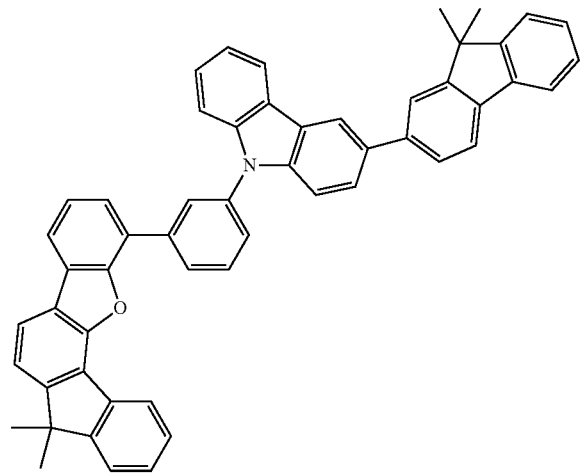
[Chemical Formula D-190]
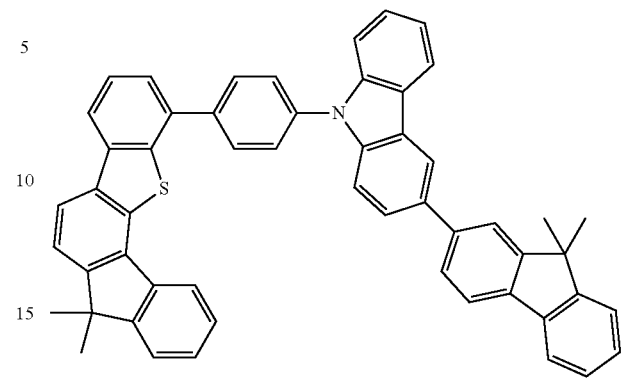
[Chemical Formula D-191]
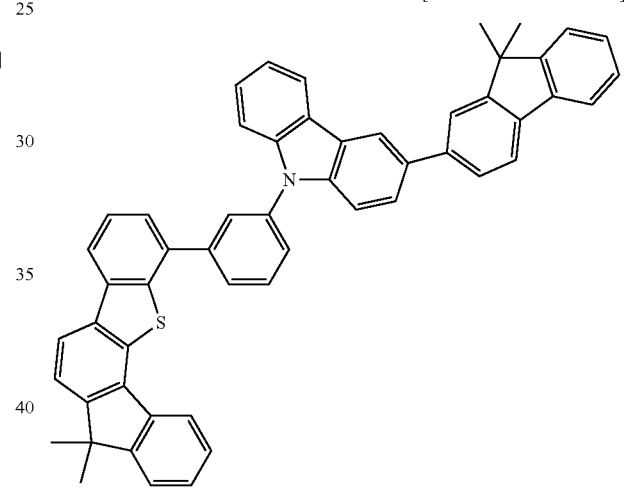
[Chemical Formula D-193]
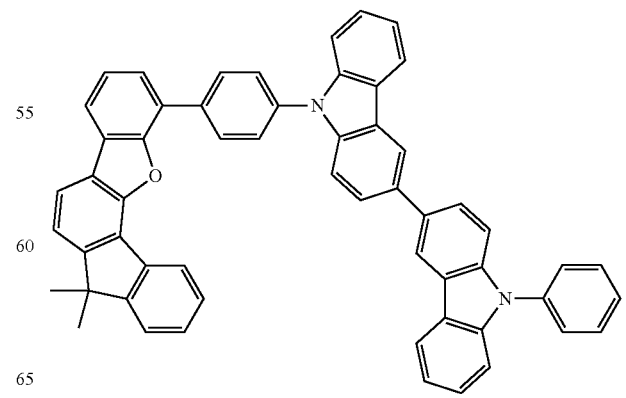

[Chemical Formula D-194]
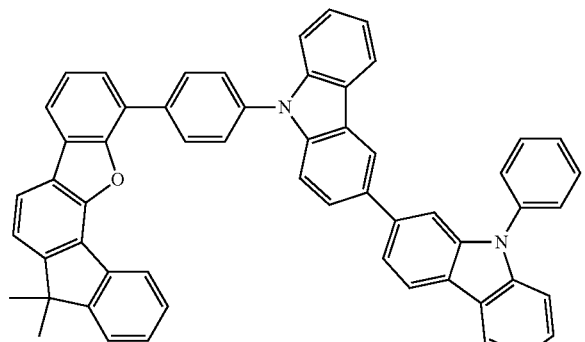
[Chemical Formula D-196]
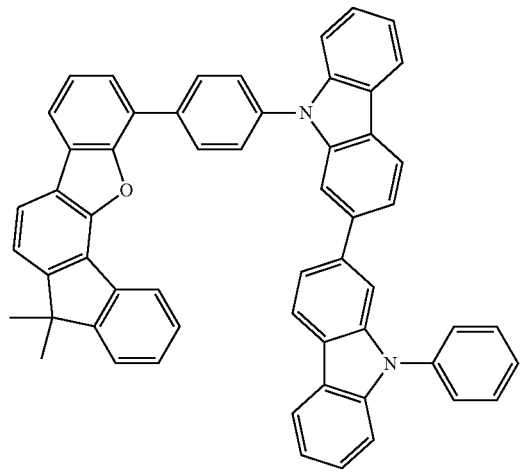
[Chemical Formula D-197]
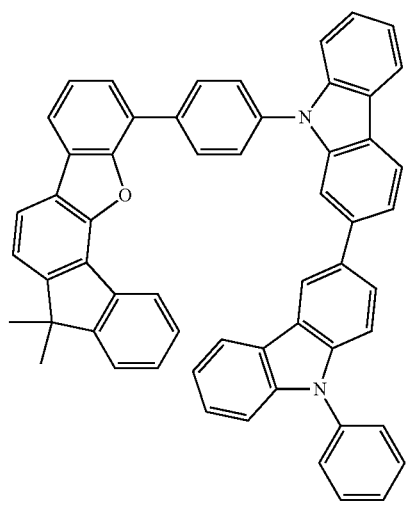
[Chemical Formula D-199]
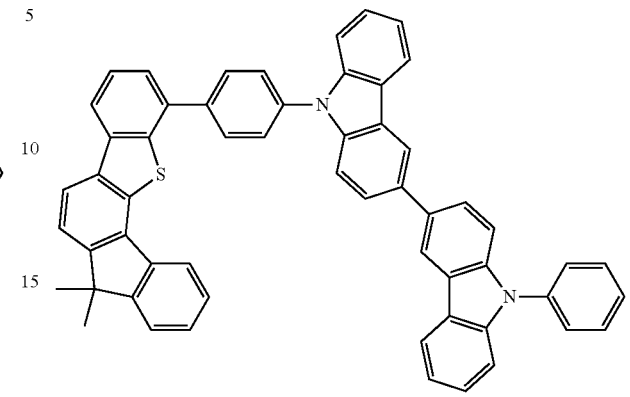
[Chemical Formula D-200]
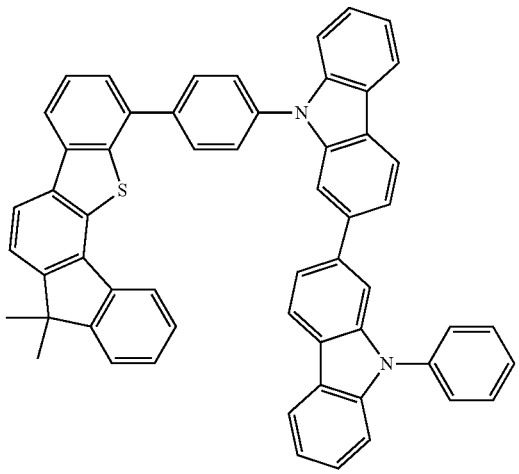
[Chemical Formula D-202]

[Chemical Formula D-203]
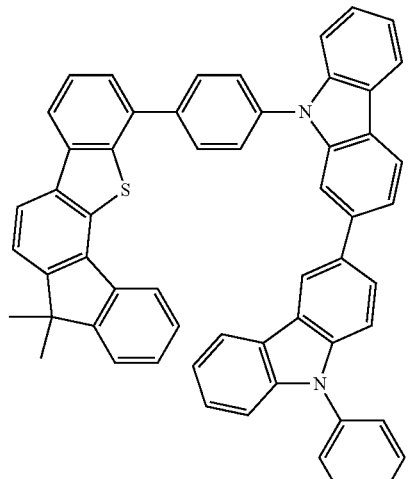
[Chemical Formula D-205]
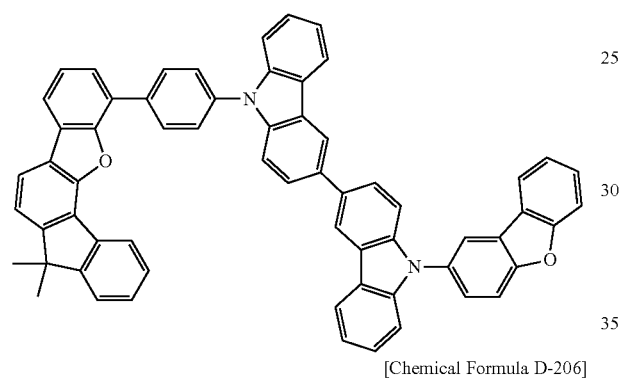
[Chemical Formula D-206]
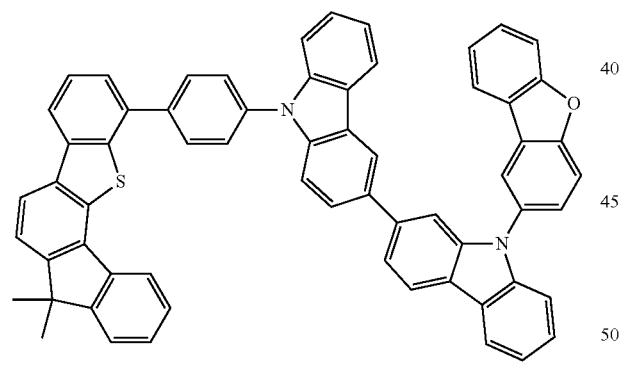
[Chemical Formula D-208]
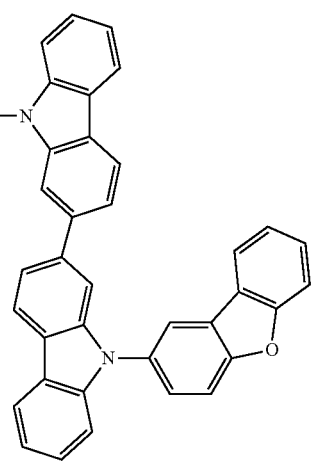
[Chemical Formula D-209]
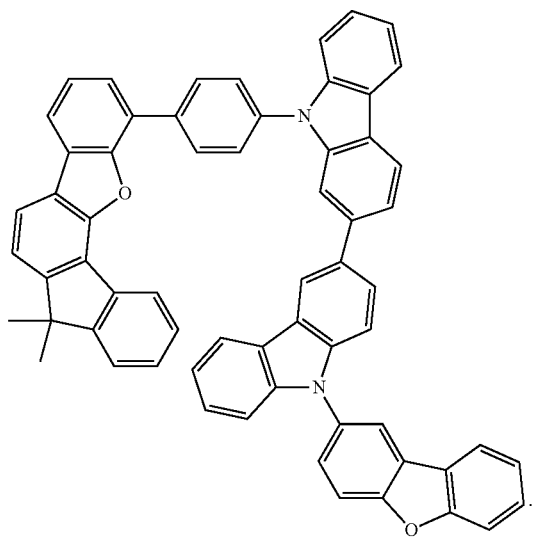
* * * * *